US011753478B2

(12) United States Patent
Lippincott et al.

(10) Patent No.: US 11,753,478 B2
(45) Date of Patent: Sep. 12, 2023

(54) ANTI-CD115 ANTIBODIES

(71) Applicant: Ablexis, LLC, San Diego, CA (US)

(72) Inventors: John Lippincott, San Diego, CA (US); Dana Duey, San Diego, CA (US)

(73) Assignee: ABLEXIS, LLC, San Diego, CA (US)

( * ) Notice: Subject to any disclaimer, the term of this patent is extended or adjusted under 35 U.S.C. 154(b) by 446 days.

(21) Appl. No.: 16/902,940

(22) Filed: Jun. 16, 2020

(65) Prior Publication Data

US 2020/0308291 A1 Oct. 1, 2020

Related U.S. Application Data

(62) Division of application No. 15/760,322, filed as application No. PCT/US2016/052063 on Sep. 16, 2016, now Pat. No. 10,759,861.

(60) Provisional application No. 62/220,147, filed on Sep. 17, 2015, provisional application No. 62/219,578, filed on Sep. 16, 2015.

(51) Int. Cl.
*C07K 16/28* (2006.01)

(52) U.S. Cl.
CPC ...... *C07K 16/2866* (2013.01); *C07K 2317/21* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
CPC .......... C07K 16/2866; C07K 2317/565; C07K 2317/21; C07K 2317/24; C07K 2317/33; C07K 2317/76; C07K 2317/77; C07K 2317/92
See application file for complete search history.

(56) References Cited

U.S. PATENT DOCUMENTS

| | | | | |
|---|---|---|---|---|
| 5,595,756 | A * | 1/1997 | Bally | A61K 9/1272 264/4.1 |
| 10,759,861 | B2 | 9/2020 | Lippincott et al. | |
| 2006/0246071 | A1 | 11/2006 | Green | |
| 2009/0155164 | A1 | 6/2009 | Brasel | |
| 2011/0027286 | A1 | 2/2011 | Thurston | |
| 2011/0178278 | A1 | 7/2011 | Haegel | |
| 2013/0216547 | A1 | 8/2013 | Morton | |
| 2014/0322757 | A1 | 10/2014 | Wong | |

FOREIGN PATENT DOCUMENTS

| | | | |
|---|---|---|---|
| WO | WO2005068503 | 7/2005 | |
| WO | WO2011070024 | 6/2011 | |
| WO | WO-2011070024 A1 * | 6/2011 | A61P 19/08 |
| WO | WO2014096333 | 6/2016 | |

OTHER PUBLICATIONS

O'Brien et al. Activity of tumor-associated macrophage depletion by CSF1R blockade is highly dependent on the tumor model and timing of treatment. Cancer Immunol Immunother 70, 2401-2410 (2021) (Year: 2021).*
Heppner et al. Tumor heterogeneity: biological implications and therapeutic consequences. Cancer Metastasis Review 2:5-23; 1983 (Year: 1983).*
Sporn et al. Chemoprevention of Cancer. Carcinogenesis, vol. 21 (2000), 525-530 (Year: 2000).*
Auerbach et al. Cancer and Metastasis Reviews, 2000, 19: 167-172 (Year: 2000).*
Jain RK. Barriers to drug delivery in solid tumors. Scientific American, Jul. 1994,58-65 (Year: 1994).*
Hait. Anticancer drug development: the grand challenges. Nature Reviews/Drug Discovery, 2010, 9, pp. 253-254 (Year: 2010).*
Gravanis et al. The changing word of cancer drug development: the regulatory bodies' perspective. Chin Clin Oncol, 2014, 3, pp. 1-5) (Year: 2014).*
Beans. Targeting metastasis to halt cancer's spread. PNAS 2018; 115(50): 12539-12543) (Year: 2018).*
Steinman et al. Optimization of current and future therapy for autoimmune diseases. Nat Med. Jan. 6, 2012;18(1):59-65 (Year: 2012).*
Blumberg et al. Optimization of current and future therapy for autoimmune diseases. Nat Med. 2012; 18(1): 35-41) (Year: 2012).*
Tockman et al. Considerations in bringing a cancer biomarker to clinical application. Cancer Res., 1992, 52:2711s-2718s (Year: 1992).*
Kurosawa, et al., "Immunoglobulin Heavy Chain VHDJ Region, Partial (*Homo sapiens*)," National Center for Biotechnology Information, Genbank entry, Jul. 25, 2001 (https://www.ncbi.nlm.nih.gov/protein/21670603) (2 pages).
Stanley, et al., "CSF-1 Receptor Signaling in Myeloid Cells," Cold Spring Harbor Perspectives in Biology; 2014; 6:a021857 (23 Pages).
Kunkik, et al., "Structural Consensus among Antibodies Defines the Antigen Binding Site," PLOS Computational Biology, 8(2):e1002388 (12 pages) (2012).

* cited by examiner

*Primary Examiner* — Vanessa L. Ford
*Assistant Examiner* — Sandra Dillahunt
(74) *Attorney, Agent, or Firm* — HALEY GUILIANO LLP; James F. Haley, Jr.; Brian M. Gummow

(57) ABSTRACT

The present invention provides anti-CD115 monoclonal antibodies and related compositions, which may be used in any of a variety of therapeutic and diagnostic methods for the treatment of cancer, autoimmune, and other diseases.

13 Claims, 16 Drawing Sheets

Specification includes a Sequence Listing.

| | GeoMean FL1 | |
|---|---|---|
| CCL212A | 4.1 | 1 |
| CCL225A | 4.4 | |
| CCL207A | 4.8 | |
| CCL310A | 4.8 | |
| CCL333A | 5.1 | |
| CCL311A | 5.4 | |
| CCL340A | 5.4 | |
| CCL338A | 6.1 | 2 |
| CCL229A | 6.5 | |
| CCL339A | 6.6 | |
| CCL324A | 7.4 | |
| CCL231A | 7.5 | |
| CCL314A | 7.6 | |
| CCL313A | 8.9 | |
| CCL349A | 9.3 | |
| CCL220A | 9.6 | |
| CCL206A | 10 | |
| CCL335A | 10.2 | 3 |
| CCL211A | 12 | |
| CCL223A | 13.3 | |
| CCL332A | 13.6 | |
| CCL218A | 13.9 | |
| CCL312A | 14.9 | |
| CCL320A | 16.2 | 4 |
| CCL303A | 16.9 | |
| CCL327A | 16.9 | |
| CCL322A | 17.5 | |
| CCL315A | 17.7 | |
| CCL205A | 18.1 | |
| CCL216A | 18.3 | |
| CCL255A | 19.3 | |
| CCL328A | 19.4 | |
| CCL209A | 20.1 | |
| CCL329A | 21.7 | 5 |
| CCL201A | 21.8 | |
| CCL238A | 22.1 | |
| CCL346A | 22.7 | |
| CCL226A | 23.5 | |
| CCL203A | 23.6 | |
| CCL249A | 23.9 | |
| CCL309A | 24.2 | |
| CCL325A | 24.9 | |
| CCL245A | 25.6 | |
| CCL321A | 26.3 | |
| CCL217A | 26.4 | |
| CCL208A | 26.5 | |
| CCL337A | 26.5 | |
| CCL213A | 26.9 | |
| CCL204A | 27 | |
| CCL253A | 27 | |
| CCL305A | 30 | |
| CCL235A | 30.3 | 6 |
| CCL215A | 34.9 | |
| CCL301A | 35.3 | |
| CCL221A | 35.8 | |
| CCL344A | 36 | |
| CCL341A | 38.5 | |
| CCL252A | 42.1 | |
| CCL331A | 60 | |
| CCL247A | 69.7 | |

Ranking of cell surface binding
1=little to none
5=good
6=strong

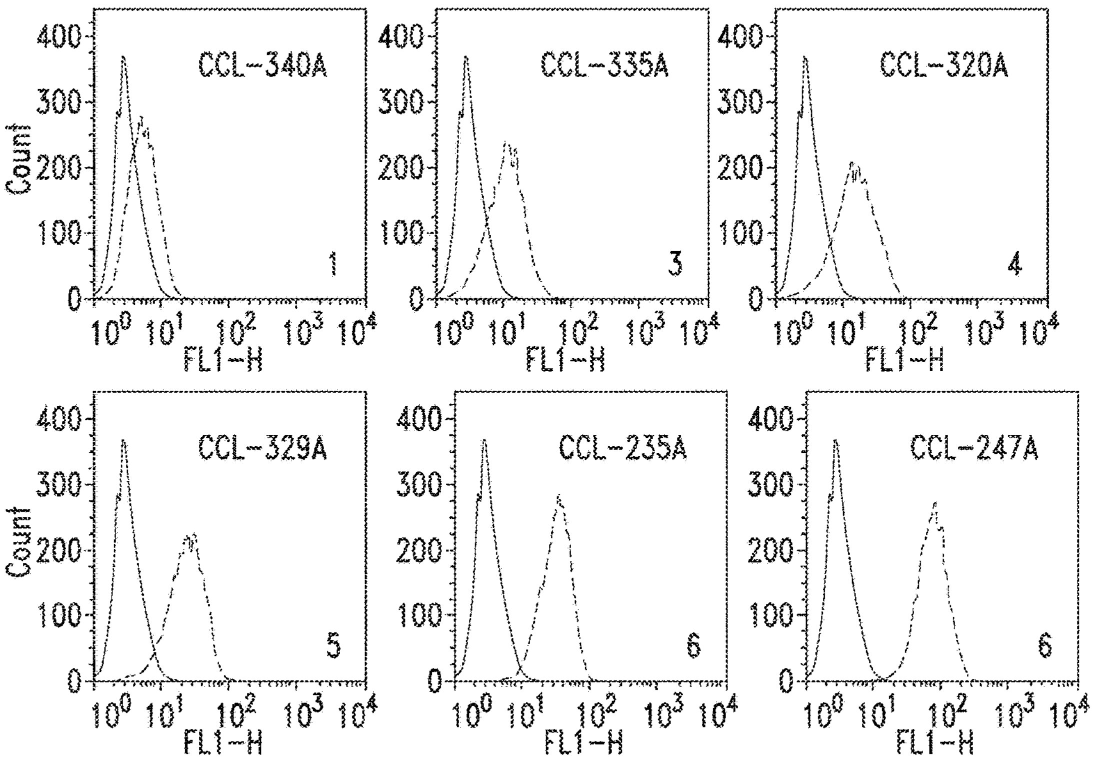

*FIG. 7*

ANTI-CD115 ANTIBODIES

CROSS REFERENCE TO RELATED APPLICATIONS

This application is a divisional application under 35 U.S.C. § 121 of U.S. patent application Ser. No. 15/760,322, filed Mar. 15, 2018; which is a U.S. National Phase Application filed under 35 U.S.C. § 371 from International Patent Application No. PCT/US2016/052063, filed Sep. 16, 2016, which claims the benefit under 35 U.S.C. § 119(e) of U.S. Provisional Application No. 62/220,147, filed Sep. 17, 2015 and U.S. Provisional Application No. 62/219,578, filed Sep. 16, 2015, each of which is incorporated by reference herein in its entirety.

SEQUENCE LISTING

The Sequence Listing associated with this application is provided in text format in lieu of a paper copy and is hereby incorporated by reference into the specification. The name of the text file containing the Sequence Listing is 000118-0006-302.txt. The text file is 537,274 bytes, was created on Jun. 16, 2020, and is being submitted electronically via EFS-Web.

BACKGROUND

Technical Field

The present invention relates generally to anti-CD115 antibodies, compositions and methods of using same. Such antibodies are useful, for example, for treating a variety of diseases, such as oncological and immunological diseases.

Description of the Related Art

CD115, also known as Colony-Stimulating Factor 1 Receptor (CSF1R) and macrophage-colony stimulating factor receptor (M-CSFR), is a cell surface receptor tyrosine kinase belonging to the platelet-derived growth factor family. CD115 has two structurally unrelated ligands, namely CSF-1 (M-CSF) and IL-34. CD115 is expressed by hematopoietic stem cells, myeloid cells, including monocytes, macrophages, osteoclasts, dendritic cells, and microglia, neural progenitor cells, and epithelial cells, including Paneth cells (Stanley and Chitu, Cold Spring Harb Perspect Biol 2014; 6:a021857).

Dysregulation of CD115, and/or its ligands, is associated with proliferative diseases and disorders (e.g., neoplasms, tumors and metastases), as well as immunological and neurological diseases and disorders. The present invention provides chimeric and fully human anti-CD115 antibodies, including CD115 antagonists.

SUMMARY OF THE INVENTION

The present invention relates to anti-CD115 antibodies. More specifically, it relates to chimeric anti-CD115 antibodies generated from an AlivaMab® Mouse, fully human anti-CD115 antibodies produced therefrom, and methods of use thereof.

One aspect of the invention provides an isolated anti-CD115 antibody, or an antigen-binding fragment thereof, comprising i) a heavy chain variable region comprising a VHCDR1 selected from any of SEQ ID NOs:436-543, a VHCDR2 selected from any of SEQ ID NOs:868-975, and a VHCDR3 selected from any of SEQ ID NOs:1300-1407 and ii) a light chain variable region comprising a VLCDR1 selected from any of SEQ ID NOs:652-759, a VLCDR2 selected from any of SEQ ID NOs:1084-1191, and a VLCDR3 selected from any of SEQ ID NOs:1516-1623.

In one embodiment, the VHCDR1, VHCDR2, and VHCDR3 of the anti-CD115 antibody, or antigen-binding fragment thereof, comprise SEQ ID NOs:450, 882, and 1314, respectively. In one embodiment, the VLCDR1, VLCDR2, and VLCDR3 comprise SEQ ID NOs:666, 1098, and 1530, respectively. In another embodiment, the VH is selected from any one of SEQ ID NOs:109-216. In yet another embodiment, the VL is selected from any one of SEQ ID NOs:325-432. In one embodiment, the VH comprises SEQ ID NO:123. In another embodiment, the VL comprises SEQ ID NO:339. In another embodiment, the VH comprises SEQ ID NO:123, and the VL comprises SEQ ID NO:339.

In one embodiment, the anti-CD115 antibody, or antigen-binding fragment thereof, is human. In one embodiment, the antibody is chimeric. In certain embodiments, the antibody is selected from a single-variable domain antibody, single chain antibody, a scFv, a bispecific antibody, a multi-specific antibody, a Fab, a F(ab')2, and a whole antibody.

One aspect of the invention provides a recombinant polynucleotide encoding the anti-CD115 antibody, or antigen-binding fragment thereof, described above. Another aspect of the invention provides an expression vector comprising the recombinant polynucleotide. In another aspect of the invention provides an isolated host cell that comprises the expression vector. One aspect of the invention provides a composition comprising an anti-CD115 antibody, or antigen-binding fragment thereof, described herein and a physiologically acceptable carrier.

BRIEF DESCRIPTION OF THE FIGURES

FIG. 7 shows binding of anti-CD115 IgGλ mAbs to OCI-AML5 cells.

BRIEF DESCRIPTION OF THE SEQUENCES

Figure 1:
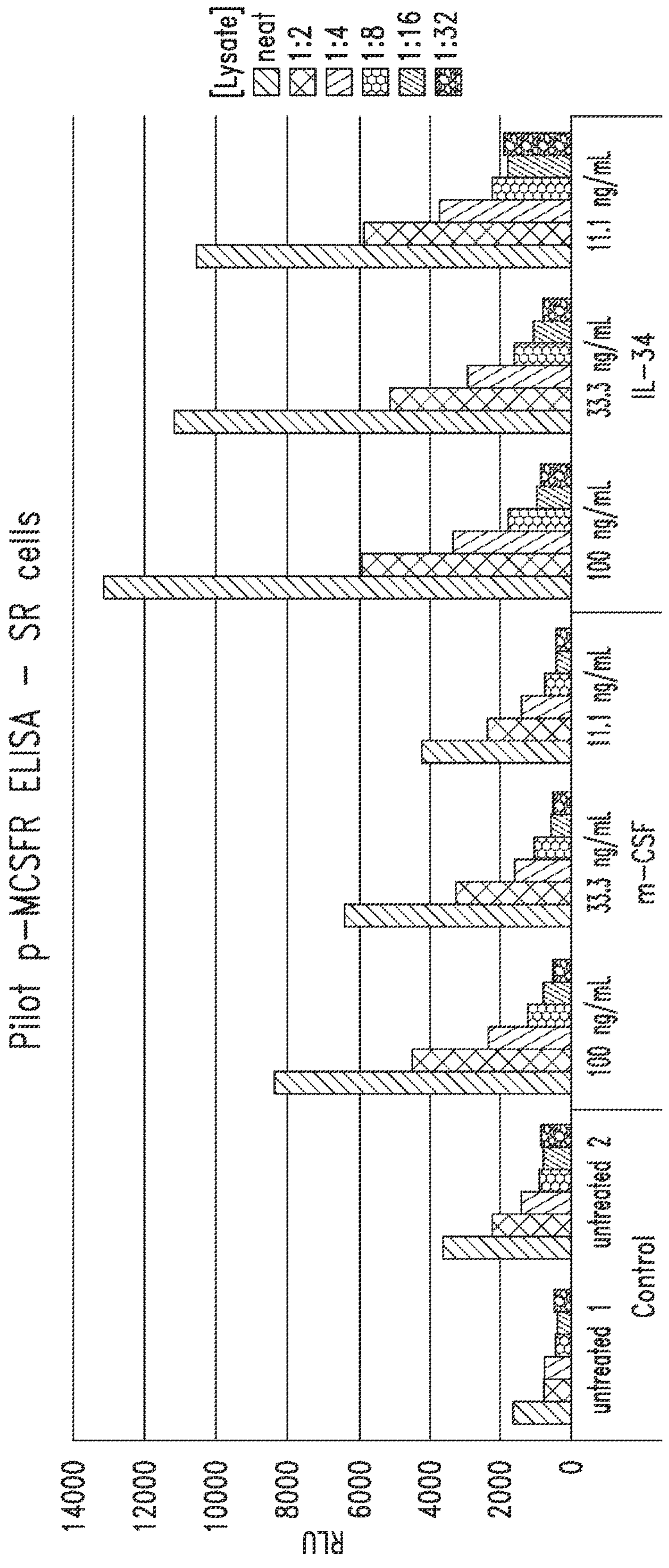
FIG. 1 shows ELISA can detect an increase in p-MCSFR. For each grouping of bars, the lysate ratio is neat, 1:2, 1:4, 1:8, 1:16 and 1:32 from left to right.

SEQ ID NOs:1-108 are polynucleotide sequences encoding VH regions of the anti-CD115 antibodies listed in Table 2.

SEQ ID NOs:109-216 are amino acid sequences of VH regions of the anti-CD115 antibodies listed in Table 2.

SEQ ID NOs:217-324 are polynucleotide sequences encoding VL regions of the anti-CD115 antibodies listed in Table 2.

SEQ ID NOs:325-432 are amino acid sequences of VL regions of the anti-CD115 antibodies listed in Table 2.

SEQ ID NO:433 is an IgG specific primer.

SEQ ID NO:434 is an Igλ specific primer.

SEQ ID NO:435 is an Igκ specific primer.

SEQ ID NOs:436-543 are amino acid sequences of the VHCDR1 of the anti-CD115 antibodies listed in Table 2.

SEQ ID NOs:544-651 are polynucleotide sequences encoding the VHCDR1 of the anti-CD115 antibodies listed in Table 2.

SEQ ID NOs:652-759 are amino acid sequences of the VLCDR1 of the anti-CD115 antibodies listed in Table 2.

SEQ ID NOs:760-867 are polynucleotide sequences encoding the VLCDR1 of the anti-CD115 antibodies listed in Table 2.

SEQ ID NOs:868-975 are amino acid sequences of the VHCDR2 of the anti-CD115 antibodies listed in Table 2.

SEQ ID NOs:976-1083 are polynucleotide sequences encoding the VHCDR2 of the anti-CD115 antibodies listed in Table 2.

SEQ ID NOs:1084-1191 are amino acid sequences of the VLCDR2 of the anti-CD115 antibodies listed in Table 2.

SEQ ID NOs:1192-1299 are polynucleotide sequences encoding the VLCDR2 of the anti-CD115 antibodies listed in Table 2.

SEQ ID NOs:1300-1407 are amino acid sequences of the VHCDR3 of the anti-CD115 antibodies listed in Table 2.

SEQ ID NOs:1408-1515 are polynucleotide sequences encoding the VHCDR3 of the anti-CD115 antibodies listed in Table 2.

SEQ ID NOs:1516-1623 are amino acid sequences of the VLCDR3 of the anti-CD115 antibodies listed in Table 2.

SEQ ID NOs:1624-1731 are polynucleotide sequences encoding the VLCDR3 of the anti-CD115 antibodies listed in Table 2.

DETAILED DESCRIPTION

The present disclosure relates to anti-CD115 antibodies. Ablexis has used its proprietary AlivaMab® Mouse technology (See WO 2010/039900 and WO 2011/123708, incorporated herein in their entirety) to generate panels of monoclonal antibodies (mAbs) against human CD115. Antibodies that potently neutralize CD115 signaling induced by CSF-1 were identified within the panel of CD115 AlivaMab® antibodies. In one embodiment, anti-CD115 AlivaMab® antibodies potently neutralize CD115 signaling induced by IL-34. In one embodiment, anti-CD115 AlivaMab® antibodies that potently neutralize CD115 signaling induced by both CSF-1 and IL-34. CD115 (colony-stimulating factor 1 receptor, CSF1R, C-FMS) is a member of the receptor tyrosine kinase superfamily. For a review of CD115 biology, refer to Stanley and Chitu, Cold Spring Harb. Perspect. Biol. 2014 Jun. 2; 6(6).

Embodiments of the invention pertain to the use of anti-CD115 antibodies, or antigen-binding fragments thereof, for the diagnosis, assessment and treatment of diseases and disorders associated with CD115, CSF-1 and/or IL-34 or aberrant expression thereof. The subject antibodies are used in the treatment or prevention of neoplasms and/or the treatment or prevention of autoimmune and/or inflammatory diseases, among other diseases.

Portions of variable regions from the AlivaMab® antibodies may include all or a combination of the complementarity determining regions (CDRs) of the VH and/or VL. The variable regions may be formatted with constant regions, either native or modified for various desired effector functions, in a standard antibody structure (two heavy chains with two light chains). The variable regions may also be formatted as multi-specific antibodies, e.g., bispecific antibodies binding to two different epitopes on CD115 or to two different antigens, one of which is CD115. The variable regions may also be formatted as antibody fragments, e.g., single-domain antibodies comprising a single VH or VL, Fabs or Fab'2. The antibodies may also be used as antibody-drug conjugates, or carry other additions such as small molecule toxins, biologic toxins, cytokines, oligopeptides, or RNAs to increase therapeutic modality and/or increase safety.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al., Short Protocols in Molecular Biology, 3rd ed., Wiley & Sons, 1995; Sambrook and Russell, Molecular Cloning: A Laboratory Manual (3rd Edition, 2001); Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

The terms "antibody" and "immunoglobulin" (Ig) are used interchangeably herein. An antibody may be either membrane bound or secreted. As used herein, the term encompasses not only intact, or "whole", polyclonal or monoclonal antibodies, but also fragments thereof (such as single-variable domain (VH, VL or combination thereof) antibodies, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

Antibody, or Ig, molecules are typically comprised of two identical heavy chains and two identical light chains linked together through disulfide bonds. Both heavy chains (IgH) and light chains (IgL) contain a variable (V) region or domain and a constant (C) region or domain. The portion of the IgH locus encoding the V region comprises multiple copies of variable (V), diversity (D), and joining (J) gene segments. The portion of the IgL loci encoding the V region comprises multiple copies of V and J gene segments. The V region encoding portion of the IgH and IgL loci undergo gene segment rearrangement, e.g., different combinations of a V, (D) and J gene segments arrange to form the IgH and IgL variable regions, to develop diverse antigen specificity in antibodies. Each variable region comprises three complementarity-determining regions (CDRs) interspersed between the less variable framework regions (FRs). The heavy chain comprises VHCDR1, VHCDR2, and VHCDR3. The light chain comprises VLCDR1, VLCDR2, and VLCDR3. The secreted form of the IgH C region is made up of three C domains, CH1, CH2, CH3, optionally CH4 (CO, and a hinge region except for Cμ, which lacks a hinge region. The membrane-bound form of the IgH C region also has membrane and intra-cellular domains. The IgH constant region determines the isotype of the antibody, e.g. IgM, IgD, IgG1, IgG2, IgG3, IgG4, IgA and IgE. It will be appreciated that non-human mammals, such as an AlivaMab® Mouse, encoding multiple Ig isotypes will be able to undergo isotype class switching. There are two types of human IgL, Igκ and Igλ.

The term "antigen-binding fragment" as used herein refers to a polypeptide fragment that contains at least one CDR of an immunoglobulin heavy and/or light chain that binds to CD115. In this regard, an antigen-binding fragment of the antibodies may comprise 1, 2, 3, 4, 5, or all 6 CDRs of a VH and VL sequence set forth herein from anti-CD115 antibodies described herein. An antigen-binding fragment of the CD115-specific antibodies described herein is capable of binding to CD115. In certain embodiments, an antigen-binding fragment or an antibody comprising an antigen-binding fragment, prevents or inhibits CSF-1 and/or IL-34 binding to CD115 and subsequent signaling events. In other embodiments, an anti-CD115 antibody, or an antigen-binding fragment thereof, prevents signaling events mediated by CD115 by preventing dimerization of CD115, including dimerization that is induced by CSF-1 or IL-34 binding or that may happen spontaneously under certain conditions of expression CD115. In certain embodiments, the antigen-binding fragment binds specifically to and/or inhibits or modulates the biological activity of human CD115.

In certain embodiments, antibodies and antigen-binding fragments thereof as described herein include a heavy chain and a light chain CDR set, respectively interposed between a heavy chain and a light chain framework region (FR) set that provide conformational support to the CDRs and define the spatial relationship of the CDRs relative to each other. As used herein, the term "CDR set" refers to the three hypervariable regions of a heavy or light chain V region. Proceeding from the N terminus of a heavy or light chain, these regions are denoted as "CDR1," "CDR2," and "CDR3" respectively. An antigen-binding site, therefore, includes six CDRs, comprising the CDR set from each of a heavy and a light chain V region.

A "Fab" domain or fragment comprises the N-terminal portion of the IgH, which includes the V region and the CH1 domain of the IgH, and the entire IgL. A "$F(ab')_2$" domain comprises the Fab domain and a portion of the hinge region, wherein the 2 IgH are linked together via disulfide linkage in the middle hinge region. Both the Fab and $F(ab')_2$ are "antigen-binding fragments." The C-terminal portion of the IgH, comprising the CH2 and CH3 domains, is the "Fc" domain. The Fc domain is the portion of the Ig recognized by cell receptors, such as the FcR, and to which the complement-activating protein, C1q, binds. The lower hinge region, which is encoded in the 5' portion of the CH2 exon, provides flexibility within the antibody for binding to FcR receptors. An "Fv" fragment includes a non-covalent VH::VL heterodimer including an antigen-binding site. In certain embodiments, single chain Fv (scFv) antibodies are contemplated. A scFv is a covalently linked VH::VL heterodimer which is expressed from a gene fusion including VH- and VL-encoding genes linked by a peptide-encoding linker (Huston et al. (1988) Proc. Nat. Acad. Sci. USA 85(16): 5879-5883).

Where bispecific antibodies are to be used, these may be conventional bispecific antibodies, which can be manufactured in a variety of ways (Holliger, P. and Winter G. Current Opinion Biotechnol. 4, 446-449 (1993)), e.g., prepared chemically or from hybrid hybridomas, or may be any of the bispecific antibody fragments mentioned above.

As used herein "chimeric antibody" refers to an antibody encoded by a polynucleotide sequence containing polynucleotide sequences from two or more species, e.g., human and mouse.

As used herein "chimeric Ig chain" refers to an Ig heavy chain or an Ig light chain encoded by a polynucleotide sequence containing polynucleotide sequences from two or more species, e.g., human and mouse. For example, a chimeric Ig heavy chain may comprise a human VH domain, DH domain, JH domain, CH1 domain, and upper hinge region and mouse CH2 and CH3 domains. In one embodiment, the middle hinge region is mouse. In one embodiment, the middle hinge region is human. In one embodiment, the middle hinge region is chimeric.

"Polypeptide," "peptide" or "protein" are used interchangeably herein to describe a chain of amino acids that are linked together by chemical bonds. A polypeptide or protein may be an IgH, IgL, V domain, C domain, or an antibody.

The strength, or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant, $K_D$. See, generally, Davies et al. (1990) Annual Rev. Biochem. 59:439-473.

"Polynucleotide" refers to a chain of nucleic acids that are linked together by chemical bonds. Polynucleotides include, but are not limited to, DNA, cDNA, RNA, mRNA, and gene sequences and segments. Polynucleotides may be isolated from a living source such as a eukaryotic cell, prokaryotic cell or virus, or may be derived through in vitro manipulation by using standard techniques of molecular biology, or by DNA synthesis, or by a combination of a number of techniques.

As used herein, the term "vector" refers to a nucleic acid molecule into which another nucleic acid fragment can be integrated without loss of the vector's ability to replicate. Vectors may originate from a virus, a plasmid or the cell of a higher organism. Vectors are utilized to introduce foreign or recombinant DNA into a host cell, wherein the vector is replicated.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes an RNA, for expressing the encoded RNA in a particular cell, either for subsequent translation of the RNA into a polypeptide or for subsequent trans regulatory activity by the RNA in the cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, alpha virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb 25:37-42, 1993; Kirshenbaum et al., J. Clin. Invest 92:381-387, 1993; each of which is incorporated herein by reference).

The term "construct" as used herein refers to a sequence of DNA artificially constructed by genetic engineering, recombineering or synthesis. In one embodiment, the DNA constructs are linearized prior to recombination. In another embodiment, the DNA constructs are not linearized prior to recombination.

The terms "inhibit", "neutralize", and "antagonize" are used interchangeably herein and encompass anti-CD115 antibodies that block, inhibit, and/or decrease the activity of CD115. Examples of CD115 activity include kinase function and ligand binding, e.g., binding to CSF-1 and/or IL-34.

The term "treating" with regard to a subject, refers to improving at least one symptom of the subject's disease or disorder. Treating includes curing, improving, or at least partially ameliorating the disease or disorder.

As used herein, the term "disorder" refers to, and is used interchangeably with, the terms disease, condition, or illness.

The term "pharmaceutically acceptable carrier" refers generally to any material (e.g., carrier, excipient, or stabilizer) that may accompany a therapeutic agent and is non-toxic to the subject or patient being exposed thereto.

The term "administering," as used herein, refers to any mode of transferring, delivering, introducing, or transporting a pharmaceutical composition or other agent, such as an anti-CD115 antibody, to a subject. Such modes include oral administration, topical contact, intravenous, intraperitoneal, intramuscular, intranasal, or subcutaneous administration.

The term "inhibit" or "neutralize" or "block" may relate generally to the ability of one or more anti-CD115 antibodies of the invention to decrease a biological activity of CD115, such as intracellular signaling and/or ligand binding. The inhibition/blocking of CSF-1 and/or IL-34 to CD115 preferably reduces or alters the normal level or type of cell signaling that occurs when CSF-1 and/or IL-34 binds to CD115 without inhibition or blocking. Inhibition and blocking are also intended to include any measurable decrease in the binding of CSF-1 and/or IL-34 to CD115 when in contact with an anti CD115 antibody as disclosed herein as compared to the ligand not in contact with an anti CD115 antibody, e.g., the blocking of CSF-1 and/or IL-34 to CD115 by at least about a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease, including all integers in between. In one embodiment, a neutralizing anti-CD115 antibody inhibits binding of CSF-1 and/or IL-34 to CD115 by at least about a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease, including all integers in between.

An antibody, or antigen-binding fragment thereof, is said to "specifically bind," "immunologically bind," and/or is "immunologically reactive" to CD115 if it reacts at a detectable level (within, for example, an ELISA assay) with CD115, and does not react detectably with unrelated polypeptides under similar conditions. Antibodies are considered to specifically bind to a target polypeptide when the binding affinity is at least $1\times10^{-7}$ M or, preferably, at least $1\times10^{-8}$ M.

In one embodiment, the antibody, or antigen-binding fragment thereof, specifically binds human CD115.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

CD115

CD115 is expressed by a variety of cells, including, but not limited to, hematopoietic stem cells (HSCs); myeloid cells, including monocytes, macrophages, osteoclasts, dendritic cells, and microglia; neural progenitor cells; and epithelial cells, including Paneth cells (Stanley and Chitu, Cold Spring Harb Perspect Biol 2014; 6:a021857). Dysregulation of CD115, and/or its ligands, is associated with proliferative diseases and disorders (e.g., neoplasms, tumors and metastases), as well as immunological and neurological diseases and disorders, making it an important therapeutic target.

Anti-CD115 Antibodies

AlivaMab® Mouse anti-CD115 antibodies were generated using both AlivaMab® Mouse Kappa mice and AlivaMab® Mouse Lambda mice (also referred to herein interchangeably as AlivaMab® Kappa Mice and AlivaMab® Lambda Mice, respectively). Antibodies produced by AlivaMab® Kappa Mice comprise a chimeric immunoglobulin heavy (IgH) chain and a human immunoglobulin kappa (Igκ) light chain. Antibodies produced by AlivaMab® Lambda Mice comprise a chimeric IgH chain and a human immunoglobulin lambda (Igλ) light chain. The chimeric IgH chain of the AlivaMab® Mouse antibodies comprises a human variable region comprising a human variable heavy (VH) domain, a human diversity heavy (DH) domain, and a human joining heavy (JH) domain, a human constant heavy 1 (CH1) domain, a human upper hinge region (except for Cμ, which is naturally missing an upper hinge region), a mouse middle hinge region, a mouse CH2 domain, and a mouse CH3 domain. Upon identification of a lead candidate antibody, e.g., an anti-CD115 antibody, the human heavy chain variable region is readily appended to a fully human constant region while maintaining the antigen-binding characteristics of the parent chimeric antibody that were developed in vivo in the AlivaMab® Mouse. In one embodiment, the human heavy chain variable region, CH1 and, optionally, upper hinge region of the chimeric antibody are appended to human hinge, a human CH2 domain and a human CH3 domain in order to produce a fully human antibody.

Accordingly, in one embodiment, an anti-CD115 antibody, or an antigen-binding fragment thereof, of the invention is chimeric. In one embodiment, the chimeric anti-CD115 antibody, or an antigen-binding fragment thereof, comprises a chimeric IgH chain and a human Igκ chain. In one embodiment, the chimeric anti-CD115 antibody, or an antigen-binding fragment thereof, comprises a chimeric IgH chain and a human Igλ chain. In one embodiment, the chimeric anti-CD115 antibody is human and mouse. In one embodiment, an anti-CD115 antibody, or an antigen-binding fragment thereof, of the invention is human. In one embodiment, the human anti-CD115 antibody, or an antigen-binding fragment thereof, comprises a human IgH chain and a human Igκ chain. In one embodiment, the human anti-CD115 antibody, or an antigen-binding fragment thereof, comprises a human IgH chain and a human Igλ chain. In one embodiment, the isotype of the anti-CD115 antibody is selected from IgM, IgD, IgG1, IgG2, IgG3, IgG4, IgA and IgE. In one embodiment, the isotype of the anti-CD115 antibody is selected from IgG1, IgG2, IgG3, and IgG4.

In one embodiment, the anti-CD115 antibody binds an Fc receptor (FcR) selected from an FcγR, an FcεR, and an FcαR. In one embodiment, the anti-CD115 antibody binds an FcγR selected from FcγRI (CD64), FcγRII (CD32), and FcγRIII (CD16), including isoforms thereof. In one embodiment, the Fc region of the anti-CD115 antibody comprises a mutation so that it preferentially binds a particular FcγR (see, e.g., U.S. Pat. No. 6,737,056 and U.S. 2015/0031862).

In one aspect of the invention, the CDRs of an anti-CD115 antibody, or antigen-binding fragment thereof, may be mixed and matched between the CDRs of antibody clones described herein. In one embodiment, an anti-CD115 antibody, or antigen-binding fragment thereof, comprises a VHCDR1 comprising any one of SEQ ID NOs:436-543, a VHCDR2 comprising any one of SEQ ID NOs:868-975, and a VHCDR3 comprising any one of SEQ ID NOs:1300-1407. In one embodiment, the VHCDR1, VHCDR2 and VHCDR3 are selected from three different anti-CD115 clones disclosed herein. In one embodiment, the VHCDR1, VHCDR2 and VHCDR3 are selected from two different anti-CD115 clones disclosed herein.

In one embodiment, an anti-CD115 antibody, or an antigen-binding fragment thereof, comprises a VLCDR1 comprising any one of SEQ ID NOs:652-759, a VLCDR2 comprising any one of SEQ ID NOs:1084-1191, and a VLCDR3 comprising any one of SEQ ID NOs:1516-1623. In one embodiment, the VLCDR1, VLCDR2 and VLCDR3 are selected from three different anti-CD115 clones disclosed herein. In one embodiment, the VLCDR1, VLCDR2 and VLCDR3 are selected from two different anti-CD115 clones disclosed herein.

In one embodiment, an anti-CD115 antibody, or an antigen-binding fragment thereof, comprises 1) comprises a VHCDR1 comprising any one of SEQ ID NOs: 436-543, a VHCDR2 comprising any one of SEQ ID NOs: 868-975, and a VHCDR3 comprising any one of SEQ ID NOs: 300-1407, and 2) a VLCDR1 comprising any one of SEQ ID NOs: 652-759, a VLCDR2 comprising any one of SEQ ID NOs: 1084-1191, and a VLCDR3 comprising any one of SEQ ID NOs: 1516-1623.

In one aspect of the invention, the CDRs of an anti-CD115 antibody, or antigen-binding fragment thereof, are from the same anti-CD115 antibody clone disclosed herein. In one embodiment, an anti-CD115 antibody, or an antigen-binding fragment thereof, comprises a VHCDR1, a VHCDR2 and a VHCDR3 from the same anti-CD115 clone disclosed herein. In one embodiment, an anti-CD115 antibody, or an antigen-binding fragment thereof, comprises a VHCDR1, a VHCDR2, and a VHCDR3 of a VH selected from any one of SEQ ID NOs:109-216. In one embodiment, an anti-CD115 antibody, or an antigen-binding fragment thereof, comprises a VHCDR1, a VHCDR2, and a VHCDR3 comprising the corresponding sequences listed in Table 3.

Accordingly, in one embodiment, an anti-CD115 antibody, or an antigen-binding fragment thereof, comprises a VHCDR1, a VHCDR2, and a VHCDR3 selected from: SEQ ID NOs:436, 868, and 1300; SEQ ID NOs:437, 869, and 1301; SEQ ID NOs:438, 870, and 1302; SEQ ID NOs:439, 871, and 1303; SEQ ID NOs:440, 872, and 1304; SEQ ID NOs:441, 873, and 1305; SEQ ID NOs:442, 874, and 1306; SEQ ID NOs:443, 875, and 1307; SEQ ID NOs:444, 876, and 1308; SEQ ID NOs:445, 877, and 1309; SEQ ID NOs:446, 878, and 1310; SEQ ID NOs:447, 879, and 1311; SEQ ID NOs:448, 880, and 1312; SEQ ID NOs:449, 881, and 1313; SEQ ID NOs:450, 882, and 1314; SEQ ID NOs:451, 883, and 1315; SEQ ID NOs:452, 884, and 1316; SEQ ID NOs:453, 885, and 1317; SEQ ID NOs:454, 886, and 1318; SEQ ID NOs:455, 887, and 1319; SEQ ID NOs:456, 888, and 1320; SEQ ID NOs:457, 889, and 1321; SEQ ID NOs:458, 890, and 1322; SEQ ID NOs:459, 891, and 1323; SEQ ID NOs:460, 892, and 1324; SEQ ID NOs:461, 893, and 1325; SEQ ID NOs:462, 894, and 1326; SEQ ID NOs:463, 895, and 1327; SEQ ID NOs:464, 896, and 1328; SEQ ID NOs:465, 897, and 1329; SEQ ID NOs:466, 898, and 1330; SEQ ID NOs:467, 899, and 1331; SEQ ID NOs:468, 900, and 1332; SEQ ID NOs:469, 901, and 1333; SEQ ID NOs:470, 902, and 1334; SEQ ID NOs:471, 903, and 1335; SEQ ID NOs:472, 904, and 1336; SEQ ID NOs:473, 905, and 1337; SEQ ID NOs:474, 906, and 1338; SEQ ID NOs:475, 907, and 1339; SEQ ID NOs:476, 908, and 1340; SEQ ID NOs:477, 909, and 1341; SEQ ID NOs:478, 910, and 1342; SEQ ID NOs:479, 911, and 1343; SEQ ID NOs:480, 912, and 1344; SEQ ID NOs:481, 913, and 1345; SEQ ID NOs:482, 914, and 1346; SEQ ID NOs:483, 915, and 1347; SEQ ID NOs:484, 916, and 1348; SEQ ID NOs:485, 917, and 1349; SEQ ID NOs:486, 918, and 1350; SEQ ID NOs:487, 919, and 1351; SEQ ID NOs:488, 920, and 1352; SEQ ID NOs:489, 921, and 1353; SEQ ID NOs:490, 922, and 1354; SEQ ID NOs:491, 923, and 1355; SEQ ID NOs:492, 924, and 1356; SEQ ID NOs:493, 925, and 1357; SEQ ID NOs:494, 926, and 1358; SEQ ID NOs:495, 927, and 1359; SEQ ID NOs:496, 928, and 1360; SEQ ID NOs:497, 929, and 1361; SEQ ID NOs:498, 930, and 1362; SEQ ID NOs:499, 931, and 1363; SEQ ID NOs:500, 932, and 1364; SEQ ID NOs:501, 933, and 1365; SEQ ID NOs:502, 934, and 1366; SEQ ID NOs:503, 935, and 1367; SEQ ID NOs:504, 936, and 1368; SEQ ID NOs:505, 937, and 1369; SEQ ID NOs:506, 938, and 1370; SEQ ID NOs:507, 939, and 1371; SEQ ID NOs:508, 940, and 1372; SEQ ID NOs:509, 941, and 1373; SEQ ID NOs:510, 942, and 1374; SEQ ID NOs:511, 943, and 1375; SEQ ID NOs:512, 944, and 1376; SEQ ID NOs:513, 945, and 1377; SEQ ID NOs:514, 946, and 1378; SEQ ID NOs:515, 947, and 1379; SEQ ID NOs:516, 948, and 1380; SEQ ID NOs:517, 949, and 1381; SEQ ID NOs:518, 950, and 1382; SEQ ID NOs:519, 951, and 1383; SEQ ID NOs:520, 952, and 1384; SEQ ID NOs:521, 953, and 1385; SEQ ID NOs:522, 954, and 1386; SEQ ID NOs:523, 955, and 1387; SEQ ID NOs:524, 956, and 1388; SEQ ID NOs:525, 957, and 1389; SEQ ID NOs:526, 958, and 1390; SEQ ID NOs:527, 959, and 1391; SEQ ID NOs:528, 960, and 1392; SEQ ID NOs:529, 961, and 1393; SEQ ID NOs:530, 962, and 1394; SEQ ID NOs:531, 963, and 1395; SEQ ID NOs:532, 964, and 1396; SEQ ID NOs:533, 965, and 1397; SEQ ID NOs:534, 966, and 1398; SEQ ID NOs:535, 967, and 1399; SEQ ID NOs:536, 968, and 1400; SEQ ID NOs:537, 969, and 1401; SEQ ID NOs:538, 970, and 1402; SEQ ID NOs:539, 971, and 1403; SEQ ID NOs:540, 972, and 1404; SEQ ID NOs:541, 973, and 1405; SEQ ID NOs:542, 974, and 1406; and SEQ ID NOs:543, 975, and 1407.

In one embodiment, an anti-CD115 antibody, or an antigen-binding fragment thereof, comprises a VLCDR1, a VLCDR2 and a VLCDR3 from the same anti-CD115 clone disclosed herein. In one embodiment, an anti-CD115 antibody, or an antigen-binding fragment thereof, comprises a VLCDR1, a VLCDR2, and a VLCDR3 of a VL selected from any one of SEQ ID NOs:325-432. In one embodiment, an anti-CD115 antibody, or an antigen-binding fragment thereof, comprises a VLCDR1, a VLCDR2, and a VLCDR3 comprising the corresponding sequences listed in Table 3.

Accordingly, in one embodiment, an anti-CD115 antibody, or an antigen-binding fragment thereof, comprises a VLCDR1, a VLCDR2, and a VLCDR3 selected from: SEQ ID NOs:652, 1084, and 1516; SEQ ID NOs:653, 1085, and 1517; SEQ ID NOs:654, 1086, and 1518; SEQ ID NOs:655, 1087, and 1519; SEQ ID NOs:656, 1088, and 1520; SEQ ID NOs:657, 1089, and 1521; SEQ ID NOs:658, 1090, and 1522; SEQ ID NOs:659, 1091, and 1523; SEQ ID NOs:660, 1092, and 1524; SEQ ID NOs:661, 1093, and 1525; SEQ ID NOs:662, 1094, and 1526; SEQ ID NOs:663, 1095, and 1527; SEQ ID NOs:664, 1096, and 1528; SEQ ID NOs:665, 1097, and 1529; SEQ ID NOs:666, 1098, and 1530; SEQ ID NOs:667, 1099, and 1531; SEQ ID NOs:668, 1100, and 1532; SEQ ID NOs:669, 1101, and 1533; SEQ ID NOs:670, 1102, and 1534; SEQ ID NOs:671, 1103, and 1535; SEQ ID NOs:672, 1104, and 1536; SEQ ID NOs:673, 1105, and 1537; SEQ ID NOs:674, 1106, and 1538; SEQ ID NOs:675, 1107, and 1539; SEQ ID NOs:676, 1108, and 1540; SEQ ID NOs:677, 1109, and 1541; SEQ ID NOs:678, 1110, and 1542; SEQ ID NOs:679, 1111, and 1543; SEQ ID NOs:680, 1112, and 1544; SEQ ID NOs:681, 1113, and 1545; SEQ ID NOs:682, 1114, and 1546; SEQ ID NOs:683, 1115, and 1547; SEQ ID NOs:684, 1116, and 1548; SEQ ID NOs:685, 1117, and 1549; SEQ ID NOs:686, 1118, and 1550; SEQ ID NOs:687, 1119, and 1551; SEQ ID NOs:688, 1120, and 1552; SEQ ID NOs:689, 1121, and 1553; SEQ ID NOs:690, 1122, and 1554; SEQ ID NOs:691, 1123, and 1555; SEQ ID NOs:692, 1124, and 1556; SEQ ID NOs:693, 1125, and 1557; SEQ ID NOs:694, 1126, and 1558; SEQ ID NOs:695, 1127, and 1559; SEQ ID NOs:696, 1128, and 1560; SEQ ID NOs:697, 1129, and 1561; SEQ ID NOs:698, 1130, and 1562; SEQ ID NOs:699, 1131, and 1563; SEQ ID NOs:700, 1132, and 1564; SEQ ID NOs:701, 1133, and 1565; SEQ ID NOs:702, 1134, and 1566; SEQ ID NOs:703, 1135, and 1567; SEQ ID NOs:704, 1136, and 1568; SEQ ID NOs:705, 1137, and 1569; SEQ ID NOs:706, 1138, and 1570; SEQ ID NOs:707, 1139, and 1571; SEQ ID NOs:708, 1140, and 1572; SEQ ID NOs:709, 1141, and 1573; SEQ ID NOs:710, 1142, and 1574; SEQ ID NOs:711, 1143, and 1575; SEQ ID NOs:712, 1144, and 1576; SEQ ID NOs:713, 1145, and 1577; SEQ ID NOs:714, 1146, and 1578; SEQ ID NOs:715, 1147, and 1579; SEQ ID NOs:716, 1148, and 1580; SEQ ID NOs:717, 1149, and 1581; SEQ ID NOs:718, 1150, and 1582; SEQ ID NOs:719, 1151, and 1583; SEQ ID NOs:720, 1152, and 1584; SEQ ID NOs:721, 1153, and 1585; SEQ ID NOs:722, 1154, and 1586; SEQ ID NOs:723, 1155, and 1587; SEQ ID NOs:724, 1156, and 1588; SEQ ID NOs:725, 1157, and 1589; SEQ ID NOs:726, 1158, and 1590; SEQ ID NOs:727, 1159, and 1591; SEQ ID NOs:728, 1160, and 1592; SEQ ID NOs:729, 1161, and 1593; SEQ ID NOs:730, 1162, and 1594; SEQ ID NOs:731, 1163, and 1595; SEQ ID NOs:732, 1164, and 1596; SEQ ID NOs:733, 1165, and 1597; SEQ ID NOs:734, 1166, and 1598; SEQ ID NOs:735, 1167, and 1599; SEQ ID NOs:736, 1168, and 1600; SEQ ID NOs:737, 1169, and 1601; SEQ ID NOs:738, 1170, and 1602; SEQ ID NOs:739, 1171, and 1603; SEQ ID NOs:740, 1172, and 1604; SEQ ID NOs:741, 1173, and 1605; SEQ ID NOs:742, 1174, and 1606; SEQ ID NOs:743, 1175, and 1607; SEQ ID NOs:744, 1176, and 1608; SEQ ID NOs:745, 1177, and 1609; SEQ ID NOs:746, 1178, and 1610; SEQ ID NOs:747, 1179, and 1611; SEQ ID NOs:748, 1180, and 1612; SEQ ID NOs:749, 1181, and 1613; SEQ ID NOs:750, 1182, and 1614; SEQ ID NOs:751, 1183, and 1615; SEQ ID NOs:752, 1184, and 1616; SEQ ID NOs:753, 1185, and 1617; SEQ ID NOs:754, 1186, and 1618; SEQ ID NOs:755, 1187, and 1619; SEQ ID NOs:756, 1188, and 1620; SEQ ID NOs:757, 1189, and 1621; SEQ ID NOs:758, 1190, and 1622; and SEQ ID NOs:759, 1191, and 1623.

In another aspect of the invention, the CDRs of an anti-CD115 antibody, or antigen-binding fragment thereof, are selected from the corresponding VH and VL of a single clone described herein. In one embodiment, an anti-CD115 antibody, or an antigen-binding fragment thereof, comprises 1) a VHCDR1, a VHCDR2, and a VHCDR3 selected from the VHCDR1, VHCDR2 and VHCDR3 of one VH selected from any one of SEQ ID NOs: 109-216 and 2) a VLCDR1, a VLCDR2, and a VLCDR3 selected from the VLCDR1, VLCDR2 and VLCDR3 of one VL selected from any one of SEQ ID NOs:325-432. In one embodiment, an anti-CD115 antibody, or antigen-binding fragment thereof, comprises a VHCDR1, a VHCDR2, a VHCDR3, a VLCDR1, a VLCDR2, and a VLCDR3 within the corresponding VH and VL amino acid sequences of a single clone as set forth in Table 3.

Accordingly, in one embodiment, an anti-CD115 antibody, or an antigen-binding fragment thereof, comprises a VHCDR1, a VHCDR2, a VHCDR3, a VLCDR1, a VLCDR2, and a VLCDR3 selected from: SEQ ID NOs:436, 868, 1300, 652, 1084, and 1516; SEQ ID NOs:437, 869, 1301, 653, 1085, and 1517; SEQ ID NOs:438, 870, 1302, 654, 1086, and 1518; SEQ ID NOs:439, 871, 1303, 655, 1087, and 1519; SEQ ID NOs:440, 872, 1304, 656, 1088, and 1520; SEQ ID NOs:441, 873, 1305, 657, 1089, and 1521; SEQ ID NOs:442, 874, 1306, 658, 1090, and 1522; SEQ ID NOs:443, 875, 1307, 659, 1091, and 1523; SEQ ID NOs:444, 876, 1308, 660, 1092, and 1524; SEQ ID NOs: 445, 877, 1309, 661, 1093, and 1525; SEQ ID NOs:446, 878, 1310, 662, 1094, and 1526; SEQ ID NOs:447, 879, 1311, 663, 1095, and 1527; SEQ ID NOs:448, 880, 1312, 664, 1096, and 1528; SEQ ID NOs:449, 881, 1313, 665, 1097, and 1529; SEQ ID NOs:450, 882, 1314, 666, 1098, and 1530; SEQ ID NOs:451, 883, 1315, 667, 1099, and 1531; SEQ ID NOs:452, 884, 1316, 668, 1100, and 1532; SEQ ID NOs:453, 885, 1317, 669, 1101, and 1533; SEQ ID NOs:454, 886, 1318, 670, 1102, and 1534; SEQ ID NOs: 455, 887, 1319, 671, 1103, and 1535; SEQ ID NOs:456, 888, 1320, 672, 1104, and 1536; SEQ ID NOs:457, 889, 1321, 673, 1105, and 1537; SEQ ID NOs:458, 890, 1322, 674, 1106, and 1538; SEQ ID NOs:459, 891, 1323, 675, 1107, and 1539; SEQ ID NOs:460, 892, 1324, 676, 1108, and 1540; SEQ ID NOs:461, 893, 1325, 677, 1109, and 1541; SEQ ID NOs:462, 894, 1326, 678, 1110, and 1542; SEQ ID NOs:463, 895, 1327, 679, 1111, and 1543; SEQ ID NOs: 464, 896, 1328, 680, 1112, and 1544; SEQ ID NOs:465, 897, 1329, 681, 1113, and 1545; SEQ ID NOs:466, 898, 1330, 682, 1114, and 1546; SEQ ID NOs:467, 899, 1331, 683, 1115, and 1547; SEQ ID NOs:468, 900, 1332, 684, 1116, and 1548; SEQ ID NOs:469, 901, 1333, 685, 1117, and 1549; SEQ ID NOs:470, 902, 1334, 686, 1118, and 1550; SEQ ID NOs:471, 903, 1335, 687, 1119, and 1551; SEQ ID NOs:472, 904, 1336, 688, 1120, and 1552; SEQ ID NOs: 473, 905, 1337, 689, 1121, and 1553; SEQ ID NOs:474, 906, 1338, 690, 1122, and 1554; SEQ ID NOs:475, 907, 1339, 691, 1123, and 1555; SEQ ID NOs:476, 908, 1340, 692, 1124, and 1556; SEQ ID NOs:477, 909, 1341, 693, 1125, and 1557; SEQ ID NOs:478, 910, 1342, 694, 1126, and 1558; SEQ ID NOs:479, 911, 1343, 695, 1127, and 1559; SEQ ID NOs:480, 912, 1344, 696, 1128, and 1560; SEQ ID NOs:481, 913, 1345, 697, 1129, and 1561; SEQ ID NOs: 482, 914, 1346, 698, 1130, and 1562; SEQ ID NOs:483, 915, 1347, 699, 1131, and 1563; SEQ ID NOs:484, 916, 1348, 700, 1132, and 1564; SEQ ID NOs:485, 917, 1349, 701, 1133, and 1565; SEQ ID NOs:486, 918, 1350, 702, 1134, and 1566; SEQ ID NOs:487, 919, 1351, 703, 1135, and 1567; SEQ ID NOs:488, 920, 1352, 704, 1136, and 1568; SEQ ID NOs:489, 921, 1353, 705, 1137, and 1569; SEQ ID NOs:490, 922, 1354, 706, 1138, and 1570; SEQ ID NOs: 491, 923, 1355, 707, 1139, and 1571; SEQ ID NOs:492, 924, 1356, 708, 1140, and 1572; SEQ ID NOs:493, 925, 1357, 709, 1141, and 1573; SEQ ID NOs:494, 926, 1358, 710, 1142, and 1574; SEQ ID NOs:495, 927, 1359, 711, 1143, and 1575; SEQ ID NOs:496, 928, 1360, 712, 1144, and 1576; SEQ ID NOs:497, 929, 1361, 713, 1145, and 1577; SEQ ID NOs:498, 930, 1362, 714, 1146, and 1578; SEQ ID NOs:499, 931, 1363, 715, 1147, and 1579; SEQ ID NOs: 500, 932, 1364, 716, 1148, and 1580; SEQ ID NOs:501, 933, 1365, 717, 1149, and 1581; SEQ ID NOs:502, 934, 1366, 718, 1150, and 1582; SEQ ID NOs:503, 935, 1367, 719, 1151, and 1583; SEQ ID NOs:504, 936, 1368, 720, 1152, and 1584; SEQ ID NOs:505, 937, 1369, 721, 1153, and 1585; SEQ ID NOs:506, 938, 1370, 722, 1154, and 1586; SEQ ID NOs:507, 939, 1371, 723, 1155, and 1587; SEQ ID NOs:508, 940, 1372, 724, 1156, and 1588; SEQ ID NOs: 509, 941, 1373, 725, 1157, and 1589; SEQ ID NOs:510, 942, 1374, 726, 1158, and 1590; SEQ ID NOs:511, 943, 1375, 727, 1159, and 1591; SEQ ID NOs:512, 944, 1376, 728, 1160, and 1592; SEQ ID NOs:513, 945, 1377, 729, 1161, and 1593; SEQ ID NOs:514, 946, 1378, 730, 1162, and 1594; SEQ ID NOs:515, 947, 1379, 731, 1163, and 1595; SEQ ID NOs:516, 948, 1380, 732, 1164, and 1596; SEQ ID NOs:517, 949, 1381, 733, 1165, and 1597; SEQ ID NOs: 518, 950, 1382, 734, 1166, and 1598; SEQ ID NOs:519, 951, 1383, 735, 1167, and 1599; SEQ ID NOs:520, 952, 1384, 736, 1168, and 1600; SEQ ID NOs:521, 953, 1385, 737, 1169, and 1601; SEQ ID NOs:522, 954, 1386, 738, 1170, and 1602; SEQ ID NOs:523, 955, 1387, 739, 1171, and 1603; SEQ ID NOs:524, 956, 1388, 740, 1172, and 1604; SEQ ID NOs:525, 957, 1389, 741, 1173, and 1605; SEQ ID NOs:526, 958, 1390, 742, 1174, and 1606; SEQ ID NOs: 527, 959, 1391, 743, 1175, and 1607; SEQ ID NOs:528, 960, 1392, 744, 1176, and 1608; SEQ ID NOs:529, 961, 1393, 745, 1177, and 1609; SEQ ID NOs:530, 962, 1394, 746, 1178, and 1610; SEQ ID NOs:531, 963, 1395, 747, 1179, and 1611; SEQ ID NOs:532, 964, 1396, 748, 1180, and 1612; SEQ ID NOs:533, 965, 1397, 749, 1181, and 1613; SEQ ID NOs:534, 966, 1398, 750, 1182, and 1614; SEQ ID NOs:535, 967, 1399, 751, 1183, and 1615; SEQ ID NOs: 536, 968, 1400, 752, 1184, and 1616; SEQ ID NOs:537, 969, 1401, 753, 1185, and 1617; SEQ ID NOs:538, 970, 1402, 754, 1186, and 1618; SEQ ID NOs:539, 971, 1403, 755, 1187, and 1619; SEQ ID NOs:540, 972, 1404, 756, 1188, and 1620; SEQ ID NOs:541, 973, 1405, 757, 1189, and 1621; SEQ ID NOs:542, 974, 1406, 758, 1190, and 1622; and SEQ ID NOs:543, 975, 1407, 759, 1191, and 1623.

In one embodiment, an anti-CD115 antibody, or antigen-binding fragment thereof, comprises a VH comprising any one of SEQ ID NOs: 109-216. In one embodiment, an anti-CD115 antibody, or antigen-binding fragment thereof, comprises a VL comprising any one of SEQ ID NOs:325-432. In one embodiment, an anti-CD115 antibody, or an antigen-binding fragment thereof, comprises a corresponding VH and VL of a single clone as set forth in Table 3.

Accordingly, in one embodiment, an anti-CD115 antibody, or an antigen-binding fragment thereof, comprises a VH and a VL selected from: SEQ ID NOs:109 and 325; SEQ ID NOs:110 and 326; SEQ ID NOs:111 and 327; SEQ ID NOs:112 and 328; SEQ ID NOs:113 and 329; SEQ ID NOs:114 and 330; SEQ ID NOs:115 and 331; SEQ ID NOs:116 and 332; SEQ ID NOs:117 and 333; SEQ ID NOs:118 and 334; SEQ ID NOs:119 and 335; SEQ ID NOs:120 and 336; SEQ ID NOs:121 and 337; SEQ ID NOs:122 and 338; SEQ ID NOs:123 and 339; SEQ ID NOs:124 and 340; SEQ ID NOs:125 and 341; SEQ ID NOs:126 and 342; SEQ ID NOs:127 and 343; SEQ ID NOs:128 and 344; SEQ ID NOs:129 and 345; SEQ ID NOs:130 and 346; SEQ ID NOs:131 and 347; SEQ ID NOs:132 and 348; SEQ ID NOs:133 and 349; SEQ ID NOs:134 and 350; SEQ ID NOs:135 and 351; SEQ ID NOs:136 and 352; SEQ ID NOs:137 and 353; SEQ ID NOs:138 and 354; SEQ ID NOs:139 and 355; SEQ ID NOs:140 and 356; SEQ ID NOs:141 and 357; SEQ ID NOs:142 and 358; SEQ ID NOs:143 and 359; SEQ ID NOs:144 and 360; SEQ ID NOs:145 and 361; SEQ ID NOs:146 and 362; SEQ ID NOs:147 and 363; SEQ ID NOs:148 and 364; SEQ ID NOs:149 and 365; SEQ ID NOs:150 and 366; SEQ ID NOs:151 and 367; SEQ ID NOs:152 and 368; SEQ ID NOs:153 and 369; SEQ ID NOs:154 and 370; SEQ ID NOs:155 and 371; SEQ ID NOs:156 and 372; SEQ ID NOs:157 and 373; SEQ ID NOs:158 and 374; SEQ ID NOs:159 and 375; SEQ ID NOs:160 and 376; SEQ ID NOs:161 and 377; SEQ ID NOs:162 and 378; SEQ ID NOs:163 and 379; SEQ ID NOs:164 and 380; SEQ ID NOs:165 and 381; SEQ ID NOs:166 and 382; SEQ ID NOs:167 and 383; SEQ ID NOs:168 and 384; SEQ ID NOs:169 and 385; SEQ ID NOs:170 and 386; SEQ ID NOs:171 and 387; SEQ ID NOs:172 and 388; SEQ ID NOs:173 and 389; SEQ ID NOs:174 and 390; SEQ ID NOs:175 and 391; SEQ ID NOs:176 and 392; SEQ ID NOs:177 and 393; SEQ ID NOs:178 and 394; SEQ ID NOs:179 and 395; SEQ ID NOs:180 and 396; SEQ ID NOs:181 and 397; SEQ ID NOs:182 and 398; SEQ ID NOs:183 and 399; SEQ ID NOs:184 and 400; SEQ ID NOs:185 and 401; SEQ ID NOs:186 and 402; SEQ ID NOs:187 and 403; SEQ ID NOs:188 and 404; SEQ ID NOs:189 and 405; SEQ ID NOs:190 and 406; SEQ ID NOs:191 and 407; SEQ ID NOs:192 and 408; SEQ ID NOs:193 and 409; SEQ ID NOs:194 and 410; SEQ ID NOs:195 and 411; SEQ ID NOs:196 and 412; SEQ ID NOs:197 and 413; SEQ ID NOs:198 and 414; SEQ ID NOs:199 and 415; SEQ ID NOs:200 and 416; SEQ ID NOs:201 and 417; SEQ ID NOs:202 and 418; SEQ ID NOs:203 and 419; SEQ ID NOs:204 and 420; SEQ ID NOs:205 and 421; SEQ ID NOs:206 and 422; SEQ ID NOs:207 and 423; SEQ ID NOs:208 and 424; SEQ ID NOs:209 and 425; SEQ ID NOs:210 and 426; SEQ ID NOs:211 and 427; SEQ ID NOs:212 and 428; SEQ ID NOs:213 and 429; SEQ ID NOs:214 and 430; SEQ ID NOs:215 and 431; and SEQ ID NOs:216 and 432.

In one embodiment, an anti-CD115 antibody is a whole antibody. In one embodiment, an anti-CD115 antibody is a single chain antibody. In one embodiment, an anti-CD115 antibody is a scFv. In one embodiment, an anti-CD115 antibody is a Fab. In one embodiment, an anti-CD115 antibody is a $F(ab')_2$. In one embodiment, an anti-CD115 antibody is a Fv.

In one embodiment, an anti-CD115 antibody is a bispecific antibody. In one embodiment, a bispecific anti-CD115 antibody specifically recognizes two different epitopes of CD115. In one embodiment, a bispecific anti-CD115 comprises a first CDR set comprising the VHCDR1, VHCDR2, VHCDR3, VLCDR1, VLCDR2, and VLCDR3 from a first anti-CD115 antibody clone disclosed herein and a second CDR set comprising the VHCDR1, VHCDR2, VHCDR3, VLCDR1, VLCDR2, and VLCDR3 of a second anti-CD115 antibody clone disclosed herein. In one embodiment, a bispecific anti-CD115 comprises a corresponding first VH and first VL of a first anti-CD115 antibody clone disclosed herein and a corresponding second VH and second VL of a second anti-CD115 antibody clone disclosed herein. In one embodiment, a bispecific anti-CD115 antibody specifically recognizes CD115 and another antigen.

Neutralizing Anti-CD115 Antibodies

One aspect of the present invention provides anti-CD115 antibodies, and antigen-binding fragments thereof, that are CD115 antagonists. In one embodiment, an antagonist anti-CD115 antibody, or antigen-binding fragment thereof, neutralizes or inhibits one or more ligands of CD115 from binding CD115. In one embodiment, an antagonist anti-CD115 antibody, or antigen-binding fragment thereof, inhibits CSF-1 from binding CD115. In one embodiment, an antagonist anti-CD115 antibody, or antigen-binding fragment thereof, inhibits IL-34 from binding CD115. In one embodiment, an antagonist anti-CD115 antibody, or antigen-binding fragment thereof, inhibits CSF-1 and IL-34 from binding CD115. In one embodiment, an antagonist anti-CD115 antibody, or antigen-binding fragment thereof, prevents dimerization of CD115, including dimerization that is induced by CSF-1 or IL-34 binding or that may happen spontaneously under certain conditions of expression CD115. In one embodiment, an antagonist anti-CD115 antibody, or antigen-binding fragment thereof, inhibits CD115 signaling. In one embodiment, an antagonist anti-CD115 antibody, or antigen-binding fragment thereof, inhibits ligand-induced phosphorylation of CD115.

Polynucleotides

One aspect of the present invention provides a polynucleotide sequence that encodes an anti-CD115 antibody, or antigen-binding fragment thereof, disclosed herein. In one embodiment, the polynucleotide is a recombinant polynucleotide. In one embodiment, the polynucleotide is cDNA.

In one embodiment, a polynucleotide sequence encodes a CDR of an anti-CD115 antibody disclosed herein. In one embodiment, the polynucleotide comprises a VHCDR1 polynucleotide sequence selected from any one of SEQ ID NOs:544-651. In one embodiment, the polynucleotide comprises a VHCDR2 polynucleotide sequence selected from any one of SEQ ID NOs:976-1083. In one embodiment, the polynucleotide comprises a VHCDR3 polynucleotide sequence selected from any one of SEQ ID NOs:1408-1515. In one embodiment, the polynucleotide comprises a VLCDR1 polynucleotide sequence selected from any one of SEQ ID NOs:760-867. In one embodiment, the polynucleotide comprises a VLCDR2 polynucleotide sequence selected from any one of SEQ ID NOs:1192-1299. In one embodiment, the polynucleotide comprises a VLCDR3 polynucleotide sequence selected from any one of SEQ ID NOs: 1624-1731.

In one embodiment, a polynucleotide sequence encodes a VH of an anti-CD115 antibody disclosed herein. In one embodiment, the polynucleotide comprises a VH polynucleotide sequence selected from any one of SEQ ID NOs:1-108. In one embodiment, a polynucleotide sequence encodes a VL of an anti-CD115 antibody disclosed herein. In one embodiment, the polynucleotide comprises a VL polynucleotide sequence selected from any one of SEQ ID NOs:217-324. In one embodiment, a polynucleotide sequence encodes a VH and a VL of an anti-CD115 antibody disclosed herein.

One embodiment of the invention provides a vector comprising a polynucleotide sequence encoding an anti-CD115 antibody, or an antigen-binding fragment thereof, disclosed herein. In one embodiment, the vector is an expression vector. In one embodiment, the vector is a cloning vector. One embodiment of the invention provides a host cell comprising the vector.

Methods of Use

The AlivaMab® antibodies against CD115, and in particular fully human antibodies incorporating all or portions of the heavy chain and light chain variable regions from the AlivaMab® antibodies, may have utility for the treatment of human disease including, but not limited to, diseases in oncology and autoimmunity and inflammation. As the understanding of CD115 biology and disease association becomes better known, it is expected that opportunities for human clinical therapeutic indications may expand. In particular, oncological, immunological, and neurological diseases and disorders are contemplated.

An anti-CD115 antibody, or antigen-binding fragment thereof, disclosed herein may be used in research, diagnostic, and/or therapeutic methods. In one embodiment, an anti-CD115 antibody, or antigen-binding fragment thereof, disclosed herein is used to treat diseases and disorders associated with CD115, CSF-1 and/or IL-34. In one embodiment, an anti-CD115 antibody, or antigen-binding fragment thereof, disclosed herein is used to treat diseases and disorders associated with CD115 overexpression. In one embodiment, an anti-CD115 antibody, or antigen-binding fragment thereof, disclosed herein is used to treat diseases and disorders associated with CSF-1 overexpression. In one embodiment, an anti-CD115 antibody, or antigen-binding fragment thereof, disclosed herein is used to treat diseases and disorders associated with IL-34 overexpression. In one embodiment, an anti-CD115 antibody, or antigen-binding fragment thereof, disclosed herein is used to treat diseases and disorders associated with aberrant CD115 signaling.

Embodiments of the invention pertain to the use of anti-CD115 antibodies, or antigen-binding fragments thereof, for the diagnosis and prognosis of diseases and disorders associated with CD115, CSF-1 and/or IL-34 or aberrant expression thereof.

Modified Anti-CD115 Antibodies and Compositions

Anti-CD115 antibodies of the present invention, and antigen-binding fragments and variants thereof, may also be conjugated or operably linked to another compound (e.g., therapeutic agent, label, or tag), referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents are contemplated. In one embodiment, the antibody is conjugated or operably linked to a toxin, including but not limited to small molecule toxins and enzymatically active toxins of bacterial, fungal, plant, animal or synthetic origin, including fragments and/or variants thereof.

There are many linking groups known in the art for making antibody conjugates, including, for example, those disclosed in U.S. Pat. No. 5,208,020 or EP Patent 0425235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

The present invention further relates to pharmaceutical compositions and methods of use. The pharmaceutical compositions of the present invention include an antibody, or fragment thereof, in a pharmaceutically acceptable carrier. Pharmaceutical compositions may be administered in vivo for the treatment or prevention of a disease or disorder. Furthermore, pharmaceutical compositions comprising an antibody, or a fragment thereof, of the present invention may include one or more agents for use in combination, or may be administered in conjunction with one or more agents. Agents for use in combination with an anti-CD115 antibody disclosed herein include, but are not limited to cytotoxic agents, chemotherapeutic agents, cytokines, anti-angiogenic agents, tyrosine kinase inhibitors, toxins, and radioisotopes.

The present invention also provides kits relating to any of the antibodies, or fragments thereof, and/or methods described herein. Kits of the present invention may include diagnostic or therapeutic agents. A kit of the present invention may further provide instructions for use of a composition or antibody and packaging. A kit of the present invention may include devices, reagents, containers or other components. Furthermore, a kit of the present invention may also require the use of an apparatus, instrument or device, including a computer.

EXAMPLES

Figure 3:
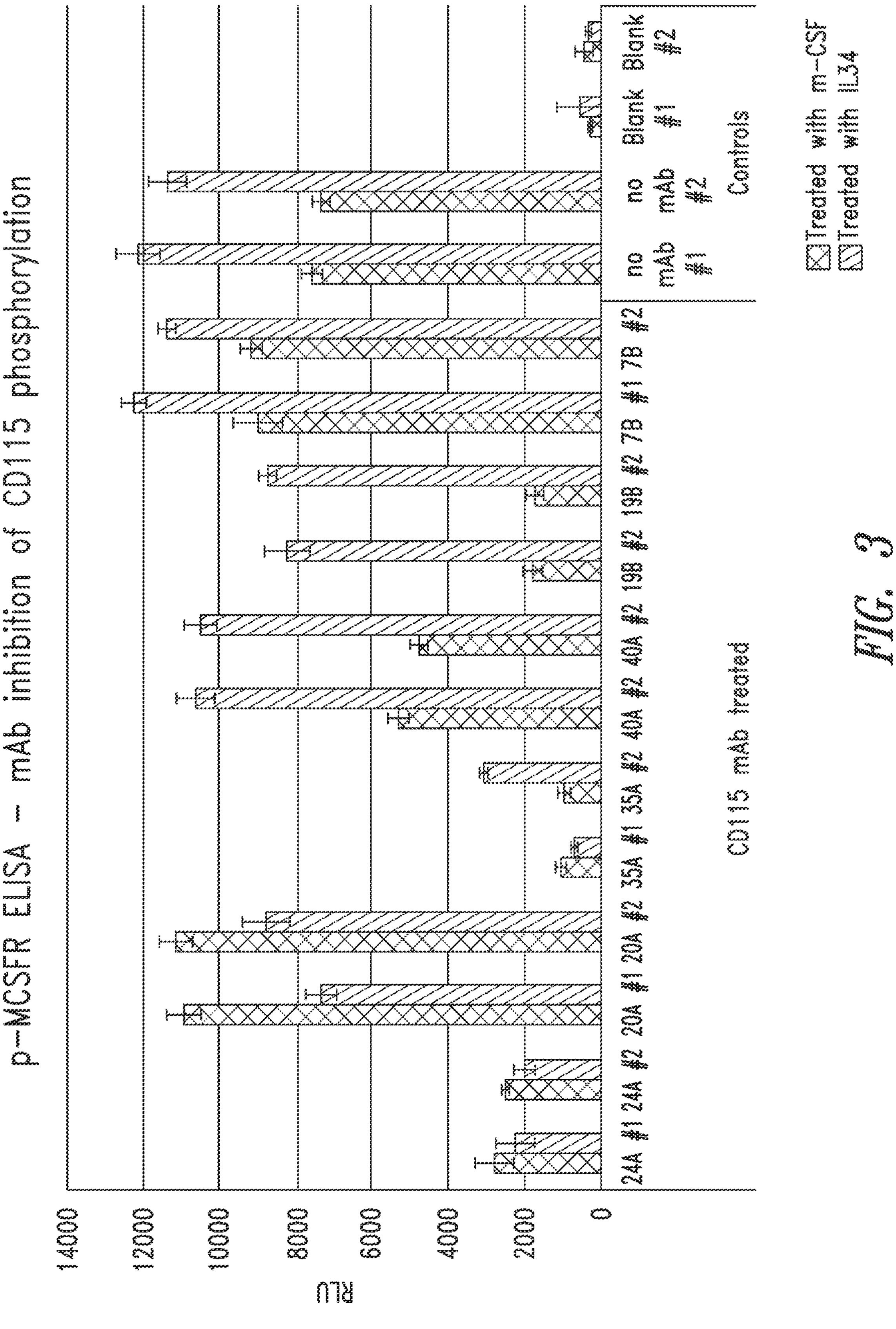
FIG. 3 shows CD115 phosphorylation (p-CD115 or p-MCSFR) measured by ELISA.

The Examples below utilize a CD115 phosphorylation assay in order to detect phospho-CD115. SR cells (confirmed CD115 expression by FACS) were serum starved overnight (1% FBS). Cells were treated with M-CSF or IL-34 in the presence of CD115 mAbs for 30 minutes on ice. Cells were lysed in buffer containing phosphatase and protease inhibitors. Lysates were run on R&D systems p-MCSFR DUOSET, which is an ELISA comprising validated phospho-CD115-specific antibody pairs. Exemplary results from a p-CD115 (MCSFR) ELISA using SR cells are shown in FIGS. 1 and 3.

Example 1

Preparation of Monoclonal Antibodies to Cd 115

Monoclonal antibodies were prepared in accordance with a general method as described in "Antibodies: A Laboratory Manual" (Harlow and Lane 1988 CSH Press). Eight-week old AlivaMab® Kappa Mice and eight-week old AlivaMab® Lambda Mice mice were immunized using a RIMMS protocol. 50 ug of human CD115 extracellular domain (Sino Biological, China 10161-H08H) was mixed with 40 ul (first immunization), 20 ul (immunizations 2-4) or 0 ul (final immunization) Gerbu MM adjuvant (C-C Biotech, Valley Center, Calif. #3001-6030) and PBS was added to a final volume of 100 ul. The 50 ug mixture was injected in 20 ul portions in 5 locations per mouse; right and left flanks and right and left shoulder/armpit subcutaneously, and the remaining 20 ul intraperitoneally. This was done 5 times per mouse on days, 1, 4, 7, 9, and 11. On Day 14 mice were sacrificed and terminal materials were collected. Spleens and lymph nodes were prepared and fused with CRL-2016 myeloma cells (ATCC) using a PEG based method as generally described in "Antibodies: A Laboratory Manual" (Harlow and Lane 1988 CSH Press) to establish hybridomas.

Figure 5:
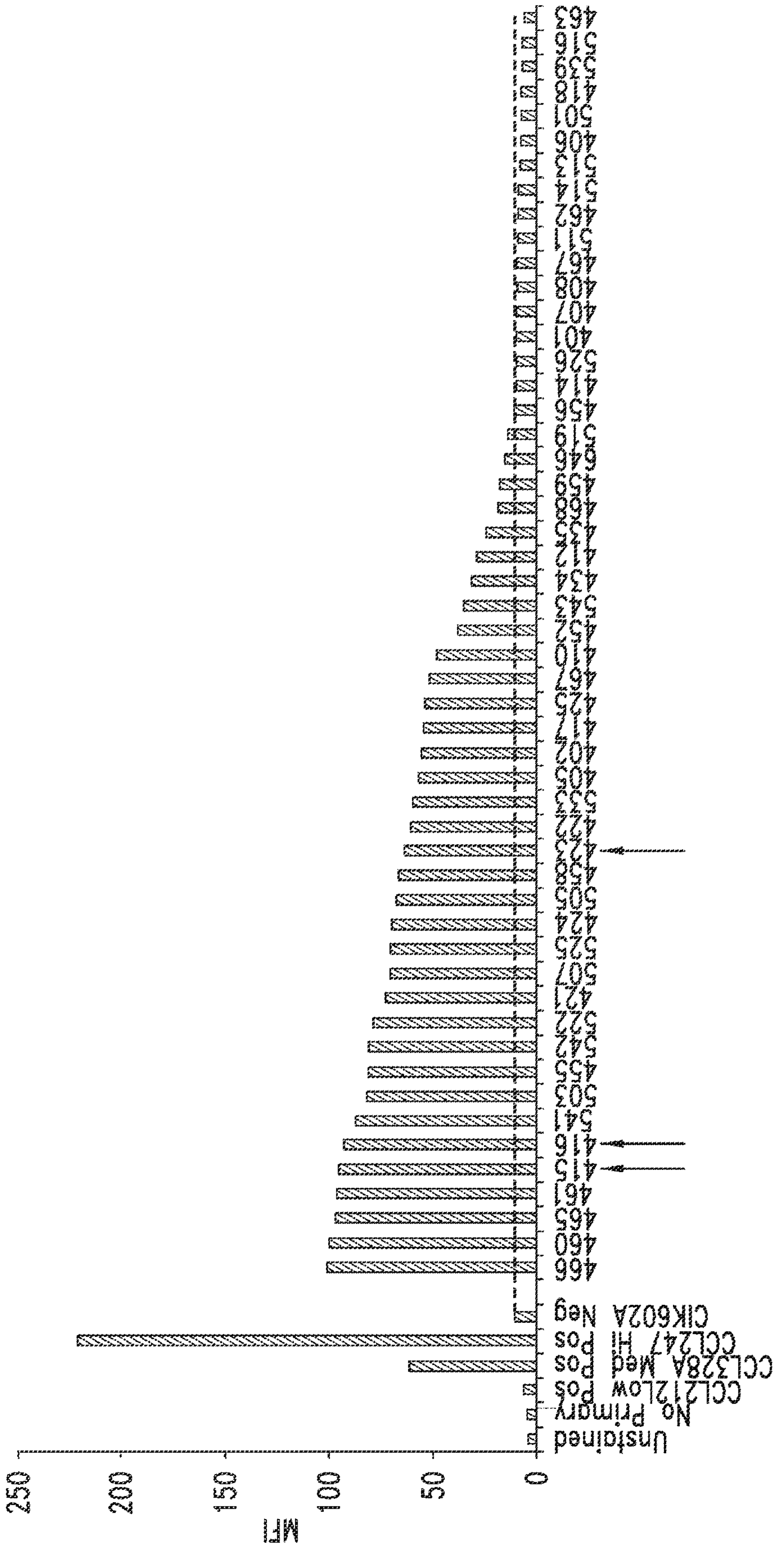
FIG. 5 shows binding of anti-CD115 IgGκ mAbs to CD115 expressed on OCI-AML5 cells.

Hybridomas were grown in 384-well tissue culture plates and supernatants from individual wells were screened by ELISA for production of antibodies recognizing huCD115. Positive wells were then transferred to 48-well plates, expanded, and supernatants were collected for huCD115 binding confirmation by ELISA. Positive supernatants were also counter-screened against a non-related histidine-tagged protein. Fifty to sixty hybridoma lines each from AlivaMab® Kappa Mice and AlivaMab® Lambda Mice confirmed to bind CD115 specifically by ELISA were picked at random and single-cell cloned into 96-well plates. One hundred and eight (108) hybridoma lines were cloned. They were grown into colonies and the supernatant from these individual colonies was screened by ELISA to re-confirm monoclonal antibody binding to huCD115. These supernatants were then screened by FACS to confirm binding to native CD115 on OCI-AML5 cells (DSMZ #ACC-247, Table 1 shows results for select antibodies, and FIG. 7). Seventy-five hybridoma clones were confirmed to produce mAb that bound to CD115-expressing OCI-AML5 cells (FIG. 5).

TABLE 1

Summary of Screening for Binding to CD115 on cell Surface

| HYBRIDOMA | FACS Binding |
|---|---|
| CCL-247A | + |
| CCK-423A | + |
| CCK-415A | + |
| CCK-416A | + |
| CCK-541A | + |
| CCK-424A | + |
| CCK-507A | + |
| CCK-461A | + |
| CCK-421A | + |
| CCL-331A | + |
| CCK-422A | + |
| CCK-437A | + |
| CCL-327A | + |
| CCK-522A | + |
| CCL-309A | + |

TABLE 1-continued

Summary of Screening for Binding to CD115 on cell Surface

| HYBRIDOMA | FACS Binding |
|---|---|
| CCL-321A | + |
| CCL-332A | + |
| CCL-217A | + |
| CCL-328A | + |
| CCL-221A | + |
| CCK-402A | + |
| CCL-238A | + |
| CCL-245A | + |
| CCK-417A | + |
| CCL-215A | + |
| CCL-346A | + |
| CCL-213A | + |
| CCL-205A | + |
| CCL-216A | + |
| CCL-211A | + |
| CCL-204A | + |
| CCL-325A | + |
| CCL-337A | + |
| CCL-249A | + |

Example 2

Sequences of Anti-CD115 VH and VL

Total RNA was extracted from hybridomas producing anti-CD115 monoclonal antibodies using the Qiagen RNeasy Mini kit (Cat No. 74104), followed by 5' RACE, using the 5' RACE system kit (Life Technologies, US cat #18734-058) with the following 3' gene specific primers IgG 5'-GGTTCGGGGAAGTAGTCCTTGACC-3' (SEQ ID NO:433) IgL 5'-CTGTAGCTTCTGTGGGACTTC-CACTGCTC-3' (SEQ ID NO:434) IgK 5'-CCGATTG-GAGGGCGTTATCCAC-3' (SEQ ID NO:435). RACE products were gel purified and cloned into pCR4-TOPO using TOPO TA cloning kit for sequencing with One Shot Top 10 chemically competent *E. coli* (Life Technologies, US Cat #K4575-01). Sequencing of vector containing colonies was performed by Sequetech (Mountain View, Calif.) using M13F or M13R sequencing primers. The reported nucleotide sequences start at the first nucleotide in the first codon for the amino terminal amino acid in framework 1. The reported polypeptide sequences are based on an in silico translation of the nucleic acid sequence and start at the first amino acid at the amino terminus of framework 1.

TABLE 2

Anti-CD115 mAb Amino Acid (aa) and Polynucleotide (nt) Sequences

| | VH | | VHCDR1 | | VHCDR2 | | VHCDR3 | | VL | | VLCDR1 | | VLCDR2 | | VLCDR3 | |
|---|---|---|---|---|---|---|---|---|---|---|---|---|---|---|---|---|
| Clone | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: |
| CCK-401A | 109 | 1 | 436 | 544 | 868 | 976 | 1300 | 1408 | 325 | 217 | 652 | 760 | 1084 | 1192 | 1516 | 1624 |
| CCK-402A | 110 | 2 | 437 | 545 | 869 | 977 | 1301 | 1409 | 326 | 218 | 653 | 761 | 1085 | 1193 | 1517 | 1625 |
| CCK-406A | 111 | 3 | 438 | 546 | 870 | 978 | 1302 | 1410 | 327 | 219 | 654 | 762 | 1086 | 1194 | 1518 | 1626 |
| CCK-407A | 112 | 4 | 439 | 547 | 871 | 979 | 1303 | 1411 | 328 | 220 | 655 | 763 | 1087 | 1195 | 1519 | 1627 |
| CCK-408A | 113 | 5 | 440 | 548 | 872 | 980 | 1304 | 1412 | 329 | 221 | 656 | 764 | 1088 | 1196 | 1520 | 1628 |
| CCK-410A | 114 | 6 | 441 | 549 | 873 | 981 | 1305 | 1413 | 330 | 222 | 657 | 765 | 1089 | 1197 | 1521 | 1629 |
| CCK-412A | 115 | 7 | 442 | 550 | 874 | 982 | 1306 | 1414 | 331 | 223 | 658 | 766 | 1090 | 1198 | 1522 | 1630 |
| CCK-414A | 116 | 8 | 443 | 551 | 875 | 983 | 1307 | 1415 | 332 | 224 | 659 | 767 | 1091 | 1199 | 1523 | 1631 |
| CCK-415A | 117 | 9 | 444 | 552 | 876 | 984 | 1308 | 1416 | 333 | 225 | 660 | 768 | 1092 | 1200 | 1524 | 1632 |
| CCK-416A | 118 | 10 | 445 | 553 | 877 | 985 | 1309 | 1417 | 334 | 226 | 661 | 769 | 1093 | 1201 | 1525 | 1633 |
| CCK-417A | 119 | 11 | 446 | 554 | 878 | 986 | 1310 | 1418 | 335 | 227 | 662 | 770 | 1094 | 1202 | 1526 | 1634 |

TABLE 2-continued

Anti-CD115 mAb Amino Acid (aa) and Polynucleotide (nt) Sequences

| Clone | VH | | VHCDR1 | | VHCDR2 | | VHCDR3 | | VL | | VLCDR1 | | VLCDR2 | | VLCDR3 | |
|---|---|---|---|---|---|---|---|---|---|---|---|---|---|---|---|---|
| | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: |
| CCK-418A | 120 | 12 | 447 | 555 | 879 | 987 | 1311 | 1419 | 336 | 228 | 663 | 771 | 1095 | 1203 | 1527 | 1635 |
| CCK-421A | 121 | 13 | 448 | 556 | 880 | 988 | 1312 | 1420 | 337 | 229 | 664 | 772 | 1096 | 1204 | 1528 | 1636 |
| CCK-422A | 122 | 14 | 449 | 557 | 881 | 989 | 1313 | 1421 | 338 | 230 | 665 | 773 | 1097 | 1205 | 1529 | 1637 |
| CCK-423A | 123 | 15 | 450 | 558 | 882 | 990 | 1314 | 1422 | 339 | 231 | 666 | 774 | 1098 | 1206 | 1530 | 1638 |
| CCK-424A | 124 | 16 | 451 | 559 | 883 | 991 | 1315 | 1423 | 340 | 232 | 667 | 775 | 1099 | 1207 | 1531 | 1639 |
| CCK-425A | 125 | 17 | 452 | 560 | 884 | 992 | 1316 | 1424 | 341 | 233 | 668 | 776 | 1100 | 1208 | 1532 | 1640 |
| CCK-434A | 126 | 18 | 453 | 561 | 885 | 993 | 1317 | 1425 | 342 | 234 | 669 | 777 | 1101 | 1209 | 1533 | 1641 |
| CCK-435A | 127 | 19 | 454 | 562 | 886 | 994 | 1318 | 1426 | 343 | 235 | 670 | 778 | 1102 | 1210 | 1534 | 1642 |
| CCK-436A | 128 | 20 | 455 | 563 | 887 | 995 | 1319 | 1427 | 344 | 236 | 671 | 779 | 1103 | 1211 | 1535 | 1643 |
| CCK-437A | 129 | 21 | 456 | 564 | 888 | 996 | 1320 | 1428 | 345 | 237 | 672 | 780 | 1104 | 1212 | 1536 | 1644 |
| CCK-455A | 130 | 22 | 457 | 565 | 889 | 997 | 1321 | 1429 | 346 | 238 | 673 | 781 | 1105 | 1213 | 1537 | 1645 |
| CCK-456A | 131 | 23 | 458 | 566 | 890 | 998 | 1322 | 1430 | 347 | 239 | 674 | 782 | 1106 | 1214 | 1538 | 1646 |
| CCK-458A | 132 | 24 | 459 | 567 | 891 | 999 | 1323 | 1431 | 348 | 240 | 675 | 783 | 1107 | 1215 | 1539 | 1647 |
| CCK-459A | 133 | 25 | 460 | 568 | 892 | 1000 | 1324 | 1432 | 349 | 241 | 676 | 784 | 1108 | 1216 | 1540 | 1648 |
| CCK-460A | 134 | 26 | 461 | 569 | 893 | 1001 | 1325 | 1433 | 350 | 242 | 677 | 785 | 1109 | 1217 | 1541 | 1649 |
| CCK-461A | 135 | 27 | 462 | 570 | 894 | 1002 | 1326 | 1434 | 351 | 243 | 678 | 786 | 1110 | 1218 | 1542 | 1650 |
| CCK-464A | 136 | 28 | 463 | 571 | 895 | 1003 | 1327 | 1435 | 352 | 244 | 679 | 787 | 1111 | 1219 | 1543 | 1651 |
| CCK-465A | 137 | 29 | 464 | 572 | 896 | 1004 | 1328 | 1436 | 253 | 245 | 680 | 788 | 1112 | 1220 | 1544 | 1652 |
| CCK-467A | 138 | 30 | 465 | 573 | 897 | 1005 | 1329 | 1437 | 354 | 246 | 681 | 789 | 1113 | 1221 | 1545 | 1653 |
| CCK-468A | 139 | 31 | 466 | 574 | 898 | 1006 | 1330 | 1438 | 355 | 247 | 682 | 790 | 1114 | 1222 | 1546 | 1654 |
| CCK-501A | 140 | 32 | 467 | 575 | 899 | 1007 | 1331 | 1439 | 356 | 248 | 683 | 791 | 1115 | 1223 | 1547 | 1655 |
| CCK-503A | 141 | 33 | 468 | 576 | 900 | 1008 | 1332 | 1440 | 357 | 249 | 684 | 792 | 1116 | 1224 | 1548 | 1656 |
| CCK-505A | 142 | 34 | 469 | 577 | 901 | 1009 | 1333 | 1441 | 358 | 250 | 685 | 793 | 1117 | 1225 | 1549 | 1657 |
| CCK-507A | 143 | 35 | 470 | 578 | 902 | 1010 | 1334 | 1442 | 359 | 251 | 686 | 794 | 1118 | 1226 | 1550 | 1658 |
| CCK-511A | 144 | 36 | 471 | 579 | 903 | 1011 | 1335 | 1443 | 360 | 252 | 687 | 795 | 1119 | 1227 | 1551 | 1659 |
| CCK-513A | 145 | 37 | 472 | 580 | 904 | 1012 | 1336 | 1444 | 361 | 253 | 688 | 796 | 1120 | 1228 | 1552 | 1660 |
| CCK-514A | 146 | 38 | 473 | 581 | 905 | 1013 | 1337 | 1445 | 362 | 254 | 689 | 797 | 1121 | 1229 | 1553 | 1661 |
| CCK-516A | 147 | 39 | 474 | 582 | 906 | 1014 | 1338 | 1446 | 363 | 255 | 690 | 798 | 1122 | 1230 | 1554 | 1662 |
| CCK-519A | 148 | 40 | 475 | 583 | 907 | 1015 | 1339 | 1447 | 364 | 256 | 691 | 799 | 1123 | 1231 | 1555 | 1663 |
| CCK-522A | 149 | 41 | 476 | 584 | 908 | 1016 | 1340 | 1448 | 365 | 257 | 692 | 800 | 1124 | 1232 | 1556 | 1664 |
| CCK-525A | 150 | 42 | 477 | 585 | 909 | 1017 | 1341 | 1449 | 366 | 258 | 693 | 801 | 1125 | 1233 | 1557 | 1665 |
| CCK-526A | 151 | 43 | 478 | 586 | 910 | 1018 | 1342 | 1450 | 367 | 259 | 694 | 802 | 1126 | 1234 | 1558 | 1666 |
| CCK-533A | 152 | 44 | 479 | 587 | 911 | 1019 | 1343 | 1451 | 368 | 260 | 695 | 803 | 1127 | 1235 | 1559 | 1667 |
| CCK-539A | 153 | 45 | 480 | 588 | 912 | 1020 | 1344 | 1452 | 369 | 261 | 696 | 804 | 1128 | 1236 | 1560 | 1668 |
| CCK-541A | 154 | 46 | 481 | 589 | 913 | 1021 | 1345 | 1453 | 370 | 262 | 697 | 805 | 1129 | 1237 | 1561 | 1669 |
| CCK-542A | 155 | 47 | 482 | 590 | 914 | 1022 | 1346 | 1454 | 371 | 263 | 698 | 806 | 1130 | 1238 | 1562 | 1670 |
| CCK-543A | 156 | 48 | 483 | 591 | 915 | 1023 | 1347 | 1455 | 372 | 264 | 699 | 807 | 1131 | 1239 | 1563 | 1671 |
| CCL-201A | 157 | 49 | 484 | 592 | 916 | 1024 | 1348 | 1456 | 373 | 265 | 700 | 808 | 1132 | 1240 | 1564 | 1672 |
| CCL-203A | 158 | 50 | 485 | 593 | 917 | 1025 | 1349 | 1457 | 374 | 266 | 701 | 809 | 1133 | 1241 | 1565 | 1673 |
| CCL-204A | 159 | 51 | 486 | 594 | 918 | 1026 | 1350 | 1458 | 375 | 267 | 702 | 810 | 1134 | 1242 | 1566 | 1674 |
| CCL-205A | 160 | 52 | 487 | 595 | 919 | 1027 | 1351 | 1459 | 376 | 268 | 703 | 811 | 1135 | 1243 | 1567 | 1675 |
| CCL-206A | 161 | 53 | 488 | 596 | 920 | 1028 | 1352 | 1460 | 377 | 269 | 704 | 812 | 1136 | 1244 | 1568 | 1676 |
| CCL-207A | 162 | 54 | 489 | 597 | 921 | 1029 | 1353 | 1461 | 378 | 270 | 705 | 813 | 1137 | 1245 | 1569 | 1677 |
| CCL-208A | 163 | 55 | 490 | 598 | 922 | 1030 | 1354 | 1462 | 379 | 271 | 706 | 814 | 1138 | 1246 | 1570 | 1678 |
| CCL-209A | 164 | 56 | 491 | 599 | 923 | 1031 | 1355 | 1463 | 380 | 272 | 707 | 815 | 1139 | 1247 | 1571 | 1679 |
| CCL-211A | 165 | 57 | 492 | 600 | 924 | 1032 | 1356 | 1464 | 381 | 273 | 708 | 816 | 1140 | 1248 | 1572 | 1680 |
| CCL-212A | 166 | 58 | 493 | 601 | 925 | 1033 | 1357 | 1465 | 382 | 274 | 709 | 817 | 1141 | 1249 | 1573 | 1681 |
| CCL-213A | 167 | 59 | 494 | 602 | 926 | 1034 | 1358 | 1466 | 383 | 275 | 710 | 818 | 1142 | 1250 | 1574 | 1682 |
| CCL-215A | 168 | 60 | 495 | 603 | 927 | 1035 | 1359 | 1467 | 384 | 276 | 711 | 819 | 1143 | 1251 | 1575 | 1683 |
| CCL-216A | 169 | 61 | 496 | 604 | 928 | 1036 | 1360 | 1468 | 385 | 277 | 712 | 820 | 1144 | 1252 | 1576 | 1684 |
| CCL-217A | 170 | 62 | 497 | 605 | 929 | 1037 | 1361 | 1469 | 386 | 278 | 713 | 821 | 1145 | 1253 | 1577 | 1685 |
| CCL-218A | 171 | 63 | 498 | 606 | 930 | 1038 | 1362 | 1470 | 387 | 279 | 714 | 822 | 1146 | 1254 | 1578 | 1686 |
| CCL-220A | 172 | 64 | 499 | 607 | 931 | 1039 | 1363 | 1471 | 388 | 280 | 715 | 823 | 1147 | 1255 | 1579 | 1687 |
| CCL-221A | 173 | 65 | 500 | 608 | 932 | 1040 | 1364 | 1472 | 389 | 281 | 716 | 824 | 1148 | 1256 | 1580 | 1688 |
| CCL-223A | 174 | 66 | 501 | 609 | 933 | 1041 | 1365 | 1473 | 390 | 282 | 717 | 825 | 1149 | 1257 | 1581 | 1689 |
| CCL-225A | 175 | 67 | 502 | 610 | 934 | 1042 | 1366 | 1474 | 391 | 283 | 718 | 826 | 1150 | 1258 | 1582 | 1690 |
| CCL-226A | 176 | 68 | 503 | 611 | 935 | 1043 | 1367 | 1475 | 392 | 284 | 719 | 827 | 1151 | 1259 | 1583 | 1691 |
| CCL-229A | 177 | 69 | 504 | 612 | 936 | 1044 | 1368 | 1476 | 393 | 285 | 720 | 828 | 1152 | 1260 | 1584 | 1692 |
| CCL-231A | 178 | 70 | 505 | 613 | 937 | 1045 | 1369 | 1477 | 394 | 286 | 721 | 829 | 1153 | 1261 | 1585 | 1693 |
| CCL-235A | 179 | 71 | 506 | 614 | 938 | 1046 | 1370 | 1478 | 395 | 287 | 722 | 830 | 1154 | 1262 | 1586 | 1694 |
| CCL-238A | 180 | 72 | 507 | 615 | 939 | 1047 | 1371 | 1479 | 396 | 288 | 723 | 831 | 1155 | 1263 | 1587 | 1695 |
| CCL-245A | 181 | 73 | 508 | 616 | 940 | 1048 | 1372 | 1480 | 397 | 289 | 724 | 832 | 1156 | 1264 | 1588 | 1696 |
| CCL-247A | 182 | 74 | 509 | 617 | 941 | 1049 | 1373 | 1481 | 398 | 290 | 725 | 833 | 1157 | 1265 | 1589 | 1697 |
| CCL-249A | 183 | 75 | 510 | 618 | 942 | 1050 | 1374 | 1482 | 399 | 291 | 726 | 834 | 1158 | 1266 | 1590 | 1698 |
| CCL-252A | 184 | 76 | 511 | 619 | 943 | 1051 | 1375 | 1483 | 400 | 292 | 727 | 835 | 1159 | 1267 | 1591 | 1699 |
| CCL-253A | 185 | 77 | 512 | 620 | 944 | 1052 | 1376 | 1484 | 401 | 293 | 728 | 836 | 1160 | 1268 | 1592 | 1700 |
| CCL-255A | 186 | 78 | 513 | 621 | 945 | 1053 | 1377 | 1485 | 402 | 294 | 729 | 837 | 1161 | 1269 | 1593 | 1701 |
| CCL-301A | 187 | 79 | 514 | 622 | 946 | 1054 | 1378 | 1486 | 403 | 295 | 730 | 838 | 1162 | 1270 | 1594 | 1702 |
| CCL-303A | 188 | 80 | 515 | 623 | 947 | 1055 | 1379 | 1487 | 404 | 296 | 731 | 839 | 1163 | 1271 | 1595 | 1703 |
| CCL-305A | 189 | 81 | 516 | 624 | 948 | 1056 | 1380 | 1488 | 405 | 297 | 732 | 840 | 1164 | 1272 | 1596 | 1704 |
| CCL-309A | 190 | 82 | 517 | 625 | 949 | 1057 | 1381 | 1489 | 406 | 298 | 733 | 841 | 1165 | 1273 | 1597 | 1705 |

TABLE 2-continued

| Anti-CD115 mAb Amino Acid (aa) and Polynucleotide (nt) Sequences | | | | | | | | | | | | | | | | |
|---|---|---|---|---|---|---|---|---|---|---|---|---|---|---|---|---|
| | VH | | VHCDR1 | | VHCDR2 | | VHCDR3 | | VL | | VLCDR1 | | VLCDR2 | | VLCDR3 | |
| Clone | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: | aa SEQ ID NO: | nt SEQ ID NO: |
| CCL-310A | 191 | 83 | 518 | 626 | 950 | 1058 | 1382 | 1490 | 407 | 299 | 734 | 842 | 1166 | 1274 | 1598 | 1706 |
| CCL-311A | 192 | 84 | 519 | 627 | 951 | 1059 | 1383 | 1491 | 408 | 300 | 735 | 843 | 1167 | 1275 | 1599 | 1707 |
| CCL-312A | 193 | 85 | 520 | 628 | 952 | 1060 | 1384 | 1492 | 409 | 301 | 736 | 844 | 1168 | 1276 | 1600 | 1708 |
| CCL-313A | 194 | 86 | 521 | 629 | 953 | 1061 | 1385 | 1493 | 410 | 302 | 737 | 845 | 1169 | 1277 | 1601 | 1709 |
| CCL-314A | 195 | 87 | 522 | 630 | 954 | 1062 | 1386 | 1494 | 411 | 303 | 738 | 846 | 1170 | 1278 | 1602 | 1710 |
| CCL-315A | 196 | 88 | 523 | 631 | 955 | 1063 | 1387 | 1495 | 412 | 304 | 739 | 847 | 1171 | 1279 | 1603 | 1711 |
| CCL-320A | 197 | 89 | 524 | 632 | 956 | 1064 | 1388 | 1496 | 413 | 305 | 740 | 848 | 1172 | 1280 | 1604 | 1712 |
| CCL-321A | 198 | 90 | 525 | 633 | 957 | 1065 | 1389 | 1497 | 414 | 306 | 741 | 849 | 1173 | 1281 | 1605 | 1713 |
| CCL-322A | 199 | 91 | 526 | 634 | 958 | 1066 | 1390 | 1498 | 415 | 307 | 742 | 850 | 1174 | 1282 | 1606 | 1714 |
| CCL-324A | 200 | 92 | 527 | 635 | 959 | 1067 | 1391 | 1499 | 416 | 308 | 743 | 851 | 1175 | 1283 | 1607 | 1715 |
| CCL-325A | 201 | 93 | 528 | 636 | 960 | 1068 | 1392 | 1500 | 417 | 309 | 744 | 852 | 1176 | 1284 | 1608 | 1716 |
| CCL-327A | 202 | 94 | 529 | 637 | 961 | 1069 | 1393 | 1501 | 418 | 310 | 745 | 853 | 1177 | 1285 | 1609 | 1717 |
| CCL-328A | 203 | 95 | 530 | 638 | 962 | 1070 | 1394 | 1502 | 419 | 311 | 746 | 854 | 1178 | 1286 | 1610 | 1718 |
| CCL-329A | 204 | 96 | 531 | 639 | 963 | 1071 | 1395 | 1503 | 420 | 312 | 747 | 855 | 1179 | 1287 | 1611 | 1719 |
| CCL-331A | 205 | 97 | 532 | 640 | 964 | 1072 | 1396 | 1504 | 421 | 313 | 748 | 856 | 1180 | 1288 | 1612 | 1720 |
| CCL-332A | 206 | 98 | 533 | 641 | 965 | 1073 | 1397 | 1505 | 422 | 314 | 749 | 857 | 1181 | 1289 | 1613 | 1721 |
| CCL-333A | 207 | 99 | 534 | 642 | 966 | 1074 | 1398 | 1506 | 423 | 315 | 750 | 858 | 1182 | 1290 | 1614 | 1799 |
| CCL-335A | 208 | 100 | 535 | 643 | 967 | 1075 | 1399 | 1507 | 424 | 316 | 751 | 859 | 1183 | 1291 | 1615 | 1723 |
| CCL-337A | 209 | 101 | 536 | 644 | 968 | 1076 | 1400 | 1508 | 425 | 317 | 752 | 860 | 1184 | 1292 | 1616 | 1724 |
| CCL-338A | 210 | 102 | 537 | 645 | 969 | 1077 | 1401 | 1509 | 426 | 318 | 753 | 861 | 1185 | 1293 | 1617 | 1725 |
| CCL-339A | 211 | 103 | 538 | 646 | 970 | 1078 | 1402 | 1510 | 427 | 319 | 754 | 862 | 1186 | 1294 | 1618 | 1726 |
| CCL-340A | 212 | 104 | 539 | 647 | 971 | 1079 | 1403 | 1511 | 428 | 320 | 755 | 863 | 1187 | 1295 | 1619 | 1727 |
| CCL-341A | 213 | 105 | 540 | 648 | 972 | 1080 | 1404 | 1512 | 429 | 321 | 756 | 864 | 1188 | 1296 | 1620 | 1728 |
| CCL-344A | 214 | 106 | 541 | 649 | 973 | 1081 | 1405 | 1513 | 430 | 322 | 757 | 865 | 1189 | 1297 | 1621 | 1729 |
| CCL-346A | 215 | 107 | 542 | 650 | 974 | 1082 | 1406 | 1514 | 431 | 323 | 758 | 866 | 1190 | 1298 | 1622 | 1730 |
| CCL-349A | 216 | 108 | 543 | 651 | 975 | 1083 | 1407 | 1515 | 432 | 324 | 759 | 867 | 1191 | 1299 | 1623 | 1731 |

Example 3

Epitope Binning

A competition ELISA was performed to establish competitive binding bins. ELISA plates were coated with 1 ug/ml huCD115 protein (Sino Biological, China 10161-H08H) and blocked with Superblock (Thermo Scientific #37518). After washing, wells were incubated with a mouse monoclonal antibody representing one of six unique competition bins and for some of which, exhibit different activities in blocking CSF-1 and/or IL-34 binding to CD115 (Table 7) (these mouse mAbs were generated by hybridoma by immunizing wild-type mice as described in Example 1 as part of a comparator CD115 antibody generation program as part of the first tests of the newly-created AlivaMab® Mouse technology). After 1 hour the wells were washed and incubated with individual clonal anti-huCD115 AlivaMab® hybridoma supernatants. After another hour the wells were washed and incubated with a specific secondary antibody that either recognized human kappa LC or human lambda LC depending on which AlivaMab® Mouse supernatants were being detected (Southern Biotech Goat X hu kappa LC #2061-05 or Bethyl Goat X hu lambda LC #A80-116P) and detected with Supersignal ELISA Pico Chemiluminescent substrate (Thermo Scientific—Product #37069) (Tables 5 and 6). Individual AlivaMab® Mouse antibodies that were able to bind in the presence of a mouse antibody are considered to be in a unique epitope bin from that particular mouse antibody. Individual AlivaMab® Mouse antibodies that were unable to bind in the presence of a mouse antibody are considered to be in the same epitope bin as that particular mouse antibody. In this way multiple epitope bins were defined for huCD115 binding antibodies (Tables 3 and 6).

TABLE 3

| Multiple Epitope Bins | | | |
|---|---|---|---|
| | IgGκ | IgGλ | TOTAL |
| BIN 1 | 4 | 0 | 4 |
| BIN 2 | 18 | 16 | 34 |
| BIN 3 | 6 | 28 | 34 |
| BIN 4 | 6 | 8 | 14 |
| BIN 5 | 1 | 5 | 6 |
| BIN 6 | 7 | 2 | 9 |
| BIN 7 | 2 | 0 | 2 |
| BIN 8 | 6 | 0 | 6 |

TABLE 4

| Binning of AlivaMab Kappa Mouse Anti-CD115 mAbs | | | | | | | | | | | | | | | | |
|---|---|---|---|---|---|---|---|---|---|---|---|---|---|---|---|---|
| | | 1A | | 1B | | 1C | | 1D | | 1E | 3 | | 4 | | 5 | |
| | | 522 | 505 | 417 | 462 | 511 | 526 | 542 | 519 | 412 | 402 | 503 | 435 | 437 | 401 | 406 |
| Bin 1 | TMR 95A | 7 | 1 | 3 | 3 | 3 | 9 | 23 | 36 | 3 | 131 | 82 | 86 | 84 | 94 | 87 |
| Bin 1.5 | TMR 44B | 24 | 10 | 19 | 23 | 2 | 3 | 10 | 12 | 110 | 126 | 89 | 75 | 78 | 93 | 88 |
| Bin 1.7 | TMR 24A | 33 | 0 | 6 | 12 | 99 | 68 | 94 | 110 | 13 | 131 | 97 | 79 | 86 | 96 | 96 |

TABLE 4-continued

Binning of AlivaMab Kappa Mouse Anti-CD115 mAbs

| | | | | | | | | | | | | | | | | |
|---|---|---|---|---|---|---|---|---|---|---|---|---|---|---|---|---|
| Bin 2 | TMR 20A | 34 | 53 | 110 | 93 | 77 | 92 | 7 | 6 | 70 | 145 | 95 | 85 | 95 | 104 | 103 |
| Bin 3 | TMR 35A | 83 | 110 | 110 | 77 | 76 | 82 | 111 | 110 | 78 | 11 | 23 | 96 | 101 | 98 | 99 |
| Bin 4 | TMR 100A | 67 | 111 | 113 | 89 | 91 | 84 | 76 | 118 | 91 | 147 | 96 | 17 | 51 | 106 | 109 |
| | NO COMP | 100 | 100 | 100 | 100 | 100 | 100 | 100 | 100 | 100 | 100 | 100 | 100 | 100 | 100 | 100 |

| | 1A | | | | 1B | | | | | |
|---|---|---|---|---|---|---|---|---|---|---|
| | 455 | 458 | 522 | 585 | 417 | 462 | 422 | 424 | 461 | 421 |
| TMR 95A | 0 | 6 | 7 | 1 | 3 | 3 | 6 | 16 | 15 | 9 |
| TMR 44B | 28 | 17 | 24 | 10 | 19 | 23 | 31 | 53 | 41 | 55 |
| TMR 24A | −1 | 2 | 33 | 0 | 6 | 12 | 11 | 29 | 27 | 18 |
| TMR 20A | 58 | 22 | 34 | 53 | 110 | 93 | 107 | 98 | 110 | 104 |
| TMR 35A | 54 | 66 | 80 | 110 | 110 | 77 | 111 | 102 | 110 | 100 |
| TMR 100A | 79 | 79 | 67 | 111 | 113 | 89 | 111 | 98 | 110 | 99 |
| NO COMP | 100 | 100 | 100 | 100 | 100 | 100 | 100 | 100 | 100 | 100 |

| | 1B | | | | | | | | | | | |
|---|---|---|---|---|---|---|---|---|---|---|---|---|
| | 525 | 415 | 418 | 599 | 516 | 454 | 416 | 456 | 514 | 467 | 466 | 464 |
| TMR 95A | 11 | 11 | 10 | 19 | 20 | 29 | 21 | 27 | 42 | 46 | 34 | 57 |
| TMR 44B | 56 | 46 | 3 | 21 | 10 | 23 | 53 | 27 | 4 | 22 | 13 | 0 |
| TMR 24A | 13 | 31 | 35 | 51 | 39 | 37 | 37 | 42 | 53 | 58 | 58 | 39 |
| TMR 20A | 80 | 97 | 89 | 82 | 70 | 115 | 94 | 73 | 84 | 96 | 86 | 87 |
| TMR 35A | 88 | 96 | 82 | 85 | 82 | 110 | 107 | 64 | 75 | 83 | 100 | 85 |
| TMR 100A | 100 | 93 | 106 | 85 | 87 | 89 | 104 | 96 | 103 | 102 | 98 | 96 |
| NO COMP | 100 | 100 | 100 | 100 | 100 | 100 | 100 | 100 | 100 | 100 | 100 | 100 |

| | 1C | | | | | | 1D | | | | | | 1E |
|---|---|---|---|---|---|---|---|---|---|---|---|---|---|
| | 511 | 526 | 460 | 465 | 429 | 418 | 425 | 542 | 519 | 541 | 549 | 468 | 412 |
| TMR 95A | 3 | 9 | 23 | 41 | 38 | 35 | 21 | 23 | 36 | 42 | 1 | 61 | 3 |
| TMR 44B | 2 | 3 | 48 | 8 | 45 | 60 | 6 | 10 | 12 | 15 | 2 | 24 | 110 |
| TMR 24A | 99 | 68 | 61 | 81 | 75 | 75 | 78 | 94 | 110 | 109 | 111 | 85 | 13 |
| TMR 20A | 77 | 92 | 85 | 78 | 84 | 91 | 4 | 7 | 6 | 34 | 59 | 53 | 70 |
| TMR 35A | 76 | 82 | 86 | 88 | 112 | 86 | 88 | 111 | 110 | 111 | 89 | 104 | 78 |
| TMR 100A | 91 | 84 | 94 | 92 | 107 | 94 | 98 | 76 | 118 | 93 | 100 | 95 | 91 |
| NO COM | 100 | 100 | 100 | 100 | 100 | 100 | 100 | 100 | 100 | 100 | 100 | 100 | 100 |

| | 3 | | | | | | | 4 | | 5 | | | | | |
|---|---|---|---|---|---|---|---|---|---|---|---|---|---|---|---|
| | 482 | 589 | 587 | 459 | 599 | 487 | 488 | 495 | 497 | 481 | 486 | 414 | 496 | 581 | 519 |
| TMR 95A | 131 | 82 | 74 | 77 | 97 | 84 | 68 | 86 | 84 | 94 | 87 | 86 | 81 | 91 | 77 |
| TMR 44B | 126 | 89 | 87 | 84 | 92 | 94 | 80 | 75 | 78 | 93 | 88 | 87 | 91 | 106 | 86 |
| TMR 24A | 131 | 97 | 106 | 86 | 112 | 86 | 74 | 79 | 86 | 96 | 96 | 92 | 87 | 95 | 90 |
| TMR 20A | 145 | 95 | 112 | 90 | 102 | 97 | 100 | 85 | 95 | 104 | 103 | 106 | 96 | 114 | 92 |
| TMR 35A | 11 | 23 | 7 | 3 | 4 | 6 | 34 | 96 | 101 | 98 | 99 | 91 | 92 | 106 | 89 |
| TMR 100A | 147 | 96 | 123 | 95 | 109 | 103 | 101 | 17 | 51 | 106 | 109 | 101 | 100 | 116 | 93 |
| NO COM | 100 | 100 | 100 | 100 | 100 | 100 | 100 | 100 | 100 | 100 | 100 | 100 | 100 | 100 | 100 |

TABLE 5

Epitope Competition Bins in Panels of anti-CD115 mAbs

| | BIN 1 | | BIN 2 | | BIN 3 | | BIN 4 | | BIN 5 | | BIN 6 | | BIN 7 | | BIN 8 | |
|---|---|---|---|---|---|---|---|---|---|---|---|---|---|---|---|---|
| | CCK 522A | CCK 505A | CCK 417A | CCK 462A | CCK 511A | CCK 526A | CCK 542A | CCK 519A | CCK 412A | CCL 321A | CCK 402A | CCK 503A | CCK 43 5A | CCK 43 7A | CCK 401A | CCK 406A |
| TMR 4413 | 0 | 0 | 0 | 0 | 0 | 0 | 0 | 0 | 1 | 1 | 1 | 1 | 1 | 1 | 1 | 1 |
| TMR 24A | 0 | 0 | 0 | 0 | 1 | 1 | 1 | 1 | 0 | 0 | 1 | 1 | 1 | 1 | 1 | 1 |
| TMR 20A | 0 | 0 | 1 | 1 | 1 | 1 | 0 | 0 | 1 | 1 | 1 | 1 | 1 | 1 | 1 | 1 |
| TMR 35A | 1 | 1 | 1 | 1 | 1 | 1 | 1 | 1 | 1 | 1 | 0 | 0 | 1 | 1 | 1 | 1 |
| TMR 100A | 1 | 1 | 1 | 1 | 1 | 1 | 1 | 1 | 1 | 1 | 1 | 1 | 0 | 0 | 1 | 1 |
| NO COMP | 1 | 1 | 1 | 1 | 1 | 1 | 1 | 1 | 1 | 1 | 1 | 1 | 1 | 1 | 1 | 1 |

TABLE 6

Anti-CD115 mAb Epitope Bins

| HYBRIDOMA | BIN | HYBRIDOMA | BIN |
|---|---|---|---|
| CCK-401A | 5 | CCL-201A | 1C |
| CCK-402A | 3 | CCL-203A | 1C |
| CCK-406A | 5 | CCL-204A | 1C |
| CCK-407A | 3 | CCL-205A | 1C |
| CCK-408A | 3 | CCL-206A | 1B |
| CCK-410A | 1C | CCL-207A | 1C |
| CCK-412A | 1E | CCL-208A | 1D |
| CCK-414A | 5 | CCL-209A | 1D |
| CCK-415A | 1B | CCL-211A | 1C |
| CCK-416A | 1B | CCL-212A | 1B |
| CCK-417A | 1B | CCL-213A | 1B |
| CCK-418A | 1B | CCL-215A | 1C |
| CCK-421A | 1B | CCL-216A | 1C |
| CCK-422A | 1B | CCL-217A | 1C |
| CCK-423A | 1C | CCL-218A | 1B |
| CCK-424A | 1B | CCL-220A | 1C |
| CCK-425A | 1D | CCL-221A | 1E |
| CCK-434A | 1B | CCL-223A | 1C |
| CCK-435A | 4 | CCL-225A | 1B |
| CCK-436A | 5 | CCL-226A | 1C |
| CCK-437A | 4 | CCL-229A | 1B |
| CCK-455A | 1A | CCL-231A | 1E |
| CCK-456A | 1B | CCL-235A | 1B |
| CCK-458A | 1A | CCL-238A | 1C |
| CCK-459A | 3 | CCL-245A | 1C |
| CCK-460A | 1D | CCL-247A | 1C |
| CCK-461A | 1B | CCL-249A | 1C |
| CCK-464A | 1B | CCL-252A | 1B |
| CCK-465A | 1C | CCL-253A | 1C |
| CCK-467A | 1B | CCL-255A | 1C |
| CCK-468A | 1C | CCL-301A | 1D |
| CCK-501A | 5 | CCL-303A | 1C |
| CCK-503A | 3 | CCL-305A | 1D |
| CCK-505A | 1A | CCL-309A | 1E |
| CCK-507A | 3 | CCL-310A | 1C |
| CCK-511A | 1C | CCL-311A | 1B |
| CCK-513A | 5 | CCL-312A | 3 |
| CCK-514A | 1B | CCL-313A | 3 |
| CCK-516A | 1B | CCL-314A | 1B |
| CCK-519A | 1D | CCL-315A | 1B |
| CCK-522A | 1A | CCL-320A | 1B |
| CCK-525A | 1B | CCL-321A | 1E |
| CCK-526A | 1C | CCL-322A | 1C |
| CCK-533A | 3 | CCL-324A | 1B |
| CCK-539A | 1B | CCL-325A | 1C |
| CCK-541A | 1D | CCL-327A | 1D |
| CCK-542A | 1D | CCL-328A | 1D |
| CCK-543A | 1D | CCL-329A | 1C |
| | | CCL-331A | 1E |
| | | CCL-332A | 1C |
| | | CCL-333A | 1C |
| | | CCL-335A | 1B |
| | | CCL-337A | 1C |
| | | CCL-338A | 1B |
| | | CCL-339A | 1C |
| | | CCL-340A | 1C |
| | | CCL-341A | 1D |
| | | CCL-344A | 1D |
| | | CCL-346A | 1C |
| | | CCL-349A | 1B |

Figure 2:
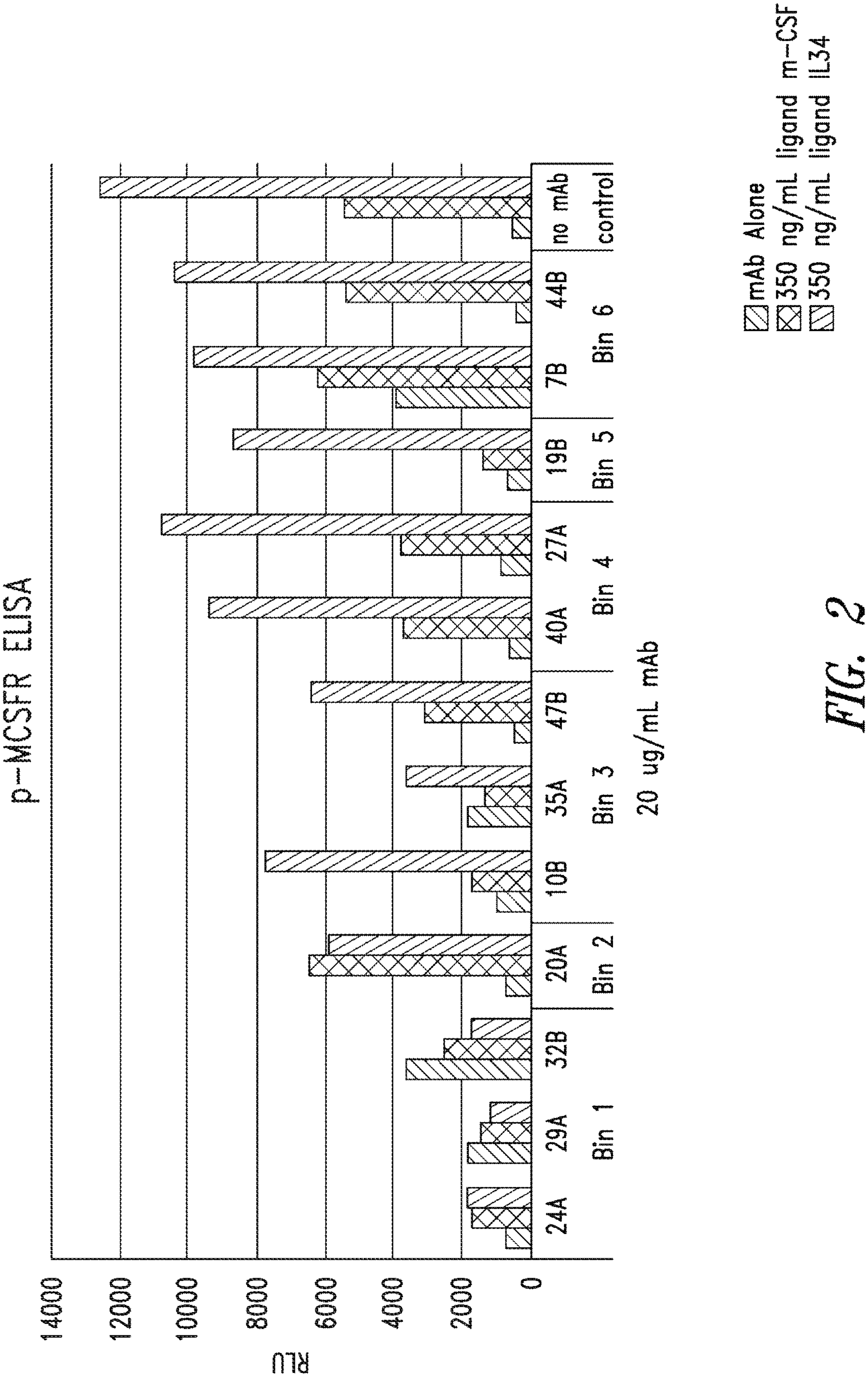
FIG. 2 shows Bin1 α-CD115 mAbs may block M-CSF and IL34 induced CD115 phosphorylation and Bin 3 35A may block all phosphorylation.
Figure 4A:
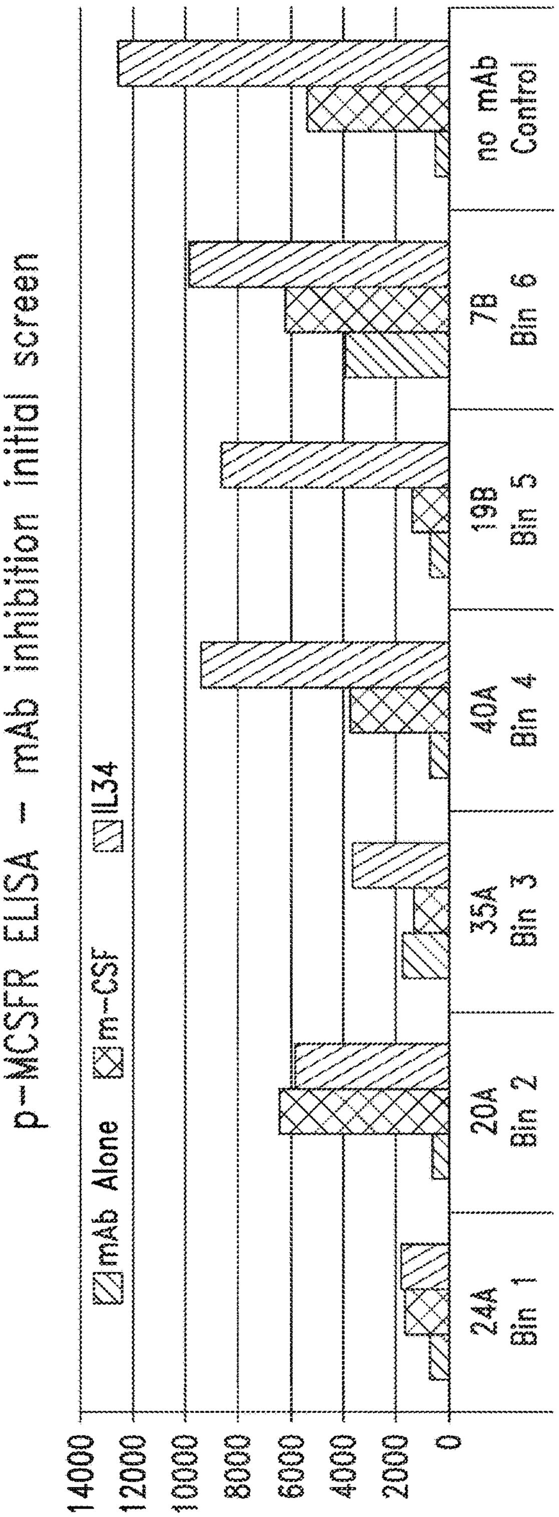
FIGS. 4A and 4B show inhibition of m-CSF- and IL-34-induced phosphorylation of CD115 (MCSFR).
Figure 4B:
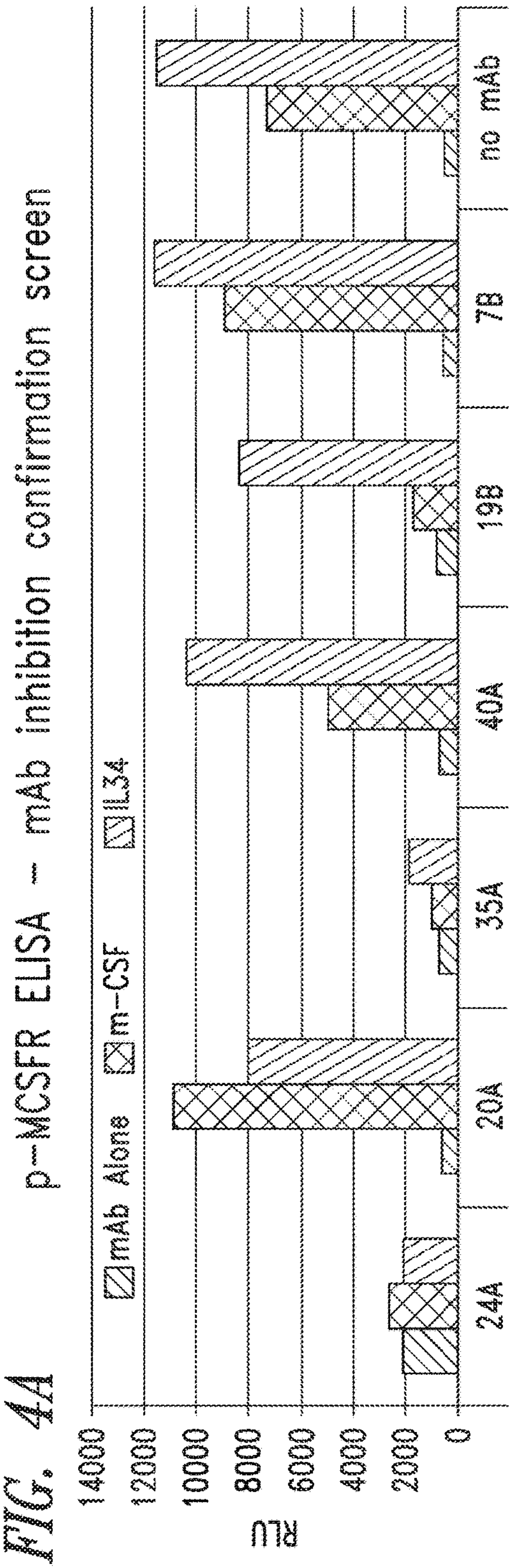

Based on functional characterization of the bin-defining mouse mAbs, some antibodies within epitope bins 1A or 1C (defined by dual IL-34- and CSF-1-neutralizing mouse mAb, TMR24A) or bin 3 (defined by dual IL-34- and CSF-1-neutralizing mouse mAb, TMR35A) may neutralize P-TYR formation induced by both CSF-1 and IL-34 (FIG. 2). Some antibodies within epitope bin 1C (defined by only CSF-1-neutralizing and IL-34 non-neutralizing mouse mAb, TMR20A) may neutralize only CSF-1-induced P-TYR formation on CD115. However, some bin 3 mAbs may neutralize both IL-34 and CSF-1 induced P-TYR formation on CD115. As summarized in Table 7 below, some of the reference wild-type mouse mAbs can block both cytokines from different locations on the receptor (e.g., bin 1 and bin3), some mAbs block M-CSF while not blocking IL-34, none of the mAbs were agonists on their own, and the bin 3 epitope region appears to contain functional diversity (e.g., all 3 mAbs listed below exhibited different activity). Also of note is that mAb 20A slightly increased/enhanced the M-CSF signal (FIGS. 4A and 4B).

TABLE 7

Summary of anti-CD115 mAb Activity

| mAb | Bin | Blocks M-CSF | Blocks IL-34 |
|---|---|---|---|
| 24A | 1 | +++ | +++ |
| 29A | 1 | +++ | +++ |
| 32B | 1 | +++ | +++ |
| 20A | 2 | Slight agonist | NO |
| 10B | 3 | +++ | NO |
| 35A | 3 | +++ | +++ |
| 47B | 3 | NO | NO |
| 40A | 4 | + | NO |
| 27A | 4 | + | NO |
| 19B | 5 | +++ | NO |
| 7B | 6 | NO | NO |
| 44B | 6 | NO | NO |

Example 4

Affinity Determination

Affinity was determined for 24 selected monoclonal hybridoma supernatants (Biosensor Tools, Salt Lake City, Utah). Binding kinetics were measured using a BioRad ProteOn XPR36 optical biosensor equipped with an anti-mouse IgG-Coated GLC sensor chip. Hybridoma supernatants were diluted 10-fold into running buffer and captured for 4 minutes on the anti-mouse IgG surface. Hu CD115 (Sino Biological, China #10161-H08H) was tested in duplicate using a 3-fold dilution series starting at 150 nM. The processed data were fit using a 1:1 interaction model that includes a mass-transport parameter (Scrubber2, Canberra Australia). Within the panel of AlivaMab® Mouse anti-CD115 antibodies, there are antibodies with KD values below a nanomolar and KD values in the low nanomolar range, and with fast $k_{on}$ and slow $k_{off}$ rates (Tables 8 and 9).

TABLE 8

Binding Kinetics of Anti-CD115 IgGλ mAbs

| mAb | ka ($M^{-1}s^{-1}$) | kd ($s^{-1}$) | $K_D$ (pM) |
|---|---|---|---|
| 329 | $1.18 \times 10^{5}$ | $4.46 \times 10^{-6}$ | 38 |
| 310 | $5.06 \times 10^{4}$ | $4.35 \times 10^{-6}$ | 79 |
| 331 | $1.86 \times 10^{5}$ | $2.20 \times 10^{-5}$ | 118 |
| 215 | $8.53 \times 10^{4}$ | $1.83 \times 10^{-5}$ | 215 |
| 225 | $5.00 \times 10^{4}$ | $1.38 \times 10^{-5}$ | 277 |
| 340 | $7.41 \times 10^{4}$ | $2.72 \times 10^{-5}$ | 367 |
| 312 | $1.39 \times 10^{5}$ | $6.03 \times 10^{-5}$ | 435 |
| 206 | $5.90 \times 10^{4}$ | $2.92 \times 10^{-5}$ | 495 |
| 231 | $8.10 \times 10^{4}$ | $4.71 \times 10^{-5}$ | 578 |
| 249 | $1.49 \times 10^{5}$ | $8.91 \times 10^{-5}$ | 599 |
| 217 | $9.81 \times 10^{4}$ | $1.20 \times 10^{-4}$ | 1,220 |
| 313 | $7.36 \times 10^{4}$ | $9.09 \times 10^{-5}$ | 1,240 |
| 327 | $1.33 \times 10^{5}$ | $1.89 \times 10^{-4}$ | 1,410 |

TABLE 9

| Binding Kinetics of Anti-CD115 IgGκ mAbs | | | |
|---|---|---|---|
| mAb | ka ($M^{-1}s^{-1}$) | kd ($s^{-1}$) | $K_D$ (pM) |
| 418 | $1.33 \times 10^5$ | $2.11 \times 10^{-5}$ | 158 |
| 533 | $1.24 \times 10^5$ | $3.92 \times 10^{-5}$ | 317 |
| 412 | $1.58 \times 10^5$ | $5.94 \times 10^{-4}$ | 376 |
| 460 | $8.92 \times 10^5$ | $5.51 \times 10^{-4}$ | 618 |
| 467 | $2.30 \times 10^4$ | $1.48 \times 10^{-5}$ | 650 |
| 459 | $5.00 \times 10^4$ | $3.38 \times 10^{-5}$ | 680 |
| 519 | $9.00 \times 10^4$ | $7.71 \times 10^{-5}$ | 860 |
| 407 | $6.90 \times 10^4$ | $6.54 \times 10^{-5}$ | 950 |
| 541 | $2.67 \times 10^5$ | $3.74 \times 10^{-4}$ | 1,400 |
| 465 | $5.31 \times 10^5$ | $7.49 \times 10^{-4}$ | 1,410 |
| 456 | $2.70 \times 10^4$ | $5.30 \times 10^{-5}$ | 1,970 |
| 539 | $3.20 \times 10^4$ | $8.50 \times 10^{-5}$ | 2,700 |

Example 5

Internalization of Anti-CD115 Antibodies

Figure 12:
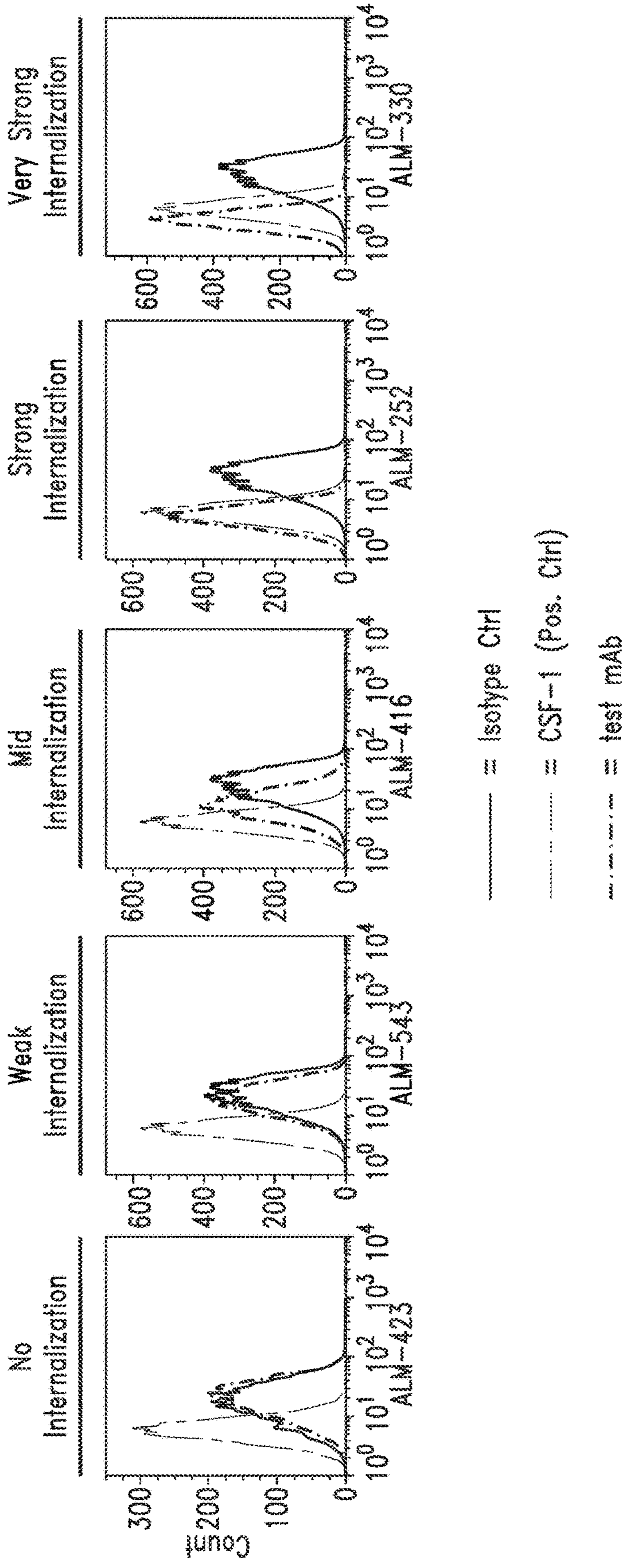
FIG. 12 shows internalization of anti-CD115 mAbs. From left to right, examples within the panel of anti-CD115 mAbs exhibiting no internalization, weak internalization, mid internalization, strong internalization and very strong internalization are depicted.

Anti-CD115 antibodies were tested for their ability to internalize upon binding to native CD115 on the surface of OCI-AML5 cells (DSMZ #ACC-247). OCI-AML5 cells were treated with individual AlivaMab® Mouse anti-CD115 supernatants for 1 hour at 37° C. The cells were then transferred to ice and stained with a fluorescently labeled anti-CD115 mAb known to be able to bind CD115 in the presence of bound test antibody (either Biolegend Rat x Hu-CD115-PE #6393 or CCK533A conjugated with Dylight488 Pierce #46403). Detection of fluorescent signal was then measured using a BD FACScalibur instrument. Cells that gave a strong fluorescent signal are considered to be non-internalizers for that individual test anti-CD115 mAb. Cells that are measured to have weak or no fluorescent signal are considered to be strong internalizers for that individual test anti-CD115 mAb. This procedure was repeated with several purified AlivaMab® Mouse anti-CD115 mAbs that showed internalization as a supernatant at 20 ug/ml. Other AlivaMab® Mouse anti-CD115 mAbs are also shown to exhibit various levels of internalization of CD115 induced by mAb binding (FIG. 12 and Table 10).

TABLE 10

| Internalization of Anti-CD115 mAbs | |
|---|---|
| mAb | Internalization |
| CCK-423A | − |
| CCK-543A | + |
| CCK-416A | ++ |
| CCL-252A | +++ |
| CCL-331A | ++++ |

(− = no internalization, 1-4 + = strength of internalization)

Example 6

Neutralization of CSF-1 Binding to CD115

Figure 10:
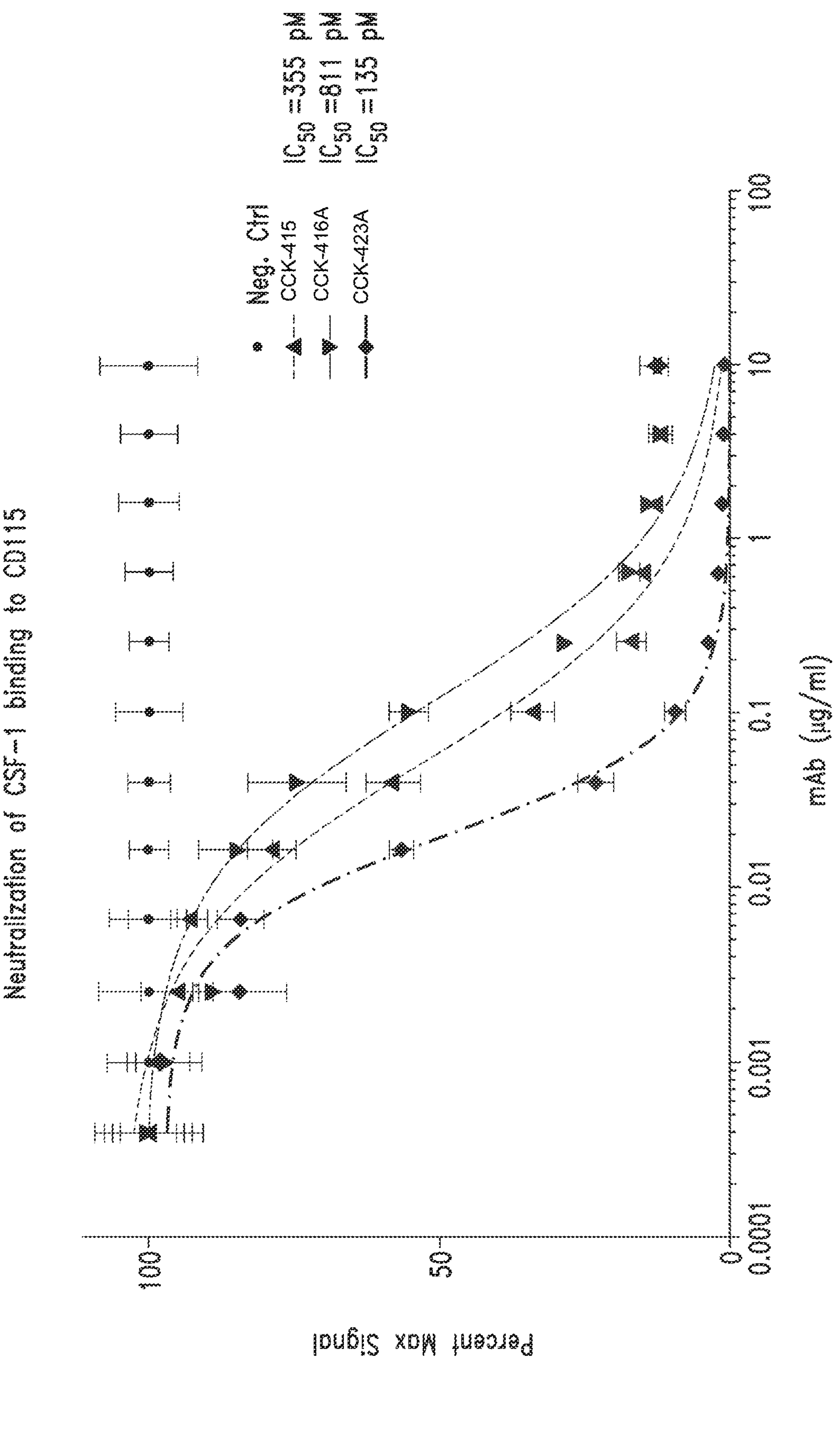
FIG. 10 shows neutralization of CSF-1 binding to CD115 by anti-CD115 mAbs.

Anti-CD115 antibodies were tested for their ability to block binding of recombinant CSF-1 to recombinant CD115. ELISA plates were coated with recombinant hu-CD115 (Sino Biological, China #10161-H08H) at 0.5 ug/ml and blocked with Superblock (Thermo Scientific #37518). Wells were incubated for 15 min with anti-CD115 mAbs, then biotinylated Hu-CSF-1 (R&D Systems, #216-MC-005) (biotinylation using NHS-Peg4-biotin, Life Technologies, #21330) was added to a final concentration of 0.25 ug/ml for an additional 15'. After a 4× wash, CSF-1-biotin was detected using 1:10,000 SAV-poly HRP (Life Technologies, #N200). Other AlivaMab® Mouse anti-CD115 mAbs are also shown to exhibit various abilities and IC50 values in blocking CSF-1 binding to CD115 (FIG. 10 and Table 11).

TABLE 11

| AlivaMab Mouse anti-CD115 mAbs block CSF-1 binding to CD115 | |
|---|---|
| mAb | $IC_{50}$ (pM) |
| CCK-415A | 355 |
| CCK-416A | 811 |
| CCK-423A | 135 |

Example 7

Inhibition of P-Tyr Formation on CD115 Induced by CSF-1

Figure 6:
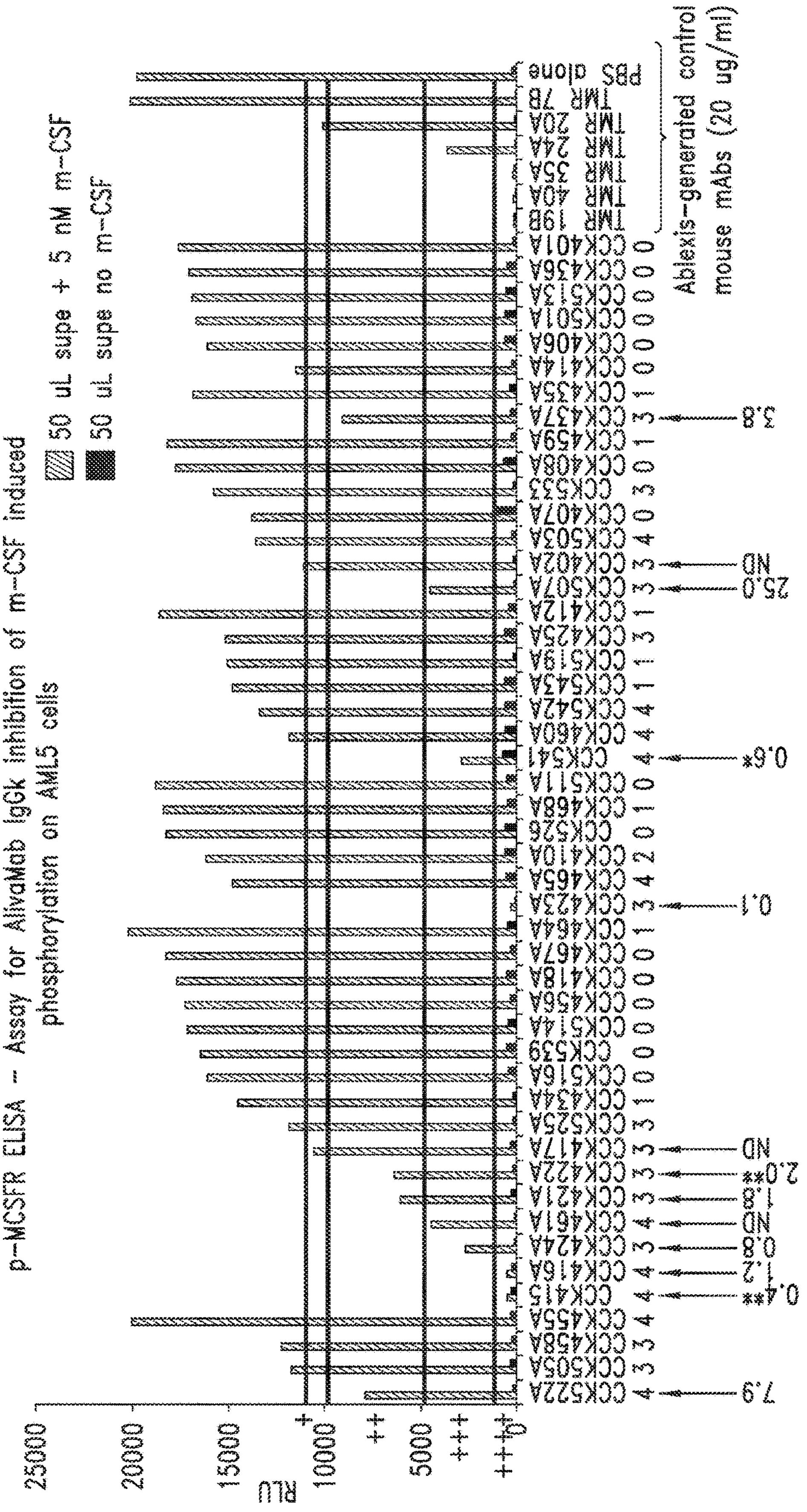
FIG. 6 shows an assay for detecting inhibition of m-CSF (CSF-1) induced phosphorylation on CD115 expressing AML5 cells by anti-CD115 IgGκ mAb.
Figure 8:
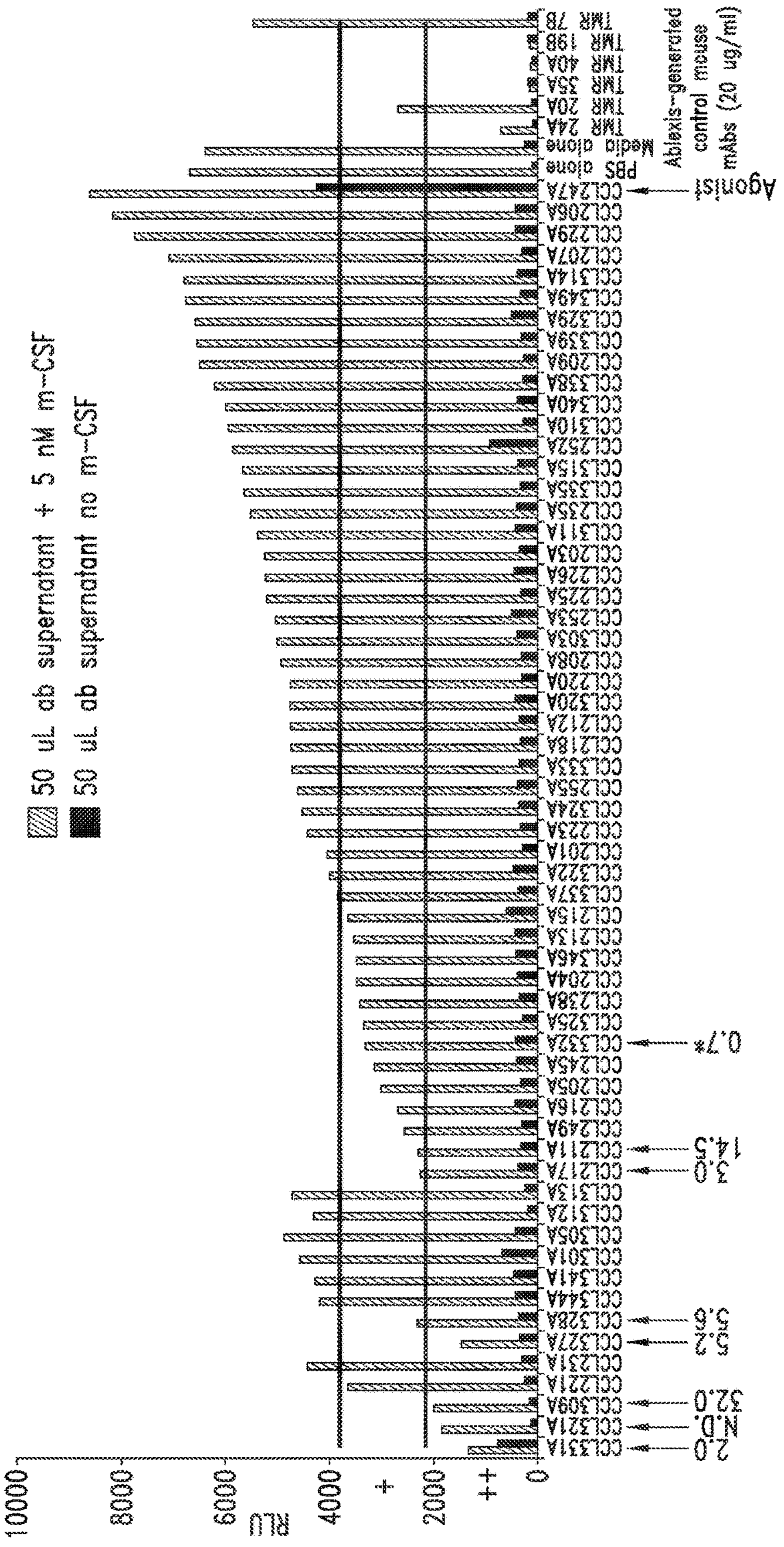
FIG. 8 shows anti-CD115 IgGλ mAb inhibition of CSF-1 induced phosphorylation of CD115.

Anti-CD115 antibodies were tested for their ability to block hu-CSF1 induced phosphorylation of native CD115. OCI-AML5 cells (DSMZ, #ACC-247) were serum starved (1% FBS) overnight, then harvested and washed twice in PBS with 0.1% BSA. 250,000 cells were plated per well into a 96-well v-bottom polypropylene plate. Anti-CD115 supernatants were added neat for 15 min while incubating the plate on ice. Hu-CSF-1 (R&D Systems, #216-MC-005) was added to each well at a final concentration of 100 ng/ml and incubated for 30' on ice. Cells were then spun down at 1500 RPM for 5' at 4° C. and supernatant was removed. Cells were then resuspended in lysis buffer (Cell Signaling, #9803 with 1×HALT protease inhibitors, Pierce, #78430) and incubated on ice for 15 min. Lysates were then measured for tyrosine phosphorylated CD115 using a p-MCSFR validated DUOSET assay (R&D Systems #CYC3268E) and detected using Supersignal Pico ELISA Substrate (Pierce, #37069) (FIGS. 6 and 8).

Figure 9:
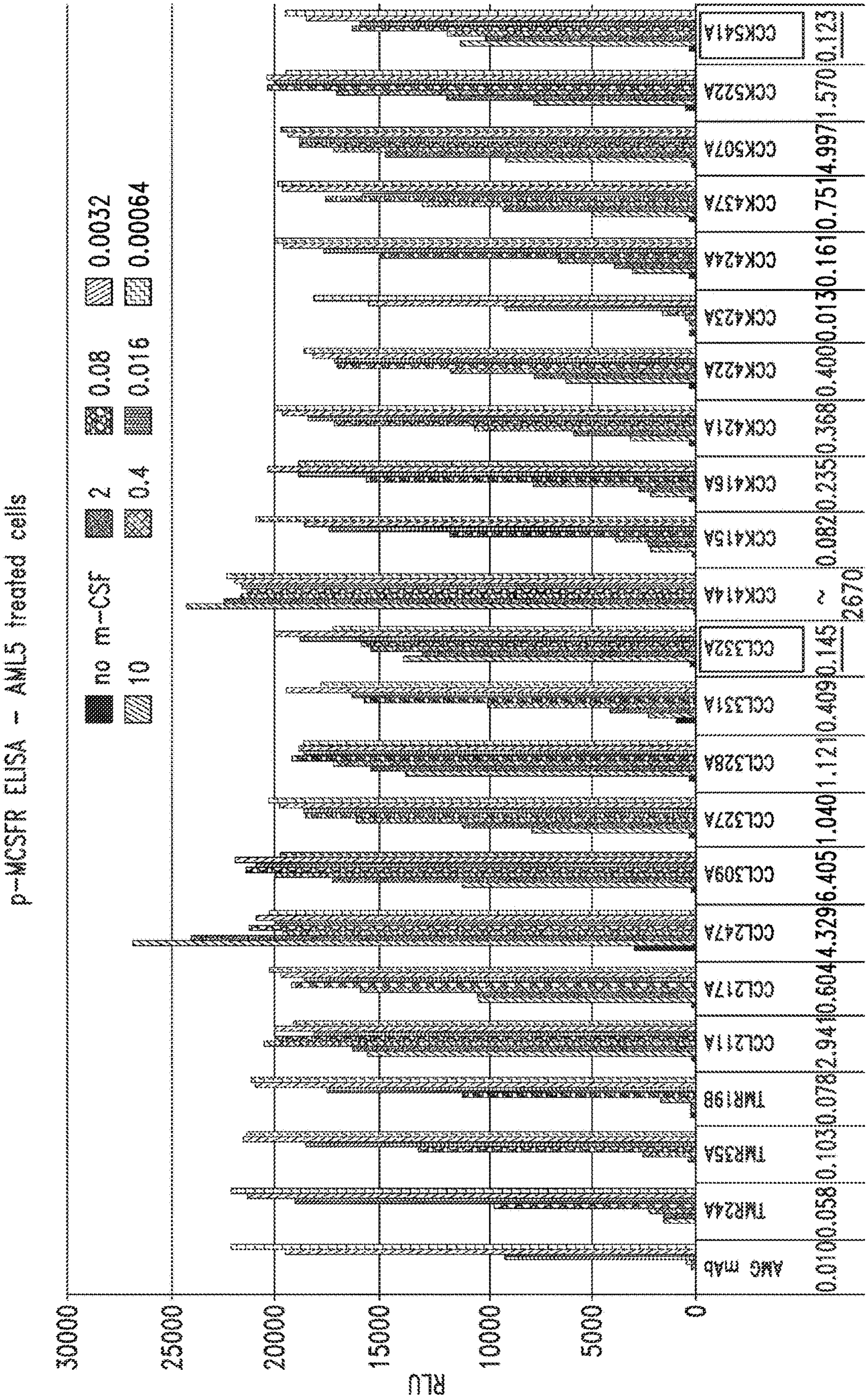
FIG. 9 shows the IC50 of selected anti-CD115 mAbs. For each grouping of bars, no M-CSF, 10, 2, 0.4, 0.08, 0.016, 0.0032, and 0.00064 ng/ml are shown from left to right.
Figure 11:
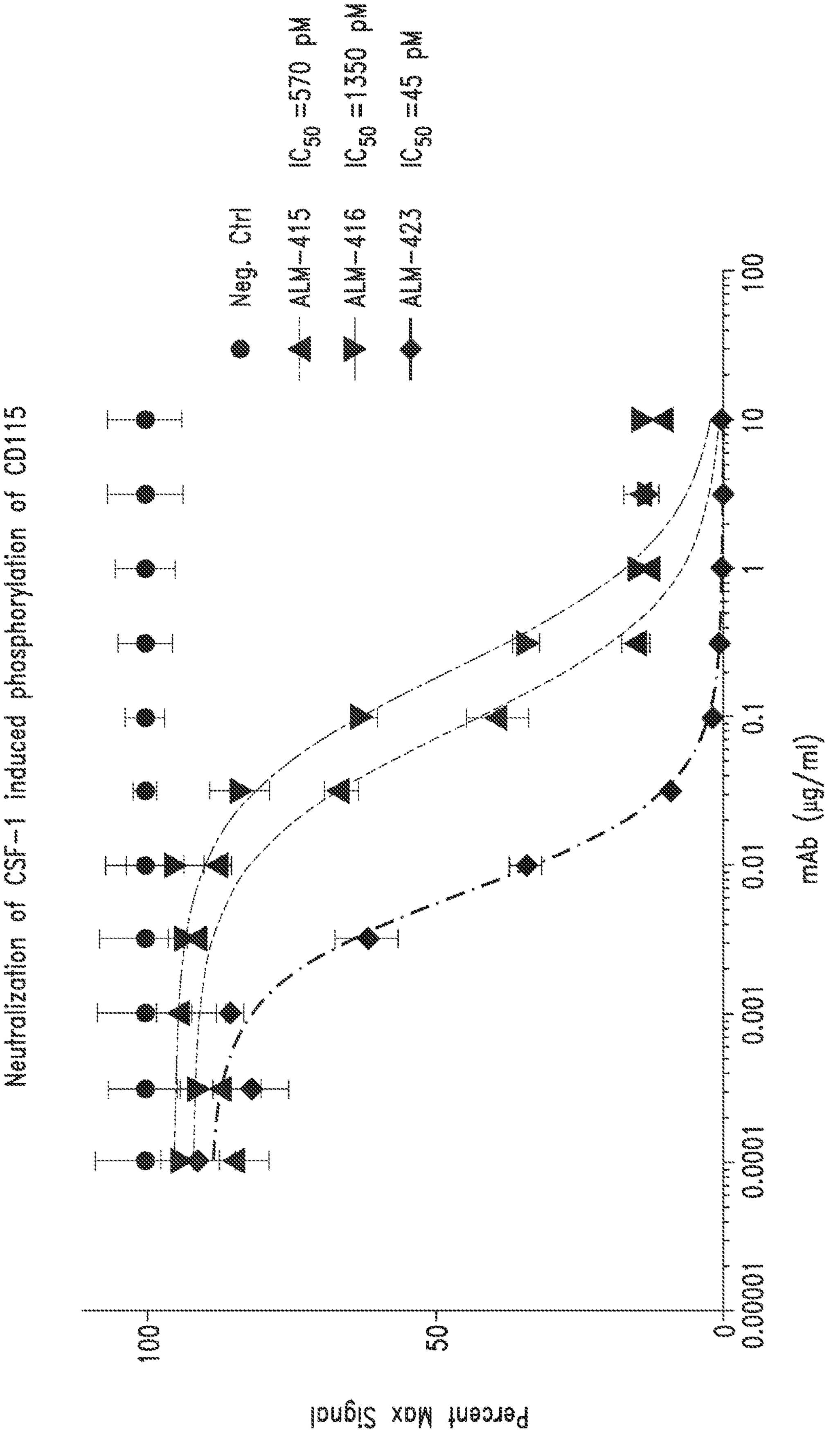
FIG. 11 shows neutralization of CSF-1 induced phosphorylation of CD115 by anti-CD115 mAbs.
Figure 16:
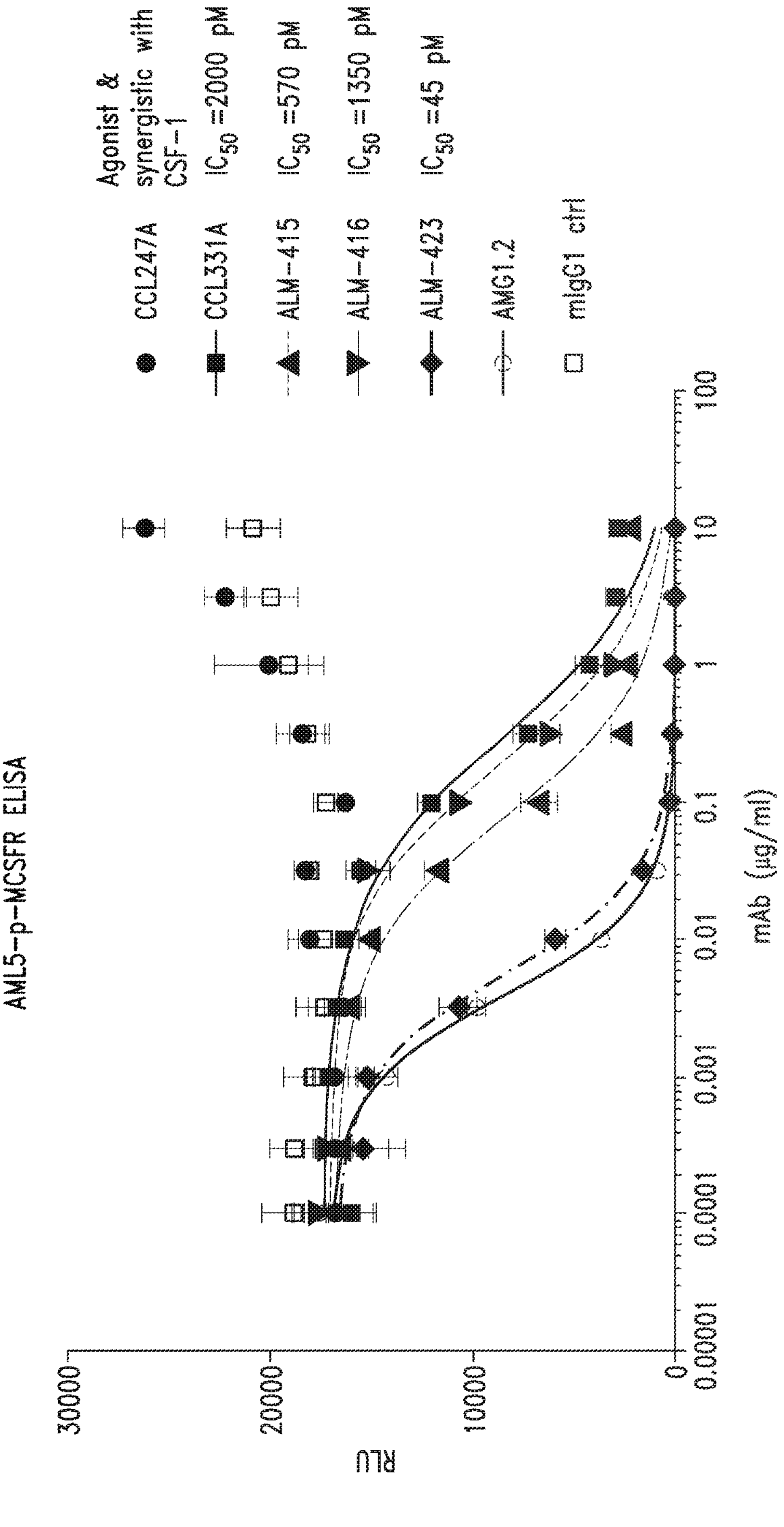
FIG. 16 shows some anti-CD115 antibodies that are antagonists of CSF-1 induce p-tyr formation on CD115.

Unpurified anti-CD115 IgGs (as identified by ELISA as described above) secreted from hybridomas into the tissue culture supernatant was assessed for neutralization of P-TYR formation induced by CSF-1. Neutralization using these unpurified, non-quantified antibodies was rank ordered. From this assessment, sets of the better neutralizing mAbs were identified, one set of IgGκ mAbs and one set of IgGλ mAbs. The hybridomas making these mAbs were grown and mAb purified using a commercially-available kit. The P-TYR neutralization assay was repeated with several purified anti-CD115 mAbs using a dilution series enabling an IC50 calculation, first in an eight-point dilution curve (FIG. 9) and then with a further subset of best neutralizing mAbs in a twelve-point dilution curve to better calculate IC50 values. Of the antibodies tested, CCK423 was identified as having the best IC50 for neutralizing CSF-1 P-TYR formation on CD115 (FIGS. 11 and 16; Table 12).

TABLE 12

| Anti-CD115 mAbs inhibit CSF-1 induced phosphorylation of CD115 | |
|---|---|
| mAb | $IC_{50}$ (pM) |
| CCK-415A | 570 |
| CCK-416A | 1350 |
| CCK-423A | 45 |

Example 8

Conversion of Alivamab® Mouse Anti-CD115 mAbs to Fully Human

Figure 13:
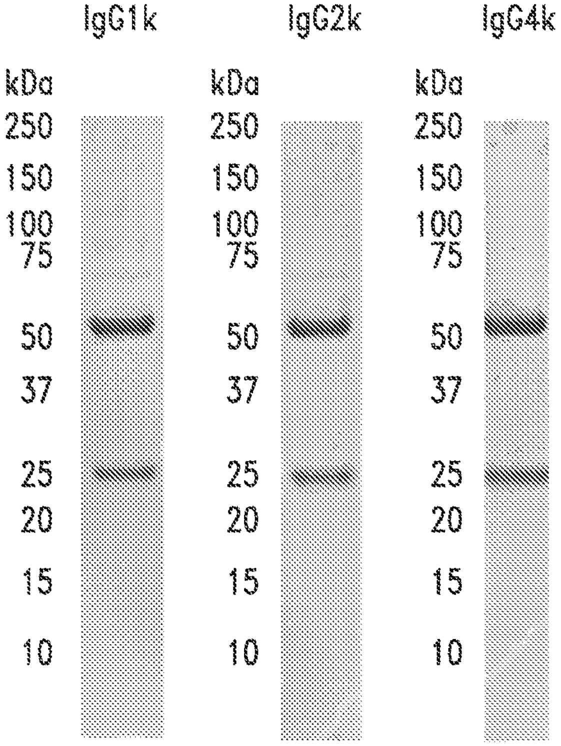
FIG. 13 shows conversion of anti-CD115 mAb ALM-423 to fully human antibodies.

The AlivaMab® Mouse anti-CD115 mAbs are easily converted, expressed recombinantly and purified as fully-human antibodies of any isotype. The recombinant fully-human antibody retains all of the characteristics of the parental AlivaMab® Mouse antibody. For example, the nucleotide sequences of the heavy and light chain variable region of CCK423A were transmitted to and synthesized into DNA by Lake Pharma (Belmont Calif.) and then, using vectors for recombinant expression in mammalian cells, the VH cloned in-frame with coding sequences for human IgG1, IgG2, or IgG4 constant regions and the Vκ cloned in-frame with coding sequences for the human Cκ region. Vectors were then transformed into HEK293 cells for expression of recombinant fully human antibody. Fully human IgG1κ, IgG2κ and IgG4κ mAb versions of CCK423A were purified from tissue culture supernatants using protein A (FIG. 13).

Example 9

Affinity of Fully Human mAbs

Affinity was determined for AlivaMab® CCK423A as well as for the 3 human variants CCK423A-I IgG1κ, CCK423A-IgG2κ, and CCK423A-IgG4κ (Biosensor Tools, Salt Lake City, Utah). Binding kinetics were measured using a BioRad ProteOn XPR36 optical biosensor equipped with a GLM sensor chip. Purified mAbs were amine coupled to the GLM sensor chip. Hu CD115 (Sino Biological, China #10161-H08H) was tested in triplicate using a 3 fold dilution series starting at 10 nM. The processed data were fit using a 1:1 interaction model that includes a mass-transport parameter (Scrubber2, Canberra Australia). All 4 constructs were found to bind hu-CD115 with the same kinetics and affinity (Table 13).

TABLE 13

| mAb | ka ($M^{-1}s^{-1}$) | kd ($s^{-1}$) | KD (nM) |
|---|---|---|---|
| AlivaMab CCK423A | $1.3 \times 10^7$ | $1.5 \times 10^{-2}$ | 1.2 |
| Human IgG1κ | $1.2 \times 10^7$ | $1.7 \times 10^{-2}$ | 1.2 |
| Human IgG2κ | $1.3 \times 10^7$ | $1.4 \times 10^{-2}$ | 1.3 |
| Human IgG4κ | $1.1 \times 10^7$ | $1.5 \times 10^{-2}$ | 1.3 |

Example 10

CSF-1 Binding Neutralization with Fully Human mAbs

Figure 14:
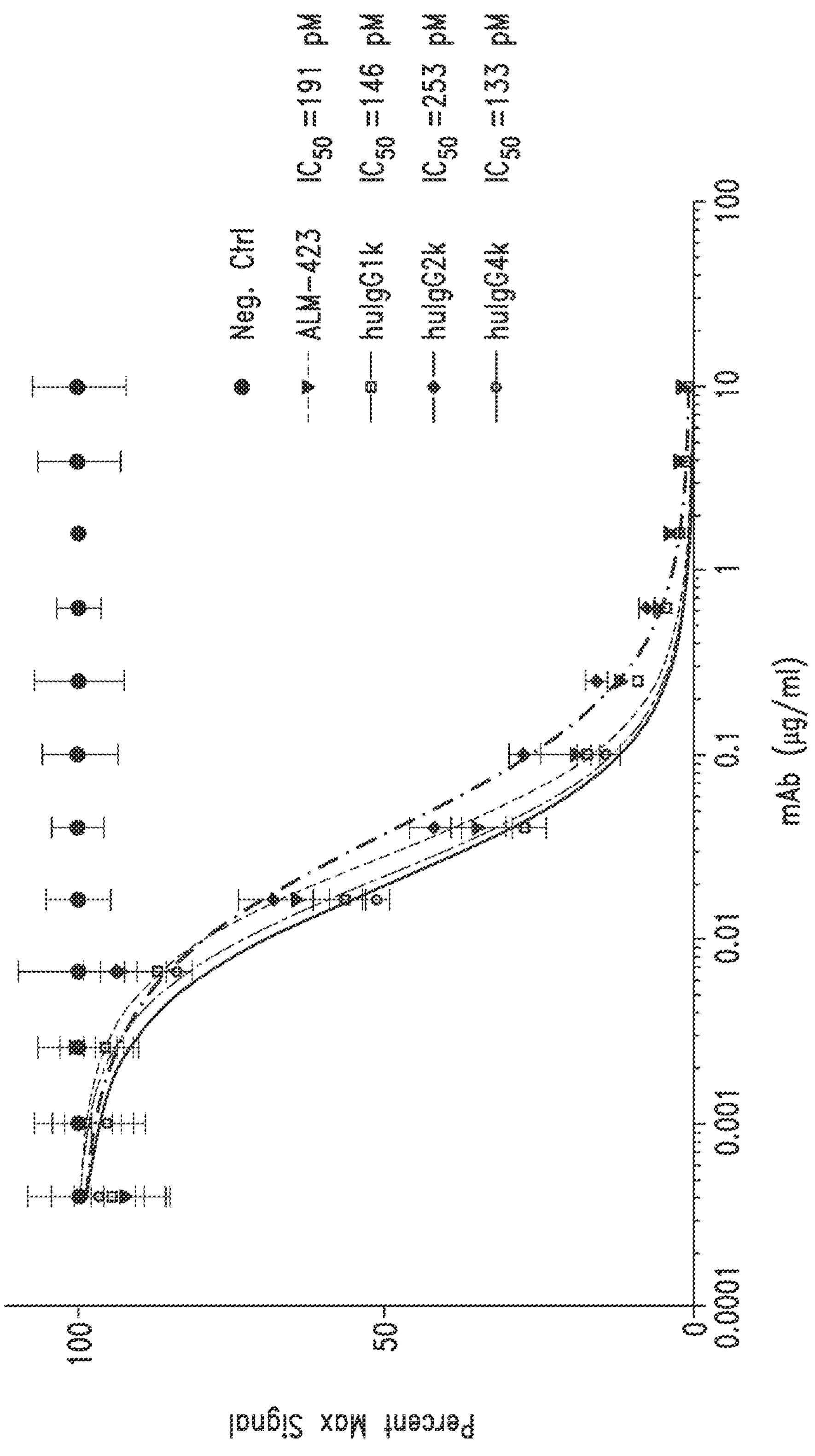
FIG. 14 shows neutralization of CSF-1 binding to CD115 by fully human anti-CD115 mAbs.

AlivaMab® Mouse CCK423A as well as the 3 human variants CCK423A-IgG1, CCK423A-IgG2, and CCK423A-IgG4 antibodies were tested for their ability to block binding of recombinant CSF-1 to recombinant CD115. ELISA plates were coated with recombinant hu-CD115 (Sino Biological, China #10161-H08H) at 0.5 ug/ml and blocked with Super-block (Thermo Scientific #37518). Wells were incubated for 15 min with anti-CD115 mAbs, then biotinylated Hu-CSF-1 (R&D Systems, #216-MC-005) (biotinylation using NHS-Peg4-biotin, Life Technologies, #21330) was added to a final concentration of 0.25 ug/ml for an additional 15'. After a 4× wash, CSF-1-biotin was detected using 1:10,000 SAV-poly HRP (Life Technologies, #N200). The fully human variants exhibited identical potency as the parental AlivaMab® antibody (FIG. 14 and Table 14).

TABLE 14

| mAb | $IC_{50}$ (pM) |
|---|---|
| AlivaMab CCK423A | 191 |
| Human IgG1κ | 146 |
| Human IgG2κ | 253 |
| Human IgG4κ | 133 |

Example 11

Inhibition of CSF-1 Induced P-Tyr with Fully Human Mabs

Figure 15:
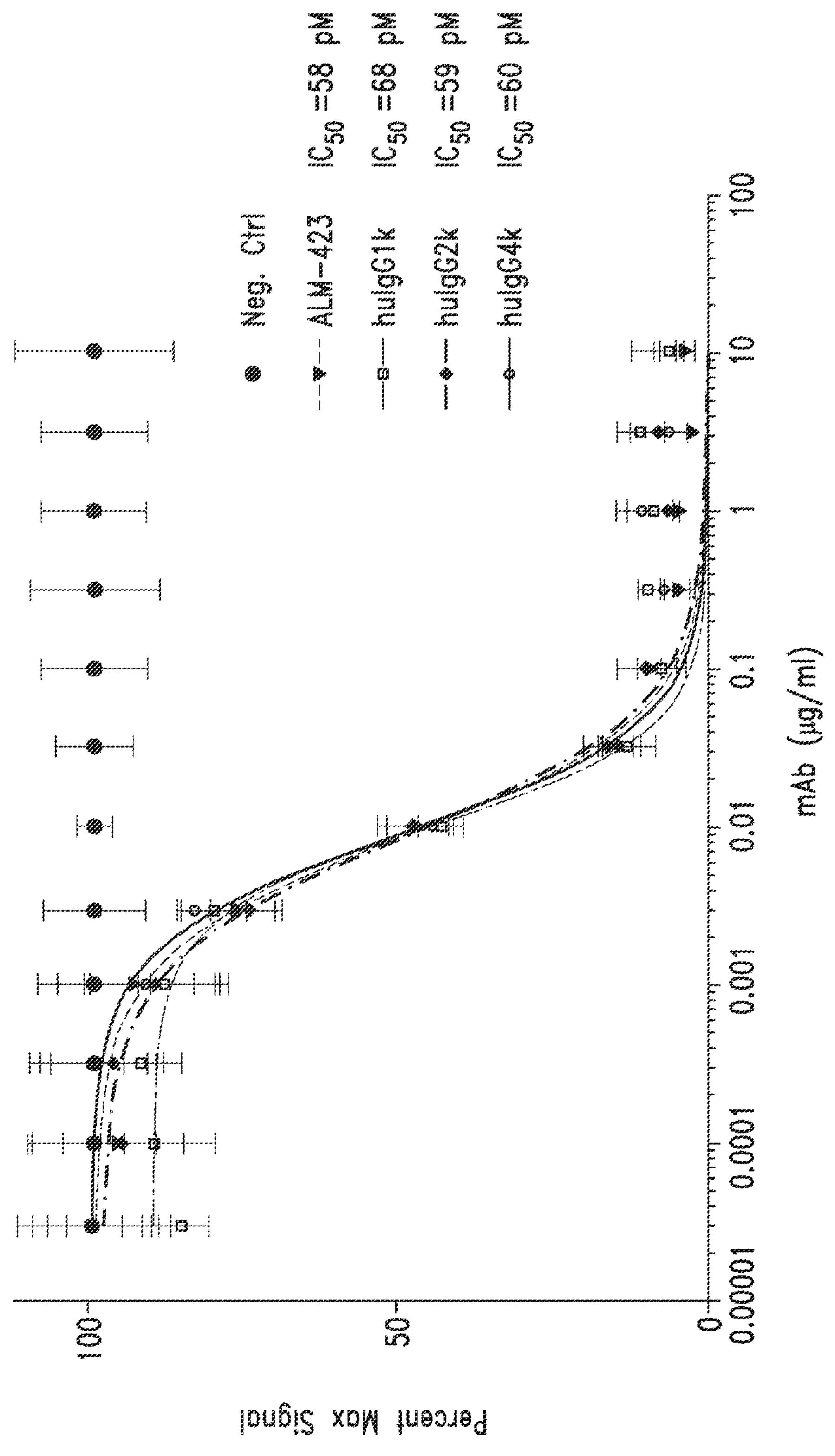
FIG. 15 shows neutralization of pTyr formation on CD115 by fully human anti-CD115 mAbs.

AlivaMab® Mouse CCK423A as well as the 3 human variants CCK423A-IgG1, CCK423A-IgG2, and CCK423A-IgG4 were tested for their ability to block hu-CSF1 induced phosphorylation of native CD115. OCI-AML5 cells (DSMZ, #ACC-247) were serum starved (1% FBS) overnight, then harvested and washed twice in PBS with 0.1% BSA. 250,000 cells were plated per well into a 96-well v-bottom polypropylene plate. Anti-CD115 mAbs were added in a dilution series for 15 min while incubating the plate on ice. Hu-CSF-1 (R&D Systems, #216-MC-005) was added to each well at a final concentration of 100 ng/ml and incubated for 30 min on ice. Cells were then spun down at 1500 RPM for 5 min at 4° C. and supernatant was removed. Cells were then resuspended in lysis buffer (Cell Signaling, #9803 with 1×HALT protease inhibitors, Pierce, #78430) and incubated on ice for 15 min. Lysates were then measured for tyrosine phosphorylated-CD115 using a p-MCSFR validated duoset assay (R&D Systems #CYC3268E) and detected using Supersignal Pico ELISA Substrate (Pierce, #37069). The fully human variants exhibited identical potency as the parental AlivaMab® antibody (FIG. 15 and Table 15).

TABLE 15

| mAb | $IC_{50}$ (pM) |
|---|---|
| AlivaMab CCK423A | 58 |
| Human IgG1κ | 68 |
| Human IgG2κ | 59 |
| Human IgG4κ | 60 |

Example 12

Inhibition of P-Tyr Formation on CD115 Induced by IL-34

Anti-CD115 antibodies of the invention were found to neutralize P-TYR formation on CD115 induced by interleukin-34 (IL-34). Some antibodies that block CSF-1 induced P-TYR formation on CD115 are found to also block IL-34 induced P-TYR formation on CD115. Other antibodies are found that block only CSF-1 induced P-TYR formation on CD115 and do not block IL-34 induced P-TYR formation on CD115. Antibodies are tested for their ability to block IL-34 induced phosphorylation of native CD115.

In an example assay, SR cells or other CD115+ IL-34 responsive cell line(s) are serum starved (1% FBS) overnight, then harvested and washed twice in PBS with 0.1% BSA. Cells are plated into a 96-well v-bottom polypropylene plate. Anti-CD115 antibodies, either in hybridoma supernatants, purified antibody, or in purified fully-human recombinant antibody format, are added for 15 min while incubating the plate on ice. Human IL-34 is added to each well at a final concentration sufficient and necessary to trigger P-TYR formation on CD115 and incubated for 30' on ice. Cells were then spun down at 1500 RPM for 5' at 4° C. and supernatant was removed. Cells were then resuspended in lysis buffer (Cell Signaling, #9803 with 1×HALT protease inhibitors, Pierce, #78430) and incubated on ice for 15 min. Lysates were then measured for tyrosine phosphorylated CD115 using a p-MCSFR validated DUOSET assay (R&D Systems #CYC3268E) and detected using Supersignal Pico ELISA Substrate (Pierce, #37069).

Example 13

Neutralization of IL-34 Binding to CD115

AlivaMab® Mouse anti-CD115 antibodies block binding of IL-34 to CD115. For example, anti-CD115 antibodies were tested for their ability to block binding of recombinant human IL-34 to recombinant CD115. ELISA plates were coated with recombinant hu-CD115 (Sino Biological, China #10161-H08H) at 0.5 ug/ml and blocked with Superblock (Thermo Scientific #37518). Wells were incubated for 15 min with anti-CD115 mAbs, then biotinylated Hu-IL-34 (biotinylation using NHS-Peg4-biotin, Life Technologies, #21330) is added for an additional 15 minutes. After a 4× wash, HU-IL-34-biotin was detected using 1:10,000 SAV-poly HRP (Life Technologies, #N200). Other AlivaMab® Mouse anti-CD115 mAbs are also shown to exhibit various abilities and IC50 values in blocking HU-IL-34 binding to CD115.

Example 14

Neutralization of P-Tyr Formation on CD115 without Neutralization of Binding of CSF-1 and IL-34

AlivaMab® Mouse anti-CD115 mAbs were found that neutralize p-Tyr formation in cells exposed to either CSF-1 or IL-34. However, these mAbs still allow binding of CSF-1 and IL-34 to CD115. This set of mAbs block p-Tyr formation through inhibition of dimerization of CD115.

Example 15

AlivaMab® Mouse Anti-CD115 Mabs and their Fully Human Derivatives Bind to and Neutralize CD115 from Cynomolgus Monkey CD115 is cloned and expressed from cynomolgus monkey using standard molecular biological techniques. The recombinant CD115 may be tagged (histidine, Fc) to support efficient purification. The recombinant cynomolgus CD115 may also be transiently or stably expressed on cell lines. The AlivaMab® Mouse anti-CD115 mAbs and their human variants are shown to bind to cynomolgus monkey CD115. The AlivaMab® Mouse anti-CD115 mAbs and their human variants are shown to neutralize cynomolgus monkey CD115 in assays as described above for human CD115.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated anti-CD115 antibody, or an antigen-binding fragment thereof, comprising:

(a)(i) a heavy chain variable region (VH) comprising a heavy chain variable complementarity determining region 1 (HCDR1) comprising SEQ ID NO: 445; a HCDR2 comprising SEQ ID NO: 877; and a HCDR3 comprising SEQ ID NO: 1309; and (ii) a light chain variable region (VL) comprising a light chain variable complementarity determining region 1 (LCDR1) comprising SEQ ID NO: 661; a LCDR2 comprising SEQ ID NO: 1093; and a LCDR3 comprising SEQ ID NO: 1525, (b)(i) a heavy chain variable region comprising a VHCDR1 comprising SEQ ID NO: 481, a VHCDR2 comprising SEQ ID NO: 913, and a VHCDR3 comprising SEQ ID NO: 1345 and (ii) a light chain variable region comprising a VLCDR1 comprising SEQ ID NO: 697, a VLCDR2 comprising SEQ ID NO: 1129, and a VLCDR3 comprising SEQ ID NO: 1561, or (c)(i) a heavy chain variable region comprising a VHCDR1 comprising SEQ ID NO: 533, a VHCDR2 comprising SEQ ID NO: 965, and a VHCDR3 comprising SEQ ID NO: 1397 and (ii) a light chain variable region comprising a VLCDR1 comprising SEQ ID NO: 749, a VLCDR2 comprising SEQ ID NO: 1181, and a VLCDR3 comprising SEQ ID NO: 1613.

2. The antibody, or antigen-binding fragment thereof, of claim 1, wherein the HCDR1, HCDR2, and HCDR3 comprise SEQ ID NOs:445, 877 and 1309, respectively; and the LCDR1, LCDR2, and LCDR3 comprise SEQ ID NOs:661, 1093 and 1525, respectively.

3. The antibody, or antigen-binding fragment thereof, of claim 1, wherein the HCDR1, HCDR2, and HCDR3 comprise SEQ ID NOs:481, 913 and 1345, respectively; and the LCDR1, LCDR2, and LCDR3 comprise SEQ ID NOs:697, 1129 and 1561, respectively.

4. The antibody, or antigen-binding fragment thereof, of claim 1, wherein the HCDR1, HCDR2, and HCDR3 comprise SEQ ID NOs: 533, 965 and 1397, respectively; and the LCDR1, LCDR2, and LCDR3 comprise SEQ ID NOs:749, 1181 and 1613, respectively.

5. The antibody, or antigen-binding fragment thereof, of claim 1, wherein the VH comprises a) SEQ ID NO: 118; b) SEQ ID NO:154; or c) SEQ ID NO: 206.

6. The antibody, or antigen-binding fragment thereof, of claim 1, wherein the VL comprises a) SEQ ID NO:334; b) SEQ ID NO:370; or c) SEQ ID NO: 422.

7. The antibody, or antigen-binding fragment thereof, of claim 2, wherein the VH comprises SEQ ID NO:118 and the VL comprises SEQ ID NO: 334.

8. The antibody, or antigen-binding fragment thereof, of claim 3, wherein the VH comprises SEQ ID NO:154 and the VL comprises SEQ ID NO: 370.

9. The antibody, or antigen-binding fragment thereof, of claim 4, wherein the VH comprises SEQ ID NO: 206 and the VL comprises SEQ ID NO: 422.

10. The antibody, or antigen-binding fragment thereof, of claim 1, wherein the antibody is human.

11. The antibody, or antigen-binding fragment thereof, of claim 1, wherein the antibody is chimeric.

12. The antibody, or antigen-binding fragment thereof, of claim 1, wherein the antibody or fragment is selected from a single-variable domain antibody, a single chain antibody, a scFv, a bispecific antibody, a multi-specific antibody, a Fab, a F(ab')2, and a whole antibody.

13. A pharmaceutical composition comprising the antibody, or antigen-binding fragment thereof, of claim 1 and a physiologically acceptable carrier.

* * * * *

SEQUENCE LISTING

```
<160> NUMBER OF SEQ ID NOS: 1731

<210> SEQ ID NO 1
<211> LENGTH: 367
<212> TYPE: DNA
<213> ORGANISM: Homo sapiens

<400> SEQUENCE: 1

gaggtgcagc tggtggagtc tgggggaggc ttggtaaagc ctgggggtc ccttagactc      60

tcctgtgcag cctctggatt cactttcagt aacgcctgga tgagctgggt ccgccaggct    120

ccagggaagg ggctggagtg ggttggccgt attaaaagca aaactgatgg tgggacaaca    180

gactacgctg cacccgtgaa aggcagattc accatctcaa gagatgattc aaaaaacacg    240

ctgtatctgc aaatgaacag cctgaaaacc gaggacacag ccgtgtatta ctgtaccacc    300

aatgactacg gtgactacga ggcttttgat atctggggcc aagggacaat ggtcaccgtc    360

tcttcag                                                               367


<210> SEQ ID NO 2
<211> LENGTH: 355
<212> TYPE: DNA
```

<213> ORGANISM: Homo sapiens

<400> SEQUENCE: 2
caggtgcagc tggtgcagtc tgggcctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta tcagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagacaggat 300
aactggaact actttgacta ctggggccag ggaaccctgg tcaccgtctc ctcag 355

<210> SEQ ID NO 3
<211> LENGTH: 370
<212> TYPE: DNA
<213> ORGANISM: Homo sapiens

<400> SEQUENCE: 3
gaggtgcagc tggtggagtc tgggggaggc ttggtaaagc ctggggggtc ccttagactt 60
tcctgtgcag cctctggatt cactttcagt aatgcctgga tgagctgggt ccgccaggct 120
ccagggaagg ggctggactg ggttggccgt gttaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtaccact 300
aatgactacg gtggtcccgt tgatgctttt gatatctggg gccaagggac aatggtcacc 360
gtctcttcag 370

<210> SEQ ID NO 4
<211> LENGTH: 349
<212> TYPE: DNA
<213> ORGANISM: Homo sapiens

<400> SEQUENCE: 4
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcat atctttagca gtgggagcac caactacaac 180
ccctccctca agagtcgagt caccatgtca gtagacacgt ccaagagcca gttctccctg 240
aagctgagct ctgtgaccgc cgcggacacg gccgtgtatt tgtgtgcgag gggggggtc 300 acttggttcg acccctgggg ccagggaacc ctggtcaccg tctcctcag 349

<210> SEQ ID NO 5
<211> LENGTH: 349
<212> TYPE: DNA
<213> ORGANISM: Homo sapiens

<400> SEQUENCE: 5
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactaccac 180
ccctccttca agagtcgagt caccatgtca gtagacacgt ccaagaccca gttctccctg 240
aagctaagct ctctgaccgc cgcggacacg gccgtgtatt actgtgcgag gggggggatt 300
acttggttcg acccctgggg ccagggaacc ctggtcaccg tctcctcag 349

-continued

<210> SEQ ID NO 6
<211> LENGTH: 361
<212> TYPE: DNA
<213> ORGANISM: Homo sapiens

<400> SEQUENCE: 6
gaggtgcagc tggtggagtc tgggggaggc ttggtacagc cagggcggtc cctgagactc 60
tcctgtacag cttctggatt cacctttggt gattatgcta tgagctggtt ccgccaggct 120
ccagggaagg ggctggagtg ggtaggtttc attagaagca aagcttatgg tgggacaaca 180
gaatacgccg cgtctgtgaa aggcagattc accatctcaa gagatgatac caaaagcatc 240
gcctatctgc aaatgaacag cctgaaaatc gaggacacag ccgtgcatta ttgtactaga 300
gagggtagtt ttggtgctct tgatatctgg ggccaaggga taatggtcac cgtctcttca 360
g 361

<210> SEQ ID NO 7
<211> LENGTH: 358
<212> TYPE: DNA
<213> ORGANISM: Homo sapiens

<400> SEQUENCE: 7
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaacaat 180
gcacagaagt ttcagggcag ggtcaccatg accagggaca cgtccatcag cacagcctac 240
atggagctga gcaggctgag atctgacgac acggccgtgt attactgtgc gagagggggg 300
tatagtgggc cctactttga ctactggggc cagggaaccc tggtcaccgt ctcctcag 358

<210> SEQ ID NO 8
<211> LENGTH: 367
<212> TYPE: DNA
<213> ORGANISM: Homo sapiens

<400> SEQUENCE: 8
gaggtgcagc tggtggagtc tgggggaggc ttggtaaagc ctggggggtc ccttagactc 60
tcctgtgcag cctctggatt cactttcagt aacgcctgga tgagctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgcatta ctgtaccaca 300
ggggactaca gttacactga tgcttttgat atctggggcc aagggacaat ggtcaccgtc 360
tcttcag 367

<210> SEQ ID NO 9
<211> LENGTH: 337
<212> TYPE: DNA
<213> ORGANISM: Homo sapiens

<400> SEQUENCE: 9
caggtgcagc tgcaggagtc gggcccagga ctggtgaagc cttcggagac cctgtccctc 60
acctgcactg tctctggtgg ctccatcagt agttcctatt ggacttggat ccggcagccc 120
ccagggaagg gactggagtg gattgggtat atccattaca gtgggagcac caactacaac 180
ccctccctca agagtcgagt caccatatca gtagacacgt ccaagaacca gttctccctg 240

-continued aagctgagct ctgtgaccgc tgcggacacg gccgtgtact actgtgcgag gggatttgac 300
tactggggcc agggaaccct ggtcaccgtc tcctcag 337

<210> SEQ ID NO 10
<211> LENGTH: 373
<212> TYPE: DNA
<213> ORGANISM: Homo sapiens

<400> SEQUENCE: 10
gaggtgcagc tggtggagtc tgggggagac ttggtacagc ctggggggtc cctgagactc 60
tcctgtgcag actctagatt caccttcagt agctatagca tgaactgggt ccgccaggct 120
ccagggaagg ggctggagtg ggtttcatac attagtccta gtagtagtac catatactac 180
gcagactctg tgaggggccg attcaccatc tccagagaca atgccaagaa ctcactctat 240
ctgcaaatga acagcctgag aaacgaggac acggctgtgt attactgtgc gagagatttt 300
ccccatgact acggttacta ccctcactac tttgactact ggggccaggg aaccctggtc 360
accgtctcct cag 373

<210> SEQ ID NO 11
<211> LENGTH: 355
<212> TYPE: DNA
<213> ORGANISM: Homo sapiens

<400> SEQUENCE: 11
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccag ggaaggccct ggagtgcctt gcactcattg attgggatga tgataaatac 180
tacagcacat ctctgaagac caggctcacc atctccaagg acacctccaa aaaccaggtg 240
gtccttacaa tgaccaacat ggaccctgtg gacacagcca cgtattattg tgcacggacc 300
caactgggga tcgcggacta ctggggccag ggaaccctgg tcaccgtctc ctcag 355

<210> SEQ ID NO 12
<211> LENGTH: 361
<212> TYPE: DNA
<213> ORGANISM: Homo sapiens

<400> SEQUENCE: 12
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggaatg gattgggcgt atctatacca gtgggaccac caacttcaac 180
ccctccctca agagtcgagt caccatgtca gtagacacgt ccaagaacca gttctccctg 240
aagctgagct ctgtgaccgc cgcggacacg gccgtgtatt actgtgcgac attgtctggt 300
acgaactggg gaagtccctt tgactactgg ggccagggaa ccctggtcac cgtctcctca 360
g 361

<210> SEQ ID NO 13
<211> LENGTH: 376
<212> TYPE: DNA
<213> ORGANISM: Homo sapiens

<400> SEQUENCE: 13
caggtgcagc tgcaggagtc gggcccagga ctggtgaagc cttcggagac cctgtccctc 60
acctgcactg tcactggtgg ctccatcagt agttactact ggagctggat ccggcagccc 120
gccgggaagg gactggagtg gattgggcgt atctatacca gtgggagcac caattacaac 180
ccctccctca agagtcgagt caccatgtca gtagacacgt ccaagaacca cttctccctg 240
aagctgagct ctgtgaccgc cgcggacacg gccgtgtatt actgtgcgag agagatttta 300
gtggtggtag ctgctactcg aactgggggg gtttttgata tctggggcca agggacaatg 360
gtcaccgtct cttcag 376

<210> SEQ ID NO 14
<211> LENGTH: 337
<212> TYPE: DNA
<213> ORGANISM: Homo sapiens

<400> SEQUENCE: 14
caggtgcagc tgcaggagtc gggcccagga ctggtgaagc cttcggagac cctgtccctc 60
acctgctctg tctctggtgg ctccatcagt agttactact ggagctggat ccggcagccc 120
ccagggaagg gactggagtg gattggatat gtctcttaca gtgggggcac caactacaac 180
ccctccctga agagtcgagt caccatatca gtagacacgt ccaagaacca gttctccctg 240
aagctgagct ctgtgaccgc tgcggacacg gccgtgtatt actgtgcgag ggatttgac 300 tactggggcc agggaaccct ggtcaccgtc tcctcag 337

<210> SEQ ID NO 15
<211> LENGTH: 358
<212> TYPE: DNA
<213> ORGANISM: Homo sapiens

<400> SEQUENCE: 15
caggtgcagc tggagcagtc tggggctgag gtgaagaggc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagaggtga cacaaactat 180
gcacagaagt ttcagggcag ggtcaccatg accagggaca cgtccatcag tacagcctac 240
atggagctga gtaggctgag atctgacgac acggccgtat attactgtgc gagagatctc 300
gaaggggggg ggccttttga ctactggggc cagggaaccc tggtcaccgt ctcctcag 358

<210> SEQ ID NO 16
<211> LENGTH: 336
<212> TYPE: DNA
<213> ORGANISM: Homo sapiens

<400> SEQUENCE: 16
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg tactggagtg gattgggtat ttctcttaca atgggaacac caactacaac 180
ccctccctca agagtcgagt caccatatca gtagacacgt ccaagaacca gttctccctg 240
aagctgagct ctgtgaccgc tgcggacacg gccgtgtatt actgtacgag ggtatggac 300 gtctggggcc aagggaccac ggtcaccgtc tcctca 336

<210> SEQ ID NO 17
<211> LENGTH: 352
<212> TYPE: DNA
<213> ORGANISM: Homo sapiens

<400> SEQUENCE: 17

```
caggtgcagc tgcaggagtc gggcccagga ctggtgaagc cttcggagac cctgtccctc     60
acctgcactg tctctggtgg ctccatcagt agttactact ggagctggat ccggcagccc    120
gccgggaagg gactggagtg gattgggcgt atctatacca gtgggagcac caactacaac    180
ccctccctca agagtcgagt caccatgtca gtagacacgt ccaagaacca gttctccctg    240
aagctgagtt ctgtgaccgc cgcggacacg gccgtgtatt actgtgcgag agatcgaact    300
ttttatgctt ttgatatgtg gggccaaggg acaatggtca ccgtctcttc ag            352
```

<210> SEQ ID NO 18
<211> LENGTH: 358
<212> TYPE: DNA
<213> ORGANISM: Homo sapiens

<400> SEQUENCE: 18

```
gaggtgcagc tggtggagtc tgggggaggc ttggtacagc ctggggggtc cctgagactc     60
tcctgtgcag cctctggatt caccttcagt agctacgaca tgcactgggt ccgccaagct    120
acaggaaaag gtctggagtg ggtctcagct attggtactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag aggtcatatt    300
gtggtggtga ctgctatgga ctactggggc cagggaaccc tggtcaccgt ctcctcag      358
```

<210> SEQ ID NO 19
<211> LENGTH: 346
<212> TYPE: DNA
<213> ORGANISM: Homo sapiens

<400> SEQUENCE: 19

```
caggtgcagc tacagcagtg gggcgcagga ctgttgaagc cttcggagac cctgtccctc     60
acctgcgctg tctatggtgg gtcctgcagt gcttactact ggagttggat ccgccagccc    120
ccagggaagg ggctggagtg gattggggaa atcaatcata gtggaagcac caactacaac    180
ccgtccctca agagtcgagt caccatatca gtagacacgt ccaggaacca gttctccctg    240
aagctgagct ctgtgaccgc cgcggacacg gctgtttatt actgtgcgag agaggctgat    300
gcttttgata tctggggcca agggacaatg gtcaccgtct cttcag                   346
```

<210> SEQ ID NO 20
<211> LENGTH: 367
<212> TYPE: DNA
<213> ORGANISM: Homo sapiens

<400> SEQUENCE: 20

```
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aaacagattc accatctcaa gagatgattc aaaaaacacg    240
ctgtatctgc aaatgaacag cctgaaaacc gaggacacag ccgtgtatta ctgtaccacc    300
tctgactacg gtgactttga tgcttttgat atctggggcc aagggacaat ggtcaccgtc    360
tcttcag                                                              367
```

<210> SEQ ID NO 21
<211> LENGTH: 346
<212> TYPE: DNA
<213> ORGANISM: Homo sapiens

<400> SEQUENCE: 21
caggtgcagc tacagcagtg ggcgcagga ctgttgaagc cttcggagac cctgtccctc 60
acctgcgctg tctatggtgg gtccttcagt gcttactact ggagctggat ccgccagccc 120
ccagggaagg ggctggagtg gattggggaa atcaatcata gtggaagcac caactacaac 180
ccgtccctca agagtcgagt caccatatca ggagacacgt ccaagaacca gttctccctg 240
aagctgagtt ctgtgaccgc cgcggacacg gctgtgtatt actgtgcgag agaggctgat 300
gcttttgata tctggggcca agggacaatg gtcaccgtct cttcag 346

<210> SEQ ID NO 22
<211> LENGTH: 358
<212> TYPE: DNA
<213> ORGANISM: Homo sapiens

<400> SEQUENCE: 22
gaggtgcagc tggtggagtc cgggggaggc ttagttcagc ctggggggtc cctgagactc 60
tcctgtgcag cctctggatt caccttcagt agctactgga tgcactgggt ccgccaagct 120
ccagggaagg ggctggtgtg ggtctcacgt attaatagtg atgggagtag cacaagctac 180
gcggactccg tgaagggccg attcaccatc tccagagaca acgccaagaa cacgctgtat 240
ctgcaaatga acagtctgag agccgaggac acggctgtgt attactgtgc aagagatgga 300
ggaactactg gtgcttttga tatctggggc caagggacaa tggtcaccgt ctcttcag 358

<210> SEQ ID NO 23
<211> LENGTH: 367
<212> TYPE: DNA
<213> ORGANISM: Homo sapiens

<400> SEQUENCE: 23
gaggtgcatc tggtggagtc tgggggaggc ctggtcaagc ctggggggtc cctgagactc 60
tcctgtgcag cctctggatt caccttcagt agctatagca tgaactggtt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtct 240
ctgcaaatga acagcctgag agccgaggac acggctgtgt attactgtgc gagagctgga 300
gcagtggctg ccctgtacaa ctggttcgac ccctggggcc agggaaccct ggtcaccgtc 360
tcctcag 367

<210> SEQ ID NO 24
<211> LENGTH: 361
<212> TYPE: DNA
<213> ORGANISM: Homo sapiens

<400> SEQUENCE: 24
cagatcacct tgaaggagtc tggtcctccg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacagc 300
ccccgatata gtggctactt tgactactgg ggccagggaa ccctggtcac cgtctcctca 360
g 361

<210> SEQ ID NO 25
<211> LENGTH: 355
<212> TYPE: DNA
<213> ORGANISM: Homo sapiens

<400> SEQUENCE: 25
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggcaa attcaccatg accagggaca cgtccatcag cacagcctac 240
atggagctga gcaggctgag atctgacgac acggccgtgt attactgtgc gagagaatct 300
ccttactggt acttcgatct ctggggccgt ggcaccctgg tcactgtctc ctcag 355

<210> SEQ ID NO 26
<211> LENGTH: 348
<212> TYPE: DNA
<213> ORGANISM: Homo sapiens

<400> SEQUENCE: 26
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caaaaacccc 180
tccctcaaga gtcgagtaac catatcagta gacacgtcca agaaccagtt ctccctgaag 240
ctgagctctg tgaccgctgc ggacacggcc gtgtattact gtgcgagatg gagaaccttt 300
tacggtatgg acgtctgggg ccaagggacc acggtcaccg tctcctca 348

<210> SEQ ID NO 27
<211> LENGTH: 340
<212> TYPE: DNA
<213> ORGANISM: Homo sapiens

<400> SEQUENCE: 27
caggtgcagc tgcaggagtc gggcccagga ctggtgaagc cttcggagac cctgtccctc 60
acctgcactg tctctggtgg ctccatcagt agttactact ggacctggat ccggcagccc 120
ccagggaagg gactggagtg gattgggtat atctcttaca gtgggggcac caactacaac 180
ccctccctca agagtcgagt caccatatca gtagacacgt ccaagaacca gttctccctg 240
aagctgagct ctgtgaccgc tgcggacacg gccgtgtatt actgtgcgag agaactgggg 300
aactactggg gccagggaac cctggtcacc gtctcctcag 340

<210> SEQ ID NO 28
<211> LENGTH: 369
<212> TYPE: DNA
<213> ORGANISM: Homo sapiens

<400> SEQUENCE: 28
gaggtgcagc tggtggagtc tgggggaggc ctggtcaagc ctgggggtc cctgagactc 60 tcctgtgcag cctctggatt caccttcagt agctataaca tgaactgggt ccgccaggct 120
ccagggaagg gactggagtg ggtctcatcc attagtagta gtagtactta catatactac 180
gcagactcac tgaagggccg attcaccatc tccagagaca acgccatgaa ctcactgtat 240
ctgcaaatga gcagcctgag agccgaggac acggctgtgt attactgtgc gagagatagt 300
gggacctacc cctactacta cttcggtatg gacgtctggg gccaagggac cacggtcacc 360

-continued gtctcctca 369

<210> SEQ ID NO 29
<211> LENGTH: 351
<212> TYPE: DNA
<213> ORGANISM: Homo sapiens

<400> SEQUENCE: 29
caggtgcagc tgcaggagtc gggcccagga ctggtgaagc cttcggagac cctgtccctc 60
agttgcactg tctctggtgg ctccatcagt agttactact ggagctggat ccggcagccc 120
gccgggaagg gactggagtg gattgggcgt atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag agataggagt 300
ttttacggta tggacgtctg gggccaaggg accacggtca ccgtctcctc a 351

<210> SEQ ID NO 30
<211> LENGTH: 361
<212> TYPE: DNA
<213> ORGANISM: Homo sapiens

<400> SEQUENCE: 30
gaggtgcagc tggtggagtc tgggggaggc ctggtcaagc ctgggggtc cctgagactc 60 tcctgtgcag cctctggatt caccttcagt agctatagca tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgttt 240
ctgcaaatga acagcctgag agccgaggac acggctgtgt attactgtgc gagaggtggg 300
agcttccctt ataactggtt cgacccctgg ggccagggaa ccctggtcac cgtctcctca 360
g 361

<210> SEQ ID NO 31
<211> LENGTH: 361
<212> TYPE: DNA
<213> ORGANISM: Homo sapiens

<400> SEQUENCE: 31
gaggtgcagc tggtggagtc tgggggaggc ttggtacagc cagggcggtc cctgagactc 60
tcctgtacag cttctggatt cacctttggt gattatgcta tgacctggtt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
gagggtagtt ttggtgctct tgatatctgg ggccaaggga caatggtcac cgtctcttca 360
g 361

<210> SEQ ID NO 32
<211> LENGTH: 364
<212> TYPE: DNA
<213> ORGANISM: Homo sapiens

<400> SEQUENCE: 32
gaggtgcagc tggtggagtc tgggggaggc ttggtaaagc ctgggggtc ccttagactc 60 tcctgtgcag cctctggatt cactttcagt aacgcctgga tgaactgggt ccgccaggct 120
ccagggaagg ggctggagtg ggttggccgt attaatagca aaactgatgg tgggacaaca 180
gactacgctg cacccgtgaa aggcagattc accatctcaa gagatgattc aaaaaccacg 240
ctgtatctgc aaatgaacag cctgaagacc gaggacacag ccgtgtatta ctgtaccaca 300
gatggggtat accccgatgt ttttgatatc tggggccaag ggacaatggt caccgtctct 360
tcag 364

<210> SEQ ID NO 33
<211> LENGTH: 355
<212> TYPE: DNA
<213> ORGANISM: Homo sapiens

<400> SEQUENCE: 33
caggtgcagg tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaggt ttcagggcag ggtcaccatg accagggaca cgtccatcag cacagcctac 240
atggagctga gcaggctgag atctgacgac acggccgtat attactgtgc gagattatcc 300
ccttactggt acttcgatct ctggggccgt ggcaccctgg tcactgtctc ctcag 355

<210> SEQ ID NO 34
<211> LENGTH: 379
<212> TYPE: DNA
<213> ORGANISM: Homo sapiens

<400> SEQUENCE: 34
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agacgaggac acggctgtgt attactgtgc gagagaaggg 300
gagagatttt gtggtgctga ctgctatccc cactggttcg accccctgggg ccagggaacc 360 ctggtcaccg tctcctcag 379

<210> SEQ ID NO 35
<211> LENGTH: 378
<212> TYPE: DNA
<213> ORGANISM: Homo sapiens

<400> SEQUENCE: 35
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gggggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag agataactgg 300
aactacggag ggcccactta ctactactac tacggtatgg acgtctgggg ccaagggacc 360
acggtcaccg tctcctca 378

<210> SEQ ID NO 36
<211> LENGTH: 349
<212> TYPE: DNA
<213> ORGANISM: Homo sapiens

<400> SEQUENCE: 36
gaggtgcagg tggtggagtc tgggggaggc ttggtccagc ctgggaagtc cctgagactc 60
tcctgtgcag cctctggatt cccctttagt gtctattgga tgacctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attgctgtgc gagcggatac 300
catttatttg actactgggg ccagggaacc ctggtcaccg tctcctcag 349

<210> SEQ ID NO 37
<211> LENGTH: 367
<212> TYPE: DNA
<213> ORGANISM: Homo sapiens

<400> SEQUENCE: 37
gaggtgcagc tggtggagtc tgggggaggc ttggtaaagc ctggggggtc ccttagactc 60
tcctgtgcag cctctggatt cactttcagt aacgcctgga tgatctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtacctca 300
acggactacg gtgactacga tgcttttgat atctggggcc aagggacaat ggtcaccgtc 360
tcttcag 367

<210> SEQ ID NO 38
<211> LENGTH: 361
<212> TYPE: DNA
<213> ORGANISM: Homo sapiens

<400> SEQUENCE: 38
gaggtgcagc tggtggagtc tgggggaggc ctggtcaagc ctggggggtc cctgagactc 60
tcctgtgcag cctctggatt caccttcagt agttatagca tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggctgtgt attactgtgc gagaggtggg 300
agctaccctt ataactggtt cgacccctgg ggccagggaa ccctggtcac cgtctcctca 360
g 361

<210> SEQ ID NO 39
<211> LENGTH: 355
<212> TYPE: DNA
<213> ORGANISM: Homo sapiens

<400> SEQUENCE: 39
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaaat ttcagggcag ggtcaccatg accagggaca cgtccatcag cacagcctac 240
atggagctga gcaggctgag atctgacgac acggccgtgt attactgtgc gagagataac 300
cacgacggtg cttttgatat ctggggccaa gggacaatgg tcaccgtctc ttcag 355

<210> SEQ ID NO 40
<211> LENGTH: 358
<212> TYPE: DNA
<213> ORGANISM: Homo sapiens

<400> SEQUENCE: 40
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagagatgag 300
gatagtggga gctactttga ctactggggc cagggaaccc tggtcaccgt ctcctcag 358

<210> SEQ ID NO 41
<211> LENGTH: 364
<212> TYPE: DNA
<213> ORGANISM: Homo sapiens

<400> SEQUENCE: 41
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180
tacagcccat ctctgaagag cagactcacc atcaccaagg acacctccaa aaaccaggtg 240
gtccttacaa tgaccaacat ggaccctgtg gacacagcca catattactg tgcacatcaa 300
gagaggcgca gtggctggtc ctttgactac tggggccagg gaaccctggt ctccgtctcc 360
tcag 364

<210> SEQ ID NO 42
<211> LENGTH: 379
<212> TYPE: DNA
<213> ORGANISM: Homo sapiens

<400> SEQUENCE: 42
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtat taaatactat 180
gcagactccg tgaagggccg attcaccatc tccagagaca attccaagaa cacgctgtat 240
ctgcaaatga acagcctgag agccgaggac acggctgtgt attactgtgc gagagctacg 300
tattactatg atagtagtgg ttattactct aactggttcg acccctgggg ccagggaacc 360
ctggtcaccg tctcctcag 379

<210> SEQ ID NO 43
<211> LENGTH: 349
<212> TYPE: DNA
<213> ORGANISM: Homo sapiens

<400> SEQUENCE: 43
gaggtgcagg tggtggagtc tgggggaggc ttggtccagc ctgggaagtc cctgagactc 60
tcctgtgcag cctctggatt cacctttagt acctattgga tgacctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attgctgtgc gagcggatac 300
catttatttg actactgggg ccagggaacc ctggtcaccg tctcctcag 349

<210> SEQ ID NO 44
<211> LENGTH: 355
<212> TYPE: DNA
<213> ORGANISM: Homo sapiens

<400> SEQUENCE: 44
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggacgg atcaacccta acagtggtgg cacatactat 180
gctcagaagt ttcagggcag ggtcaccatg accagggaca cgtccatcag cacagcctac 240
gtggagctga gcaggctgag atctgacgac acggccgtgt attactgtgc gagaaagaat 300
ccctggggtc actttgacta ctggggccag ggaaccctgg tcaccgtctc ctcag 355

<210> SEQ ID NO 45
<211> LENGTH: 355
<212> TYPE: DNA
<213> ORGANISM: Homo sapiens

<400> SEQUENCE: 45
caggtgcagc tggtggagtc tgggggaggc gtggtccagc ctgggaggtc cctgagactc 60
tcctgtgcag cctctggatt caccttcagt acctttgcca tgcactgggt ccgccaggct 120
ccaggcaagg ggctggagtg ggtggcagtt atatcatatg atggaagtaa taaatactat 180
gtagactccg tgaagggccg attcaccatc tccagagaca attccaagaa cacgctgtat 240
ctgcaaatga acagcctgag agctgaggac acggctatgt actactgtgc gagagatggg 300
actggggatg ctttggatat ctggggccaa gggacaatgg tcaccgtctc ttcag 355

<210> SEQ ID NO 46
<211> LENGTH: 351
<212> TYPE: DNA
<213> ORGANISM: Homo sapiens

<400> SEQUENCE: 46
caggtgcagc tgcaggagtc gggcccagga ctggtgaagc cttcggagac cctgtccctc 60
acctgcactg tctctggtgc ctccatcagt acttacttct ggagctggct ccggcagccc 120
ccagggaagg gactggagtg gattgggtat atcttttaca gtgggagcat caactataac 180
ccctccctca agagtcgagt caccatatca gtagacacat ccaagaacca gttctccctg 240
gaactgagct ctgtgaccgc tgcggacacg gccgtgtatt actgtgcgag agatcggacc 300
ttttacggta tggacgtctg gggccaaggg accacggtca ccgtctcctc a 351

<210> SEQ ID NO 47
<211> LENGTH: 351
<212> TYPE: DNA
<213> ORGANISM: Homo sapiens

<400> SEQUENCE: 47
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatagca gtgggagcat taactacaat 180
ccctccctca agagtcgagt caccatgtca gtagacacgt ccaagaacca gttctccctg 240
aagctgagct ctgtgaccgc cgcggacacg gccgtgtttt actgtgcgag agatcgggct 300
ttttacggta tggacgtctg ggccaaggg accacggtca ccgtctcctc a 351

<210> SEQ ID NO 48
<211> LENGTH: 352
<212> TYPE: DNA
<213> ORGANISM: Homo sapiens

<400> SEQUENCE: 48
caggtgcagt ttgtggagtc tgggggaggc gtggtccagc ctgggaggtc cctgagactc 60
tcctgtgcag cgtctggatt caccctcagt agctatggca tgcactgggt ccgccaggct 120
ccaggcaagg ggctggagtg ggtggcagtt atatggtatg atggaagtaa tgaatactat 180
gcagactccg tgaagggccg attcaccata tccagagaca attccaagaa cacgctgtat 240
ctgcaaatga acagcctgag agccgaggac acggctgtgt attactgtgc gagagatcga 300
gcctggggat caggagactg gggccaggga accctggtca ccgtctcctc ag 352

<210> SEQ ID NO 49
<211> LENGTH: 352
<212> TYPE: DNA
<213> ORGANISM: Homo sapiens

<400> SEQUENCE: 49
caggtgcagc tgcaggagtc gggcccagga ctggtgaagc cttcggagac cctgtccctc 60
acctgcactg tctctggtgg ctccatcagt agttactact ggatctggat ccggcagccc 120
ccagggaagg gactggagtg gattgggtat ttctattaca gtgggagcac caactacaac 180
ccctccctca agagtcgagt caccatatca gtaggcacgt ccaagaacca gttctccctg 240
aagctgagct ctgtgaccgc tgcggacacg gccgtgtatt actgtgcgag gagccggttg 300
gggagcatat ttgactactg gggccaggga accctggtca ccgtctcctc ag 352

<210> SEQ ID NO 50
<211> LENGTH: 352
<212> TYPE: DNA
<213> ORGANISM: Homo sapiens

<400> SEQUENCE: 50
caggtgcagc tgcaggagtc gggcccagga ctggtgaagc cttcggagac cctgtccctc 60
acctgcactg tctctggtgg ctccatcagt agttactact ggaactggat ccggcagccc 120
ccagggaagg gactggagtg gattggatat atctattaca gtgggagtac caactacaac 180
ccctccctca agagtcgagt caccatatca ttagacacgt ccaagaacca gttctccctg 240
aagctgagct ctgtgaccgc tgcggacacg gccgtgtatc actgtgcgag aggacgtcta 300
aatggggcct ttgactactg gggccaggga accctggtca ccgtctcctc ag 352

<210> SEQ ID NO 51
<211> LENGTH: 352
<212> TYPE: DNA
<213> ORGANISM: Homo sapiens

<400> SEQUENCE: 51
caggtgcagc tgcaggagtc gggcccagga ctggtgaagc cttcggagac cctgtccctc 60
acctgcacta tctcgagtgg ctccatcagt agttactact ggagctggat ccggcagccc 120
gccgggaagg gactggagtg gattgggcgt atctatacca gtgggagcac caactaccac 180
ccctccctca agagtcgagt caccatgtca gtagacacgt ccaagaacca cttctccctg 240
aagttgacct ctgtgaccgc cgcggacacg gccgtgtatt actgtgcgag agaaaggcta 300
actgggttct ttgactactg gggccaggga accctggtca ccgtctcctc ag 352

<210> SEQ ID NO 52
<211> LENGTH: 352
<212> TYPE: DNA
<213> ORGANISM: Homo sapiens

<400> SEQUENCE: 52
caggtgcagc tgcaggagtc gggcccagga ctggtgaagc cttcggagac cctgtccctc 60
acctgcactg tctctggtgg ttccatcagt agttattact ggagctggat ccggcagccc 120
gccgggaagg gactggagtg gattgggcgt atttatatca gtgggagtat ttacaacaac 180
ccctccctca agagtcgagt caccatgtcg gtagacacgt ccaagaacca gttctccctg 240
aagctgagct ctgtgaccgc cgcggacacg gccgtgtatt actgtgcgag agatcgggtg 300
gggatgactt ttgatatctg gggccaaggg acaatggtca ccgtctcttc ag 352

<210> SEQ ID NO 53
<211> LENGTH: 352
<212> TYPE: DNA
<213> ORGANISM: Homo sapiens

<400> SEQUENCE: 53
caggtgcagc tgcaggagtc gggcccagga ctggtgaagc cttcggagac cctgtccctc 60
acctgcactg tctctggtgg ctccatcagt agttactact ggacctggat ccggcagccc 120
ccagggaagg gactggagtg gattggctat atctattaca gtgggatcac caactacaac 180
ccctccctca agagtcgagt caccatgtca atggacacgt ccaagaacca gttctccctg 240
aggctgagct ctgtgaccgc tgcggacacg gccgtgtatt actgtgcgag agggcgtatt 300
attggagctt ttgatatctg gggccaaggg acaatggtca ccgtctcttc ag 352

<210> SEQ ID NO 54
<211> LENGTH: 349
<212> TYPE: DNA
<213> ORGANISM: Homo sapiens

<400> SEQUENCE: 54
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggaccac caactacaac 180
ccctccctca agagtcgagt caccatgtca gtagacacgt ccaagaacca gttctccctg 240
aagctgaact ctgtgaccgc cgcggacacg gccgtgtatt attgtgcgag agaaagggta 300
atttggttcg acccctgggg ccagggaacc ctggtcaccg tctcctcag 349

<210> SEQ ID NO 55
<211> LENGTH: 352
<212> TYPE: DNA
<213> ORGANISM: Homo sapiens

<400> SEQUENCE: 55
caggtgcagc tggtgcagtc tggggctgag gtgaagaagc ctggggcctc agtgaaggtc 60
tcctgcaagg cttctggata caccttcacc gactactata tgcactgggt gcgacaggcc 120
cctggacaag ggcttgagtg gatgggatgg atcaacccta acagtggtgg cgcaaactat 180
gcacagaagt ttcagggcag ggtcaccatg accagggaca cgtccatcag tatagcctac 240
atggagctga gcaggctgag atctgacgac acggccatat attactgtgc gagaggaagg 300
ctaactttct ttgactactg gggccaggga accctggtca ccgtctcctc ag 352

<210> SEQ ID NO 56
<211> LENGTH: 352
<212> TYPE: DNA
<213> ORGANISM: Homo sapiens

<400> SEQUENCE: 56
caggtgcagc tgcaggagtc gggcccagga ctggtgaagc cttcggagac cctgtccctc 60
acctgcactg tctctggtgg ctccatcagt agtttctact ggagctggat ccggcagtcc 120
ccagggaggg gactggaatg gattgggtat atcttttaca gtgggagcac aaagtacaac 180
ccctccctca tgagtcgagt caccatatca gcagacacgt ccaagaacca gttctccctg 240
aaactgagtt ctgtgaccgc tgcggacacg gccgtgtatt actgtgcgag agggagactg 300
gggaactact ttgactactg gggccaggga accctggtca ccgtctcctc ag 352

<210> SEQ ID NO 57
<211> LENGTH: 352
<212> TYPE: DNA
<213> ORGANISM: Homo sapiens

<400> SEQUENCE: 57
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattggacgt atctatatta gtgggaccac caactacaac 180
ccctccctca tgagtcgagt caccatgtca gtagacacgt ccaagaacca gttctccctg 240
aagctgacct ctgtgaccgc cgcggacacg gccgtgtatt actgtgcgag agaaaggctg 300
gtgagggctt ttgatatctg gggccaaggg acaatggtca ccgtctcttc ag 352

<210> SEQ ID NO 58
<211> LENGTH: 352
<212> TYPE: DNA
<213> ORGANISM: Homo sapiens

<400> SEQUENCE: 58
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caagtacaac 180
ccctccctca agagtcgagt caccatgtca gtagacacgt ccaagaacca gttctccctg 240
aagctgagct ctgtgaccgc cgcggacacg gccgtgtatt actgtgcgag agagggagta 300
acgggtgggt tcgacccctg gggccaggga accctggtca ccgtctcctc ag 352

<210> SEQ ID NO 59
<211> LENGTH: 349
<212> TYPE: DNA
<213> ORGANISM: Homo sapiens

<400> SEQUENCE: 59
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caaaaatccc 180
tccctcaaga gtcgagtcac catgtcagta gacacgtcca agaaccagtt ctccctgaag 240
ctgagctctg tgaccgccgc ggacacggcc gtgtattact gtgcgagatt gaccgtagtg 300
ggagctcttg actactgggg ccagggaacc ctggtcaccg tctcctcag 349

<210> SEQ ID NO 60
<211> LENGTH: 355
<212> TYPE: DNA
<213> ORGANISM: Homo sapiens

<400> SEQUENCE: 60
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagtgaca atgccaagaa ctcactgtat 240
ctgcaaatgg acagcctgag agacgaggac acggctgtgt attactgtgc gagagatagg 300
ctggggatac cctttgacta ctggggccag ggaaccctgg tcaccgtctc ctcag 355

<210> SEQ ID NO 61
<211> LENGTH: 349
<212> TYPE: DNA
<213> ORGANISM: Homo sapiens

<400> SEQUENCE: 61
caggtgcagc tgcaggagtc gggcccagga ctggtgaagc cttcggagac cctgtccctc 60
acctgcactg tctctggtga ctccatcagt aattactact ggagctggat ccggcagccc 120
gccgggaagg gactggagtg gattgggcgt atctatacca gtgggagcac caataacaac 180
ccctccctca agagtcgagt caccatgtca gtagacacgt ccaagaacca gttctccctg 240
aagctgagct ctgtgaccgc cgcggacacg gccgtgtatt actgtgcgag agaaaggatc 300
aactggttcg acccctgggg ccagggaacc ctggtcaccg tctcctcag 349

<210> SEQ ID NO 62
<211> LENGTH: 352
<212> TYPE: DNA
<213> ORGANISM: Homo sapiens

<400> SEQUENCE: 62
caggtgcagc tgcaggagtc gggcccagga ctggtgaaac cttcggagac cctgtccctc 60
acctgcactg tctctggtgg ctccatcagt agttactact ggagctggat ccggcagccc 120
gccgggaagg gactggagtg gattgggcgt atctatagca gtgggaccac caactacaac 180
ccctccctca agagtcgagt caccatgtca gtagaaacgt ccaagaacca gttctccctg 240
aacctgagct ctgtgaccgc cgcggacacg gccgtgtatt attgtgcgag agagaggata 300
actgggcact ttgactactg gggccaggga accctggtca ccgtctcctc ag 352

<210> SEQ ID NO 63
<211> LENGTH: 352
<212> TYPE: DNA
<213> ORGANISM: Homo sapiens

<400> SEQUENCE: 63
caggtgcagc tgcaggagtc gggcccagga ctggtgaagc cttcggagac cctgtccctc 60

-continued

```
acctgcactg tctctggtgg ctccatcagt agttactact ggagctggat ccggcagccc    120

gccgggaagg gactggagtg gattgggcgt atctatacca gtgggagcac caactacaac    180

ccctccctca agagtcgagt caccatgtca gtagacacgt ccaagaacca gttctccctg    240

aaactgagct ctgtgaccgc cgcggacacg gccgtgtatt actgtgcgag agaggtactg    300

gggtactact ttgactactg gggccaggga accctggtca ccgtctcctc ag            352
```

<210> SEQ ID NO 64
<211> LENGTH: 348
<212> TYPE: DNA
<213> ORGANISM: Homo sapiens

<400> SEQUENCE: 64

```
caggtgcagc tgcaggagtc gggcccagga ctggtgaagc cttcggagac cctgtccctc     60

acctgcactg tctccggtgg ctccatcagt agttactact ggagctggat ccggcagccc    120

gccgggaagg gactggaggg gattgggcgt atctatacca gtgggagcac caactacaac    180

ccctccctca agagtcgagt caccatgtca gtagacacgt ccaagaacca gttctccctg    240

aagctgagct ctgtgaccgc cgcggacacg gccgtgtatt actgtgcgag agaaagactc    300

tacggtatgg acgtctgggg ccaagggacc acggtcaccg tctcctca                 348
```

<210> SEQ ID NO 65
<211> LENGTH: 358
<212> TYPE: DNA
<213> ORGANISM: Homo sapiens

<400> SEQUENCE: 65

```
caggtgcagc tgcaggagtc gggcccagga ctggtgaagc cttcggagac cctgtccctc     60

acctgcactg tctctggtgg ctccatcagt agttactact ggagctggat ccggcagccc    120

gccgggaagg gactggagtg gattgggcgt atctatacca gtgggaacac caactacaac    180

ccctccctca agagtcgagt caccatgtca ctagacacgt ccaagaacca gttctccctg    240

aagctgagct ctgtgaccgc cgcggacacg gccgtgtatt actgtgcgag agtgggagct    300

atcggggttg atgcttttga tatctggggc caagggacaa tggtcaccgt ctcttcag      358
```

<210> SEQ ID NO 66
<211> LENGTH: 349
<212> TYPE: DNA
<213> ORGANISM: Homo sapiens

<400> SEQUENCE: 66

```
caggtgcagc tgcaggagtc gggcccagga ctggtgaagc cttcggagac cctgtccctc     60

acctgcactg tctctggtgg ctccatcagt agttactact ggagctggat ccggcagccc    120

gccgggaagg gactggagtg gattgggcgt atctatacca gtgggagcac caactacaac    180

ccctccctca agagtcgagt ctccatgtca gtagacacgt ccaagaacca gttttccctg    240

aagctgagct ctgtgaccgc cgcggacacg gccgtgtatt attgtgcgag agaaaggata    300

atttggttcg acccctgggg ccagggaacc ctggtcaccg tctcctcag                349
```

<210> SEQ ID NO 67
<211> LENGTH: 355
<212> TYPE: DNA
<213> ORGANISM: Homo sapiens

<400> SEQUENCE: 67

```
gaggtgcagc tggtggagtc tgggggaggc ctggtcaagc ctgggggtc cctgagactc     60
```

tcctgtgcag cctctggatt caccttcagt agttataaca tgaactgggt ccgccaggct 120
ccagggaagg ggctggagtg ggtctcatcc attagtagta gtagtaatta catatactac 180
gcagactcag tgaagggccg attcaccatc tccggagaca ccgccaagaa ctcactgttt 240
ctgcaaatga tcagcctgag agtcgaggac acggctgtgt attactgtgc gagagatcga 300
ttggggatcc cctttgacta ctggggccag ggatccctgg tcaccgtctc ctcag 355

<210> SEQ ID NO 68
<211> LENGTH: 352
<212> TYPE: DNA
<213> ORGANISM: Homo sapiens

<400> SEQUENCE: 68
caggtgcagc tgcaggagtc gggcccagga ctggtgaagc cttcggagac cctgtccctc 60
acctgcactg tctctggtgc ctccatcagt agttactact ggagctggat ccggcagccc 120
ccaggaaagg gactggagtg gattgggtat ttctattaca gtgggagtac caactacagc 180
ccctccctca agagtcgagt caccttttca gtggacacgt ccaagaacca gttctccctg 240
aagctgagct ctgtgaccgc tgcggacacg gccgtgtatt tctgtgcgag agggaaggtc 300
ggggtccctt ttgactactg gggccaggga accctggtca ccgtctcctc ag 352

<210> SEQ ID NO 69
<211> LENGTH: 352
<212> TYPE: DNA
<213> ORGANISM: Homo sapiens

<400> SEQUENCE: 69
caggtgcagc tccaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caagtacaac 180
ccctccctca agagtcgagt caccatgtca gtagacacgt ccaagaacca gttctccctg 240
aagctgagct ctgtgaccgc cgcggacacg gccgtgtatt actgtgcgag agagggagta 300
acgggtgggt tcgacccctg gggccaggga accctggtca ccgtctcctc ag 352

<210> SEQ ID NO 70
<211> LENGTH: 358
<212> TYPE: DNA
<213> ORGANISM: Homo sapiens

<400> SEQUENCE: 70
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggaacac caactacaac 180
ccctccctca agagtcgagt caccatgtca ctagacacgt ccaagaacca gttctccctg 240
aagctgagct ctgtgaccgc cgcggacacg gccgtgtatt actgtgcgag agtgggagct 300
atcggggttg atgcttttga tatctggggc caagggacaa tggtcaccgt ctcttcag 358

<210> SEQ ID NO 71
<211> LENGTH: 352
<212> TYPE: DNA
<213> ORGANISM: Homo sapiens

<400> SEQUENCE: 71

-continued

```
caggtgcagc tgcaggagtc gggcccagga ctggtgaagc cttcggagac cctgtccctc     60

acctgcactg tctctggtgg ctccatcagt agttactact ggagttggat ctggcagccc    120

gccgggaagg gactggagtg gattgggcgt atctatacca gtgggagcac caactacaac    180

ccctccctca agagtcgagt caccatgtca gtagacacgc ccaagaacca gttctccctg    240

aagctgagct ctgtgaccgc cgcggacacg gccgtgtatt attgtgcgag agagaggtta    300

actggcgctt ttgatatctg gggccaaggg acaatggtca ccgtctcttc ag            352
```

<210> SEQ ID NO 72
<211> LENGTH: 352
<212> TYPE: DNA
<213> ORGANISM: Homo sapiens

<400> SEQUENCE: 72

```
caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatggtatgg atcaacccta acagtggtgg cacaaactat    180

gcacagaagt ttcagggcag ggtcaccatg accagggaca cgtccatcag cacagcctac    240

atggagctga gcaggctgag atctgacgac acggccgtgt attactgtgc gagaggaagg    300

ctaactttct ttgactactg gggccaggga accctggtca ccgtctcctc ag            352
```

<210> SEQ ID NO 73
<211> LENGTH: 352
<212> TYPE: DNA
<213> ORGANISM: Homo sapiens

<400> SEQUENCE: 73

```
caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatgggatgg atcaacccta acagtggtgg cacatactgt    180

gcacagaagt ttcagggcag ggtcaccatg accagggaca cgtccatcag cacagcctac    240

atggagctga gcaggctgag atctgacgac acggccgtgt attactgtgc gagaggaagg    300

ctaactttct ttgactactg gggccaggga accctggtca ccgtctcctc ag            352
```

<210> SEQ ID NO 74
<211> LENGTH: 352
<212> TYPE: DNA
<213> ORGANISM: Homo sapiens

<400> SEQUENCE: 74

```
caggtgcagc tgcaggagtc gggcccagga ctggtgaagc cttcggagac cctgtccctc     60

acctgcactg tctctgatgg ctccatcagt agttactact ggagctggat ccggcagccc    120

gccgggaagg gactggagtg gattgggcgt atctatacca gtgggagcac caactacaac    180

ccctccctca agagtcgagt caccatgtca gtagacacgt ccaagaacca gttctccctg    240

aagctgacct ctgtgaccgc cgcggacacg gccgtgtatt actgtgcgag agaaaggatt    300

acttcgtttt tcgacccctg gggccaggga accctggtca ccgtctcctc ag            352
```

<210> SEQ ID NO 75
<211> LENGTH: 352
<212> TYPE: DNA
<213> ORGANISM: Homo sapiens

<400> SEQUENCE: 75
caggtgcagc tgcaggagtc gggcccagga ctggtgaagc cttcggagac cctgtccctc 60
acctgcactg tctctggtgg ctccatcagt agttactact ggagctggat ccggcagccc 120
gccggaaagg gactggagtg ggttgggcgt ctctttacca gtgggagcac caactacaac 180
ccctccctca agagtcgagt caccatgtca gtagacacgt ccaagaacca gttctccctg 240
aagctgagtt ctgtgatcgc cgcggacacg gccgtgtatt actgtgcgag agagagacta 300
actgggtact ttgactactg gggccaggga accctggtca ccgtctcctc ag 352

<210> SEQ ID NO 76
<211> LENGTH: 352
<212> TYPE: DNA
<213> ORGANISM: Homo sapiens

<400> SEQUENCE: 76
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag agaacgactg 300
gtgatagctt ttgatatctg gggccaaggg acaatggtca ccgtctcttc ag 352

<210> SEQ ID NO 77
<211> LENGTH: 352
<212> TYPE: DNA
<213> ORGANISM: Homo sapiens

<400> SEQUENCE: 77
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactacaat 180
ccctccctca agagtcgagt caccatgtca gtagacacgt ccaagaacca gttctccctg 240
aagctgagct ctatgaccgc cgcggacacg gccgtgtatt actgtgcgag agacagactg 300
gggagggctt ttgatatctg gggccaaggg acaatggtca ccgtctcttc ag 352

<210> SEQ ID NO 78
<211> LENGTH: 352
<212> TYPE: DNA
<213> ORGANISM: Homo sapiens

<400> SEQUENCE: 78
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag agggcggcta 300
actggtcact ttgactactg gggccaggga accctggtca ccgtctcctc ag 352

<210> SEQ ID NO 79
<211> LENGTH: 352
<212> TYPE: DNA
<213> ORGANISM: Homo sapiens

<400> SEQUENCE: 79
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggtacac caactacaac 180
ccctccctca agagtcgagt ctccatgtca gtagacacgt ccaagaacca gttctccctg 240
aagctgagct ctgtgaccgc cgcggacacg gccgtgtatt actgtgcgag agagaggttg 300
ggagctttct ttgactactg gggccaggga accctggtca ccgtctcctc ag 352

<210> SEQ ID NO 80
<211> LENGTH: 352
<212> TYPE: DNA
<213> ORGANISM: Homo sapiens

<400> SEQUENCE: 80
caggtgcagc tgcaggagtc gggcccagga ctggtgaagc cttcggagac cctgtctctc 60
acctgcactg tgtctggtgg ctccatcagt agttattact ggagctggat ccggcagccc 120
ccagggaagg gactggagtg gattggttac atctattaca gtgggagcac caactacaac 180
ccctccctca agagtcgagt caccatatca gtagacacgt ccaagaacca attctccctg 240
aagctgagtt ctgtgaccgc tgcggacacg gccgtgtttt actgtgcgag aattacggtg 300
acttctgctt ttgatatctg gggccaaggg acaatggtca ccgtctcttc ag 352

<210> SEQ ID NO 81
<211> LENGTH: 349
<212> TYPE: DNA
<213> ORGANISM: Homo sapiens

<400> SEQUENCE: 81
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caaaaaaccc 180
tccctcaaga gtcgagtcac catatcagta gacacgtcca agaaccagtt ctccctgaag 240
ctgagctctg tgaccgctgc ggacacggcc gtgtattact gtgcgagaag tacggtggta 300
aatgcttttg atatctgggg ccaagggaca atggtcaccg tctcttcag 349

<210> SEQ ID NO 82
<211> LENGTH: 379
<212> TYPE: DNA
<213> ORGANISM: Homo sapiens

<400> SEQUENCE: 82
gaggtgcagc tggtggagtc tgggggaggc ttggtacagc ctgggggtc cctgagactc 60 tcctgtgcag cctctggatt caccttcagt acctatagca tgaactgggt ccgccaggct 120
ccagggaagg ggctggagtg ggtttcatac attagtagta gtagtgctat catatactac 180
gcagactctg tgaagggccg tttcaccatc tccagagaca atgccaagaa ctcactgtat 240
ctgcaaatga acagcctgag agacgaggac acggctgtgt attactgtgc gagagatctc 300
cccattacta tgatagtagt ggttatgcct gatgcttttg atatctgggg ccaagggaca 360
atggtcaccg tctcttcag 379

<210> SEQ ID NO 83
<211> LENGTH: 352

<212> TYPE: DNA
<213> ORGANISM: Homo sapiens

<400> SEQUENCE: 83
gaggtgcagc tggtggagtc tgggggaggc ttggtccagc ctggggggtc cctgagactc 60
tcctgtgcag cctctggatt cacctttagt aactattgga tgcgctgggt ccgccaggct 120
ccagggaagg ggctggagtg ggtggccaac ataaagcaag atggaagtga gaaatactat 180
gtggactctg tgaagggccg attcaccatc tccagagaca acgccaagta ctcactgtat 240
ctgcaaatga acagcctgag agccgaggac acggctgtgt attactgtgc gagagataga 300
ctggggatat ttgactactg gggccaggga accctggtca ccgtctcctc ag 352

<210> SEQ ID NO 84
<211> LENGTH: 352
<212> TYPE: DNA
<213> ORGANISM: Homo sapiens

<400> SEQUENCE: 84
gaggtgcagc tggtgcagtc tggagcagag gtgaaaaagc ccggggagtc tctgaagatc 60
tcctgtaagg gttctggata cagttttacc aactactgga tcggctgggt gcgccagatg 120
cccgggaaag gcctggagtg gatggggatc atctatcctg gtgactctga taccagatac 180
agcccgtcct tccaaggcca ggtcaccatc tcagccgaca tatccatcac caccgcctac 240
cttcagtgga gcagcctgaa ggcctcggac accgccatgt attactgtgc gagacatcga 300
ctggggttct ttgactactg gggccaggga accctggtca ccgtctcctc ag 352

<210> SEQ ID NO 85
<211> LENGTH: 354
<212> TYPE: DNA
<213> ORGANISM: Homo sapiens

<400> SEQUENCE: 85
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gaggctttac 300
tactactaca atatggacgt ctggggccaa gggaccacgg tcaccgtctc ctca 354

<210> SEQ ID NO 86
<211> LENGTH: 355
<212> TYPE: DNA
<213> ORGANISM: Homo sapiens

<400> SEQUENCE: 86
caggtgcagc tgcaggagtc gggcccagga ctggtgaagc cttcggagac cctgtccctc 60
acctgcactg tctctggtgg gtccatcagt agttactact ggagctggat ccggcagccc 120
ccagggaagg gactggagtg gattgggtat atctattaca ctgggagtac caactacaac 180
ccctccctca agagtcgagt caccatatca gtagacacgt ccaagaacca gttctccctg 240
aagctgagct ctgtgaccgc tgcggacacg gccgtgtatt actgtgcgag agggtggtgg 300
gagctaactt tctttgacta ctggggccag ggaaccctgg tcaccgtctc ctcag 355

<210> SEQ ID NO 87

<211> LENGTH: 349
<212> TYPE: DNA
<213> ORGANISM: Homo sapiens

<400> SEQUENCE: 87
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatgcca gtgggggcac caactacaac 180
ccctccctca agagtcgagt caccatgtca gtagacacgt ccaagaacca gttctccctg 240
aaggtgagct ctgtgatcgc cgcggacacg gccatatatt actgtgcgag aaatcggctg 300
gggatctatg actactgggg ccagggatcc ctggtcaccg tctcctcag 349

<210> SEQ ID NO 88
<211> LENGTH: 352
<212> TYPE: DNA
<213> ORGANISM: Homo sapiens

<400> SEQUENCE: 88
caggtgcagc tgcaggagtc gggcccagga ctggtgaagc cttcggagac cctgtccctc 60
acctgcactg tctctggtgg ctccatcagt agttattatt ggagctggat ccggcagtcc 120
ccagggaagg gactggagtg gattgggtat atctattata gtgggagcac caactacaat 180
ccctccctca agagtcgagt caccatatca gtagacacgt ccaagaacca gttctccctg 240
aagctgagtt ctgtgaccgc tgcggacacg gccgtgtatt tctgtgcgag agccctcctt 300
acgggagggt ttgcctattg gggccaggga accctggtca ccgtctcctc ag 352

<210> SEQ ID NO 89
<211> LENGTH: 352
<212> TYPE: DNA
<213> ORGANISM: Homo sapiens

<400> SEQUENCE: 89
caggtgcagc tgcaggagtc gggcccagga ctggtgaagc cttcggagac cctgtccctc 60
acctgcactg tctctgttgg ctccatcagt agttactact ggagctggat ccggcagccc 120
gccgggaagg gactggagtg gattgggcgt atctatgcca gtgggagcac caattacaat 180
ccctccctca agagtcgagt caccatgtca gtagacacgt ccaagaacca gttctccctg 240
aagctgacct ctgtgaccgc cgcggacacg gccgtgtatt actgtgcgag agagagggtg 300
ggaatctact ttgactactg gggccaggga accctggtca ccgtctcctc ag 352

<210> SEQ ID NO 90
<211> LENGTH: 376
<212> TYPE: DNA
<213> ORGANISM: Homo sapiens

<400> SEQUENCE: 90
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
tcagactctg tgaggggccg attcaccatc tccagagaca atgccaagaa ctcgctgtat 240
ctgcaaatgg acagcctgag agacgaggac acggctgttt attactgtgc gagagatagt 300
actatgatag tagtggttaa ggttcctgat gcttttgata tctggggcca agggacaatg 360
gtcaccgtct cttcag 376

<210> SEQ ID NO 91
<211> LENGTH: 352
<212> TYPE: DNA
<213> ORGANISM: Homo sapiens

<400> SEQUENCE: 91
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagtat caaatacaac 180
ccctccctca agagtcgagt cgccatgtca gtagacacgt ccaagaacca gttctccctg 240
aagctgagct ctgtgaccgc cgcggacacg gccgtgtatt actgtgcgag agaggggata 300
ctggggtact ttgactactg gggccaggga accctggtca ccgtctcctc ag 352

<210> SEQ ID NO 92
<211> LENGTH: 352
<212> TYPE: DNA
<213> ORGANISM: Homo sapiens

<400> SEQUENCE: 92
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat gtctattaca gtgggagcac caactacaac 180
ccctccctca agagtcgagt caccacatca gtagacacgt ccaagaatca gttctccctg 240
aagctgaggt ctgtgaccgc tgcggacacg gccgtgtatt actgtgcgag agatagactg 300
ggaatagctt ttgatatctg gggccaaggg acaatggtca ccgtctcttc ag 352

<210> SEQ ID NO 93
<211> LENGTH: 355
<212> TYPE: DNA
<213> ORGANISM: Homo sapiens

<400> SEQUENCE: 93
caggtgcagc tgcaggagtc gggcccagga ctggtgaagc cttcggagac cctgtccctc 60
acctgcactg tctctggtgg ctccatcagt agttactact ggagctggat ccggcagtcc 120
gccgggaagg gactggagtg gattgggcat atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag agagaggacg 300
gtggtaacct actttgacta ctggggccag ggaaccctgg tcaccgtctc ctcag 355

<210> SEQ ID NO 94
<211> LENGTH: 352
<212> TYPE: DNA
<213> ORGANISM: Homo sapiens

<400> SEQUENCE: 94
caggtgcagc tgcaggagtc gggcccagga ctggtgaagc cttcggagac cctgtccctc 60
acctgcagtg tctctggtgg ctccataagt agttaccact ggagctggat ccggcagccc 120
gccgggaagg gactggagtg gattgggcgt atctataccg gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag agagcggcta 300
actgggtact ttgactactg gggccaggga accctggtca ccgtctcctc ag 352

<210> SEQ ID NO 95
<211> LENGTH: 349
<212> TYPE: DNA
<213> ORGANISM: Homo sapiens

<400> SEQUENCE: 95
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactacaac 180
ccctccctca agagtcgagt caccatgtca atagacacgt ccaagaacca gttctccctg 240
aagctgagct ctgtgaccgc cgcggacacg gccgtgtatt actgtgcgag atcccgtctg 300
gggatctttg actactgggg ccagggaacc ctggtcaccg tctcctcag 349

<210> SEQ ID NO 96
<211> LENGTH: 352
<212> TYPE: DNA
<213> ORGANISM: Homo sapiens

<400> SEQUENCE: 96
caggtgcagc cgcaggagtc gggcccagga ctggtgaagc cttcggagac cctgtccctc 60
acctgcactg tctctggtgg ctccatcagt ggttactact ggagctggat ccggcagccc 120
gccgggacgg gactggagtg gattgggcgt atctatacca gtgggagcac caactacaac 180
tcctccctca agagtcgagt caccatgtca gtagacacgt ccaagaacca gttctccctg 240
aagctgagct ctgtgaccgc cgcggacacg gccgtgtatt actgtgcgag agaacggatg 300
gctacaatct ttgactactg gggccaggga accctggtca ccgtctcctc ag 352

<210> SEQ ID NO 97
<211> LENGTH: 349
<212> TYPE: DNA
<213> ORGANISM: Homo sapiens

<400> SEQUENCE: 97
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag agagggactt 300
cggggattcg acccctgggg ccagggaacc ctggtcaccg tctcctcag 349

<210> SEQ ID NO 98
<211> LENGTH: 376
<212> TYPE: DNA
<213> ORGANISM: Homo sapiens

<400> SEQUENCE: 98
gaggtgcagc tggtggagtc tgggggaggc ttggtacagc ctggggggtc cctgagactc 60
tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agacgaggac acggctgtgt attactgtgc gagagattac 300
tatggtagta gtggttatta ctaccctcat gcttttgata tctggggcca agggacaatg 360
gtcaccgtct cttcag 376

<210> SEQ ID NO 99
<211> LENGTH: 349
<212> TYPE: DNA
<213> ORGANISM: Homo sapiens

<400> SEQUENCE: 99
gaggtgcagc tggtggagtc tgggggaggc ctggtcaagc ctggggggtc cctgagactc 60
tcctgtgcag cctctggatt caccttcagt tactatagca tgaactgggt ccgccaggct 120
ccagggaagg ggctggagtg ggtctcatcc attagtgata gtagtgatta catatactac 180
gcagactcag tgaagggccg attcaccatc tccagagaca acgccaagaa ctcactgtat 240
ctgcaaatga acagcctgag agccgaggac acggctgtgt attactgtgc gagaggcgga 300
ctacggtttg actactgggg ccagggaacc ctggtcaccg tctcctcag 349

<210> SEQ ID NO 100
<211> LENGTH: 352
<212> TYPE: DNA
<213> ORGANISM: Homo sapiens

<400> SEQUENCE: 100
caggtgcagc tgcaggagtc gggcccagga ctggtgaagc cttcggagac cctgtccctc 60
acctgcactg tctctggtgg ctccatcagt agttactact ggagctggat ccggcagtcc 120
ccagggaagg gactggagtg gattgggtat atctattata gtgggagcac caactacaat 180
ccctccctca agagtcgagt caccatatca gtagacacgt ccaagaacca gttctccctg 240
aagctgagtt ctgtgaccgc tgcggacacg gccgtgtatt actgtgcgag agccctcctt 300
acgggagggt ttgcctattg gggccaggga accctggtca ccgtctcctc ag 352

<210> SEQ ID NO 101
<211> LENGTH: 352
<212> TYPE: DNA
<213> ORGANISM: Homo sapiens

<400> SEQUENCE: 101
caggtgcagc tgcaggagtc gggcccagga ctggtgaagc cttcggagac cctgtccctc 60
acctgcactg tctctggtgg ctccatcaat agttactact ggagctggat ccggcagccc 120
gccgggaagg gactggagtg gattgggcgt atctatacca gtgggaacac caactacaac 180
ccctccctca agagtcgagt caccatgtca gtagacacgt ccaagaacct gttctccctg 240
aagctgagct ctgtgaccgc cgcggacacg gccgtgtatt actgtgcgag agaacggcta 300
actgggtact ttgactactg ggcccaggga accctggtca ccgtctcctc ag 352

<210> SEQ ID NO 102
<211> LENGTH: 352
<212> TYPE: DNA
<213> ORGANISM: Homo sapiens

<400> SEQUENCE: 102
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggaccac caactacaac 180

```
ccctccctca agagtcgagt caccatatca gtagacacgt ccaagaacca gttctccctg    240

aagctgagct ctgtgaccgc tgcggacacg gccgtatatt actgtgcgag agcccttata    300

gtgggagctt ttgcctactg gggccaggga accctggtca ccgtctcctc ag            352
```

<210> SEQ ID NO 103
<211> LENGTH: 352
<212> TYPE: DNA
<213> ORGANISM: Homo sapiens

<400> SEQUENCE: 103

```
caggtgcagc tgcaggagtc gggcccagga ctggtgaagc cttcggagac cctgtccctc     60

acctgcactg tctctggtgg ctccatcagt agtaactact ggagctggat ccggcagccc    120

gccgggaagg gactggagtg gattgggcgt atctatacca gtgggagcac caagtacaac    180

ccctccctca agagtcgagt caccatgtca gtagacacgt ccaagaacca gttctccctg    240

aagctgagct ctgtgaccgc cgcggacacg gccgtgtatt attgtgcgag agagggtata    300

gtgggagctt tccactattg gggccaggga gccctggtca ccgtctcctc ag            352
```

<210> SEQ ID NO 104
<211> LENGTH: 355
<212> TYPE: DNA
<213> ORGANISM: Homo sapiens

<400> SEQUENCE: 104

```
gaggtgcagc tggtggagtc tgggggaggc ctggtcaagc ctgggggtc cctgagactc      60

tcctgtgcag cctctggatt caccttcagt agctatagca tgaagtgggt ccgccaggct    120

ccagtgaagg ggctggagtg ggtctcatcc attagtagta gtagtagtta catatactac    180

ggagactcag tgaagggccg attcaccatc tccagagaca acgccaagaa ctcactgtat    240

ctgcaaatga acagcctgag agccgaggac acggctgtgt attactgtgc gagagagagg    300

ctggggaggg cttttgatat ctggggccaa gggacaatgg tcaccgtctc ttcag         355
```

<210> SEQ ID NO 105
<211> LENGTH: 352
<212> TYPE: DNA
<213> ORGANISM: Homo sapiens

<400> SEQUENCE: 105

```
caggtgcagc tgcaggagtc gggcccagga ctggtgaagc cttcggagac cctgtccctc     60

acctgcactg tctctggtgg ctccatcagt agttactact ggagctggat ccggcagccc    120

gccgggaagg gactggagtg gattgggcgt atctatacca gtgggagcac caactacaac    180

ccctccctca agagtcgagt caccatgtca gtagacacgt ccaagaacca gttctccctg    240

aagctgagtt ctgtgaccgc cgcggacacg gccgtgtatt actgtgcgag agagaggctg    300

gggatgttct ttgactactg gggccaggga accctggtca ccgtctcctc ag            352
```

<210> SEQ ID NO 106
<211> LENGTH: 352
<212> TYPE: DNA
<213> ORGANISM: Homo sapiens

<400> SEQUENCE: 106

```
caggtgcagc tgcaggagtc gggcccagga ctggtgaagc cttcggagac cctgtccctc     60

acctgcactg tctctggtgg ctccatcagt agttactact ggagctggat ccggcagccc    120

gccgggaagg gactggagtg gattgggcgt atctatacca gtgggagcac caactacaac    180
```

```
ccctccctca agagtcgagt caccatgtca gtagacacgt ccaagaacca gttctccctg    240

aagctgagtt ctgtgaccgc cgcggacacg gccgtgtatt actgtgcgag agagaggctg    300

gggatgttct ttgactactg gggccaggga accctggtca ccgtctcctc ag            352


<210> SEQ ID NO 107
<211> LENGTH: 352
<212> TYPE: DNA
<213> ORGANISM: Homo sapiens

<400> SEQUENCE: 107

caggtgcagc tacaggagtc gggcccagga ctggtgaagc cttcggagac cctgtccctc     60

acctgcactg tctctggtgg ctccatcagt agttactact ggagctggat ccggcagccc    120

gccgggaagg gactggagtg gattggacgt ttctatacca gtgggagcac cagctgcaac    180

ccctccctca agagtcgagt caccatgtca gtagacacgt ccaagaacca gttctccctg    240

aagctgagct ctgtgaccgc cgcggacacg gccgtgtatt actgtgcgag agaggggata    300

ctggggtatt ttgactattg gggccaggga accctggtca ccgtctcctc ag            352


<210> SEQ ID NO 108
<211> LENGTH: 352
<212> TYPE: DNA
<213> ORGANISM: Homo sapiens

<400> SEQUENCE: 108

caggtgcagc tgcaggagtc gggcccagga ctggtgaagc cttcggagac cctgtccctc     60

acctgcactg tctctggtgg ctccatcagt atttactact ggaactggat ccggcagccc    120

ccagggaagg gactggagtg gattgggtat atctattaca ttgggagcac caactacaac    180

ccctccctca agagtcgagt caccatatca gtagacacgt ccaagaacca gttctccctg    240

aagctgagtt ctgtgaccgc tgcggacacg gccgtgtatt actgtgcgcg aggaaggcta    300

acttatgctt ttgatatctg gggccaaggg acaatggtca ccgtctcttc ag            352


<210> SEQ ID NO 109
<211> LENGTH: 122
<212> TYPE: PRT
<213> ORGANISM: Homo sapiens

<400> SEQUENCE: 109

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asn Asp Tyr Gly Asp Tyr Glu Ala Phe Asp Ile Trp
            100                 105                 110

Gly Gln Gly Thr Met Val Thr Val Ser Ser
        115                 120
```

<210> SEQ ID NO 110
<211> LENGTH: 118
<212> TYPE: PRT
<213> ORGANISM: Homo sapiens

<400> SEQUENCE: 110

```
Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ile Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Asp Asn Trp Asn Tyr Phe Asp Tyr Trp Gly Gln Gly Thr
            100                 105                 110

Leu Val Thr Val Ser Ser
        115
```

<210> SEQ ID NO 111
<211> LENGTH: 123
<212> TYPE: PRT
<213> ORGANISM: Homo sapiens

<400> SEQUENCE: 111

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Asp Trp Val
        35                  40                  45

Gly Arg Val Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asn Asp Tyr Gly Gly Pro Val Asp Ala Phe Asp Ile
            100                 105                 110

Trp Gly Gln Gly Thr Met Val Thr Val Ser Ser
        115                 120
```

<210> SEQ ID NO 112
<211> LENGTH: 116
<212> TYPE: PRT
<213> ORGANISM: Homo sapiens

<400> SEQUENCE: 112

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
```

```
        35                  40                  45

Gly His Ile Phe Ser Ser Gly Ser Thr Asn Tyr Asn Pro Ser Leu Lys
    50                  55                  60

Ser Arg Val Thr Met Ser Val Asp Thr Ser Lys Ser Gln Phe Ser Leu
65                  70                  75                  80

Lys Leu Ser Ser Val Thr Ala Ala Asp Thr Ala Val Tyr Leu Cys Ala
                85                  90                  95

Arg Gly Gly Val Thr Trp Phe Asp Pro Trp Gly Gln Gly Thr Leu Val
            100                 105                 110

Thr Val Ser Ser
        115


<210> SEQ ID NO 113
<211> LENGTH: 116
<212> TYPE: PRT
<213> ORGANISM: Homo sapiens

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr His Pro Ser Phe Lys
    50                  55                  60

Ser Arg Val Thr Met Ser Val Asp Thr Ser Lys Thr Gln Phe Ser Leu
65                  70                  75                  80

Lys Leu Ser Ser Leu Thr Ala Ala Asp Thr Ala Val Tyr Tyr Cys Ala
                85                  90                  95

Arg Gly Gly Ile Thr Trp Phe Asp Pro Trp Gly Gln Gly Thr Leu Val
            100                 105                 110

Thr Val Ser Ser
        115


<210> SEQ ID NO 114
<211> LENGTH: 120
<212> TYPE: PRT
<213> ORGANISM: Homo sapiens

<400> SEQUENCE: 114

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Thr Lys Ser Ile
65                  70                  75                  80

Ala Tyr Leu Gln Met Asn Ser Leu Lys Ile Glu Asp Thr Ala Val His
                85                  90                  95

Tyr Cys Thr Arg Glu Gly Ser Phe Gly Ala Leu Asp Ile Trp Gly Gln
            100                 105                 110

Gly Ile Met Val Thr Val Ser Ser
```

115 120

<210> SEQ ID NO 115
<211> LENGTH: 119
<212> TYPE: PRT
<213> ORGANISM: Homo sapiens

<400> SEQUENCE: 115

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Asn Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Gly Tyr Ser Gly Pro Tyr Phe Asp Tyr Trp Gly Gln Gly
100 105 110

Thr Leu Val Thr Val Ser Ser
115

<210> SEQ ID NO 116
<211> LENGTH: 122
<212> TYPE: PRT
<213> ORGANISM: Homo sapiens

<400> SEQUENCE: 116

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val His
85 90 95

Tyr Cys Thr Thr Gly Asp Tyr Ser Tyr Thr Asp Ala Phe Asp Ile Trp
100 105 110

Gly Gln Gly Thr Met Val Thr Val Ser Ser
115 120

<210> SEQ ID NO 117
<211> LENGTH: 112
<212> TYPE: PRT
<213> ORGANISM: Homo sapiens

<400> SEQUENCE: 117

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

```
Tyr Trp Thr Trp Ile Arg Gln Pro Pro Gly Lys Gly Leu Glu Trp Ile
        35                  40                  45

Gly Tyr Ile His Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Phe Asp Tyr Trp Gly Gln Gly Thr Leu Val Thr Val Ser Ser
            100                 105                 110


<210> SEQ ID NO 118
<211> LENGTH: 124
<212> TYPE: PRT
<213> ORGANISM: Homo sapiens

<400> SEQUENCE: 118

Glu Val Gln Leu Val Glu Ser Gly Gly Asp Leu Val Gln Pro Gly Gly
1               5                   10                  15

Ser Leu Arg Leu Ser Cys Ala Asp Ser Arg Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Pro Ser Ser Ser Thr Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Asn Glu Asp Thr Ala Val Tyr Tyr Cys
                85                  90                  95

Ala Arg Asp Phe Pro His Asp Tyr Gly Tyr Tyr Pro His Tyr Phe Asp
            100                 105                 110

Tyr Trp Gly Gln Gly Thr Leu Val Thr Val Ser Ser
        115                 120


<210> SEQ ID NO 119
<211> LENGTH: 118
<212> TYPE: PRT
<213> ORGANISM: Homo sapiens

<400> SEQUENCE: 119

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Cys Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Gln Leu Gly Ile Ala Asp Tyr Trp Gly Gln Gly Thr
            100                 105                 110

Leu Val Thr Val Ser Ser
        115
```

<210> SEQ ID NO 120
<211> LENGTH: 120
<212> TYPE: PRT
<213> ORGANISM: Homo sapiens

<400> SEQUENCE: 120

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Thr Thr Asn Phe Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Leu Ser Gly Thr Asn Trp Gly Ser Pro Phe Asp Tyr Trp Gly Gln
            100                 105                 110

Gly Thr Leu Val Thr Val Ser Ser
        115                 120
```

<210> SEQ ID NO 121
<211> LENGTH: 125
<212> TYPE: PRT
<213> ORGANISM: Homo sapiens

<400> SEQUENCE: 121

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Glu Ile Leu Val Val Val Ala Ala Thr Arg Thr Gly Gly Val Phe
            100                 105                 110

Asp Ile Trp Gly Gln Gly Thr Met Val Thr Val Ser Ser
        115                 120                 125
```

<210> SEQ ID NO 122
<211> LENGTH: 112
<212> TYPE: PRT
<213> ORGANISM: Homo sapiens

<400> SEQUENCE: 122

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Ser Tyr
            20                  25                  30
```

```
Tyr Trp Ser Trp Ile Arg Gln Pro Pro Gly Lys Gly Leu Glu Trp Ile
        35                  40                  45

Gly Tyr Val Ser Tyr Ser Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Phe Asp Tyr Trp Gly Gln Gly Thr Leu Val Thr Val Ser Ser
            100                 105                 110


<210> SEQ ID NO 123
<211> LENGTH: 119
<212> TYPE: PRT
<213> ORGANISM: Homo sapiens

<400> SEQUENCE: 123

Gln Val Gln Leu Glu Gln Ser Gly Ala Glu Val Lys Arg Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Arg Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Glu Gly Gly Gly Pro Phe Asp Tyr Trp Gly Gln Gly
            100                 105                 110

Thr Leu Val Thr Val Ser Ser
        115


<210> SEQ ID NO 124
<211> LENGTH: 112
<212> TYPE: PRT
<213> ORGANISM: Homo sapiens

<400> SEQUENCE: 124

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Val Leu Glu Trp Ile
        35                  40                  45

Gly Tyr Phe Ser Tyr Asn Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Gly Met Asp Val Trp Gly Gln Gly Thr Thr Val Thr Val Ser Ser
            100                 105                 110


<210> SEQ ID NO 125
<211> LENGTH: 117
```

<212> TYPE: PRT
<213> ORGANISM: Homo sapiens

<400> SEQUENCE: 125

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Asp Arg Thr Phe Tyr Ala Phe Asp Met Trp Gly Gln Gly Thr Met
100 105 110

Val Thr Val Ser Ser
115

<210> SEQ ID NO 126
<211> LENGTH: 119
<212> TYPE: PRT
<213> ORGANISM: Homo sapiens

<400> SEQUENCE: 126

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met His Trp Val Arg Gln Ala Thr Gly Lys Gly Leu Glu Trp Val
35 40 45

Ser Ala Ile Gly Thr Ala Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Gly His Ile Val Val Val Thr Ala Met Asp Tyr Trp Gly Gln Gly
100 105 110

Thr Leu Val Thr Val Ser Ser
115

<210> SEQ ID NO 127
<211> LENGTH: 115
<212> TYPE: PRT
<213> ORGANISM: Homo sapiens

<400> SEQUENCE: 127

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Cys Ser Ala Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys

```
    50                  55                  60

Ser Arg Val Thr Ile Ser Val Asp Thr Ser Arg Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Asp Ala Phe Asp Ile Trp Gly Gln Gly Thr Met Val Thr
            100                 105                 110

Val Ser Ser
        115


<210> SEQ ID NO 128
<211> LENGTH: 122
<212> TYPE: PRT
<213> ORGANISM: Homo sapiens

<400> SEQUENCE: 128

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Asn Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Asp Tyr Gly Asp Phe Asp Ala Phe Asp Ile Trp
            100                 105                 110

Gly Gln Gly Thr Met Val Thr Val Ser Ser
        115                 120


<210> SEQ ID NO 129
<211> LENGTH: 115
<212> TYPE: PRT
<213> ORGANISM: Homo sapiens

<400> SEQUENCE: 129

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Gly Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Asp Ala Phe Asp Ile Trp Gly Gln Gly Thr Met Val Thr
            100                 105                 110

Val Ser Ser
        115
```

<210> SEQ ID NO 130
<211> LENGTH: 119
<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met His Trp Val Arg Gln Ala Pro Gly Lys Gly Leu Val Trp Val
35 40 45

Ser Arg Ile Asn Ser Asp Gly Ser Ser Thr Ser Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Gly Thr Thr Gly Ala Phe Asp Ile Trp Gly Gln Gly
100 105 110

Thr Met Val Thr Val Ser Ser
115

<210> SEQ ID NO 131
<211> LENGTH: 122
<212> TYPE: PRT
<213> ORGANISM: Homo sapiens

<400> SEQUENCE: 131

Glu Val His Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Phe Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Ser
65 70 75 80

Leu Gln Met Asn Ser Leu Arg Ala Glu Asp Thr Ala Val Tyr Tyr Cys
85 90 95

Ala Arg Ala Gly Ala Val Ala Ala Leu Tyr Asn Trp Phe Asp Pro Trp
100 105 110

Gly Gln Gly Thr Leu Val Thr Val Ser Ser
115 120

<210> SEQ ID NO 132
<211> LENGTH: 120
<212> TYPE: PRT
<213> ORGANISM: Homo sapiens

<400> SEQUENCE: 132

Gln Ile Thr Leu Lys Glu Ser Gly Pro Pro Leu Val Lys Pro Thr Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Pro Arg Tyr Ser Gly Tyr Phe Asp Tyr Trp Gly Gln
            100                 105                 110

Gly Thr Leu Val Thr Val Ser Ser
        115                 120

<210> SEQ ID NO 133
<211> LENGTH: 118
<212> TYPE: PRT
<213> ORGANISM: Homo sapiens

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Lys Phe Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Pro Tyr Trp Tyr Phe Asp Leu Trp Gly Arg Gly Thr
            100                 105                 110

Leu Val Thr Val Ser Ser
        115

<210> SEQ ID NO 134
<211> LENGTH: 116
<212> TYPE: PRT
<213> ORGANISM: Homo sapiens

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Asn Pro Ser Leu Lys Ser
    50                  55                  60

Arg Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Trp Arg Thr Phe Tyr Gly Met Asp Val Trp Gly Gln Gly Thr Thr Val
            100                 105                 110

Thr Val Ser Ser
        115

<210> SEQ ID NO 135
<211> LENGTH: 113
<212> TYPE: PRT
<213> ORGANISM: Homo sapiens

<400> SEQUENCE: 135

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Ser Tyr Ser Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Leu Gly Asn Tyr Trp Gly Gln Gly Thr Leu Val Thr Val Ser
            100                 105                 110

Ser
```

<210> SEQ ID NO 136
<211> LENGTH: 123
<212> TYPE: PRT
<213> ORGANISM: Homo sapiens

<400> SEQUENCE: 136

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Ser Ile Ser Ser Ser Ser Thr Tyr Ile Tyr Tyr Ala Asp Ser Leu
    50                  55                  60

Lys Gly Arg Phe Thr Ile Ser Arg Asp Asn Ala Met Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Asp Ser Gly Thr Tyr Pro Tyr Tyr Tyr Phe Gly Met Asp Val
            100                 105                 110

Trp Gly Gln Gly Thr Thr Val Thr Val Ser Ser
        115                 120
```

<210> SEQ ID NO 137
<211> LENGTH: 117
<212> TYPE: PRT
<213> ORGANISM: Homo sapiens

<400> SEQUENCE: 137

```
Gln Val Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
```

```
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Ser Phe Tyr Gly Met Asp Val Trp Gly Gln Gly Thr Thr
            100                 105                 110

Val Thr Val Ser Ser
        115


<210> SEQ ID NO 138
<211> LENGTH: 120
<212> TYPE: PRT
<213> ORGANISM: Homo sapiens

<400> SEQUENCE: 138

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Ser Phe Pro Tyr Asn Trp Phe Asp Pro Trp Gly Gln
            100                 105                 110

Gly Thr Leu Val Thr Val Ser Ser
        115                 120


<210> SEQ ID NO 139
<211> LENGTH: 120
<212> TYPE: PRT
<213> ORGANISM: Homo sapiens

<400> SEQUENCE: 139

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Thr Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Glu Gly Ser Phe Gly Ala Leu Asp Ile Trp Gly Gln
            100                 105                 110

Gly Thr Met Val Thr Val Ser Ser
```

```
        115                 120


<210> SEQ ID NO 140
<211> LENGTH: 121
<212> TYPE: PRT
<213> ORGANISM: Homo sapiens

<400> SEQUENCE: 140

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Asn Ser Lys Thr Asp Gly Gly Thr Thr Asp Tyr Ala Ala
    50                  55                  60

Pro Val Lys Gly Arg Phe Thr Ile Ser Arg Asp Asp Ser Lys Thr Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Val Tyr Pro Asp Val Phe Asp Ile Trp Gly
            100                 105                 110

Gln Gly Thr Met Val Thr Val Ser Ser
        115                 120


<210> SEQ ID NO 141
<211> LENGTH: 118
<212> TYPE: PRT
<213> ORGANISM: Homo sapiens

<400> SEQUENCE: 141

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Arg Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ser Pro Tyr Trp Tyr Phe Asp Leu Trp Gly Arg Gly Thr
            100                 105                 110

Leu Val Thr Val Ser Ser
        115


<210> SEQ ID NO 142
<211> LENGTH: 126
<212> TYPE: PRT
<213> ORGANISM: Homo sapiens

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Glu Arg Phe Cys Gly Ala Asp Cys Tyr Pro His Trp
            100                 105                 110

Phe Asp Pro Trp Gly Gln Gly Thr Leu Val Thr Val Ser Ser
        115                 120                 125


<210> SEQ ID NO 143
<211> LENGTH: 126
<212> TYPE: PRT
<213> ORGANISM: Homo sapiens

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asn Trp Asn Tyr Gly Gly Pro Thr Tyr Tyr Tyr Tyr Tyr Gly
            100                 105                 110

Met Asp Val Trp Gly Gln Gly Thr Thr Val Thr Val Ser Ser
        115                 120                 125


<210> SEQ ID NO 144
<211> LENGTH: 116
<212> TYPE: PRT
<213> ORGANISM: Homo sapiens

<400> SEQUENCE: 144

Glu Val Gln Val Val Glu Ser Gly Gly Gly Leu Val Gln Pro Gly Lys
1               5                   10                  15

Ser Leu Arg Leu Ser Cys Ala Ala Ser Gly Phe Pro Phe Ser Val Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Cys Cys
                85                  90                  95

Ala Ser Gly Tyr His Leu Phe Asp Tyr Trp Gly Gln Gly Thr Leu Val
            100                 105                 110
```

Thr Val Ser Ser
115

<210> SEQ ID NO 145
<211> LENGTH: 122
<212> TYPE: PRT
<213> ORGANISM: Homo sapiens

<400> SEQUENCE: 145

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ile Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Ser Thr Asp Tyr Gly Asp Tyr Asp Ala Phe Asp Ile Trp
100 105 110

Gly Gln Gly Thr Met Val Thr Val Ser Ser
115 120

<210> SEQ ID NO 146
<211> LENGTH: 120
<212> TYPE: PRT
<213> ORGANISM: Homo sapiens

<400> SEQUENCE: 146

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Gly Ser Tyr Pro Tyr Asn Trp Phe Asp Pro Trp Gly Gln
100 105 110

Gly Thr Leu Val Thr Val Ser Ser
115 120

<210> SEQ ID NO 147
<211> LENGTH: 118
<212> TYPE: PRT
<213> ORGANISM: Homo sapiens

<400> SEQUENCE: 147

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asn His Asp Gly Ala Phe Asp Ile Trp Gly Gln Gly Thr
            100                 105                 110

Met Val Thr Val Ser Ser
        115


<210> SEQ ID NO 148
<211> LENGTH: 119
<212> TYPE: PRT
<213> ORGANISM: Homo sapiens

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Glu Asp Ser Gly Ser Tyr Phe Asp Tyr Trp Gly Gln Gly
            100                 105                 110

Thr Leu Val Thr Val Ser Ser
        115


<210> SEQ ID NO 149
<211> LENGTH: 121
<212> TYPE: PRT
<213> ORGANISM: Homo sapiens

<400> SEQUENCE: 149

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95
```

Cys Ala His Gln Glu Arg Arg Ser Gly Trp Ser Phe Asp Tyr Trp Gly
100 105 110

Gln Gly Thr Leu Val Ser Val Ser Ser
115 120

<210> SEQ ID NO 150
<211> LENGTH: 126
<212> TYPE: PRT
<213> ORGANISM: Homo sapiens

<400> SEQUENCE: 150

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Ile Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ala Thr Tyr Tyr Tyr Asp Ser Ser Gly Tyr Tyr Ser Asn Trp
100 105 110

Phe Asp Pro Trp Gly Gln Gly Thr Leu Val Thr Val Ser Ser
115 120 125

<210> SEQ ID NO 151
<211> LENGTH: 116
<212> TYPE: PRT
<213> ORGANISM: Homo sapiens

<400> SEQUENCE: 151

Glu Val Gln Val Val Glu Ser Gly Gly Gly Leu Val Gln Pro Gly Lys
1 5 10 15

Ser Leu Arg Leu Ser Cys Ala Ala Ser Gly Phe Thr Phe Ser Thr Tyr
20 25 30

Trp Met Thr Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Cys Cys
85 90 95

Ala Ser Gly Tyr His Leu Phe Asp Tyr Trp Gly Gln Gly Thr Leu Val
100 105 110

Thr Val Ser Ser
115

<210> SEQ ID NO 152
<211> LENGTH: 118
<212> TYPE: PRT
<213> ORGANISM: Homo sapiens

<400> SEQUENCE: 152

Gln Val Gln Leu Val Gln Ser Gly Ala Glu Val Lys Lys Pro Gly Ala

```
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Tyr Tyr Ala Gln Lys Phe
    50                  55                  60

Gln Gly Arg Val Thr Met Thr Arg Asp Thr Ser Ile Ser Thr Ala Tyr
65                  70                  75                  80

Val Glu Leu Ser Arg Leu Arg Ser Asp Asp Thr Ala Val Tyr Tyr Cys
                85                  90                  95

Ala Arg Lys Asn Pro Trp Gly His Phe Asp Tyr Trp Gly Gln Gly Thr
            100                 105                 110

Leu Val Thr Val Ser Ser
        115


<210> SEQ ID NO 153
<211> LENGTH: 118
<212> TYPE: PRT
<213> ORGANISM: Homo sapiens

<400> SEQUENCE: 153

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Phe
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Gly Thr Gly Asp Ala Leu Asp Ile Trp Gly Gln Gly Thr
            100                 105                 110

Met Val Thr Val Ser Ser
        115


<210> SEQ ID NO 154
<211> LENGTH: 117
<212> TYPE: PRT
<213> ORGANISM: Homo sapiens

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Thr Tyr
            20                  25                  30

Phe Trp Ser Trp Leu Arg Gln Pro Pro Gly Lys Gly Leu Glu Trp Ile
        35                  40                  45

Gly Tyr Ile Phe Tyr Ser Gly Ser Ile Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Glu Leu Ser Ser Val Thr Ala Ala Asp Thr Ala Val Tyr Tyr Cys Ala
```

```
                85                  90                  95

Arg Asp Arg Thr Phe Tyr Gly Met Asp Val Trp Gly Gln Gly Thr Thr
            100                 105                 110

Val Thr Val Ser Ser
        115
```

<210> SEQ ID NO 155
<211> LENGTH: 117
<212> TYPE: PRT
<213> ORGANISM: Homo sapiens

<400> SEQUENCE: 155

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ser Ser Gly Ser Ile Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Arg Asp Arg Ala Phe Tyr Gly Met Asp Val Trp Gly Gln Gly Thr Thr
            100                 105                 110

Val Thr Val Ser Ser
        115
```

<210> SEQ ID NO 156
<211> LENGTH: 117
<212> TYPE: PRT
<213> ORGANISM: Homo sapiens

<400> SEQUENCE: 156

```
Gln Val Gln Phe Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Trp Gly Ser Gly Asp Trp Gly Gln Gly Thr Leu
            100                 105                 110

Val Thr Val Ser Ser
        115
```

<210> SEQ ID NO 157
<211> LENGTH: 117
<212> TYPE: PRT
<213> ORGANISM: Homo sapiens

<400> SEQUENCE: 157

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ile Trp Ile Arg Gln Pro Pro Gly Lys Gly Leu Glu Trp Ile
        35                  40                  45

Gly Tyr Phe Tyr Tyr Ser Gly Ser Thr Asn Tyr Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Arg Leu Gly Ser Ile Phe Asp Tyr Trp Gly Gln Gly Thr Leu
            100                 105                 110

Val Thr Val Ser Ser
        115
```

<210> SEQ ID NO 158
<211> LENGTH: 117
<212> TYPE: PRT
<213> ORGANISM: Homo sapiens

<400> SEQUENCE: 158

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Ser Ser Val Thr Ala Ala Asp Thr Ala Val Tyr His Cys Ala
                85                  90                  95

Arg Gly Arg Leu Asn Gly Ala Phe Asp Tyr Trp Gly Gln Gly Thr Leu
            100                 105                 110

Val Thr Val Ser Ser
        115
```

<210> SEQ ID NO 159
<211> LENGTH: 117
<212> TYPE: PRT
<213> ORGANISM: Homo sapiens

<400> SEQUENCE: 159

```
Gln Val Gln Leu Gln Glu Ser Gly Pro Gly Leu Val Lys Pro Ser Glu
1               5                   10                  15

Thr Leu Ser Leu Thr Cys Thr Ile Ser Ser Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr His Pro Ser Leu Lys
    50                  55                  60

Ser Arg Val Thr Met Ser Val Asp Thr Ser Lys Asn His Phe Ser Leu
65                  70                  75                  80
```

Lys Leu Thr Ser Val Thr Ala Ala Asp Thr Ala Val Tyr Tyr Cys Ala
85 90 95

Arg Glu Arg Leu Thr Gly Phe Phe Asp Tyr Trp Gly Gln Gly Thr Leu
100 105 110

Val Thr Val Ser Ser
115

<210> SEQ ID NO 160
<211> LENGTH: 117
<212> TYPE: PRT
<213> ORGANISM: Homo sapiens

<400> SEQUENCE: 160

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Ile Ser Gly Ser Ile Tyr Asn Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Asp Arg Val Gly Met Thr Phe Asp Ile Trp Gly Gln Gly Thr Met
100 105 110

Val Thr Val Ser Ser
115

<210> SEQ ID NO 161
<211> LENGTH: 117
<212> TYPE: PRT
<213> ORGANISM: Homo sapiens

<400> SEQUENCE: 161

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Thr Trp Ile Arg Gln Pro Pro Gly Lys Gly Leu Glu Trp Ile
35 40 45

Gly Tyr Ile Tyr Tyr Ser Gly Ile Thr Asn Tyr Asn Pro Ser Leu Lys
50 55 60

Ser Arg Val Thr Met Ser Met Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Gly Arg Ile Ile Gly Ala Phe Asp Ile Trp Gly Gln Gly Thr Met
100 105 110

Val Thr Val Ser Ser
115

<210> SEQ ID NO 162
<211> LENGTH: 116
<212> TYPE: PRT
<213> ORGANISM: Homo sapiens

<400> SEQUENCE: 162

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Thr Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Glu Arg Val Ile Trp Phe Asp Pro Trp Gly Gln Gly Thr Leu Val
            100                 105                 110

Thr Val Ser Ser
        115

<210> SEQ ID NO 163
<211> LENGTH: 117
<212> TYPE: PRT
<213> ORGANISM: Homo sapiens

<400> SEQUENCE: 163

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Ala Asn Tyr Ala Gln Lys Phe
    50                  55                  60

Gln Gly Arg Val Thr Met Thr Arg Asp Thr Ser Ile Ser Ile Ala Tyr
65                  70                  75                  80

Met Glu Leu Ser Arg Leu Arg Ser Asp Asp Thr Ala Ile Tyr Tyr Cys
                85                  90                  95

Ala Arg Gly Arg Leu Thr Phe Phe Asp Tyr Trp Gly Gln Gly Thr Leu
            100                 105                 110

Val Thr Val Ser Ser
        115

<210> SEQ ID NO 164
<211> LENGTH: 117
<212> TYPE: PRT
<213> ORGANISM: Homo sapiens

<400> SEQUENCE: 164

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Phe
            20                  25                  30

Tyr Trp Ser Trp Ile Arg Gln Ser Pro Gly Arg Gly Leu Glu Trp Ile
        35                  40                  45

Gly Tyr Ile Phe Tyr Ser Gly Ser Thr Lys Tyr Asn Pro Ser Leu Met
    50                  55                  60

Ser Arg Val Thr Ile Ser Ala Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Arg Leu Gly Asn Tyr Phe Asp Tyr Trp Gly Gln Gly Thr Leu
100 105 110

Val Thr Val Ser Ser
115

<210> SEQ ID NO 165
<211> LENGTH: 117
<212> TYPE: PRT
<213> ORGANISM: Homo sapiens

<400> SEQUENCE: 165

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Ile Ser Gly Thr Thr Asn Tyr Asn Pro Ser Leu Met
50 55 60

Ser Arg Val Thr Met Ser Val Asp Thr Ser Lys Asn Gln Phe Ser Leu
65 70 75 80

Lys Leu Thr Ser Val Thr Ala Ala Asp Thr Ala Val Tyr Tyr Cys Ala
85 90 95

Arg Glu Arg Leu Val Arg Ala Phe Asp Ile Trp Gly Gln Gly Thr Met
100 105 110

Val Thr Val Ser Ser
115

<210> SEQ ID NO 166
<211> LENGTH: 117
<212> TYPE: PRT
<213> ORGANISM: Homo sapiens

<400> SEQUENCE: 166

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Thr Lys Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Gly Val Thr Gly Gly Phe Asp Pro Trp Gly Gln Gly Thr Leu
100 105 110

Val Thr Val Ser Ser
115

<210> SEQ ID NO 167
<211> LENGTH: 116

<212> TYPE: PRT
<213> ORGANISM: Homo sapiens

<400> SEQUENCE: 167

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Lys Asn Pro Ser Leu Lys Ser
    50                  55                  60

Arg Val Thr Met Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Leu Thr Val Val Gly Ala Leu Asp Tyr Trp Gly Gln Gly Thr Leu Val
            100                 105                 110

Thr Val Ser Ser
        115

<210> SEQ ID NO 168
<211> LENGTH: 118
<212> TYPE: PRT
<213> ORGANISM: Homo sapiens

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Ser Asp Asn Ala Lys Asn Ser Leu Tyr
65                  70                  75                  80

Leu Gln Met Asp Ser Leu Arg Asp Glu Asp Thr Ala Val Tyr Tyr Cys
                85                  90                  95

Ala Arg Asp Arg Leu Gly Ile Pro Phe Asp Tyr Trp Gly Gln Gly Thr
            100                 105                 110

Leu Val Thr Val Ser Ser
        115

<210> SEQ ID NO 169
<211> LENGTH: 116
<212> TYPE: PRT
<213> ORGANISM: Homo sapiens

<400> SEQUENCE: 169

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Asn Asn Pro Ser Leu Lys

```
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ile Asn Trp Phe Asp Pro Trp Gly Gln Gly Thr Leu Val
            100                 105                 110

Thr Val Ser Ser
        115


<210> SEQ ID NO 170
<211> LENGTH: 117
<212> TYPE: PRT
<213> ORGANISM: Homo sapiens

<400> SEQUENCE: 170

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ser Ser Gly Thr Thr Asn Tyr Asn Pro Ser Leu Lys
    50                  55                  60

Ser Arg Val Thr Met Ser Val Glu Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Glu Arg Ile Thr Gly His Phe Asp Tyr Trp Gly Gln Gly Thr Leu
            100                 105                 110

Val Thr Val Ser Ser
        115


<210> SEQ ID NO 171
<211> LENGTH: 117
<212> TYPE: PRT
<213> ORGANISM: Homo sapiens

<400> SEQUENCE: 171

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Val Leu Gly Tyr Tyr Phe Asp Tyr Trp Gly Gln Gly Thr Leu
            100                 105                 110

Val Thr Val Ser Ser
        115
```

<210> SEQ ID NO 172
<211> LENGTH: 116
<212> TYPE: PRT
<213> ORGANISM: Homo sapiens

<400> SEQUENCE: 172

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Gly Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Tyr Gly Met Asp Val Trp Gly Gln Gly Thr Thr Val
            100                 105                 110

Thr Val Ser Ser
        115
```

<210> SEQ ID NO 173
<211> LENGTH: 119
<212> TYPE: PRT
<213> ORGANISM: Homo sapiens

<400> SEQUENCE: 173

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Asn Thr Asn Tyr Asn Pro Ser Leu Lys
    50                  55                  60

Ser Arg Val Thr Met Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Ala Ile Gly Val Asp Ala Phe Asp Ile Trp Gly Gln Gly
            100                 105                 110

Thr Met Val Thr Val Ser Ser
        115
```

<210> SEQ ID NO 174
<211> LENGTH: 116
<212> TYPE: PRT
<213> ORGANISM: Homo sapiens

<400> SEQUENCE: 174

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45
```

Gly Arg Ile Tyr Thr Ser Gly Ser Thr Asn Tyr Asn Pro Ser Leu Lys
50 55 60

Ser Arg Val Ser Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Arg Ile Ile Trp Phe Asp Pro Trp Gly Gln Gly Thr Leu Val
100 105 110

Thr Val Ser Ser
115

<210> SEQ ID NO 175
<211> LENGTH: 118
<212> TYPE: PRT
<213> ORGANISM: Homo sapiens

<400> SEQUENCE: 175

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Asn Met Asn Trp Val Arg Gln Ala Pro Gly Lys Gly Leu Glu Trp Val
35 40 45

Ser Ser Ile Ser Ser Ser Ser Asn Tyr Ile Tyr Tyr Ala Asp Ser Val
50 55 60

Lys Gly Arg Phe Thr Ile Ser Gly Asp Thr Ala Lys Asn Ser Leu Phe
65 70 75 80

Leu Gln Met Ile Ser Leu Arg Val Glu Asp Thr Ala Val Tyr Tyr Cys
85 90 95

Ala Arg Asp Arg Leu Gly Ile Pro Phe Asp Tyr Trp Gly Gln Gly Ser
100 105 110

Leu Val Thr Val Ser Ser
115

<210> SEQ ID NO 176
<211> LENGTH: 117
<212> TYPE: PRT
<213> ORGANISM: Homo sapiens

<400> SEQUENCE: 176

Gln Val Gln Leu Gln Glu Ser Gly Pro Gly Leu Val Lys Pro Ser Glu
1 5 10 15

Thr Leu Ser Leu Thr Cys Thr Val Ser Gly Ala Ser Ile Ser Ser Tyr
20 25 30

Tyr Trp Ser Trp Ile Arg Gln Pro Pro Gly Lys Gly Leu Glu Trp Ile
35 40 45

Gly Tyr Phe Tyr Tyr Ser Gly Ser Thr Asn Tyr Ser Pro Ser Leu Lys
50 55 60

Ser Arg Val Thr Phe Ser Val Asp Thr Ser Lys Asn Gln Phe Ser Leu
65 70 75 80

Lys Leu Ser Ser Val Thr Ala Ala Asp Thr Ala Val Tyr Phe Cys Ala
85 90 95

Arg Gly Lys Val Gly Val Pro Phe Asp Tyr Trp Gly Gln Gly Thr Leu
100 105 110

Val Thr Val Ser Ser
115

<210> SEQ ID NO 177
<211> LENGTH: 117
<212> TYPE: PRT
<213> ORGANISM: Homo sapiens

<400> SEQUENCE: 177

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Lys Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Val Thr Gly Gly Phe Asp Pro Trp Gly Gln Gly Thr Leu
            100                 105                 110

Val Thr Val Ser Ser
        115
```

<210> SEQ ID NO 178
<211> LENGTH: 119
<212> TYPE: PRT
<213> ORGANISM: Homo sapiens

<400> SEQUENCE: 178

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Asn Thr Asn Tyr Asn Pro Ser Leu Lys
    50                  55                  60

Ser Arg Val Thr Met Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Ala Ile Gly Val Asp Ala Phe Asp Ile Trp Gly Gln Gly
            100                 105                 110

Thr Met Val Thr Val Ser Ser
        115
```

<210> SEQ ID NO 179
<211> LENGTH: 117
<212> TYPE: PRT
<213> ORGANISM: Homo sapiens

<400> SEQUENCE: 179

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30
```

```
Tyr Trp Ser Trp Ile Trp Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Pro Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Thr Gly Ala Phe Asp Ile Trp Gly Gln Gly Thr Met
            100                 105                 110

Val Thr Val Ser Ser
        115


<210> SEQ ID NO 180
<211> LENGTH: 117
<212> TYPE: PRT
<213> ORGANISM: Homo sapiens

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Val Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Arg Leu Thr Phe Phe Asp Tyr Trp Gly Gln Gly Thr Leu
            100                 105                 110

Val Thr Val Ser Ser
        115


<210> SEQ ID NO 181
<211> LENGTH: 117
<212> TYPE: PRT
<213> ORGANISM: Homo sapiens

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Tyr Cys Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Arg Leu Thr Phe Phe Asp Tyr Trp Gly Gln Gly Thr Leu
            100                 105                 110
```

```
Val Thr Val Ser Ser
        115


<210> SEQ ID NO 182
<211> LENGTH: 117
<212> TYPE: PRT
<213> ORGANISM: Homo sapiens

<400> SEQUENCE: 182

Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Arg Ile Thr Ser Phe Phe Asp Pro Trp Gly Gln Gly Thr Leu
            100                 105                 110

Val Thr Val Ser Ser
        115


<210> SEQ ID NO 183
<211> LENGTH: 117
<212> TYPE: PRT
<213> ORGANISM: Homo sapiens

<400> SEQUENCE: 183

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Val
        35                  40                  45

Gly Arg Leu Phe Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Ile Ala Ala Asp Thr Ala Val Tyr Tyr Cys Ala
                85                  90                  95

Arg Glu Arg Leu Thr Gly Tyr Phe Asp Tyr Trp Gly Gln Gly Thr Leu
            100                 105                 110

Val Thr Val Ser Ser
        115


<210> SEQ ID NO 184
<211> LENGTH: 117
<212> TYPE: PRT
<213> ORGANISM: Homo sapiens

<400> SEQUENCE: 184

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
```

-continued

```
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Val Ile Ala Phe Asp Ile Trp Gly Gln Gly Thr Met
            100                 105                 110

Val Thr Val Ser Ser
        115


<210> SEQ ID NO 185
<211> LENGTH: 117
<212> TYPE: PRT
<213> ORGANISM: Homo sapiens

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Arg Leu Gly Arg Ala Phe Asp Ile Trp Gly Gln Gly Thr Met
            100                 105                 110

Val Thr Val Ser Ser
        115


<210> SEQ ID NO 186
<211> LENGTH: 117
<212> TYPE: PRT
<213> ORGANISM: Homo sapiens

<400> SEQUENCE: 186

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Leu Thr Gly His Phe Asp Tyr Trp Gly Gln Gly Thr Leu
```

```
            100                 105                 110

Val Thr Val Ser Ser
        115


<210> SEQ ID NO 187
<211> LENGTH: 117
<212> TYPE: PRT
<213> ORGANISM: Homo sapiens

<400> SEQUENCE: 187

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Tyr Thr Asn Tyr Asn Pro Ser Leu Lys
    50                  55                  60

Ser Arg Val Ser Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Gly Ala Phe Phe Asp Tyr Trp Gly Gln Gly Thr Leu
            100                 105                 110

Val Thr Val Ser Ser
        115


<210> SEQ ID NO 188
<211> LENGTH: 117
<212> TYPE: PRT
<213> ORGANISM: Homo sapiens

<400> SEQUENCE: 188

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Arg Ile Thr Val Thr Ser Ala Phe Asp Ile Trp Gly Gln Gly Thr Met
            100                 105                 110

Val Thr Val Ser Ser
        115


<210> SEQ ID NO 189
<211> LENGTH: 116
<212> TYPE: PRT
<213> ORGANISM: Homo sapiens

<400> SEQUENCE: 189

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Lys Pro Ser Leu Lys Ser
    50                  55                  60

Arg Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95

Ser Thr Val Val Asn Ala Phe Asp Ile Trp Gly Gln Gly Thr Met Val
            100                 105                 110

Thr Val Ser Ser
        115


<210> SEQ ID NO 190
<211> LENGTH: 126
<212> TYPE: PRT
<213> ORGANISM: Homo sapiens

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ala Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Leu Pro Ile Thr Met Ile Val Val Val Met Pro Asp Ala
            100                 105                 110

Phe Asp Ile Trp Gly Gln Gly Thr Met Val Thr Val Ser Ser
        115                 120                 125


<210> SEQ ID NO 191
<211> LENGTH: 117
<212> TYPE: PRT
<213> ORGANISM: Homo sapiens

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Arg Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Tyr Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Arg Leu Gly Ile Phe Asp Tyr Trp Gly Gln Gly Thr Leu
            100                 105                 110

Val Thr Val Ser Ser
        115


<210> SEQ ID NO 192
<211> LENGTH: 117
<212> TYPE: PRT
<213> ORGANISM: Homo sapiens

<400> SEQUENCE: 192

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Ile Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Arg Leu Gly Phe Phe Asp Tyr Trp Gly Gln Gly Thr Leu
            100                 105                 110

Val Thr Val Ser Ser
        115


<210> SEQ ID NO 193
<211> LENGTH: 118
<212> TYPE: PRT
<213> ORGANISM: Homo sapiens

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Tyr Tyr Tyr Tyr Asn Met Asp Val Trp Gly Gln Gly Thr
            100                 105                 110

Thr Val Thr Val Ser Ser
        115


<210> SEQ ID NO 194
<211> LENGTH: 118
<212> TYPE: PRT
<213> ORGANISM: Homo sapiens

<400> SEQUENCE: 194
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Thr Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Trp Trp Glu Leu Thr Phe Phe Asp Tyr Trp Gly Gln Gly Thr
            100                 105                 110

Leu Val Thr Val Ser Ser
        115


<210> SEQ ID NO 195
<211> LENGTH: 116
<212> TYPE: PRT
<213> ORGANISM: Homo sapiens

<400> SEQUENCE: 195

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ala Ser Gly Gly Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Val Ser Ser Val Ile Ala Ala Asp Thr Ala Ile Tyr Tyr Cys Ala
                85                  90                  95

Arg Asn Arg Leu Gly Ile Tyr Asp Tyr Trp Gly Gln Gly Ser Leu Val
            100                 105                 110

Thr Val Ser Ser
        115


<210> SEQ ID NO 196
<211> LENGTH: 117
<212> TYPE: PRT
<213> ORGANISM: Homo sapiens

<400> SEQUENCE: 196

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ser Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Phe Cys Ala
                85                  90                  95

Arg Ala Leu Leu Thr Gly Gly Phe Ala Tyr Trp Gly Gln Gly Thr Leu
            100                 105                 110

Val Thr Val Ser Ser
        115


<210> SEQ ID NO 197
<211> LENGTH: 117
<212> TYPE: PRT
<213> ORGANISM: Homo sapiens

<400> SEQUENCE: 197

Gln Val Gln Leu Gln Glu Ser Gly Pro Gly Leu Val Lys Pro Ser Glu
1               5                   10                  15

Thr Leu Ser Leu Thr Cys Thr Val Ser Val Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ala Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Arg Val Gly Ile Tyr Phe Asp Tyr Trp Gly Gln Gly Thr Leu
            100                 105                 110

Val Thr Val Ser Ser
        115


<210> SEQ ID NO 198
<211> LENGTH: 125
<212> TYPE: PRT
<213> ORGANISM: Homo sapiens

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ser Asp Ser Val
    50                  55                  60

Arg Gly Arg Phe Thr Ile Ser Arg Asp Asn Ala Lys Asn Ser Leu Tyr
65                  70                  75                  80

Leu Gln Met Asp Ser Leu Arg Asp Glu Asp Thr Ala Val Tyr Tyr Cys
                85                  90                  95

Ala Arg Asp Ser Thr Met Ile Val Val Val Lys Val Pro Asp Ala Phe
            100                 105                 110

Asp Ile Trp Gly Gln Gly Thr Met Val Thr Val Ser Ser
        115                 120                 125


<210> SEQ ID NO 199
<211> LENGTH: 117
<212> TYPE: PRT
<213> ORGANISM: Homo sapiens
```

<400> SEQUENCE: 199

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Ile Lys Tyr Asn Pro Ser Leu Lys
50 55 60

Ser Arg Val Ala Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Gly Ile Leu Gly Tyr Phe Asp Tyr Trp Gly Gln Gly Thr Leu
100 105 110

Val Thr Val Ser Ser
115

<210> SEQ ID NO 200
<211> LENGTH: 117
<212> TYPE: PRT
<213> ORGANISM: Homo sapiens

<400> SEQUENCE: 200

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Tyr Val Tyr Tyr Ser Gly Ser Thr Asn Tyr Asn Pro Ser Leu Lys
50 55 60

Ser Arg Val Thr Thr Ser Val Asp Thr Ser Lys Asn Gln Phe Ser Leu
65 70 75 80

Lys Leu Arg Ser Val Thr Ala Ala Asp Thr Ala Val Tyr Tyr Cys Ala
85 90 95

Arg Asp Arg Leu Gly Ile Ala Phe Asp Ile Trp Gly Gln Gly Thr Met
100 105 110

Val Thr Val Ser Ser
115

<210> SEQ ID NO 201
<211> LENGTH: 118
<212> TYPE: PRT
<213> ORGANISM: Homo sapiens

<400> SEQUENCE: 201

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Ser Ala Gly Lys Gly Leu Glu Trp Ile
35 40 45

Gly His Ile Tyr Thr Ser Gly Ser Thr Asn Tyr Asn Pro Ser Leu Lys
50 55 60

Ser Arg Val Thr Met Ser Val Asp Thr Ser Lys Asn Gln Phe Ser Leu 65 70 75 80

Lys Leu Ser Ser Val Thr Ala Ala Asp Thr Ala Val Tyr Tyr Cys Ala
85 90 95

Arg Glu Arg Thr Val Val Thr Tyr Phe Asp Tyr Trp Gly Gln Gly Thr
100 105 110

Leu Val Thr Val Ser Ser
115

<210> SEQ ID NO 202
<211> LENGTH: 117
<212> TYPE: PRT
<213> ORGANISM: Homo sapiens

<400> SEQUENCE: 202

Gln Val Gln Leu Gln Glu Ser Gly Pro Gly Leu Val Lys Pro Ser Glu
1 5 10 15

Thr Leu Ser Leu Thr Cys Ser Val Ser Gly Gly Ser Ile Ser Ser Tyr
20 25 30

His Trp Ser Trp Ile Arg Gln Pro Ala Gly Lys Gly Leu Glu Trp Ile
35 40 45

Gly Arg Ile Tyr Thr Gly Gly Ser Thr Asn Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Arg Leu Thr Gly Tyr Phe Asp Tyr Trp Gly Gln Gly Thr Leu
100 105 110

Val Thr Val Ser Ser
115

<210> SEQ ID NO 203
<211> LENGTH: 116
<212> TYPE: PRT
<213> ORGANISM: Homo sapiens

<400> SEQUENCE: 203

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Ile Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ser Arg Leu Gly Ile Phe Asp Tyr Trp Gly Gln Gly Thr Leu Val
100 105 110

Thr Val Ser Ser
115

<210> SEQ ID NO 204
<211> LENGTH: 117
<212> TYPE: PRT

<213> ORGANISM: Homo sapiens

<400> SEQUENCE: 204

Gln Val Gln Pro Gln Glu Ser Gly Pro Gly Leu Val Lys Pro Ser Glu
1 5 10 15

Thr Leu Ser Leu Thr Cys Thr Val Ser Gly Gly Ser Ile Ser Gly Tyr
20 25 30

Tyr Trp Ser Trp Ile Arg Gln Pro Ala Gly Thr Gly Leu Glu Trp Ile
35 40 45

Gly Arg Ile Tyr Thr Ser Gly Ser Thr Asn Tyr Asn Ser Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Arg Met Ala Thr Ile Phe Asp Tyr Trp Gly Gln Gly Thr Leu
100 105 110

Val Thr Val Ser Ser
115

<210> SEQ ID NO 205
<211> LENGTH: 116
<212> TYPE: PRT
<213> ORGANISM: Homo sapiens

<400> SEQUENCE: 205

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Ala Gly Lys Gly Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Gly Leu Arg Gly Phe Asp Pro Trp Gly Gln Gly Thr Leu Val
100 105 110

Thr Val Ser Ser
115

<210> SEQ ID NO 206
<211> LENGTH: 125
<212> TYPE: PRT
<213> ORGANISM: Homo sapiens

<400> SEQUENCE: 206

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Asp Tyr Tyr Gly Ser Ser Gly Tyr Tyr Tyr Pro His Ala Phe
100 105 110

Asp Ile Trp Gly Gln Gly Thr Met Val Thr Val Ser Ser
115 120 125

<210> SEQ ID NO 207
<211> LENGTH: 116
<212> TYPE: PRT
<213> ORGANISM: Homo sapiens

<400> SEQUENCE: 207

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Tyr Tyr
20 25 30

Ser Met Asn Trp Val Arg Gln Ala Pro Gly Lys Gly Leu Glu Trp Val
35 40 45

Ser Ser Ile Ser Asp Ser Ser Asp Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Gly Leu Arg Phe Asp Tyr Trp Gly Gln Gly Thr Leu Val
100 105 110

Thr Val Ser Ser
115

<210> SEQ ID NO 208
<211> LENGTH: 117
<212> TYPE: PRT
<213> ORGANISM: Homo sapiens

<400> SEQUENCE: 208

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Ser Pro Gly Lys Gly Leu Glu Trp Ile
35 40 45

Gly Tyr Ile Tyr Tyr Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Leu Leu Thr Gly Gly Phe Ala Tyr Trp Gly Gln Gly Thr Leu
100 105 110

Val Thr Val Ser Ser
115

<210> SEQ ID NO 209

<211> LENGTH: 117
<212> TYPE: PRT
<213> ORGANISM: Homo sapiens

<400> SEQUENCE: 209

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Asn Thr Asn Tyr Asn Pro Ser Leu Lys
    50                  55                  60

Ser Arg Val Thr Met Ser Val Asp Thr Ser Lys Asn Leu Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Thr Gly Tyr Phe Asp Tyr Trp Ala Gln Gly Thr Leu
            100                 105                 110

Val Thr Val Ser Ser
        115

<210> SEQ ID NO 210
<211> LENGTH: 117
<212> TYPE: PRT
<213> ORGANISM: Homo sapiens

<400> SEQUENCE: 210

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Ile Val Gly Ala Phe Ala Tyr Trp Gly Gln Gly Thr Leu
            100                 105                 110

Val Thr Val Ser Ser
        115

<210> SEQ ID NO 211
<211> LENGTH: 117
<212> TYPE: PRT
<213> ORGANISM: Homo sapiens

<400> SEQUENCE: 211

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30

Tyr Trp Ser Trp Ile Arg Gln Pro Ala Gly Lys Gly Leu Glu Trp Ile
        35                  40                  45

```
Gly Arg Ile Tyr Thr Ser Gly Ser Thr Lys Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Ile Val Gly Ala Phe His Tyr Trp Gly Gln Gly Ala Leu
            100                 105                 110

Val Thr Val Ser Ser
        115


<210> SEQ ID NO 212
<211> LENGTH: 118
<212> TYPE: PRT
<213> ORGANISM: Homo sapiens

<400> SEQUENCE: 212

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Lys Trp Val Arg Gln Ala Pro Val Lys Gly Leu Glu Trp Val
        35                  40                  45

Ser Ser Ile Ser Ser Ser Ser Ser Tyr Ile Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Leu Gly Arg Ala Phe Asp Ile Trp Gly Gln Gly Thr
            100                 105                 110

Met Val Thr Val Ser Ser
        115


<210> SEQ ID NO 213
<211> LENGTH: 117
<212> TYPE: PRT
<213> ORGANISM: Homo sapiens

<400> SEQUENCE: 213

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Gly Met Phe Phe Asp Tyr Trp Gly Gln Gly Thr Leu
            100                 105                 110

Val Thr Val Ser Ser
        115
```

<210> SEQ ID NO 214
<211> LENGTH: 117
<212> TYPE: PRT
<213> ORGANISM: Homo sapiens

<400> SEQUENCE: 214

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Leu Gly Met Phe Phe Asp Tyr Trp Gly Gln Gly Thr Leu
            100                 105                 110

Val Thr Val Ser Ser
        115
```

<210> SEQ ID NO 215
<211> LENGTH: 117
<212> TYPE: PRT
<213> ORGANISM: Homo sapiens

<400> SEQUENCE: 215

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Phe Tyr Thr Ser Gly Ser Thr Ser Cys Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Ile Leu Gly Tyr Phe Asp Tyr Trp Gly Gln Gly Thr Leu
            100                 105                 110

Val Thr Val Ser Ser
        115
```

<210> SEQ ID NO 216
<211> LENGTH: 117
<212> TYPE: PRT
<213> ORGANISM: Homo sapiens

<400> SEQUENCE: 216

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Tyr Trp Asn Trp Ile Arg Gln Pro Pro Gly Lys Gly Leu Glu Trp Ile
```

```
        35                  40                  45

Gly Tyr Ile Tyr Tyr Ile Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Leu Thr Tyr Ala Phe Asp Ile Trp Gly Gln Gly Thr Met
            100                 105                 110

Val Thr Val Ser Ser
        115


<210> SEQ ID NO 217
<211> LENGTH: 319
<212> TYPE: DNA
<213> ORGANISM: Homo sapiens

<400> SEQUENCE: 217

gacatccaga tgacccagtc tccatcctcc ctgtctgcat ctgtaggaga cagagtcacc     60

atcacttgcc aggcgagtca ggacattagc gactatttaa attggtatca gcagaaacca    120

gggaaagccc ctaagctcct gatctacgat gaatccaatt tggaaacagg ggtcccatca    180

aggttcagtg gaagtggatc tgggacagat tttactttca ccatcagcag cctgcagcct    240

gaagatattg gaacatatta ctgtcaacag tatgataatc ttctcacttt cggccctggg    300

accaaagtgg atatcaaac                                                 319


<210> SEQ ID NO 218
<211> LENGTH: 340
<212> TYPE: DNA
<213> ORGANISM: Homo sapiens

<400> SEQUENCE: 218

gatattgtga tgacccagac tccactctcc ctgcccgtca cccctggaga gccggcctcc     60

atctcctgca ggtctagtca gagcctcttg gatagtgatg atggaaacac ctatttggac    120

tggttcctgc agaagccagg gcagtctcca cagctcctga tctatacgct ttcctatcgg    180

gcctctggag tcccagacag gttcagtggc agtgggtcag gcactgattt cacactgaaa    240

atcagcaggg tggaggctga cgatgttgga gtttattact gcatgcaacg tatagagttt    300

ccgttcactt ttggccaggg gaccaagctg gagatcaaac                          340


<210> SEQ ID NO 219
<211> LENGTH: 340
<212> TYPE: DNA
<213> ORGANISM: Homo sapiens

<400> SEQUENCE: 219

gacatcgtga tgacccagtc tccagactcc ctggctgtgt ctctgggcga gagggccacc     60

atcaactgca agtccagcca gagtgtttta tacagttcca acaaaaagaa ctacttaact    120

tggtaccagc agaaagtagg acagcctccg aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcaata ttatagtact    300

ccgttcactt tcggcggagg gaccaaggtg gagatcaaac                          340


<210> SEQ ID NO 220
```

<211> LENGTH: 322
<212> TYPE: DNA
<213> ORGANISM: Homo sapiens

<400> SEQUENCE: 220
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcgctcac tttcggcgga 300
gggaccaagg tggagatcaa ac 322

<210> SEQ ID NO 221
<211> LENGTH: 322
<212> TYPE: DNA
<213> ORGANISM: Homo sapiens

<400> SEQUENCE: 221
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcgctcac tttcggcgga 300
gggaccaagg tggagatcaa ac 322

<210> SEQ ID NO 222
<211> LENGTH: 337
<212> TYPE: DNA
<213> ORGANISM: Homo sapiens

<400> SEQUENCE: 222
gatattgtga tgactcagtc tccactttcc ctgcccgtca cccctggaga gccggcctcc 60
atctcctgca ggtctagtca gagcctcctg catagtaatg gatacaacta tttggaatgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaac 337

<210> SEQ ID NO 223
<211> LENGTH: 322
<212> TYPE: DNA
<213> ORGANISM: Homo sapiens

<400> SEQUENCE: 223
gacatccaga tgacccagtc tccatcttcc gtgtctgcat ctgtaggaga cagagtcacc 60
atcacttgtc gggcgagtcc gggtattagc agctggttag cctggtatca gcagaaacca 120
gagaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gcttacagtt tcccgtacac ttttggccag 300
gggaccaagc tggagatcaa ac 322

<210> SEQ ID NO 224
<211> LENGTH: 340
<212> TYPE: DNA
<213> ORGANISM: Homo sapiens

<400> SEQUENCE: 224
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca ttttctgggc atctacccgg 180
gattccgggg tccctgaccg attcagtggc agcgggtctg ggacagattt cactctcacc 240
atcagcagcc tgcaggctga agatgtggca gtttattact gtcagcaata ttatagtact 300
ccgctcactt tcggcggagg gaccaaggtg gagatcaaac 340

<210> SEQ ID NO 225
<211> LENGTH: 319
<212> TYPE: DNA
<213> ORGANISM: Homo sapiens

<400> SEQUENCE: 225
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctatatg gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attggacgtt cggccaaggg 300
accaaggtgg aaatcaaac 319

<210> SEQ ID NO 226
<211> LENGTH: 322
<212> TYPE: DNA
<213> ORGANISM: Homo sapiens

<400> SEQUENCE: 226
gacatccaga tgacccagtc tccatcctcc ctgtctgcat ctgtaggaga cagagtcacc 60
atcacttgcc aggcgagtca ggacattagc gactatttaa attggtatca gcagaaacca 120
gggaaagccc ctaagctcct gatctacgat gcatccaatt tggaaacagg ggtcccatca 180
aggttcagtg gaagtggatc tgggacagat tttactttca ccatcagtag cctgcagcct 240
gaagatattg caacatatta ctgtcaacag tatgataatc tccctcccac tttcggcgga 300
gggaccaagg tggagatcaa ac 322

<210> SEQ ID NO 227
<211> LENGTH: 322
<212> TYPE: DNA
<213> ORGANISM: Homo sapiens

<400> SEQUENCE: 227
gccatccgga tgacccagtc tccatcctca ttctctgcat ctacaggaga cagagtcacc 60
atcacttgtc gggcgagtca gggtattagc agttatttag cctggtatca gcaaaaacca 120
gggaaagccc ctaagctcct gatctatgct gcatccactt tgcaaagtgg ggtcccatca 180
aggttcagcg gcagtggatc tgggacagat ttcactctca ccatcagctg cctgcagtct 240
gaagattttg caacttatta ctgtcaacag tattatagtt acccattcac tttcggccct 300
gggaccaaag tggatatcaa ac 322

<210> SEQ ID NO 228
<211> LENGTH: 337
<212> TYPE: DNA
<213> ORGANISM: Homo sapiens

<400> SEQUENCE: 228
gatattgtga tgactcagtc tccactctcc ctgcccgtca cccctggaga gccggcctcc 60
atctcctgca ggtctagtca gagcctcctg tatagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaac 337

<210> SEQ ID NO 229
<211> LENGTH: 319
<212> TYPE: DNA
<213> ORGANISM: Homo sapiens

<400> SEQUENCE: 229
gacatccaga tgacccagtc tccttccacc ctgtctgcat ctgtaggaga cagagtcacc 60
atcacttgcc gggccagtca gagtattagt agctggttgg cctggtatca gcggaaacca 120
gggaaagccc ctaagctcct gatctataag gcgtctactt tagaaagtgg ggtcccatca 180
aggttcagcg gcagtggatc tgggacagaa ttcactctca ccatcagcag cctgcagcct 240
gatgattttg caacttatta ctgccaacag tttaatagtt attggacgtt cggccaaggg 300
accaaggtgg aaatcaaac 319

<210> SEQ ID NO 230
<211> LENGTH: 319
<212> TYPE: DNA
<213> ORGANISM: Homo sapiens

<400> SEQUENCE: 230
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attggacgtt cggccaaggg 300
accaaggtgg aaatcaaac 319

<210> SEQ ID NO 231
<211> LENGTH: 340
<212> TYPE: DNA
<213> ORGANISM: Homo sapiens

<400> SEQUENCE: 231
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
ccttcgacct tcggccaagg gacacgactg gagattaaac 340

<210> SEQ ID NO 232
<211> LENGTH: 319
<212> TYPE: DNA
<213> ORGANISM: Homo sapiens

<400> SEQUENCE: 232
gacatccaga tgacccagtc tccttccacc ctgtctgcat ctgtaggaga cagagtcacc 60
atcacttgcc gggccagtca gagtattagt gactggttgg cctggtatct gcagaaacca 120
gggaaagccc ctaagctcct gatctataag gcgtctagtt tagaaagtgg ggtcccatca 180
aggttcagcg gcagtggatc tgggacagca ttcactctca ccatcagcag cctgcagcct 240
gatgattttg caacttatta ctgccaacag tataatagtc attggacgtt cggccaaggg 300
accaaggtgg aaatcaaac 319

<210> SEQ ID NO 233
<211> LENGTH: 325
<212> TYPE: DNA
<213> ORGANISM: Homo sapiens

<400> SEQUENCE: 233
gaaattgtgt tgacgcagtc tccaggcacc ctgtctttgt ctccagggga aagagccacc 60
ctctcctgca gggccagtca gagtgttagc agcacctact tagcctggta ccagcagaga 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccgta cacttttggc 300
caggggacca agctggagat caaac 325

<210> SEQ ID NO 234
<211> LENGTH: 322
<212> TYPE: DNA
<213> ORGANISM: Homo sapiens

<400> SEQUENCE: 234
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggaaacagg ggtcccatca 180
aggttcagtg gaagtggatc tgggacagat tttactttca ccatcagcag cctgcagcct 240
gaagatattg caacatatta ctgtcaacag tatgataatc tccctctcac tttcggcgga 300
gggaccaagg tggagatcaa ac 322

<210> SEQ ID NO 235
<211> LENGTH: 325
<212> TYPE: DNA
<213> ORGANISM: Homo sapiens

<400> SEQUENCE: 235
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccgta cacttttggc 300
caggggacca agctggagat caaac 325

<210> SEQ ID NO 236
<211> LENGTH: 340
<212> TYPE: DNA
<213> ORGANISM: Homo sapiens

<400> SEQUENCE: 236
gacatcgtga tgacccagtc tccagactcc ctggctgtgt ctctgggcga gggggccacc 60
atcaactgca agtccagcca gagtgtttta tacagctcca acaataagaa ctacttagct 120
tggtatcagc agaaaccagg acagcctcct aaactgctca tttactgggc atctacccgg 180
gaatccgggg tccctgaccg attcagcggc agcgggtctg ggacagattt cactctcacc 240
atcagcagcc tgcaggctga agatgaggca gtttattact gtcagcaata ttattatact 300
ccgtacactt ttggccaggg gaccaagctg gagatcaaac 340

<210> SEQ ID NO 237
<211> LENGTH: 325
<212> TYPE: DNA
<213> ORGANISM: Homo sapiens

<400> SEQUENCE: 237
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccgta cacttttggc 300
caggggacca agctggagat caaac 325

<210> SEQ ID NO 238
<211> LENGTH: 340
<212> TYPE: DNA
<213> ORGANISM: Homo sapiens

<400> SEQUENCE: 238
gacatcgtga tgacccagtc tccagactcc ctggctgtgt ctctgggcga gagggccacc 60
atcaactgca agtccagcca gagtgtttta tacagctcca acaataagaa ctacttatct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
ccgctcactt tcggcggagg gaccaaggtg gagatcaaac 340

<210> SEQ ID NO 239
<211> LENGTH: 325
<212> TYPE: DNA
<213> ORGANISM: Homo sapiens

<400> SEQUENCE: 239
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcactatt cactttcggc 300
cctgggacca aagtggatat caaac 325

<210> SEQ ID NO 240
<211> LENGTH: 340
<212> TYPE: DNA
<213> ORGANISM: Homo sapiens

<400> SEQUENCE: 240
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccaac agaaaccagg acagcctcct aaggtgctca tttactgggc atctatccgg 180
gaatccgggg tctctgaccg attcagtggc agcgggtctg ggacagattt cactctcacc 240
atcagcagcc tgcaggctga agatgtggca gtttattact gtcagcaata ttatagtact 300
ccgtacactt ttggccaggg gaccaagctg gagatcaaac 340

<210> SEQ ID NO 241
<211> LENGTH: 340
<212> TYPE: DNA
<213> ORGANISM: Homo sapiens

<400> SEQUENCE: 241
gacatcgtga tgacccagtc tccagactcc ctggctgtgt ctctgggcga gagggccacc 60
atcaactgca agtccagcca gactgtttta tacagctccg acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
cctcggacgt tcggccaagg gaccaaggtg gaaatcaaac 340

<210> SEQ ID NO 242
<211> LENGTH: 325
<212> TYPE: DNA
<213> ORGANISM: Homo sapiens

<400> SEQUENCE: 242
gaaattgtgt tgacgcagtc tccaggcacc ctgtctttgt ctccagggga aagagccacc 60
ctctcctgca gggccagtca gagtattagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccgta cacttttggc 300
caggggacca agctggagat caaac 325

<210> SEQ ID NO 243
<211> LENGTH: 319
<212> TYPE: DNA
<213> ORGANISM: Homo sapiens

<400> SEQUENCE: 243
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccgtcagcag cctgcagcct 240
gatgattttg caacttatta ctgccaacag tataatagtt attggacgtt cggccaaggg 300
accaaggtgg aaatcaaac 319

<210> SEQ ID NO 244
<211> LENGTH: 322
<212> TYPE: DNA
<213> ORGANISM: Homo sapiens

<400> SEQUENCE: 244
gacatccagt tgacccagtc tccatccttc ctgtctgcat ctgtaggaga cagagtcacc 60
atcacttgcc gggccagtca gggcattagc agttatttag cctggtatca gcaaaaacca 120
gggaaagccc ctaagctcct gatctatgct gcatccactt tgcaaagtgg ggtcccatca 180
aggttcagcg gcagtggatc tgggacagaa ttcactctca caatcagcag cctgcagcct 240
gaagattttg caacttatta ctgtcaacag cttaatactt accctcggac gttcggccaa 300
gggaccaagg tggaaatcaa ac 322

<210> SEQ ID NO 245
<211> LENGTH: 322
<212> TYPE: DNA
<213> ORGANISM: Homo sapiens

<400> SEQUENCE: 245
gacatccaga tgacccagtc tccatcctcc ctgtctgcat ctgtaggaga cagagtcacc 60
atcacttgcc gggcgagtca gggctttagc aattatttag cctggtatca gcagaaacca 120
gggaaagttc ctaagctcct gatctatgct gcatccactt tgcaatcagg ggtcccatct 180
cggttcagtg gcagtggatc tgggacagat ttcactctca ccatcagcag cctgcagcct 240
gaagatgttg caacttatta ctgtcaaaag tataacagtg ccccgctcac tttcggcgga 300
gggaccaagg tggagatcaa ac 322

<210> SEQ ID NO 246
<211> LENGTH: 337
<212> TYPE: DNA
<213> ORGANISM: Homo sapiens

<400> SEQUENCE: 246
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttggattc taatcgggcc 180
tccggggtcc ctgacaggtt cagtggcagt ggatcaggca cagattttac actgagaatc 240
agcagagtgg aggctgagga tgttggggtt tattactgca tgcaaactct acaaactccg 300
tacacttttg gccaggggac caagctggag atcaaac 337

<210> SEQ ID NO 247
<211> LENGTH: 337
<212> TYPE: DNA
<213> ORGANISM: Homo sapiens

<400> SEQUENCE: 247
gatattgtga tgactcagtc tccactctcc ctgcccgtca cccctggaga gccggcctcc 60
atctcctgca ggtctagtca gagcctcctg catagtaatg gatacaacta tttggaatgg 120
tacctgcaga agccagggca gtctccacag ctcctgatct atttgggttc taatcgggcc 180
tccggggtcc ctgacaggtt cagtggcagt ggatcaggca cagattttac actgaaaatc 240

```
agcagagtgg aggctgagga tgttggggtt tattactgca tgcaagctct acaaactccg    300

ctcactttcg gcggagggac caaggtggag atcaaac                             337


<210> SEQ ID NO 248
<211> LENGTH: 337
<212> TYPE: DNA
<213> ORGANISM: Homo sapiens

<400> SEQUENCE: 248

gatattgtga tgactcagtc tccactctcc ctgcccgtca cccctggaga gccggcctcc     60

atctcctgca ggtctagtca gagcctcctg catagtaatg gatacaacta tttggattgg    120

tacctgcaga agtcagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaagctct acaaactccg    300

ctcactttcg gcggagggac caaggtggag atcaaac                             337


<210> SEQ ID NO 249
<211> LENGTH: 340
<212> TYPE: DNA
<213> ORGANISM: Homo sapiens

<400> SEQUENCE: 249

gacatcgtga tgacccagtc tccagactcc ctggctgtgt ctctgggcga gagggccacc     60

atcaactgca agtccagcca gagtgtttta tacagctcca acaataaaaa ctacttaact    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcaata ttatagtact    300

cctccgacgt tcggccaagg gaccaaggtg gaaatcaaac                          340


<210> SEQ ID NO 250
<211> LENGTH: 322
<212> TYPE: DNA
<213> ORGANISM: Homo sapiens

<400> SEQUENCE: 250

gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatatta ctgtcaacag tatgataatc tccccatcac cttcggccaa    300

gggacacgac tggagattaa ac                                             322


<210> SEQ ID NO 251
<211> LENGTH: 340
<212> TYPE: DNA
<213> ORGANISM: Homo sapiens

<400> SEQUENCE: 251

gatattgtga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttc taatcgggcc    180
```

tccggggtcc ctgacaggtt cagtggcagt ggatcaggca cagattttac actgaaaatc 240
agcagagtgg aggctgagga tgttggggtt tattactgca tgcaagctct acaaactcct 300
ccgtacactt ttggccaggg gaccaagctg gagatcaaac 340

<210> SEQ ID NO 252
<211> LENGTH: 337
<212> TYPE: DNA
<213> ORGANISM: Homo sapiens

<400> SEQUENCE: 252
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaagatc 240
agcagagtgg aggctgagga tgttggggtt tattactgca tgcaagctct acaaactcca 300
ctcactttcg gcggagggac caaggtggag atcaaac 337

<210> SEQ ID NO 253
<211> LENGTH: 340
<212> TYPE: DNA
<213> ORGANISM: Homo sapiens

<400> SEQUENCE: 253
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatcgtact 300
atgtacactt ttggccaggg gaccaagctg gagatcaaac 340

<210> SEQ ID NO 254
<211> LENGTH: 337
<212> TYPE: DNA
<213> ORGANISM: Homo sapiens

<400> SEQUENCE: 254
gatattgtga tgactcagtc tccactctcc ctgcccgtca cccctggaga gccggcctcc 60
atctcctgca ggtctagtca gagcctcctg catagtaatg gatacaacta tttggattgg 120
tccctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaactct acaaattccg 300
tatacttttg gccaggggac caagctggag atcaaac 337

<210> SEQ ID NO 255
<211> LENGTH: 340
<212> TYPE: DNA
<213> ORGANISM: Homo sapiens

<400> SEQUENCE: 255
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
cctctcactt tcggcggagg gaccaaggtg gagatcaaac 340

<210> SEQ ID NO 256
<211> LENGTH: 340
<212> TYPE: DNA
<213> ORGANISM: Homo sapiens

<400> SEQUENCE: 256
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
ccgatcacct tcggccaagg gacacgactg gagattaaac 340

<210> SEQ ID NO 257
<211> LENGTH: 340
<212> TYPE: DNA
<213> ORGANISM: Homo sapiens

<400> SEQUENCE: 257
gacatcgtga tgacccagtc tccagactcc ctggctgtgt ctctgggcga gagggccacc 60
atcaactgca agtccagcca gagtgtttta tacagctcca acaataaaaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagttct 300
ccgtggacgt tcggccaagg gaccaaggaa ctgtggctgc 340

<210> SEQ ID NO 258
<211> LENGTH: 322
<212> TYPE: DNA
<213> ORGANISM: Homo sapiens

<400> SEQUENCE: 258
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacactt tccccttcac tgtcggccct 300
gggaccaaag tggatatcaa ac 322

<210> SEQ ID NO 259
<211> LENGTH: 337
<212> TYPE: DNA
<213> ORGANISM: Homo sapiens

<400> SEQUENCE: 259
gatattgtga tgactcagtc tccactctcc ctgcccgtca cccctggaga gccggcctcc 60
atctcctgca ggtctagtca gagcctcctc catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgct tgcaagctct acaaactccg 300
ctcactttcg gcggagggac caaggtggaa atcaaac 337

<210> SEQ ID NO 260
<211> LENGTH: 340
<212> TYPE: DNA
<213> ORGANISM: Homo sapiens

<400> SEQUENCE: 260
gatattgtga tgacccagac tccactctcc ctgcccgtca cccctggaga gccggcctcc 60
atctcctgca ggtctagtca gagcctcttg gatagtgatg atggaaacac ctatttggac 120
tggtacctgc agaagccagg gcagtctcca cagctcctga tctatacgct ttcctatcgg 180
gcctctggag tcccagacag gttcagtggc agtgggtcag gcactgattt cacactgaaa 240
atcagcaggg tggaggctga ggatgttgga gtttattact gcatgcaacg tatagagttt 300
ccttacactt ttggccaggg gaccaagctg gagatcaaac 340

<210> SEQ ID NO 261
<211> LENGTH: 337
<212> TYPE: DNA
<213> ORGANISM: Homo sapiens

<400> SEQUENCE: 261
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttggcttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcattctcg gcggagggac caaggtggag atcaaac 337

<210> SEQ ID NO 262
<211> LENGTH: 325
<212> TYPE: DNA
<213> ORGANISM: Homo sapiens

<400> SEQUENCE: 262
gaaattgtgt tgacgcagtc tccaggcacc ctgtctttgc ctccagggga aagagccacc 60
ctctcctgca gggccagtca gaatgttagc agcacctact tagcctggta ccaccagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcccctcg gacgttcggc 300
caagggacca aggtggaaat caaac 325

<210> SEQ ID NO 263
<211> LENGTH: 325
<212> TYPE: DNA
<213> ORGANISM: Homo sapiens

<400> SEQUENCE: 263
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta actcaccgct cactttcggc 300
ggagggacca aggtggagat caaac 325

<210> SEQ ID NO 264
<211> LENGTH: 337
<212> TYPE: DNA
<213> ORGANISM: Homo sapiens

<400> SEQUENCE: 264
gatattgtga tgactcagtc tccaatctcc ctgcccgtca cccctggaga gccggcctcc 60
atctcctgca ggtctagtca gagcctcctc tatagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggcgtt tattactgca tgcaagctct acaaaccccg 300
tggacgttcg gccaagggac caaggtggaa atcaaac 337

<210> SEQ ID NO 265
<211> LENGTH: 331
<212> TYPE: DNA
<213> ORGANISM: Homo sapiens

<400> SEQUENCE: 265
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggtg 300
ttcggcggag ggaccaagct gaccgtccta g 331

<210> SEQ ID NO 266
<211> LENGTH: 331
<212> TYPE: DNA
<213> ORGANISM: Homo sapiens

<400> SEQUENCE: 266
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta tgactgtgca gcatgggatg acagtctgaa tggtccggtg 300
ttcggcggag ggaccaagct gaccgtccta g 331

<210> SEQ ID NO 267
<211> LENGTH: 331
<212> TYPE: DNA
<213> ORGANISM: Homo sapiens

<400> SEQUENCE: 267
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
ggccgattct ctggctccaa gtctggcacc tcagcctccc tggccatcag tgggctccag 240
tctgacgatg aggctgatta ttactgtgca gcatgggatg acagcctgaa tggtccggta 300
ttcggcggag ggaccaagct gaccgtccta g 331

<210> SEQ ID NO 268
<211> LENGTH: 331
<212> TYPE: DNA
<213> ORGANISM: Homo sapiens

<400> SEQUENCE: 268
cagtctgtgc tgactcagcc accctcagcg tctgggaccc ccgggcagag ggtcaccatc 60
tcttgttctg gaagcagctc caacatcgga agtaattctg taaactggtt ccagcagctc 120
ccaggcacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 269
<211> LENGTH: 331
<212> TYPE: DNA
<213> ORGANISM: Homo sapiens

<400> SEQUENCE: 269
cagtctgtgc tgactcagcc accctcagcg tctgggaccc ccgggcagag ggtcaccatc 60
tcttgttctg gaagcagttc caacatcgga agtaatactg taaactggta ccagcaactc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 270
<211> LENGTH: 331
<212> TYPE: DNA
<213> ORGANISM: Homo sapiens

<400> SEQUENCE: 270
cagtctgtgc tgactcagcc accctcagcg tctgggaccc ccgggcagag ggtcaccatc 60
tcttgttctg gaagcagctc caacatcgga agtaatgctg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 271
<211> LENGTH: 331
<212> TYPE: DNA
<213> ORGANISM: Homo sapiens

<400> SEQUENCE: 271
cagtctgtgc tgactcagcc accctcagcg tctgggaccc ccgggcagag ggtcaccatc 60

```
tcttgttctg gaagcagctc caacatcgga agtaatactg taaactggta ccagcagttc    120

ccaggaacgg cccccaaact cctcatctat agtaataatc agcggccctc aggggtccct    180

gaccgattct ctggctccaa gtctggcacc tcagcctccc tggccatcag tgggctccag    240

tctgaggatg aggctgatta ttactgtgca gcatgggatg acagcctgaa tggtgtggta    300

ttcggcggag ggaccaagct gaccgtccta g                                   331
```

<210> SEQ ID NO 272
<211> LENGTH: 331
<212> TYPE: DNA
<213> ORGANISM: Homo sapiens

<400> SEQUENCE: 272

```
cagtctgtgc tgactcagcc accctcagcg tctgggaccc ccgggcagag ggtcaccatc     60

tcttgttctg gaagcagctc caacatcgga aataatgctg taaactggta ccagcagctc    120

ccaggaacgg cccccaaact cctcatctat agtaataatc agcggccctc aggggttcct    180

gaccgattct ctggctccaa gtctggcacc tcagcctccc tggccatcag tgggctccag    240

tctgaggatg aggctgatta ctactgtgca gcatgggatg acagcctgaa tggtccggtt    300

ttcggcggag ggaccaagct gaccgtccta g                                   331
```

<210> SEQ ID NO 273
<211> LENGTH: 331
<212> TYPE: DNA
<213> ORGANISM: Homo sapiens

<400> SEQUENCE: 273

```
cagtctgtgc tgactcagcc accctcagcg tctgggaccc ccgggcagag ggtcaccatc     60

tcttgttctg gaagcagctc caacatcgga agtaatactg taaactggta ccagcagctc    120

ccaggaacgg cccccaacct cctcatctat agtaataatc agcggccctc aggggtccct    180

gaccgattct ctggctccaa gtctggcacc tcagcctccc tggccatcag tgggctccag    240

tctgaggatg aggctgatta tttctgtgca gcatgggatg acagcctgaa tggtgtggta    300

ttcggcggag ggaccaagct gaccgtccta g                                   331
```

<210> SEQ ID NO 274
<211> LENGTH: 331
<212> TYPE: DNA
<213> ORGANISM: Homo sapiens

<400> SEQUENCE: 274

```
cagtctgtgc tgactcagcc accctcagcg tctgggaccc ccgggcagag ggtcaccatc     60

tcttgttctg gaagcagctc caacatcgga agtaatactg taaactggta ccagcagctc    120

ccaggaacgg cccccaaact cctcatctat agtaataatc agcggccctc aggggtccct    180

gaccgattct ctggctccaa gtctggcacc tcagcctccc tggccatcag tgggctccag    240

tctgaggatg aggctgatta ttactgtgca gcatgggatg acagcctgaa tggtccggta    300

ttcggcggag ggaccaacct gaccgtccta g                                   331
```

<210> SEQ ID NO 275
<211> LENGTH: 331
<212> TYPE: DNA
<213> ORGANISM: Homo sapiens

<400> SEQUENCE: 275
cagtctgtgc tgactcagcc accctcagcg tctgggaccc ccgggcagag ggtcaccatc 60
tcttgttctg gaggcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 276
<211> LENGTH: 331
<212> TYPE: DNA
<213> ORGANISM: Homo sapiens

<400> SEQUENCE: 276
cagtctgtgc tgactcagtc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggttatgtc 300
ttcggaactg ggaccaaggt caccgtccta g 331

<210> SEQ ID NO 277
<211> LENGTH: 331
<212> TYPE: DNA
<213> ORGANISM: Homo sapiens

<400> SEQUENCE: 277
cagtctgtgc tgactcagcc accctcagcg tctgggaccc ccgggcagag ggtcaccctc 60
tcttgttctg gaagcagctc caacatcgga agtaatactg taaactggta ccaacagctc 120
ccaggaacgg cccccaaact cctcatctat agtaataatc agcggccctc aggggtccct 180
gaccgattct ctggctccaa gtctggcacc tcagcctccc tggccatcag tgggctcctg 240
tctgaggatg aggctgatta ttactgtgca gcatggcatg acagcctgaa tggtgtggtt 300
ttcggcggag ggaccaagct gaccgtccta g 331

<210> SEQ ID NO 278
<211> LENGTH: 328
<212> TYPE: DNA
<213> ORGANISM: Homo sapiens

<400> SEQUENCE: 278
cagtctgtgc tgactcagcc accctcagcg tctgggaccc ccgggcagag ggtcaccatc 60
tcttgttctg gaagcagctc caatatcgga agtaatactg taaactggta ccagcagttc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgcg gcatgggatg acagtctgaa tggtgtgttc 300
ggcggaggga ccaagctgac cgtcctag 328

<210> SEQ ID NO 279
<211> LENGTH: 331
<212> TYPE: DNA
<213> ORGANISM: Homo sapiens

<400> SEQUENCE: 279
cagtctgtgc tgactcagcc accctcagcg tctgggaccc ccgggcagag ggtcaccatc 60
tcttgttctg gaagcagctc caacatcgga agtaatactg taaactggtt ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtgtggta 300
ttcggcggag ggaccaagct gaccgtccta g 331

<210> SEQ ID NO 280
<211> LENGTH: 331
<212> TYPE: DNA
<213> ORGANISM: Homo sapiens

<400> SEQUENCE: 280
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtgtggta 300
ttcggcggag ggaccaagct gaccgtccta g 331

<210> SEQ ID NO 281
<211> LENGTH: 334
<212> TYPE: DNA
<213> ORGANISM: Homo sapiens

<400> SEQUENCE: 281
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgagggca gtaagcggcc ctcaggggtt 180
tctaatcgct tctctggctc caagtctggc aacacggcct ccctgacaat ctctgggctc 240
caggctgagg acgaggctga ttattactgc tgctcatatg caggtagtag cactttcgtg 300
gtattcggcg gagggaccaa gctgaccgtc ctag 334

<210> SEQ ID NO 282
<211> LENGTH: 331
<212> TYPE: DNA
<213> ORGANISM: Homo sapiens

<400> SEQUENCE: 282
cagtctgtgc tgactcagcc accctcagcg tctgggaccc ccgggcagag ggtcaccatc 60
tcttgttctg gaagcagctc caacatcgga agtaatactg taaactggta ccagcaggtc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 283
<211> LENGTH: 331
<212> TYPE: DNA
<213> ORGANISM: Homo sapiens

<400> SEQUENCE: 283
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggttatgtc 300
ttcggaactg ggaccaaggt caccgtccta g 331

<210> SEQ ID NO 284
<211> LENGTH: 331
<212> TYPE: DNA
<213> ORGANISM: Homo sapiens

<400> SEQUENCE: 284
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggtg 300
ttcggcggag ggaccaagct gaccgtccta g 331

<210> SEQ ID NO 285
<211> LENGTH: 331
<212> TYPE: DNA
<213> ORGANISM: Homo sapiens

<400> SEQUENCE: 285
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 286
<211> LENGTH: 334
<212> TYPE: DNA
<213> ORGANISM: Homo sapiens

<400> SEQUENCE: 286
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgagggca gtaagcggcc ctcaggggtt 180
tctaatcgct tctctggctc caagtctggc aacacggcct ccctgacaat ctctgggctc 240
caggctgagg acgaggctga ttattactgc tgctcatatg caggtagtag cactttcgtg 300
gtattcggcg gagggaccaa gctgaccgtc ctag 334

<210> SEQ ID NO 287
<211> LENGTH: 331
<212> TYPE: DNA
<213> ORGANISM: Homo sapiens

<400> SEQUENCE: 287
cagtctgtgc tgactcagcc accctcagcg tctgggaccc ccgggcagag ggtcaccatc 60
tcttgttctg gaagcagctc caacatcgga agtaatgctg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttattgtgca gcatgggatg acagcctgaa tggtccggtg 300
ttcggcggag ggaccaagct gaccgtccta g 331

<210> SEQ ID NO 288
<211> LENGTH: 331
<212> TYPE: DNA
<213> ORGANISM: Homo sapiens

<400> SEQUENCE: 288
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtgtggta 300
ttcggcggag ggaccaagct gaccgtccta g 331

<210> SEQ ID NO 289
<211> LENGTH: 331
<212> TYPE: DNA
<213> ORGANISM: Homo sapiens

<400> SEQUENCE: 289
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtgtggta 300
ttcggcggag ggaccaagct gaccgtccta g 331

<210> SEQ ID NO 290
<211> LENGTH: 331
<212> TYPE: DNA
<213> ORGANISM: Homo sapiens

<400> SEQUENCE: 290
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 291
<211> LENGTH: 331
<212> TYPE: DNA

<213> ORGANISM: Homo sapiens

<400> SEQUENCE: 291

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtccggtg   300
ttcggcggag ggaccaagct gaccgtccta g                                  331
```

<210> SEQ ID NO 292
<211> LENGTH: 331
<212> TYPE: DNA
<213> ORGANISM: Homo sapiens

<400> SEQUENCE: 292

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc aggggtcccg   180
gaccgattct ctggctccaa gtctggcacc tcagcgtccc tggccatcag tgggctccag   240
tctgaggatg aggctgatta ttactgtgca gcatgggatg acagcctgaa tggtccggta   300
ttcggcggag ggaccaagct gaccgtccta g                                  331
```

<210> SEQ ID NO 293
<211> LENGTH: 331
<212> TYPE: DNA
<213> ORGANISM: Homo sapiens

<400> SEQUENCE: 293

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta tttctgtgca gcatggcatg acagcctgaa tggtcgggtg   300
ttcggcggag ggaccaagct gaccgtccta g                                  331
```

<210> SEQ ID NO 294
<211> LENGTH: 331
<212> TYPE: DNA
<213> ORGANISM: Homo sapiens

<400> SEQUENCE: 294

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtccggta   300
ttcggcggag ggaccaagct gaccgtccta g                                  331
```

<210> SEQ ID NO 295
<211> LENGTH: 331

<212> TYPE: DNA
<213> ORGANISM: Homo sapiens

<400> SEQUENCE: 295
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttcctgtgca gcatgggatg acagcctgaa tggtccggta 300
ttcggcggag ggaccaagct gaccgtccta g 331

<210> SEQ ID NO 296
<211> LENGTH: 331
<212> TYPE: DNA
<213> ORGANISM: Homo sapiens

<400> SEQUENCE: 296
cagtctgtgc tgactcagcc accctcagcg tctgggaccc ccgggcagag ggtcaccatc 60
tcttgttctg gaagcagctc caacatcgga agtaattctg taaactggta ccagcagctc 120
ccaggaacgg cccccaaact cctcatctat agtaataatc agcgcccctc aggggtccct 180
gaccgattct ctggctccaa gtctggcacc tcagcctccc tggccatcag tgggctccag 240
tctgaggatg aggctgatta tttctgtgca gcatgggatg acagcctgaa tggtccggtg 300
ttcggcggag ggaccaagct gaccgtccta g 331

<210> SEQ ID NO 297
<211> LENGTH: 331
<212> TYPE: DNA
<213> ORGANISM: Homo sapiens

<400> SEQUENCE: 297
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 298
<211> LENGTH: 331
<212> TYPE: DNA
<213> ORGANISM: Homo sapiens

<400> SEQUENCE: 298
cagtctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccgg 240
tctgaggatg aggctgatta ttactgtgca gcatgggatg acagcctgag tggtctggta 300
ttcggcggag ggaccaagct gaccgtccta g 331

<210> SEQ ID NO 299

<211> LENGTH: 331
<212> TYPE: DNA
<213> ORGANISM: Homo sapiens

<400> SEQUENCE: 299
cagtctgtgc tgactcagcc accctcagcg tctgggaccc ccgggcagag ggtcaccatc 60
tcttgttctg gaagcagctc caacatcgga agtaatgctg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgag tggtgtggta 300
ttcggcggag ggaccaagct gaccgtccta g 331

<210> SEQ ID NO 300
<211> LENGTH: 331
<212> TYPE: DNA
<213> ORGANISM: Homo sapiens

<400> SEQUENCE: 300
cagtctgtgc tgactcagcc accctcagcg tctgggaccc ccgggcagag ggtcaccatc 60
tcttgttctg gaagcagctc caacatcgga agtaatactg taaactggta ccagcttctc 120
ccaggaacgg cccccaaact cctcatctat agtaataatc agcggccctc aggggtccct 180
gaccgattct ctggctccca gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 301
<211> LENGTH: 331
<212> TYPE: DNA
<213> ORGANISM: Homo sapiens

<400> SEQUENCE: 301
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 302
<211> LENGTH: 331
<212> TYPE: DNA
<213> ORGANISM: Homo sapiens

<400> SEQUENCE: 302
cagtctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctct agtaataatc agcggccctc aggggtccct 180
gaccgattct ctggctccaa gtctggcacc tcagcctccc tggccatcag tgggctccgg 240
tctgaggatg aggctgatta ttactgtgca gcatgggatg acagcctgag tggtgtggta 300
ttcggcggag ggaccaagct gaccgtccta g 331

<210> SEQ ID NO 303
<211> LENGTH: 331
<212> TYPE: DNA
<213> ORGANISM: Homo sapiens

<400> SEQUENCE: 303
cagtctgtgc tgactcagcc tccctcagcg tctgggaccc ccgggcagag gttcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccagcag tgggctccag 240
tctgaggatg aggctgatta ttactgtgca gcatgggatg acagactgaa tggtccggtg 300
ttcggcggag ggaccaagct gaccgtccta g 331

<210> SEQ ID NO 304
<211> LENGTH: 331
<212> TYPE: DNA
<213> ORGANISM: Homo sapiens

<400> SEQUENCE: 304
cagtctgtgc tgactcagcc accctcagcg tctgggaccc ccgggcagag ggtcaccatc 60
tcttgttctg gaagcagctc caacatcgga agtaatactg taaactggta ccagcagttc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggtg 300
ttcggcggag ggaccaagct gaccgtccta g 331

<210> SEQ ID NO 305
<211> LENGTH: 331
<212> TYPE: DNA
<213> ORGANISM: Homo sapiens

<400> SEQUENCE: 305
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaagatg aggctgatta ttactgtgca gcatgggatg acagcctgaa tggtccggtg 300
ttcggcggag ggaccaagct gaccgtccta g 331

<210> SEQ ID NO 306
<211> LENGTH: 331
<212> TYPE: DNA
<213> ORGANISM: Homo sapiens

<400> SEQUENCE: 306
cagtctgtgc tgactcagcc accctcagcg tctgggaccc ccgggcagag ggtcaccatc 60
tcttgttctg gaagcagttt caacatcgga ggtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggtg 300
ttcggcggag ggaccaagct gaccgtccta g 331

<210> SEQ ID NO 307
<211> LENGTH: 331
<212> TYPE: DNA
<213> ORGANISM: Homo sapiens

<400> SEQUENCE: 307
cagtctgtgc tgactcagcc accctcagcg tctgggaccc ccgggcagag ggtcaccatc 60
tcttgttctg gaagcagctc caacatcgga agtaatactg taacctggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgag tggtccggta 300
ttcggcggag ggaccaagct gaccgtccta g 331

<210> SEQ ID NO 308
<211> LENGTH: 328
<212> TYPE: DNA
<213> ORGANISM: Homo sapiens

<400> SEQUENCE: 308
tcttctgagc tgactcagga ccctgctgtg tctgtggcct tgggacagac agtcaggatc 60
acatgccaag gagacagcct cagaagctat tatgcaagct ggtaccagca gaagccagga 120
caggccccta tacttgtcat ctatggtaaa aacaaccggc cctcagggat cccagaccga 180
ttctctggct ccagttcagg aaacacagct tccttgacca tcactggggc tcaggcggaa 240
gatgaggctg actattactg taactcccag gacaacagtg gtaaccatct agtggtattc 300
ggcagaggga ccaagctgac cgtcctag 328

<210> SEQ ID NO 309
<211> LENGTH: 331
<212> TYPE: DNA
<213> ORGANISM: Homo sapiens

<400> SEQUENCE: 309
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 310
<211> LENGTH: 331
<212> TYPE: DNA
<213> ORGANISM: Homo sapiens

<400> SEQUENCE: 310
cagtctgtgc tgactcagcc accctcagcg tctgggaccc ccgggcagag ggtcaccatc 60
tcttgttctg gaagcaattc caacatcgga agtaatactg taaattggta ccagcagctc 120
ccaggaacgg cccccagact cctcatctat agtaataatc agcggccctc aggggtccct 180
gaccgattct ctggctccaa gtctggcacc tcagcctccc tggccatcag tgggctccag 240
tctgaggatg aggctgattc ttactgtgca gcatggtatg acagcctgaa tggtccggtg 300
ttcggcggag ggaccaagct gaccgtccta g 331

<210> SEQ ID NO 311
<211> LENGTH: 331
<212> TYPE: DNA
<213> ORGANISM: Homo sapiens

<400> SEQUENCE: 311
cagtctgtgc tgactcagcc accctcagcg tctgggaccc ccgggcagag ggtcaccatc 60
tcttgttctg gaagcagctc caacatcgga agtaatactg taaactggta ccagcacctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta tttctgtgca gcatgggatg acagcctgaa tggtccggtg 300
ttcggcggag ggaccagggt gaccgtccta g 331

<210> SEQ ID NO 312
<211> LENGTH: 331
<212> TYPE: DNA
<213> ORGANISM: Homo sapiens

<400> SEQUENCE: 312
cagtctgtgt tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcaggctccc tggccatcag tgggctcaag 240
tctgaggatg aggctgatta ttactgtgca gcatgggatg acagcctgaa tggtgtggta 300
ttcggcggag ggaccaagct gaccgtccta g 331

<210> SEQ ID NO 313
<211> LENGTH: 331
<212> TYPE: DNA
<213> ORGANISM: Homo sapiens

<400> SEQUENCE: 313
cagtctgtgc tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccgg 240
tctgaggatg aggctgatta ttactgtgca gcatgggatg acagcctgag tggtgtggta 300
ttcggcggag ggaccaagtt gaccgtccta g 331

<210> SEQ ID NO 314
<211> LENGTH: 331
<212> TYPE: DNA
<213> ORGANISM: Homo sapiens

<400> SEQUENCE: 314
cagtctgtgc tgactcagcc accctcagtg tctgggaccc ccgggcagag ggtcaccatc 60
tcttgttctg gaagcagctc caacatcgga agtaacactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta tgactgtgca gcatgggatg acagcctgaa tggtccggta 300
ttcggcggag ggaccaagct gaccgtccta g 331

<210> SEQ ID NO 315
<211> LENGTH: 331
<212> TYPE: DNA
<213> ORGANISM: Homo sapiens

<400> SEQUENCE: 315
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggttgggtg 300
ttcggcggag ggaccaagct gaccgtcctg g 331

<210> SEQ ID NO 316
<211> LENGTH: 331
<212> TYPE: DNA
<213> ORGANISM: Homo sapiens

<400> SEQUENCE: 316
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggtg 300
ttcggcggag ggaccaaact gaccgtccta g 331

<210> SEQ ID NO 317
<211> LENGTH: 331
<212> TYPE: DNA
<213> ORGANISM: Homo sapiens

<400> SEQUENCE: 317
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 318
<211> LENGTH: 325
<212> TYPE: DNA
<213> ORGANISM: Homo sapiens

<400> SEQUENCE: 318
tcctatgagc tgactcagcc acactcagtg tcagtggcca cagcacagat ggccaggatc 60
acctgtgggg gaaacaacat tggaagtaaa gctgtgcact ggtaccagca aaagccaggc 120
caggaccctg tgctggtcat ctatagcgat agcaaccggc cctcagggat ccctgagcga 180
ttctctggct ccaacccagg gaacaccgcc accctaacca tcagcaggat cgaggctggg 240
gatgaggctg actattactg tcaggtgtgg gacagtagta gtgatcatcg ggtgttcggc 300
ggagggacca agctgaccgt cctag 325

<210> SEQ ID NO 319
<211> LENGTH: 331
<212> TYPE: DNA
<213> ORGANISM: Homo sapiens

<400> SEQUENCE: 319
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca ccatgggatg acagcctgaa tggtgtggta 300
ttcggcggag ggaccaagct gaccgtccta g 331

<210> SEQ ID NO 320
<211> LENGTH: 331
<212> TYPE: DNA
<213> ORGANISM: Homo sapiens

<400> SEQUENCE: 320
cagtctgtgc tgactcagcc accctcagcg tctgggaccc ccgggcagag ggtcaccatc 60
tcttgttctg gaagcagctc caacatcgga agtaatactg taaactggta ccagcaggtc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tagttgggtg 300
ttcggcggag ggaccatgct gaccgtccta g 331

<210> SEQ ID NO 321
<211> LENGTH: 331
<212> TYPE: DNA
<213> ORGANISM: Homo sapiens

<400> SEQUENCE: 321
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcacgggatg acagcctgaa tggtgtggta 300
ttcggcggag ggaccaagct gaccgtccta g 331

<210> SEQ ID NO 322
<211> LENGTH: 331
<212> TYPE: DNA
<213> ORGANISM: Homo sapiens

<400> SEQUENCE: 322
cagtctgtgc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcacgggatg acagcctgaa tggtgtggta 300
ttcggcggag ggaccaagct gaccgtccta g 331

<210> SEQ ID NO 323
<211> LENGTH: 331
<212> TYPE: DNA
<213> ORGANISM: Homo sapiens

<400> SEQUENCE: 323
cagtctgtgc tgactcagcc accctcagcg tctgggaccc ccgggcagag ggtcaccatc 60
tcttgttctg gaaccagctc caacatcgga agtaatactg tacactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtccggta 300
ttcggcggag ggaccaagct gaccgtccta g 331

<210> SEQ ID NO 324
<211> LENGTH: 331
<212> TYPE: DNA
<213> ORGANISM: Homo sapiens

<400> SEQUENCE: 324
cagtctgtgc tgactcagcc accctcagcc tctgggaccc ccgggcagag ggttaccatc 60
tcttgttctg gaagcagctc caacatcgga agtaatactg taaactggta ccagcgggtc 120
ccaggaacgg cccccaaact cctcatctat agtaatgatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtgtggta 300
ttcggcggag ggaccaagct gaccgtccta g 331

<210> SEQ ID NO 325
<211> LENGTH: 106
<212> TYPE: PRT
<213> ORGANISM: Homo sapiens

<400> SEQUENCE: 325

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asp Tyr
20 25 30

Leu Asn Trp Tyr Gln Gln Lys Pro Gly Lys Ala Pro Lys Leu Leu Ile
35 40 45

Tyr Asp Glu Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Gly Thr Tyr Tyr Cys Gln Gln Tyr Asp Asn Leu Leu Thr
85 90 95

Phe Gly Pro Gly Thr Lys Val Asp Ile Lys
100 105

<210> SEQ ID NO 326
<211> LENGTH: 113
<212> TYPE: PRT
<213> ORGANISM: Homo sapiens

<400> SEQUENCE: 326

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Phe Leu Gln Lys Pro Gly Gln
35 40 45

Ser Pro Gln Leu Leu Ile Tyr Thr Leu Ser Tyr Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Asp Asp Val Gly Val Tyr Tyr Cys Met Gln
85 90 95

Arg Ile Glu Phe Pro Phe Thr Phe Gly Gln Gly Thr Lys Leu Glu Ile
100 105 110

Lys

<210> SEQ ID NO 327
<211> LENGTH: 113
<212> TYPE: PRT
<213> ORGANISM: Homo sapiens

<400> SEQUENCE: 327

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Lys Lys Asn Tyr Leu Thr Trp Tyr Gln Gln Lys Val Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Phe Thr Phe Gly Gly Gly Thr Lys Val Glu Ile
100 105 110

Lys

<210> SEQ ID NO 328
<211> LENGTH: 107
<212> TYPE: PRT
<213> ORGANISM: Homo sapiens

<400> SEQUENCE: 328

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

```
Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 329
<211> LENGTH: 107
<212> TYPE: PRT
<213> ORGANISM: Homo sapiens

<400> SEQUENCE: 329

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 330
<211> LENGTH: 112
<212> TYPE: PRT
<213> ORGANISM: Homo sapiens

<400> SEQUENCE: 330

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Glu Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 331
<211> LENGTH: 107
<212> TYPE: PRT
<213> ORGANISM: Homo sapiens

<400> SEQUENCE: 331

Asp Ile Gln Met Thr Gln Ser Pro Ser Ser Val Ser Ala Ser Val Gly
1               5                   10                  15

Asp Arg Val Thr Ile Thr Cys Arg Ala Ser Pro Gly Ile Ser Ser Trp
            20                  25                  30

Leu Ala Trp Tyr Gln Gln Lys Pro Glu Lys Ala Pro Lys Leu Leu Ile
```

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Phe Pro Tyr
                85                  90                  95

Thr Phe Gly Gln Gly Thr Lys Leu Glu Ile Lys
            100                 105


<210> SEQ ID NO 332
<211> LENGTH: 113
<212> TYPE: PRT
<213> ORGANISM: Homo sapiens

<400> SEQUENCE: 332

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Phe Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210> SEQ ID NO 333
<211> LENGTH: 106
<212> TYPE: PRT
<213> ORGANISM: Homo sapiens

<400> SEQUENCE: 333

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Met Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105


<210> SEQ ID NO 334
<211> LENGTH: 107
<212> TYPE: PRT
<213> ORGANISM: Homo sapiens
```

<400> SEQUENCE: 334

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asp Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Pro
85 90 95

Thr Phe Gly Gly Gly Thr Lys Val Glu Ile Lys
100 105

<210> SEQ ID NO 335
<211> LENGTH: 107
<212> TYPE: PRT
<213> ORGANISM: Homo sapiens

<400> SEQUENCE: 335

Ala Ile Arg Met Thr Gln Ser Pro Ser Ser Phe Ser Ala Ser Thr Gly
1 5 10 15

Asp Arg Val Thr Ile Thr Cys Arg Ala Ser Gln Gly Ile Ser Ser Tyr
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Cys Leu Gln Ser
65 70 75 80

Glu Asp Phe Ala Thr Tyr Tyr Cys Gln Gln Tyr Tyr Ser Tyr Pro Phe
85 90 95

Thr Phe Gly Pro Gly Thr Lys Val Asp Ile Lys
100 105

<210> SEQ ID NO 336
<211> LENGTH: 112
<212> TYPE: PRT
<213> ORGANISM: Homo sapiens

<400> SEQUENCE: 336

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Tyr Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 337
<211> LENGTH: 106
<212> TYPE: PRT
<213> ORGANISM: Homo sapiens

<400> SEQUENCE: 337

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Arg Lys Pro Gly Lys Ala Pro Lys Leu Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Phe Asn Ser Tyr Trp Thr
85 90 95

Phe Gly Gln Gly Thr Lys Val Glu Ile Lys
100 105

<210> SEQ ID NO 338
<211> LENGTH: 106
<212> TYPE: PRT
<213> ORGANISM: Homo sapiens

<400> SEQUENCE: 338

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Trp Thr
85 90 95

Phe Gly Gln Gly Thr Lys Val Glu Ile Lys
100 105

<210> SEQ ID NO 339
<211> LENGTH: 113
<212> TYPE: PRT
<213> ORGANISM: Homo sapiens

<400> SEQUENCE: 339

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Tyr Leu Gln Lys Pro Gly Gln
35 40 45

Ser Pro Gln Leu Leu Ile Tyr Thr Leu Ser Tyr Arg Ala Ser Gly Val

```
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Ser Thr Phe Gly Gln Gly Thr Arg Leu Glu Ile
            100                 105                 110

Lys


<210> SEQ ID NO 340
<211> LENGTH: 106
<212> TYPE: PRT
<213> ORGANISM: Homo sapiens

<400> SEQUENCE: 340

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asp Trp
            20                  25                  30

Leu Ala Trp Tyr Leu Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Ala Phe Thr Leu Thr Ile Ser Ser Leu Gln Pro
65                  70                  75                  80

Asp Asp Phe Ala Thr Tyr Tyr Cys Gln Gln Tyr Asn Ser His Trp Thr
                85                  90                  95

Phe Gly Gln Gly Thr Lys Val Glu Ile Lys
            100                 105


<210> SEQ ID NO 341
<211> LENGTH: 108
<212> TYPE: PRT
<213> ORGANISM: Homo sapiens

<400> SEQUENCE: 341

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105


<210> SEQ ID NO 342
<211> LENGTH: 107
<212> TYPE: PRT
<213> ORGANISM: Homo sapiens

<400> SEQUENCE: 342
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105


<210> SEQ ID NO 343
<211> LENGTH: 108
<212> TYPE: PRT
<213> ORGANISM: Homo sapiens

<400> SEQUENCE: 343

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105


<210> SEQ ID NO 344
<211> LENGTH: 113
<212> TYPE: PRT
<213> ORGANISM: Homo sapiens

<400> SEQUENCE: 344

Asp Ile Val Met Thr Gln Ser Pro Asp Ser Leu Ala Val Ser Leu Gly
1               5                   10                  15

Glu Gly Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Ala Val Tyr Tyr Cys Gln Gln
                85                  90                  95

Tyr Tyr Tyr Thr Pro Tyr Thr Phe Gly Gln Gly Thr Lys Leu Glu Ile
            100                 105                 110
```

Lys

<210> SEQ ID NO 345
<211> LENGTH: 108
<212> TYPE: PRT
<213> ORGANISM: Homo sapiens

<400> SEQUENCE: 345

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Tyr Thr Phe Gly Gln Gly Thr Lys Leu Glu Ile Lys
100 105

<210> SEQ ID NO 346
<211> LENGTH: 113
<212> TYPE: PRT
<213> ORGANISM: Homo sapiens

<400> SEQUENCE: 346

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ser Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Leu Thr Phe Gly Gly Gly Thr Lys Val Glu Ile
100 105 110

Lys

<210> SEQ ID NO 347
<211> LENGTH: 108
<212> TYPE: PRT
<213> ORGANISM: Homo sapiens

<400> SEQUENCE: 347

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Leu
85 90 95

Phe Thr Phe Gly Pro Gly Thr Lys Val Asp Ile Lys
100 105

<210> SEQ ID NO 348
<211> LENGTH: 113
<212> TYPE: PRT
<213> ORGANISM: Homo sapiens

<400> SEQUENCE: 348

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Val Leu Ile Tyr Trp Ala Ser Ile Arg Glu Ser Gly Val
50 55 60

Ser Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Tyr Thr Phe Gly Gln Gly Thr Lys Leu Glu Ile
100 105 110

Lys

<210> SEQ ID NO 349
<211> LENGTH: 113
<212> TYPE: PRT
<213> ORGANISM: Homo sapiens

<400> SEQUENCE: 349

Asp Ile Val Met Thr Gln Ser Pro Asp Ser Leu Ala Val Ser Leu Gly
1 5 10 15

Glu Arg Ala Thr Ile Asn Cys Lys Ser Ser Gln Thr Val Leu Tyr Ser
20 25 30

Ser Asp Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Arg Thr Phe Gly Gln Gly Thr Lys Val Glu Ile
100 105 110

Lys

<210> SEQ ID NO 350
<211> LENGTH: 108
<212> TYPE: PRT
<213> ORGANISM: Homo sapiens

<400> SEQUENCE: 350

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Ile Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Tyr Thr Phe Gly Gln Gly Thr Lys Leu Glu Ile Lys
100 105

<210> SEQ ID NO 351
<211> LENGTH: 106
<212> TYPE: PRT
<213> ORGANISM: Homo sapiens

<400> SEQUENCE: 351

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Val Ser Ser Leu Gln Pro
65 70 75 80

Asp Asp Phe Ala Thr Tyr Tyr Cys Gln Gln Tyr Asn Ser Tyr Trp Thr
85 90 95

Phe Gly Gln Gly Thr Lys Val Glu Ile Lys
100 105

<210> SEQ ID NO 352
<211> LENGTH: 107
<212> TYPE: PRT
<213> ORGANISM: Homo sapiens

<400> SEQUENCE: 352

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Gly Ile Ser Ser Tyr
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Leu Asn Thr Tyr Pro Arg
85 90 95

```
Thr Phe Gly Gln Gly Thr Lys Val Glu Ile Lys
            100                 105


<210> SEQ ID NO 353
<211> LENGTH: 107
<212> TYPE: PRT
<213> ORGANISM: Homo sapiens

<400> SEQUENCE: 353

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Phe Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105


<210> SEQ ID NO 354
<211> LENGTH: 112
<212> TYPE: PRT
<213> ORGANISM: Homo sapiens

<400> SEQUENCE: 354

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Asp Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Thr
                85                  90                  95

Leu Gln Thr Pro Tyr Thr Phe Gly Gln Gly Thr Lys Leu Glu Ile Lys
            100                 105                 110


<210> SEQ ID NO 355
<211> LENGTH: 112
<212> TYPE: PRT
<213> ORGANISM: Homo sapiens

<400> SEQUENCE: 355

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Glu Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 356
<211> LENGTH: 112
<212> TYPE: PRT
<213> ORGANISM: Homo sapiens

<400> SEQUENCE: 356

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 357
<211> LENGTH: 113
<212> TYPE: PRT
<213> ORGANISM: Homo sapiens

<400> SEQUENCE: 357

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys


<210> SEQ ID NO 358
<211> LENGTH: 107
<212> TYPE: PRT
<213> ORGANISM: Homo sapiens

<400> SEQUENCE: 358
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys
            100                 105


<210> SEQ ID NO 359
<211> LENGTH: 113
<212> TYPE: PRT
<213> ORGANISM: Homo sapiens

<400> SEQUENCE: 359

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Tyr Thr Phe Gly Gln Gly Thr Lys Leu Glu Ile
            100                 105                 110

Lys


<210> SEQ ID NO 360
<211> LENGTH: 112
<212> TYPE: PRT
<213> ORGANISM: Homo sapiens

<400> SEQUENCE: 360

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
```

100 105 110

<210> SEQ ID NO 361
<211> LENGTH: 113
<212> TYPE: PRT
<213> ORGANISM: Homo sapiens

<400> SEQUENCE: 361

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Arg Thr Met Tyr Thr Phe Gly Gln Gly Thr Lys Leu Glu Ile
100 105 110

Lys

<210> SEQ ID NO 362
<211> LENGTH: 112
<212> TYPE: PRT
<213> ORGANISM: Homo sapiens

<400> SEQUENCE: 362

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Ser Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Thr
85 90 95

Leu Gln Ile Pro Tyr Thr Phe Gly Gln Gly Thr Lys Leu Glu Ile Lys
100 105 110

<210> SEQ ID NO 363
<211> LENGTH: 113
<212> TYPE: PRT
<213> ORGANISM: Homo sapiens

<400> SEQUENCE: 363

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Tyr Leu Gln Lys Pro Gly Gln
35 40 45

```
Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Ile
            100                 105                 110

Lys


<210> SEQ ID NO 364
<211> LENGTH: 113
<212> TYPE: PRT
<213> ORGANISM: Homo sapiens

<400> SEQUENCE: 364

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Ile Thr Phe Gly Gln Gly Thr Arg Leu Glu Ile
            100                 105                 110

Lys


<210> SEQ ID NO 365
<211> LENGTH: 113
<212> TYPE: PRT
<213> ORGANISM: Homo sapiens

<400> SEQUENCE: 365

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Trp Thr Phe Gly Gln Gly Thr Lys Glu Leu Trp
            100                 105                 110

Leu


<210> SEQ ID NO 366
<211> LENGTH: 107
```

-continued

<212> TYPE: PRT
<213> ORGANISM: Homo sapiens

<400> SEQUENCE: 366

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Phe
                85                  90                  95

Thr Val Gly Pro Gly Thr Lys Val Asp Ile Lys
            100                 105

<210> SEQ ID NO 367
<211> LENGTH: 112
<212> TYPE: PRT
<213> ORGANISM: Homo sapiens

<400> SEQUENCE: 367

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Leu Gln Thr Pro Leu Thr Phe Gly Gly Gly Thr Lys Val Glu Ile Lys
            100                 105                 110

<210> SEQ ID NO 368
<211> LENGTH: 113
<212> TYPE: PRT
<213> ORGANISM: Homo sapiens

<400> SEQUENCE: 368

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln

```
                85                  90                  95

Arg Ile Glu Phe Pro Tyr Thr Phe Gly Gln Gly Thr Lys Leu Glu Ile
            100                 105                 110

Lys


<210> SEQ ID NO 369
<211> LENGTH: 112
<212> TYPE: PRT
<213> ORGANISM: Homo sapiens

<400> SEQUENCE: 369

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ile Leu Gly Gly Gly Thr Lys Val Glu Ile Lys
            100                 105                 110


<210> SEQ ID NO 370
<211> LENGTH: 108
<212> TYPE: PRT
<213> ORGANISM: Homo sapiens

<400> SEQUENCE: 370

Glu Ile Val Leu Thr Gln Ser Pro Gly Thr Leu Ser Leu Pro Pro Gly
1               5                   10                  15

Glu Arg Ala Thr Leu Ser Cys Arg Ala Ser Gln Asn Val Ser Ser Thr
            20                  25                  30

Tyr Leu Ala Trp Tyr His Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105


<210> SEQ ID NO 371
<211> LENGTH: 108
<212> TYPE: PRT
<213> ORGANISM: Homo sapiens

<400> SEQUENCE: 371

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Leu Thr Phe Gly Gly Gly Thr Lys Val Glu Ile Lys
            100                 105


<210> SEQ ID NO 372
<211> LENGTH: 112
<212> TYPE: PRT
<213> ORGANISM: Homo sapiens

<400> SEQUENCE: 372

Asp Ile Val Met Thr Gln Ser Pro Ile Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110


<210> SEQ ID NO 373
<211> LENGTH: 110
<212> TYPE: PRT
<213> ORGANISM: Homo sapiens

<400> SEQUENCE: 373

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 374
<211> LENGTH: 110
<212> TYPE: PRT
<213> ORGANISM: Homo sapiens
```

<400> SEQUENCE: 374

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Asp Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 375
<211> LENGTH: 110
<212> TYPE: PRT
<213> ORGANISM: Homo sapiens

<400> SEQUENCE: 375

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Gly Arg Phe Ser
50 55 60

Gly Ser Lys Ser Gly Thr Ser Ala Ser Leu Ala Ile Ser Gly Leu Gln
65 70 75 80

Ser Asp Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 376
<211> LENGTH: 110
<212> TYPE: PRT
<213> ORGANISM: Homo sapiens

<400> SEQUENCE: 376

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Ser Val Asn Trp Phe Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu 100 105 110

<210> SEQ ID NO 377
<211> LENGTH: 110
<212> TYPE: PRT
<213> ORGANISM: Homo sapiens

<400> SEQUENCE: 377

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 378
<211> LENGTH: 110
<212> TYPE: PRT
<213> ORGANISM: Homo sapiens

<400> SEQUENCE: 378

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Ala Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 379
<211> LENGTH: 110
<212> TYPE: PRT
<213> ORGANISM: Homo sapiens

<400> SEQUENCE: 379

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Phe Pro Gly Thr Ala Pro Lys Leu Leu
35 40 45

Ile Tyr Ser Asn Asn Gln Arg Pro Ser Gly Val Pro Asp Arg Phe Ser
50 55 60

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 380
<211> LENGTH: 110
<212> TYPE: PRT
<213> ORGANISM: Homo sapiens

<400> SEQUENCE: 380

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 381
<211> LENGTH: 110
<212> TYPE: PRT
<213> ORGANISM: Homo sapiens

<400> SEQUENCE: 381

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Asn Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 382
<211> LENGTH: 110
<212> TYPE: PRT
<213> ORGANISM: Homo sapiens

<400> SEQUENCE: 382

Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Asn Leu Thr Val Leu
            100                 105                 110


<210> SEQ ID NO 383
<211> LENGTH: 110
<212> TYPE: PRT
<213> ORGANISM: Homo sapiens

<400> SEQUENCE: 383

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 384
<211> LENGTH: 110
<212> TYPE: PRT
<213> ORGANISM: Homo sapiens

<400> SEQUENCE: 384

Gln Ser Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110


<210> SEQ ID NO 385
<211> LENGTH: 110
```

<212> TYPE: PRT
<213> ORGANISM: Homo sapiens

<400> SEQUENCE: 385

Gln Ser Val Leu Thr Gln Pro Pro Ser Ala Ser Gly Thr Pro Gly Gln
1               5                   10                  15

Arg Val Thr Leu Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Leu
65                  70                  75                  80

Ser Glu Asp Glu Ala Asp Tyr Tyr Cys Ala Ala Trp His Asp Ser Leu
                85                  90                  95

Asn Gly Val Val Phe Gly Gly Gly Thr Lys Leu Thr Val Leu
            100                 105                 110

<210> SEQ ID NO 386
<211> LENGTH: 109
<212> TYPE: PRT
<213> ORGANISM: Homo sapiens

<400> SEQUENCE: 386

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu
            100                 105

<210> SEQ ID NO 387
<211> LENGTH: 110
<212> TYPE: PRT
<213> ORGANISM: Homo sapiens

<400> SEQUENCE: 387

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Phe Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu

```
                85                  90                  95

Asn Gly Val Val Phe Gly Gly Gly Thr Lys Leu Thr Val Leu
            100                 105                 110


<210> SEQ ID NO 388
<211> LENGTH: 110
<212> TYPE: PRT
<213> ORGANISM: Homo sapiens

<400> SEQUENCE: 388

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 389
<211> LENGTH: 111
<212> TYPE: PRT
<213> ORGANISM: Homo sapiens

<400> SEQUENCE: 389

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Val Val Phe Gly Gly Gly Thr Lys Leu Thr Val Leu
            100                 105                 110


<210> SEQ ID NO 390
<211> LENGTH: 110
<212> TYPE: PRT
<213> ORGANISM: Homo sapiens

<400> SEQUENCE: 390

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45
```

```
Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 391
<211> LENGTH: 110
<212> TYPE: PRT
<213> ORGANISM: Homo sapiens

<400> SEQUENCE: 391

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110


<210> SEQ ID NO 392
<211> LENGTH: 110
<212> TYPE: PRT
<213> ORGANISM: Homo sapiens

<400> SEQUENCE: 392

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 393
<211> LENGTH: 110
<212> TYPE: PRT
<213> ORGANISM: Homo sapiens

<400> SEQUENCE: 393
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 394
<211> LENGTH: 111
<212> TYPE: PRT
<213> ORGANISM: Homo sapiens

<400> SEQUENCE: 394

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Val Val Phe Gly Gly Gly Thr Lys Leu Thr Val Leu
            100                 105                 110


<210> SEQ ID NO 395
<211> LENGTH: 110
<212> TYPE: PRT
<213> ORGANISM: Homo sapiens

<400> SEQUENCE: 395

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 396
<211> LENGTH: 110
<212> TYPE: PRT
<213> ORGANISM: Homo sapiens

<400> SEQUENCE: 396

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 397
<211> LENGTH: 110
<212> TYPE: PRT
<213> ORGANISM: Homo sapiens

<400> SEQUENCE: 397

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 398
<211> LENGTH: 110
<212> TYPE: PRT
<213> ORGANISM: Homo sapiens

<400> SEQUENCE: 398

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
```

```
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 399
<211> LENGTH: 110
<212> TYPE: PRT
<213> ORGANISM: Homo sapiens

<400> SEQUENCE: 399

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 400
<211> LENGTH: 110
<212> TYPE: PRT
<213> ORGANISM: Homo sapiens

<400> SEQUENCE: 400

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 401
<211> LENGTH: 110
<212> TYPE: PRT
<213> ORGANISM: Homo sapiens

<400> SEQUENCE: 401

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp His Asp Ser Leu
                85                  90                  95

Asn Gly Arg Val Phe Gly Gly Gly Thr Lys Leu Thr Val Leu
            100                 105                 110


<210> SEQ ID NO 402
<211> LENGTH: 110
<212> TYPE: PRT
<213> ORGANISM: Homo sapiens

<400> SEQUENCE: 402

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 403
<211> LENGTH: 110
<212> TYPE: PRT
<213> ORGANISM: Homo sapiens

<400> SEQUENCE: 403

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Ser Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 404
<211> LENGTH: 110
<212> TYPE: PRT
<213> ORGANISM: Homo sapiens
```

<400> SEQUENCE: 404

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Ser Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Phe Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 405
<211> LENGTH: 110
<212> TYPE: PRT
<213> ORGANISM: Homo sapiens

<400> SEQUENCE: 405

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 406
<211> LENGTH: 110
<212> TYPE: PRT
<213> ORGANISM: Homo sapiens

<400> SEQUENCE: 406

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Tyr Val Tyr Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

```
Ser Gly Leu Val Phe Gly Gly Gly Thr Lys Leu Thr Val Leu
            100                 105                 110


<210> SEQ ID NO 407
<211> LENGTH: 110
<212> TYPE: PRT
<213> ORGANISM: Homo sapiens

<400> SEQUENCE: 407

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110


<210> SEQ ID NO 408
<211> LENGTH: 110
<212> TYPE: PRT
<213> ORGANISM: Homo sapiens

<400> SEQUENCE: 408

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Leu Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Gln Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 409
<211> LENGTH: 110
<212> TYPE: PRT
<213> ORGANISM: Homo sapiens

<400> SEQUENCE: 409

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
```

```
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 410
<211> LENGTH: 110
<212> TYPE: PRT
<213> ORGANISM: Homo sapiens

<400> SEQUENCE: 410

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Ser Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110


<210> SEQ ID NO 411
<211> LENGTH: 110
<212> TYPE: PRT
<213> ORGANISM: Homo sapiens

<400> SEQUENCE: 411

Gln Ser Val Leu Thr Gln Pro Pro Ser Ala Ser Gly Thr Pro Gly Gln
1               5                   10                  15

Arg Phe Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ser Ser Gly Leu Gln
65                  70                  75                  80

Ser Glu Asp Glu Ala Asp Tyr Tyr Cys Ala Ala Trp Asp Asp Arg Leu
                85                  90                  95

Asn Gly Pro Val Phe Gly Gly Gly Thr Lys Leu Thr Val Leu
            100                 105                 110


<210> SEQ ID NO 412
<211> LENGTH: 110
<212> TYPE: PRT
<213> ORGANISM: Homo sapiens

<400> SEQUENCE: 412

Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 413
<211> LENGTH: 110
<212> TYPE: PRT
<213> ORGANISM: Homo sapiens

<400> SEQUENCE: 413

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 414
<211> LENGTH: 110
<212> TYPE: PRT
<213> ORGANISM: Homo sapiens

<400> SEQUENCE: 414

Gln Ser Val Leu Thr Gln Pro Pro Ser Ala Ser Gly Thr Pro Gly Gln
1               5                   10                  15

Arg Val Thr Ile Ser Cys Ser Gly Ser Ser Phe Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 415
```

<211> LENGTH: 110
<212> TYPE: PRT
<213> ORGANISM: Homo sapiens

<400> SEQUENCE: 415

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Thr Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Ser Gly Pro Val Phe Gly Gly Gly Thr Lys Leu Thr Val Leu
100 105 110

<210> SEQ ID NO 416
<211> LENGTH: 109
<212> TYPE: PRT
<213> ORGANISM: Homo sapiens

<400> SEQUENCE: 416

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Ile Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Gln Asp Asn Ser Gly Asn His
85 90 95

Leu Val Val Phe Gly Arg Gly Thr Lys Leu Thr Val Leu
100 105

<210> SEQ ID NO 417
<211> LENGTH: 110
<212> TYPE: PRT
<213> ORGANISM: Homo sapiens

<400> SEQUENCE: 417

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

```
Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 418
<211> LENGTH: 110
<212> TYPE: PRT
<213> ORGANISM: Homo sapiens

<400> SEQUENCE: 418

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr Gln Gln Leu Pro Gly Thr Ala Pro Arg Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Ser Tyr Cys Ala Ala Trp Tyr Asp Ser Leu
                85                  90                  95

Asn Gly Pro Val Phe Gly Gly Gly Thr Lys Leu Thr Val Leu
            100                 105                 110


<210> SEQ ID NO 419
<211> LENGTH: 110
<212> TYPE: PRT
<213> ORGANISM: Homo sapiens

<400> SEQUENCE: 419

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln His Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Gly Pro Val Phe Gly Gly Gly Thr Arg Val Thr Val Leu
            100                 105                 110


<210> SEQ ID NO 420
<211> LENGTH: 110
<212> TYPE: PRT
<213> ORGANISM: Homo sapiens

<400> SEQUENCE: 420

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
```

```
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Gly Ser Leu Ala Ile Ser Gly Leu Lys
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 421
<211> LENGTH: 110
<212> TYPE: PRT
<213> ORGANISM: Homo sapiens

<400> SEQUENCE: 421

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110


<210> SEQ ID NO 422
<211> LENGTH: 110
<212> TYPE: PRT
<213> ORGANISM: Homo sapiens

<400> SEQUENCE: 422

Gln Ser Val Leu Thr Gln Pro Pro Ser Val Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Asp Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 423
<211> LENGTH: 110
<212> TYPE: PRT
<213> ORGANISM: Homo sapiens

<400> SEQUENCE: 423
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110


<210> SEQ ID NO 424
<211> LENGTH: 110
<212> TYPE: PRT
<213> ORGANISM: Homo sapiens

<400> SEQUENCE: 424

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 425
<211> LENGTH: 110
<212> TYPE: PRT
<213> ORGANISM: Homo sapiens

<400> SEQUENCE: 425

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 426
<211> LENGTH: 108
<212> TYPE: PRT
<213> ORGANISM: Homo sapiens

<400> SEQUENCE: 426

```
Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
            20                  25                  30

His Trp Tyr Gln Gln Lys Pro Gly Gln Asp Pro Val Leu Val Ile Tyr
        35                  40                  45

Ser Asp Ser Asn Arg Pro Ser Gly Ile Pro Glu Arg Phe Ser Gly Ser
    50                  55                  60

Asn Pro Gly Asn Thr Ala Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
                85                  90                  95

Arg Val Phe Gly Gly Gly Thr Lys Leu Thr Val Leu
            100                 105
```

<210> SEQ ID NO 427
<211> LENGTH: 110
<212> TYPE: PRT
<213> ORGANISM: Homo sapiens

<400> SEQUENCE: 427

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Pro Trp Asp Asp Ser Leu
                85                  90                  95

Asn Gly Val Val Phe Gly Gly Gly Thr Lys Leu Thr Val Leu
            100                 105                 110
```

<210> SEQ ID NO 428
<211> LENGTH: 110
<212> TYPE: PRT
<213> ORGANISM: Homo sapiens

<400> SEQUENCE: 428

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60
```

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ser Trp Val Phe Gly Gly Gly Thr Met Leu Thr Val Leu
            100                 105                 110


<210> SEQ ID NO 429
<211> LENGTH: 110
<212> TYPE: PRT
<213> ORGANISM: Homo sapiens

<400> SEQUENCE: 429

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Arg Asp Asp Ser Leu
                85                  90                  95

Asn Gly Val Val Phe Gly Gly Gly Thr Lys Leu Thr Val Leu
            100                 105                 110


<210> SEQ ID NO 430
<211> LENGTH: 110
<212> TYPE: PRT
<213> ORGANISM: Homo sapiens

<400> SEQUENCE: 430

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Arg Asp Asp Ser Leu
                85                  90                  95

Asn Gly Val Val Phe Gly Gly Gly Thr Lys Leu Thr Val Leu
            100                 105                 110


<210> SEQ ID NO 431
<211> LENGTH: 110
<212> TYPE: PRT
<213> ORGANISM: Homo sapiens

<400> SEQUENCE: 431

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Asn
```

```
            20                  25                  30

Thr Val His Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 432
<211> LENGTH: 110
<212> TYPE: PRT
<213> ORGANISM: Homo sapiens

<400> SEQUENCE: 432

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Arg Val Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 433
<211> LENGTH: 24
<212> TYPE: DNA
<213> ORGANISM: Artificial Sequence
<220> FEATURE:
<223> OTHER INFORMATION: Synthesized primer

<400> SEQUENCE: 433

ggttcgggga agtagtcctt gacc                                          24


<210> SEQ ID NO 434
<211> LENGTH: 29
<212> TYPE: DNA
<213> ORGANISM: Artificial Sequence
<220> FEATURE:
<223> OTHER INFORMATION: Synthesized primer

<400> SEQUENCE: 434

ctgtagcttc tgtgggactt ccactgctc                                     29


<210> SEQ ID NO 435
<211> LENGTH: 22
<212> TYPE: DNA
<213> ORGANISM: Artificial Sequence
<220> FEATURE:
<223> OTHER INFORMATION: Synthesized primer

<400> SEQUENCE: 435
```

ccgattggag ggcgttatcc ac 22

<210> SEQ ID NO 436
<211> LENGTH: 8
<212> TYPE: PRT
<213> ORGANISM: Homo sapiens

<400> SEQUENCE: 436

Gly Phe Thr Phe Ser Asn Ala Trp
1 5

<210> SEQ ID NO 437
<211> LENGTH: 8
<212> TYPE: PRT
<213> ORGANISM: Homo sapiens

<400> SEQUENCE: 437

Gly Tyr Thr Phe Thr Gly Tyr Tyr
1 5

<210> SEQ ID NO 438
<211> LENGTH: 8
<212> TYPE: PRT
<213> ORGANISM: Homo sapiens

<400> SEQUENCE: 438

Gly Phe Thr Phe Ser Asn Ala Trp
1 5

<210> SEQ ID NO 439
<211> LENGTH: 8
<212> TYPE: PRT
<213> ORGANISM: Homo sapiens

<400> SEQUENCE: 439

Gly Gly Ser Ile Ser Ser Tyr Tyr
1 5

<210> SEQ ID NO 440
<211> LENGTH: 8
<212> TYPE: PRT
<213> ORGANISM: Homo sapiens

<400> SEQUENCE: 440

Gly Gly Ser Ile Ser Ser Tyr Tyr
1 5

<210> SEQ ID NO 441
<211> LENGTH: 8
<212> TYPE: PRT
<213> ORGANISM: Homo sapiens

<400> SEQUENCE: 441

Gly Phe Thr Phe Gly Asp Tyr Ala
1 5

<210> SEQ ID NO 442
<211> LENGTH: 8
<212> TYPE: PRT
<213> ORGANISM: Homo sapiens

<400> SEQUENCE: 442

Gly Tyr Thr Phe Thr Gly Tyr Tyr
1 5

<210> SEQ ID NO 443
<211> LENGTH: 8
<212> TYPE: PRT
<213> ORGANISM: Homo sapiens

<400> SEQUENCE: 443

Gly Phe Thr Phe Ser Asn Ala Trp
1               5

<210> SEQ ID NO 444
<211> LENGTH: 8
<212> TYPE: PRT
<213> ORGANISM: Homo sapiens

<400> SEQUENCE: 444

Gly Gly Ser Ile Ser Ser Ser Tyr
1               5

<210> SEQ ID NO 445
<211> LENGTH: 8
<212> TYPE: PRT
<213> ORGANISM: Homo sapiens

<400> SEQUENCE: 445

Arg Phe Thr Phe Ser Ser Tyr Ser
1               5

<210> SEQ ID NO 446
<211> LENGTH: 10
<212> TYPE: PRT
<213> ORGANISM: Homo sapiens

<400> SEQUENCE: 446

Gly Phe Ser Leu Ser Thr Ser Gly Met Cys
1               5                   10

<210> SEQ ID NO 447
<211> LENGTH: 8
<212> TYPE: PRT
<213> ORGANISM: Homo sapiens

<400> SEQUENCE: 447

Gly Gly Ser Ile Ser Ser Tyr Tyr
1               5

<210> SEQ ID NO 448
<211> LENGTH: 8
<212> TYPE: PRT
<213> ORGANISM: Homo sapiens

<400> SEQUENCE: 448

Gly Gly Ser Ile Ser Ser Tyr Tyr
1               5

<210> SEQ ID NO 449
<211> LENGTH: 8
<212> TYPE: PRT
<213> ORGANISM: Homo sapiens

<400> SEQUENCE: 449

Gly Gly Ser Ile Ser Ser Tyr Tyr
1               5

<210> SEQ ID NO 450
<211> LENGTH: 8
<212> TYPE: PRT
<213> ORGANISM: Homo sapiens

<400> SEQUENCE: 450

Gly Tyr Thr Phe Thr Gly Tyr Tyr
1 5

<210> SEQ ID NO 451
<211> LENGTH: 8
<212> TYPE: PRT
<213> ORGANISM: Homo sapiens

<400> SEQUENCE: 451

Gly Gly Ser Ile Ser Ser Tyr Tyr
1 5

<210> SEQ ID NO 452
<211> LENGTH: 8
<212> TYPE: PRT
<213> ORGANISM: Homo sapiens

<400> SEQUENCE: 452

Gly Gly Ser Ile Ser Ser Tyr Tyr
1 5

<210> SEQ ID NO 453
<211> LENGTH: 8
<212> TYPE: PRT
<213> ORGANISM: Homo sapiens

<400> SEQUENCE: 453

Gly Phe Thr Phe Ser Ser Tyr Asp
1 5

<210> SEQ ID NO 454
<211> LENGTH: 8
<212> TYPE: PRT
<213> ORGANISM: Homo sapiens

<400> SEQUENCE: 454

Gly Gly Ser Cys Ser Ala Tyr Tyr
1 5

<210> SEQ ID NO 455
<211> LENGTH: 8
<212> TYPE: PRT
<213> ORGANISM: Homo sapiens

<400> SEQUENCE: 455

Gly Phe Thr Phe Ser Asn Ala Trp
1 5

<210> SEQ ID NO 456
<211> LENGTH: 8
<212> TYPE: PRT
<213> ORGANISM: Homo sapiens

<400> SEQUENCE: 456

Gly Gly Ser Phe Ser Ala Tyr Tyr
1 5

<210> SEQ ID NO 457
<211> LENGTH: 8

<212> TYPE: PRT
<213> ORGANISM: Homo sapiens

<400> SEQUENCE: 457

Gly Phe Thr Phe Ser Ser Tyr Trp
1 5

<210> SEQ ID NO 458
<211> LENGTH: 8
<212> TYPE: PRT
<213> ORGANISM: Homo sapiens

<400> SEQUENCE: 458

Gly Phe Thr Phe Ser Ser Tyr Ser
1 5

<210> SEQ ID NO 459
<211> LENGTH: 10
<212> TYPE: PRT
<213> ORGANISM: Homo sapiens

<400> SEQUENCE: 459

Gly Phe Ser Leu Ser Thr Ser Gly Val Gly
1 5 10

<210> SEQ ID NO 460
<211> LENGTH: 8
<212> TYPE: PRT
<213> ORGANISM: Homo sapiens

<400> SEQUENCE: 460

Gly Tyr Thr Phe Thr Gly Tyr Tyr
1 5

<210> SEQ ID NO 461
<211> LENGTH: 8
<212> TYPE: PRT
<213> ORGANISM: Homo sapiens

<400> SEQUENCE: 461

Gly Gly Ser Ile Ser Ser Tyr Tyr
1 5

<210> SEQ ID NO 462
<211> LENGTH: 8
<212> TYPE: PRT
<213> ORGANISM: Homo sapiens

<400> SEQUENCE: 462

Gly Gly Ser Ile Ser Ser Tyr Tyr
1 5

<210> SEQ ID NO 463
<211> LENGTH: 8
<212> TYPE: PRT
<213> ORGANISM: Homo sapiens

<400> SEQUENCE: 463

Gly Phe Thr Phe Ser Ser Tyr Asn
1 5

<210> SEQ ID NO 464
<211> LENGTH: 8
<212> TYPE: PRT
<213> ORGANISM: Homo sapiens

<400> SEQUENCE: 464

Gly Gly Ser Ile Ser Ser Tyr Tyr
1 5

<210> SEQ ID NO 465
<211> LENGTH: 8
<212> TYPE: PRT
<213> ORGANISM: Homo sapiens

<400> SEQUENCE: 465

Gly Phe Thr Phe Ser Ser Tyr Ser
1 5

<210> SEQ ID NO 466
<211> LENGTH: 8
<212> TYPE: PRT
<213> ORGANISM: Homo sapiens

<400> SEQUENCE: 466

Gly Phe Thr Phe Gly Asp Tyr Ala
1 5

<210> SEQ ID NO 467
<211> LENGTH: 8
<212> TYPE: PRT
<213> ORGANISM: Homo sapiens

<400> SEQUENCE: 467

Gly Phe Thr Phe Ser Asn Ala Trp
1 5

<210> SEQ ID NO 468
<211> LENGTH: 8
<212> TYPE: PRT
<213> ORGANISM: Homo sapiens

<400> SEQUENCE: 468

Gly Tyr Thr Phe Thr Gly Tyr Tyr
1 5

<210> SEQ ID NO 469
<211> LENGTH: 8
<212> TYPE: PRT
<213> ORGANISM: Homo sapiens

<400> SEQUENCE: 469

Gly Phe Thr Phe Ser Ser Tyr Ser
1 5

<210> SEQ ID NO 470
<211> LENGTH: 8
<212> TYPE: PRT
<213> ORGANISM: Homo sapiens

<400> SEQUENCE: 470

Gly Gly Ser Ile Ser Ser Tyr Tyr
1 5

<210> SEQ ID NO 471
<211> LENGTH: 8
<212> TYPE: PRT
<213> ORGANISM: Homo sapiens

<400> SEQUENCE: 471

Gly Phe Pro Phe Ser Val Tyr Trp
1 5

<210> SEQ ID NO 472
<211> LENGTH: 8
<212> TYPE: PRT
<213> ORGANISM: Homo sapiens

<400> SEQUENCE: 472

Gly Phe Thr Phe Ser Asn Ala Trp
1 5

<210> SEQ ID NO 473
<211> LENGTH: 8
<212> TYPE: PRT
<213> ORGANISM: Homo sapiens

<400> SEQUENCE: 473

Gly Phe Thr Phe Ser Ser Tyr Ser
1 5

<210> SEQ ID NO 474
<211> LENGTH: 8
<212> TYPE: PRT
<213> ORGANISM: Homo sapiens

<400> SEQUENCE: 474

Gly Tyr Thr Phe Thr Gly Tyr Tyr
1 5

<210> SEQ ID NO 475
<211> LENGTH: 8
<212> TYPE: PRT
<213> ORGANISM: Homo sapiens

<400> SEQUENCE: 475

Gly Tyr Thr Phe Thr Gly Tyr Tyr
1 5

<210> SEQ ID NO 476
<211> LENGTH: 10
<212> TYPE: PRT
<213> ORGANISM: Homo sapiens

<400> SEQUENCE: 476

Gly Phe Ser Leu Ser Thr Ser Gly Val Gly
1 5 10

<210> SEQ ID NO 477
<211> LENGTH: 8
<212> TYPE: PRT
<213> ORGANISM: Homo sapiens

<400> SEQUENCE: 477

Gly Phe Thr Phe Ser Ser Tyr Gly
1 5

<210> SEQ ID NO 478
<211> LENGTH: 8
<212> TYPE: PRT
<213> ORGANISM: Homo sapiens

<400> SEQUENCE: 478

Gly Phe Thr Phe Ser Thr Tyr Trp

-continued 1 5

<210> SEQ ID NO 479
<211> LENGTH: 8
<212> TYPE: PRT
<213> ORGANISM: Homo sapiens

<400> SEQUENCE: 479

Gly Tyr Thr Phe Thr Gly Tyr Tyr
1 5

<210> SEQ ID NO 480
<211> LENGTH: 8
<212> TYPE: PRT
<213> ORGANISM: Homo sapiens

<400> SEQUENCE: 480

Gly Phe Thr Phe Ser Thr Phe Ala
1 5

<210> SEQ ID NO 481
<211> LENGTH: 8
<212> TYPE: PRT
<213> ORGANISM: Homo sapiens

<400> SEQUENCE: 481

Gly Ala Ser Ile Ser Thr Tyr Phe
1 5

<210> SEQ ID NO 482
<211> LENGTH: 8
<212> TYPE: PRT
<213> ORGANISM: Homo sapiens

<400> SEQUENCE: 482

Gly Gly Ser Ile Ser Ser Tyr Tyr
1 5

<210> SEQ ID NO 483
<211> LENGTH: 8
<212> TYPE: PRT
<213> ORGANISM: Homo sapiens

<400> SEQUENCE: 483

Gly Phe Thr Leu Ser Ser Tyr Gly
1 5

<210> SEQ ID NO 484
<211> LENGTH: 8
<212> TYPE: PRT
<213> ORGANISM: Homo sapiens

<400> SEQUENCE: 484

Gly Gly Ser Ile Ser Ser Tyr Tyr
1 5

<210> SEQ ID NO 485
<211> LENGTH: 8
<212> TYPE: PRT
<213> ORGANISM: Homo sapiens

<400> SEQUENCE: 485

Gly Gly Ser Ile Ser Ser Tyr Tyr
1 5

<210> SEQ ID NO 486
<211> LENGTH: 8
<212> TYPE: PRT
<213> ORGANISM: Homo sapiens

<400> SEQUENCE: 486

Ser Gly Ser Ile Ser Ser Tyr Tyr
1 5

<210> SEQ ID NO 487
<211> LENGTH: 8
<212> TYPE: PRT
<213> ORGANISM: Homo sapiens

<400> SEQUENCE: 487

Gly Gly Ser Ile Ser Ser Tyr Tyr
1 5

<210> SEQ ID NO 488
<211> LENGTH: 8
<212> TYPE: PRT
<213> ORGANISM: Homo sapiens

<400> SEQUENCE: 488

Gly Gly Ser Ile Ser Ser Tyr Tyr
1 5

<210> SEQ ID NO 489
<211> LENGTH: 8
<212> TYPE: PRT
<213> ORGANISM: Homo sapiens

<400> SEQUENCE: 489

Gly Gly Ser Ile Ser Ser Tyr Tyr
1 5

<210> SEQ ID NO 490
<211> LENGTH: 8
<212> TYPE: PRT
<213> ORGANISM: Homo sapiens

<400> SEQUENCE: 490

Gly Tyr Thr Phe Thr Asp Tyr Tyr
1 5

<210> SEQ ID NO 491
<211> LENGTH: 8
<212> TYPE: PRT
<213> ORGANISM: Homo sapiens

<400> SEQUENCE: 491

Gly Gly Ser Ile Ser Ser Phe Tyr
1 5

<210> SEQ ID NO 492
<211> LENGTH: 8
<212> TYPE: PRT
<213> ORGANISM: Homo sapiens

<400> SEQUENCE: 492

Gly Gly Ser Ile Ser Ser Tyr Tyr
1 5

<210> SEQ ID NO 493

<211> LENGTH: 8
<212> TYPE: PRT
<213> ORGANISM: Homo sapiens

<400> SEQUENCE: 493

Gly Gly Ser Ile Ser Ser Tyr Tyr
1 5

<210> SEQ ID NO 494
<211> LENGTH: 8
<212> TYPE: PRT
<213> ORGANISM: Homo sapiens

<400> SEQUENCE: 494

Gly Gly Ser Ile Ser Ser Tyr Tyr
1 5

<210> SEQ ID NO 495
<211> LENGTH: 8
<212> TYPE: PRT
<213> ORGANISM: Homo sapiens

<400> SEQUENCE: 495

Gly Phe Thr Phe Ser Ser Tyr Ser
1 5

<210> SEQ ID NO 496
<211> LENGTH: 8
<212> TYPE: PRT
<213> ORGANISM: Homo sapiens

<400> SEQUENCE: 496

Gly Asp Ser Ile Ser Asn Tyr Tyr
1 5

<210> SEQ ID NO 497
<211> LENGTH: 8
<212> TYPE: PRT
<213> ORGANISM: Homo sapiens

<400> SEQUENCE: 497

Gly Gly Ser Ile Ser Ser Tyr Tyr
1 5

<210> SEQ ID NO 498
<211> LENGTH: 8
<212> TYPE: PRT
<213> ORGANISM: Homo sapiens

<400> SEQUENCE: 498

Gly Gly Ser Ile Ser Ser Tyr Tyr
1 5

<210> SEQ ID NO 499
<211> LENGTH: 8
<212> TYPE: PRT
<213> ORGANISM: Homo sapiens

<400> SEQUENCE: 499

Gly Gly Ser Ile Ser Ser Tyr Tyr
1 5

<210> SEQ ID NO 500
<211> LENGTH: 8
<212> TYPE: PRT

<213> ORGANISM: Homo sapiens

<400> SEQUENCE: 500

Gly Gly Ser Ile Ser Ser Tyr Tyr
1 5

<210> SEQ ID NO 501
<211> LENGTH: 8
<212> TYPE: PRT
<213> ORGANISM: Homo sapiens

<400> SEQUENCE: 501

Gly Gly Ser Ile Ser Ser Tyr Tyr
1 5

<210> SEQ ID NO 502
<211> LENGTH: 8
<212> TYPE: PRT
<213> ORGANISM: Homo sapiens

<400> SEQUENCE: 502

Gly Phe Thr Phe Ser Ser Tyr Asn
1 5

<210> SEQ ID NO 503
<211> LENGTH: 8
<212> TYPE: PRT
<213> ORGANISM: Homo sapiens

<400> SEQUENCE: 503

Gly Ala Ser Ile Ser Ser Tyr Tyr
1 5

<210> SEQ ID NO 504
<211> LENGTH: 8
<212> TYPE: PRT
<213> ORGANISM: Homo sapiens

<400> SEQUENCE: 504

Gly Gly Ser Ile Ser Ser Tyr Tyr
1 5

<210> SEQ ID NO 505
<211> LENGTH: 8
<212> TYPE: PRT
<213> ORGANISM: Homo sapiens

<400> SEQUENCE: 505

Gly Gly Ser Ile Ser Ser Tyr Tyr
1 5

<210> SEQ ID NO 506
<211> LENGTH: 8
<212> TYPE: PRT
<213> ORGANISM: Homo sapiens

<400> SEQUENCE: 506

Gly Gly Ser Ile Ser Ser Tyr Tyr
1 5

<210> SEQ ID NO 507
<211> LENGTH: 8
<212> TYPE: PRT
<213> ORGANISM: Homo sapiens

<400> SEQUENCE: 507

Gly Tyr Thr Phe Thr Gly Tyr Tyr
1 5

<210> SEQ ID NO 508
<211> LENGTH: 8
<212> TYPE: PRT
<213> ORGANISM: Homo sapiens

<400> SEQUENCE: 508

Gly Tyr Thr Phe Thr Gly Tyr Tyr
1 5

<210> SEQ ID NO 509
<211> LENGTH: 8
<212> TYPE: PRT
<213> ORGANISM: Homo sapiens

<400> SEQUENCE: 509

Asp Gly Ser Ile Ser Ser Tyr Tyr
1 5

<210> SEQ ID NO 510
<211> LENGTH: 8
<212> TYPE: PRT
<213> ORGANISM: Homo sapiens

<400> SEQUENCE: 510

Gly Gly Ser Ile Ser Ser Tyr Tyr
1 5

<210> SEQ ID NO 511
<211> LENGTH: 8
<212> TYPE: PRT
<213> ORGANISM: Homo sapiens

<400> SEQUENCE: 511

Gly Gly Ser Ile Ser Ser Tyr Tyr
1 5

<210> SEQ ID NO 512
<211> LENGTH: 8
<212> TYPE: PRT
<213> ORGANISM: Homo sapiens

<400> SEQUENCE: 512

Gly Gly Ser Ile Ser Ser Tyr Tyr
1 5

<210> SEQ ID NO 513
<211> LENGTH: 8
<212> TYPE: PRT
<213> ORGANISM: Homo sapiens

<400> SEQUENCE: 513

Gly Gly Ser Ile Ser Ser Tyr Tyr
1 5

<210> SEQ ID NO 514
<211> LENGTH: 8
<212> TYPE: PRT
<213> ORGANISM: Homo sapiens

<400> SEQUENCE: 514

-continued

Gly Gly Ser Ile Ser Ser Tyr Tyr
1 5

<210> SEQ ID NO 515
<211> LENGTH: 8
<212> TYPE: PRT
<213> ORGANISM: Homo sapiens

<400> SEQUENCE: 515

Gly Gly Ser Ile Ser Ser Tyr Tyr
1 5

<210> SEQ ID NO 516
<211> LENGTH: 8
<212> TYPE: PRT
<213> ORGANISM: Homo sapiens

<400> SEQUENCE: 516

Gly Gly Ser Ile Ser Ser Tyr Tyr
1 5

<210> SEQ ID NO 517
<211> LENGTH: 8
<212> TYPE: PRT
<213> ORGANISM: Homo sapiens

<400> SEQUENCE: 517

Gly Phe Thr Phe Ser Thr Tyr Ser
1 5

<210> SEQ ID NO 518
<211> LENGTH: 8
<212> TYPE: PRT
<213> ORGANISM: Homo sapiens

<400> SEQUENCE: 518

Gly Phe Thr Phe Ser Asn Tyr Trp
1 5

<210> SEQ ID NO 519
<211> LENGTH: 8
<212> TYPE: PRT
<213> ORGANISM: Homo sapiens

<400> SEQUENCE: 519

Gly Tyr Ser Phe Thr Asn Tyr Trp
1 5

<210> SEQ ID NO 520
<211> LENGTH: 8
<212> TYPE: PRT
<213> ORGANISM: Homo sapiens

<400> SEQUENCE: 520

Gly Tyr Thr Phe Thr Gly Tyr Tyr
1 5

<210> SEQ ID NO 521
<211> LENGTH: 8
<212> TYPE: PRT
<213> ORGANISM: Homo sapiens

<400> SEQUENCE: 521

Gly Gly Ser Ile Ser Ser Tyr Tyr
1 5

<210> SEQ ID NO 522
<211> LENGTH: 8
<212> TYPE: PRT
<213> ORGANISM: Homo sapiens

<400> SEQUENCE: 522

Gly Gly Ser Ile Ser Ser Tyr Tyr
1 5

<210> SEQ ID NO 523
<211> LENGTH: 8
<212> TYPE: PRT
<213> ORGANISM: Homo sapiens

<400> SEQUENCE: 523

Gly Gly Ser Ile Ser Ser Tyr Tyr
1 5

<210> SEQ ID NO 524
<211> LENGTH: 8
<212> TYPE: PRT
<213> ORGANISM: Homo sapiens

<400> SEQUENCE: 524

Val Gly Ser Ile Ser Ser Tyr Tyr
1 5

<210> SEQ ID NO 525
<211> LENGTH: 8
<212> TYPE: PRT
<213> ORGANISM: Homo sapiens

<400> SEQUENCE: 525

Gly Phe Thr Phe Ser Ser Tyr Ser
1 5

<210> SEQ ID NO 526
<211> LENGTH: 8
<212> TYPE: PRT
<213> ORGANISM: Homo sapiens

<400> SEQUENCE: 526

Gly Gly Ser Ile Ser Ser Tyr Tyr
1 5

<210> SEQ ID NO 527
<211> LENGTH: 8
<212> TYPE: PRT
<213> ORGANISM: Homo sapiens

<400> SEQUENCE: 527

Gly Gly Ser Ile Ser Ser Tyr Tyr
1 5

<210> SEQ ID NO 528
<211> LENGTH: 8
<212> TYPE: PRT
<213> ORGANISM: Homo sapiens

<400> SEQUENCE: 528

Gly Gly Ser Ile Ser Ser Tyr Tyr
1 5

<210> SEQ ID NO 529
<211> LENGTH: 8
<212> TYPE: PRT
<213> ORGANISM: Homo sapiens

<400> SEQUENCE: 529

Gly Gly Ser Ile Ser Ser Tyr His
1               5

<210> SEQ ID NO 530
<211> LENGTH: 8
<212> TYPE: PRT
<213> ORGANISM: Homo sapiens

<400> SEQUENCE: 530

Gly Gly Ser Ile Ser Ser Tyr Tyr
1               5

<210> SEQ ID NO 531
<211> LENGTH: 8
<212> TYPE: PRT
<213> ORGANISM: Homo sapiens

<400> SEQUENCE: 531

Gly Gly Ser Ile Ser Gly Tyr Tyr
1               5

<210> SEQ ID NO 532
<211> LENGTH: 8
<212> TYPE: PRT
<213> ORGANISM: Homo sapiens

<400> SEQUENCE: 532

Gly Gly Ser Ile Ser Ser Tyr Tyr
1               5

<210> SEQ ID NO 533
<211> LENGTH: 8
<212> TYPE: PRT
<213> ORGANISM: Homo sapiens

<400> SEQUENCE: 533

Gly Phe Thr Phe Ser Ser Tyr Ser
1               5

<210> SEQ ID NO 534
<211> LENGTH: 8
<212> TYPE: PRT
<213> ORGANISM: Homo sapiens

<400> SEQUENCE: 534

Gly Phe Thr Phe Ser Tyr Tyr Ser
1               5

<210> SEQ ID NO 535
<211> LENGTH: 8
<212> TYPE: PRT
<213> ORGANISM: Homo sapiens

<400> SEQUENCE: 535

Gly Gly Ser Ile Ser Ser Tyr Tyr
1               5

<210> SEQ ID NO 536
<211> LENGTH: 8

<212> TYPE: PRT
<213> ORGANISM: Homo sapiens

<400> SEQUENCE: 536

Gly Gly Ser Ile Asn Ser Tyr Tyr
1               5

<210> SEQ ID NO 537
<211> LENGTH: 8
<212> TYPE: PRT
<213> ORGANISM: Homo sapiens

<400> SEQUENCE: 537

Gly Gly Ser Ile Ser Ser Tyr Tyr
1               5

<210> SEQ ID NO 538
<211> LENGTH: 8
<212> TYPE: PRT
<213> ORGANISM: Homo sapiens

<400> SEQUENCE: 538

Gly Gly Ser Ile Ser Ser Asn Tyr
1               5

<210> SEQ ID NO 539
<211> LENGTH: 8
<212> TYPE: PRT
<213> ORGANISM: Homo sapiens

<400> SEQUENCE: 539

Gly Phe Thr Phe Ser Ser Tyr Ser
1               5

<210> SEQ ID NO 540
<211> LENGTH: 8
<212> TYPE: PRT
<213> ORGANISM: Homo sapiens

<400> SEQUENCE: 540

Gly Gly Ser Ile Ser Ser Tyr Tyr
1               5

<210> SEQ ID NO 541
<211> LENGTH: 8
<212> TYPE: PRT
<213> ORGANISM: Homo sapiens

<400> SEQUENCE: 541

Gly Gly Ser Ile Ser Ser Tyr Tyr
1               5

<210> SEQ ID NO 542
<211> LENGTH: 8
<212> TYPE: PRT
<213> ORGANISM: Homo sapiens

<400> SEQUENCE: 542

Gly Gly Ser Ile Ser Ser Tyr Tyr
1               5

<210> SEQ ID NO 543
<211> LENGTH: 8
<212> TYPE: PRT
<213> ORGANISM: Homo sapiens

<400> SEQUENCE: 543

Gly Gly Ser Ile Ser Ile Tyr Tyr
1 5

<210> SEQ ID NO 544
<211> LENGTH: 24
<212> TYPE: DNA
<213> ORGANISM: Homo sapiens

<400> SEQUENCE: 544
ggattcactt tcagtaacgc ctgg 24

<210> SEQ ID NO 545
<211> LENGTH: 24
<212> TYPE: DNA
<213> ORGANISM: Homo sapiens

<400> SEQUENCE: 545
ggatacacct tcaccggcta ctat 24

<210> SEQ ID NO 546
<211> LENGTH: 24
<212> TYPE: DNA
<213> ORGANISM: Homo sapiens

<400> SEQUENCE: 546
ggattcactt tcagtaatgc ctgg 24

<210> SEQ ID NO 547
<211> LENGTH: 24
<212> TYPE: DNA
<213> ORGANISM: Homo sapiens

<400> SEQUENCE: 547
ggtggctcca tcagtagtta ctac 24

<210> SEQ ID NO 548
<211> LENGTH: 24
<212> TYPE: DNA
<213> ORGANISM: Homo sapiens

<400> SEQUENCE: 548
ggtggctcca tcagtagtta ctac 24

<210> SEQ ID NO 549
<211> LENGTH: 24
<212> TYPE: DNA
<213> ORGANISM: Homo sapiens

<400> SEQUENCE: 549
ggattcacct ttggtgatta tgct 24

<210> SEQ ID NO 550
<211> LENGTH: 24
<212> TYPE: DNA
<213> ORGANISM: Homo sapiens

<400> SEQUENCE: 550
ggatacacct tcaccggcta ctat 24

<210> SEQ ID NO 551
<211> LENGTH: 24

<212> TYPE: DNA
<213> ORGANISM: Homo sapiens

<400> SEQUENCE: 551
ggattcactt tcagtaacgc ctgg 24

<210> SEQ ID NO 552
<211> LENGTH: 24
<212> TYPE: DNA
<213> ORGANISM: Homo sapiens

<400> SEQUENCE: 552
ggtggctcca tcagtagttc ctat 24

<210> SEQ ID NO 553
<211> LENGTH: 24
<212> TYPE: DNA
<213> ORGANISM: Homo sapiens

<400> SEQUENCE: 553
agattcacct tcagtagcta tagc 24

<210> SEQ ID NO 554
<211> LENGTH: 30
<212> TYPE: DNA
<213> ORGANISM: Homo sapiens

<400> SEQUENCE: 554
gggttctcac tcagcactag tggaatgtgt 30

<210> SEQ ID NO 555
<211> LENGTH: 24
<212> TYPE: DNA
<213> ORGANISM: Homo sapiens

<400> SEQUENCE: 555
ggtggctcca tcagtagtta ctac 24

<210> SEQ ID NO 556
<211> LENGTH: 24
<212> TYPE: DNA
<213> ORGANISM: Homo sapiens

<400> SEQUENCE: 556
ggtggctcca tcagtagtta ctac 24

<210> SEQ ID NO 557
<211> LENGTH: 24
<212> TYPE: DNA
<213> ORGANISM: Homo sapiens

<400> SEQUENCE: 557
ggtggctcca tcagtagtta ctac 24

<210> SEQ ID NO 558
<211> LENGTH: 24
<212> TYPE: DNA
<213> ORGANISM: Homo sapiens

<400> SEQUENCE: 558
ggatacacct tcaccggcta ctat 24

<210> SEQ ID NO 559

<211> LENGTH: 24
<212> TYPE: DNA
<213> ORGANISM: Homo sapiens

<400> SEQUENCE: 559
ggtggctcca tcagtagtta ctac 24

<210> SEQ ID NO 560
<211> LENGTH: 24
<212> TYPE: DNA
<213> ORGANISM: Homo sapiens

<400> SEQUENCE: 560
ggtggctcca tcagtagtta ctac 24

<210> SEQ ID NO 561
<211> LENGTH: 24
<212> TYPE: DNA
<213> ORGANISM: Homo sapiens

<400> SEQUENCE: 561
ggattcacct tcagtagcta cgac 24

<210> SEQ ID NO 562
<211> LENGTH: 24
<212> TYPE: DNA
<213> ORGANISM: Homo sapiens

<400> SEQUENCE: 562
ggtgggtcct gcagtgctta ctac 24

<210> SEQ ID NO 563
<211> LENGTH: 24
<212> TYPE: DNA
<213> ORGANISM: Homo sapiens

<400> SEQUENCE: 563
ggattcactt tcagtaacgc ctgg 24

<210> SEQ ID NO 564
<211> LENGTH: 24
<212> TYPE: DNA
<213> ORGANISM: Homo sapiens

<400> SEQUENCE: 564
ggtgggtcct tcagtgctta ctac 24

<210> SEQ ID NO 565
<211> LENGTH: 24
<212> TYPE: DNA
<213> ORGANISM: Homo sapiens

<400> SEQUENCE: 565
ggattcacct tcagtagcta ctgg 24

<210> SEQ ID NO 566
<211> LENGTH: 24
<212> TYPE: DNA
<213> ORGANISM: Homo sapiens

<400> SEQUENCE: 566
ggattcacct tcagtagcta tagc 24

<210> SEQ ID NO 567
<211> LENGTH: 30
<212> TYPE: DNA
<213> ORGANISM: Homo sapiens

<400> SEQUENCE: 567
gggttctcac tcagcactag tggagtgggt 30

<210> SEQ ID NO 568
<211> LENGTH: 24
<212> TYPE: DNA
<213> ORGANISM: Homo sapiens

<400> SEQUENCE: 568
ggatacacct tcaccggcta ctat 24

<210> SEQ ID NO 569
<211> LENGTH: 24
<212> TYPE: DNA
<213> ORGANISM: Homo sapiens

<400> SEQUENCE: 569
ggtggctcca tcagtagtta ctac 24

<210> SEQ ID NO 570
<211> LENGTH: 24
<212> TYPE: DNA
<213> ORGANISM: Homo sapiens

<400> SEQUENCE: 570
ggtggctcca tcagtagtta ctac 24

<210> SEQ ID NO 571
<211> LENGTH: 24
<212> TYPE: DNA
<213> ORGANISM: Homo sapiens

<400> SEQUENCE: 571
ggattcacct tcagtagcta taac 24

<210> SEQ ID NO 572
<211> LENGTH: 24
<212> TYPE: DNA
<213> ORGANISM: Homo sapiens

<400> SEQUENCE: 572
ggtggctcca tcagtagtta ctac 24

<210> SEQ ID NO 573
<211> LENGTH: 24
<212> TYPE: DNA
<213> ORGANISM: Homo sapiens

<400> SEQUENCE: 573
ggattcacct tcagtagcta tagc 24

<210> SEQ ID NO 574
<211> LENGTH: 24
<212> TYPE: DNA
<213> ORGANISM: Homo sapiens

<400> SEQUENCE: 574
ggattcacct ttggtgatta tgct 24

<210> SEQ ID NO 575
<211> LENGTH: 24
<212> TYPE: DNA
<213> ORGANISM: Homo sapiens

<400> SEQUENCE: 575
ggattcactt tcagtaacgc ctgg 24

<210> SEQ ID NO 576
<211> LENGTH: 24
<212> TYPE: DNA
<213> ORGANISM: Homo sapiens

<400> SEQUENCE: 576
ggatacacct tcaccggcta ctat 24

<210> SEQ ID NO 577
<211> LENGTH: 24
<212> TYPE: DNA
<213> ORGANISM: Homo sapiens

<400> SEQUENCE: 577
ggattcacct tcagtagcta tagc 24

<210> SEQ ID NO 578
<211> LENGTH: 24
<212> TYPE: DNA
<213> ORGANISM: Homo sapiens

<400> SEQUENCE: 578
ggtggctcca tcagtagtta ctac 24

<210> SEQ ID NO 579
<211> LENGTH: 24
<212> TYPE: DNA
<213> ORGANISM: Homo sapiens

<400> SEQUENCE: 579
ggattcccct ttagtgtcta ttgg 24

<210> SEQ ID NO 580
<211> LENGTH: 24
<212> TYPE: DNA
<213> ORGANISM: Homo sapiens

<400> SEQUENCE: 580
ggattcactt tcagtaacgc ctgg 24

<210> SEQ ID NO 581
<211> LENGTH: 24
<212> TYPE: DNA
<213> ORGANISM: Homo sapiens

<400> SEQUENCE: 581
ggattcacct tcagtagtta tagc 24

<210> SEQ ID NO 582
<211> LENGTH: 24
<212> TYPE: DNA
<213> ORGANISM: Homo sapiens

<400> SEQUENCE: 582
ggatacacct tcaccggcta ctat 24

<210> SEQ ID NO 583
<211> LENGTH: 24
<212> TYPE: DNA
<213> ORGANISM: Homo sapiens

<400> SEQUENCE: 583
ggatacacct tcaccggcta ctat 24

<210> SEQ ID NO 584
<211> LENGTH: 30
<212> TYPE: DNA
<213> ORGANISM: Homo sapiens

<400> SEQUENCE: 584
gggttctcac tcagcactag tggagtgggt 30

<210> SEQ ID NO 585
<211> LENGTH: 24
<212> TYPE: DNA
<213> ORGANISM: Homo sapiens

<400> SEQUENCE: 585
ggattcacct tcagtagcta tggc 24

<210> SEQ ID NO 586
<211> LENGTH: 24
<212> TYPE: DNA
<213> ORGANISM: Homo sapiens

<400> SEQUENCE: 586
ggattcacct ttagtaccta ttgg 24

<210> SEQ ID NO 587
<211> LENGTH: 24
<212> TYPE: DNA
<213> ORGANISM: Homo sapiens

<400> SEQUENCE: 587
ggatacacct tcaccggcta ctat 24

<210> SEQ ID NO 588
<211> LENGTH: 24
<212> TYPE: DNA
<213> ORGANISM: Homo sapiens

<400> SEQUENCE: 588
ggattcacct tcagtacctt tgcc 24

<210> SEQ ID NO 589
<211> LENGTH: 24
<212> TYPE: DNA
<213> ORGANISM: Homo sapiens

<400> SEQUENCE: 589
ggtgcctcca tcagtactta cttc 24

<210> SEQ ID NO 590
<211> LENGTH: 24
<212> TYPE: DNA
<213> ORGANISM: Homo sapiens

<400> SEQUENCE: 590
ggtggctcca tcagtagtta ctac 24

<210> SEQ ID NO 591
<211> LENGTH: 24
<212> TYPE: DNA
<213> ORGANISM: Homo sapiens

<400> SEQUENCE: 591
ggattcaccc tcagtagcta tggc 24

<210> SEQ ID NO 592
<211> LENGTH: 24
<212> TYPE: DNA
<213> ORGANISM: Homo sapiens

<400> SEQUENCE: 592
ggtggctcca tcagtagtta ctac 24

<210> SEQ ID NO 593
<211> LENGTH: 24
<212> TYPE: DNA
<213> ORGANISM: Homo sapiens

<400> SEQUENCE: 593
ggtggctcca tcagtagtta ctac 24

<210> SEQ ID NO 594
<211> LENGTH: 24
<212> TYPE: DNA
<213> ORGANISM: Homo sapiens

<400> SEQUENCE: 594
agtggctcca tcagtagtta ctac 24

<210> SEQ ID NO 595
<211> LENGTH: 24
<212> TYPE: DNA
<213> ORGANISM: Homo sapiens

<400> SEQUENCE: 595
ggtggttcca tcagtagtta ttac 24

<210> SEQ ID NO 596
<211> LENGTH: 24
<212> TYPE: DNA
<213> ORGANISM: Homo sapiens

<400> SEQUENCE: 596
ggtggctcca tcagtagtta ctac 24

<210> SEQ ID NO 597
<211> LENGTH: 24
<212> TYPE: DNA
<213> ORGANISM: Homo sapiens

<400> SEQUENCE: 597
ggtggctcca tcagtagtta ctac 24

<210> SEQ ID NO 598
<211> LENGTH: 24
<212> TYPE: DNA
<213> ORGANISM: Homo sapiens

<400> SEQUENCE: 598
ggatacacct tcaccgacta ctat 24

<210> SEQ ID NO 599
<211> LENGTH: 24
<212> TYPE: DNA
<213> ORGANISM: Homo sapiens

<400> SEQUENCE: 599
ggtggctcca tcagtagttt ctac 24

<210> SEQ ID NO 600
<211> LENGTH: 24
<212> TYPE: DNA
<213> ORGANISM: Homo sapiens

<400> SEQUENCE: 600
ggtggctcca tcagtagtta ctac 24

<210> SEQ ID NO 601
<211> LENGTH: 24
<212> TYPE: DNA
<213> ORGANISM: Homo sapiens

<400> SEQUENCE: 601
ggtggctcca tcagtagtta ctac 24

<210> SEQ ID NO 602
<211> LENGTH: 24
<212> TYPE: DNA
<213> ORGANISM: Homo sapiens

<400> SEQUENCE: 602
ggtggctcca tcagtagtta ctac 24

<210> SEQ ID NO 603
<211> LENGTH: 24
<212> TYPE: DNA
<213> ORGANISM: Homo sapiens

<400> SEQUENCE: 603
ggattcacct tcagtagcta tagc 24

<210> SEQ ID NO 604
<211> LENGTH: 24
<212> TYPE: DNA
<213> ORGANISM: Homo sapiens

<400> SEQUENCE: 604
ggtgactcca tcagtaatta ctac 24

<210> SEQ ID NO 605
<211> LENGTH: 24
<212> TYPE: DNA
<213> ORGANISM: Homo sapiens

<400> SEQUENCE: 605
ggtggctcca tcagtagtta ctac 24

<210> SEQ ID NO 606
<211> LENGTH: 24
<212> TYPE: DNA
<213> ORGANISM: Homo sapiens

<400> SEQUENCE: 606
ggtggctcca tcagtagtta ctac 24

<210> SEQ ID NO 607
<211> LENGTH: 24
<212> TYPE: DNA
<213> ORGANISM: Homo sapiens

<400> SEQUENCE: 607
ggtggctcca tcagtagtta ctac 24

<210> SEQ ID NO 608
<211> LENGTH: 24
<212> TYPE: DNA
<213> ORGANISM: Homo sapiens

<400> SEQUENCE: 608
ggtggctcca tcagtagtta ctac 24

<210> SEQ ID NO 609
<211> LENGTH: 24
<212> TYPE: DNA
<213> ORGANISM: Homo sapiens

<400> SEQUENCE: 609
ggtggctcca tcagtagtta ctac 24

<210> SEQ ID NO 610
<211> LENGTH: 24
<212> TYPE: DNA
<213> ORGANISM: Homo sapiens

<400> SEQUENCE: 610
ggattcacct tcagtagtta taac 24

<210> SEQ ID NO 611
<211> LENGTH: 24
<212> TYPE: DNA
<213> ORGANISM: Homo sapiens

<400> SEQUENCE: 611
ggtgcctcca tcagtagtta ctac 24

<210> SEQ ID NO 612
<211> LENGTH: 24
<212> TYPE: DNA
<213> ORGANISM: Homo sapiens

<400> SEQUENCE: 612
ggtggctcca tcagtagtta ctac 24

<210> SEQ ID NO 613
<211> LENGTH: 24
<212> TYPE: DNA
<213> ORGANISM: Homo sapiens

<400> SEQUENCE: 613
ggtggctcca tcagtagtta ctac 24

<210> SEQ ID NO 614
<211> LENGTH: 24
<212> TYPE: DNA
<213> ORGANISM: Homo sapiens

<400> SEQUENCE: 614
ggtggctcca tcagtagtta ctac 24

<210> SEQ ID NO 615
<211> LENGTH: 24
<212> TYPE: DNA
<213> ORGANISM: Homo sapiens

<400> SEQUENCE: 615
ggatacacct tcaccggcta ctat 24

<210> SEQ ID NO 616
<211> LENGTH: 24
<212> TYPE: DNA
<213> ORGANISM: Homo sapiens

<400> SEQUENCE: 616
ggatacacct tcaccggcta ctat 24

<210> SEQ ID NO 617
<211> LENGTH: 24
<212> TYPE: DNA
<213> ORGANISM: Homo sapiens

<400> SEQUENCE: 617
gatggctcca tcagtagtta ctac 24

<210> SEQ ID NO 618
<211> LENGTH: 24
<212> TYPE: DNA
<213> ORGANISM: Homo sapiens

<400> SEQUENCE: 618
ggtggctcca tcagtagtta ctac 24

<210> SEQ ID NO 619
<211> LENGTH: 24
<212> TYPE: DNA
<213> ORGANISM: Homo sapiens

<400> SEQUENCE: 619
ggtggctcca tcagtagtta ctac 24

<210> SEQ ID NO 620
<211> LENGTH: 24
<212> TYPE: DNA
<213> ORGANISM: Homo sapiens

<400> SEQUENCE: 620
ggtggctcca tcagtagtta ctac 24

<210> SEQ ID NO 621
<211> LENGTH: 24
<212> TYPE: DNA
<213> ORGANISM: Homo sapiens

<400> SEQUENCE: 621
ggtggctcca tcagtagtta ctac 24

<210> SEQ ID NO 622
<211> LENGTH: 24
<212> TYPE: DNA

<213> ORGANISM: Homo sapiens

<400> SEQUENCE: 622
ggtggctcca tcagtagtta ctac 24

<210> SEQ ID NO 623
<211> LENGTH: 24
<212> TYPE: DNA
<213> ORGANISM: Homo sapiens

<400> SEQUENCE: 623
ggtggctcca tcagtagtta ttac 24

<210> SEQ ID NO 624
<211> LENGTH: 24
<212> TYPE: DNA
<213> ORGANISM: Homo sapiens

<400> SEQUENCE: 624
ggtggctcca tcagtagtta ctac 24

<210> SEQ ID NO 625
<211> LENGTH: 24
<212> TYPE: DNA
<213> ORGANISM: Homo sapiens

<400> SEQUENCE: 625
ggattcacct tcagtaccta tagc 24

<210> SEQ ID NO 626
<211> LENGTH: 24
<212> TYPE: DNA
<213> ORGANISM: Homo sapiens

<400> SEQUENCE: 626
ggattcacct ttagtaacta ttgg 24

<210> SEQ ID NO 627
<211> LENGTH: 24
<212> TYPE: DNA
<213> ORGANISM: Homo sapiens

<400> SEQUENCE: 627
ggatacagtt ttaccaacta ctgg 24

<210> SEQ ID NO 628
<211> LENGTH: 24
<212> TYPE: DNA
<213> ORGANISM: Homo sapiens

<400> SEQUENCE: 628
ggatacacct tcaccggcta ctat 24

<210> SEQ ID NO 629
<211> LENGTH: 24
<212> TYPE: DNA
<213> ORGANISM: Homo sapiens

<400> SEQUENCE: 629
ggtgggtcca tcagtagtta ctac 24

<210> SEQ ID NO 630
<211> LENGTH: 24

<212> TYPE: DNA
<213> ORGANISM: Homo sapiens

<400> SEQUENCE: 630
ggtggctcca tcagtagtta ctac 24

<210> SEQ ID NO 631
<211> LENGTH: 24
<212> TYPE: DNA
<213> ORGANISM: Homo sapiens

<400> SEQUENCE: 631
ggtggctcca tcagtagtta ttat 24

<210> SEQ ID NO 632
<211> LENGTH: 24
<212> TYPE: DNA
<213> ORGANISM: Homo sapiens

<400> SEQUENCE: 632
gttggctcca tcagtagtta ctac 24

<210> SEQ ID NO 633
<211> LENGTH: 24
<212> TYPE: DNA
<213> ORGANISM: Homo sapiens

<400> SEQUENCE: 633
ggattcacct tcagtagcta tagc 24

<210> SEQ ID NO 634
<211> LENGTH: 24
<212> TYPE: DNA
<213> ORGANISM: Homo sapiens

<400> SEQUENCE: 634
ggtggctcca tcagtagtta ctac 24

<210> SEQ ID NO 635
<211> LENGTH: 24
<212> TYPE: DNA
<213> ORGANISM: Homo sapiens

<400> SEQUENCE: 635
ggtggctcca tcagtagtta ctac 24

<210> SEQ ID NO 636
<211> LENGTH: 24
<212> TYPE: DNA
<213> ORGANISM: Homo sapiens

<400> SEQUENCE: 636
ggtggctcca tcagtagtta ctac 24

<210> SEQ ID NO 637
<211> LENGTH: 24
<212> TYPE: DNA
<213> ORGANISM: Homo sapiens

<400> SEQUENCE: 637
ggtggctcca taagtagtta ccac 24

<210> SEQ ID NO 638

<211> LENGTH: 24
<212> TYPE: DNA
<213> ORGANISM: Homo sapiens

<400> SEQUENCE: 638
ggtggctcca tcagtagtta ctac 24

<210> SEQ ID NO 639
<211> LENGTH: 24
<212> TYPE: DNA
<213> ORGANISM: Homo sapiens

<400> SEQUENCE: 639
ggtggctcca tcagtggtta ctac 24

<210> SEQ ID NO 640
<211> LENGTH: 24
<212> TYPE: DNA
<213> ORGANISM: Homo sapiens

<400> SEQUENCE: 640
ggtggctcca tcagtagtta ctac 24

<210> SEQ ID NO 641
<211> LENGTH: 24
<212> TYPE: DNA
<213> ORGANISM: Homo sapiens

<400> SEQUENCE: 641
ggattcacct tcagtagcta tagc 24

<210> SEQ ID NO 642
<211> LENGTH: 24
<212> TYPE: DNA
<213> ORGANISM: Homo sapiens

<400> SEQUENCE: 642
ggattcacct tcagttacta tagc 24

<210> SEQ ID NO 643
<211> LENGTH: 24
<212> TYPE: DNA
<213> ORGANISM: Homo sapiens

<400> SEQUENCE: 643
ggtggctcca tcagtagtta ctac 24

<210> SEQ ID NO 644
<211> LENGTH: 24
<212> TYPE: DNA
<213> ORGANISM: Homo sapiens

<400> SEQUENCE: 644
ggtggctcca tcaatagtta ctac 24

<210> SEQ ID NO 645
<211> LENGTH: 24
<212> TYPE: DNA
<213> ORGANISM: Homo sapiens

<400> SEQUENCE: 645
ggtggctcca tcagtagtta ctac 24

<210> SEQ ID NO 646
<211> LENGTH: 24
<212> TYPE: DNA
<213> ORGANISM: Homo sapiens

<400> SEQUENCE: 646
ggtggctcca tcagtagtaa ctac 24

<210> SEQ ID NO 647
<211> LENGTH: 24
<212> TYPE: DNA
<213> ORGANISM: Homo sapiens

<400> SEQUENCE: 647
ggattcacct tcagtagcta tagc 24

<210> SEQ ID NO 648
<211> LENGTH: 24
<212> TYPE: DNA
<213> ORGANISM: Homo sapiens

<400> SEQUENCE: 648
ggtggctcca tcagtagtta ctac 24

<210> SEQ ID NO 649
<211> LENGTH: 24
<212> TYPE: DNA
<213> ORGANISM: Homo sapiens

<400> SEQUENCE: 649
ggtggctcca tcagtagtta ctac 24

<210> SEQ ID NO 650
<211> LENGTH: 24
<212> TYPE: DNA
<213> ORGANISM: Homo sapiens

<400> SEQUENCE: 650
ggtggctcca tcagtagtta ctac 24

<210> SEQ ID NO 651
<211> LENGTH: 24
<212> TYPE: DNA
<213> ORGANISM: Homo sapiens

<400> SEQUENCE: 651
ggtggctcca tcagtattta ctac 24

<210> SEQ ID NO 652
<211> LENGTH: 6
<212> TYPE: PRT
<213> ORGANISM: Homo sapiens

<400> SEQUENCE: 652

Gln Asp Ile Ser Asp Tyr
1 5

<210> SEQ ID NO 653
<211> LENGTH: 12
<212> TYPE: PRT
<213> ORGANISM: Homo sapiens

<400> SEQUENCE: 653

Gln Ser Leu Leu Asp Ser Asp Asp Gly Asn Thr Tyr

-continued 1 5 10

<210> SEQ ID NO 654
<211> LENGTH: 12
<212> TYPE: PRT
<213> ORGANISM: Homo sapiens

<400> SEQUENCE: 654

Gln Ser Val Leu Tyr Ser Ser Asn Lys Lys Asn Tyr
1 5 10

<210> SEQ ID NO 655
<211> LENGTH: 7
<212> TYPE: PRT
<213> ORGANISM: Homo sapiens

<400> SEQUENCE: 655

Gln Ser Val Ser Ser Ser Tyr
1 5

<210> SEQ ID NO 656
<211> LENGTH: 7
<212> TYPE: PRT
<213> ORGANISM: Homo sapiens

<400> SEQUENCE: 656

Gln Ser Val Ser Ser Ser Tyr
1 5

<210> SEQ ID NO 657
<211> LENGTH: 11
<212> TYPE: PRT
<213> ORGANISM: Homo sapiens

<400> SEQUENCE: 657

Gln Ser Leu Leu His Ser Asn Gly Tyr Asn Tyr
1 5 10

<210> SEQ ID NO 658
<211> LENGTH: 6
<212> TYPE: PRT
<213> ORGANISM: Homo sapiens

<400> SEQUENCE: 658

Pro Gly Ile Ser Ser Trp
1 5

<210> SEQ ID NO 659
<211> LENGTH: 12
<212> TYPE: PRT
<213> ORGANISM: Homo sapiens

<400> SEQUENCE: 659

Gln Ser Val Leu Tyr Ser Ser Asn Asn Lys Asn Tyr
1 5 10

<210> SEQ ID NO 660
<211> LENGTH: 6
<212> TYPE: PRT
<213> ORGANISM: Homo sapiens

<400> SEQUENCE: 660

Gln Ser Ile Ser Ser Trp
1 5

<210> SEQ ID NO 661
<211> LENGTH: 6
<212> TYPE: PRT
<213> ORGANISM: Homo sapiens

<400> SEQUENCE: 661

Gln Asp Ile Ser Asp Tyr
1 5

<210> SEQ ID NO 662
<211> LENGTH: 6
<212> TYPE: PRT
<213> ORGANISM: Homo sapiens

<400> SEQUENCE: 662

Gln Gly Ile Ser Ser Tyr
1 5

<210> SEQ ID NO 663
<211> LENGTH: 11
<212> TYPE: PRT
<213> ORGANISM: Homo sapiens

<400> SEQUENCE: 663

Gln Ser Leu Leu Tyr Ser Asn Gly Tyr Asn Tyr
1 5 10

<210> SEQ ID NO 664
<211> LENGTH: 6
<212> TYPE: PRT
<213> ORGANISM: Homo sapiens

<400> SEQUENCE: 664

Gln Ser Ile Ser Ser Trp
1 5

<210> SEQ ID NO 665
<211> LENGTH: 6
<212> TYPE: PRT
<213> ORGANISM: Homo sapiens

<400> SEQUENCE: 665

Gln Ser Ile Ser Ser Trp
1 5

<210> SEQ ID NO 666
<211> LENGTH: 12
<212> TYPE: PRT
<213> ORGANISM: Homo sapiens

<400> SEQUENCE: 666

Gln Ser Leu Leu Asp Ser Asp Asp Gly Asn Thr Tyr
1 5 10

<210> SEQ ID NO 667
<211> LENGTH: 6
<212> TYPE: PRT
<213> ORGANISM: Homo sapiens

<400> SEQUENCE: 667

Gln Ser Ile Ser Asp Trp
1 5

<210> SEQ ID NO 668

<211> LENGTH: 7
<212> TYPE: PRT
<213> ORGANISM: Homo sapiens

<400> SEQUENCE: 668

Gln Ser Val Ser Ser Thr Tyr
1               5

<210> SEQ ID NO 669
<211> LENGTH: 6
<212> TYPE: PRT
<213> ORGANISM: Homo sapiens

<400> SEQUENCE: 669

Gln Asp Ile Ser Asn Tyr
1               5

<210> SEQ ID NO 670
<211> LENGTH: 7
<212> TYPE: PRT
<213> ORGANISM: Homo sapiens

<400> SEQUENCE: 670

Gln Ser Val Ser Ser Ser Tyr
1               5

<210> SEQ ID NO 671
<211> LENGTH: 12
<212> TYPE: PRT
<213> ORGANISM: Homo sapiens

<400> SEQUENCE: 671

Gln Ser Val Leu Tyr Ser Ser Asn Asn Lys Asn Tyr
1               5                   10

<210> SEQ ID NO 672
<211> LENGTH: 7
<212> TYPE: PRT
<213> ORGANISM: Homo sapiens

<400> SEQUENCE: 672

Gln Ser Val Ser Ser Ser Tyr
1               5

<210> SEQ ID NO 673
<211> LENGTH: 12
<212> TYPE: PRT
<213> ORGANISM: Homo sapiens

<400> SEQUENCE: 673

Gln Ser Val Leu Tyr Ser Ser Asn Asn Lys Asn Tyr
1               5                   10

<210> SEQ ID NO 674
<211> LENGTH: 7
<212> TYPE: PRT
<213> ORGANISM: Homo sapiens

<400> SEQUENCE: 674

Gln Ser Val Ser Ser Ser Tyr
1               5

<210> SEQ ID NO 675
<211> LENGTH: 12
<212> TYPE: PRT

<213> ORGANISM: Homo sapiens

<400> SEQUENCE: 675

Gln Ser Val Leu Tyr Ser Ser Asn Asn Lys Asn Tyr
1 5 10

<210> SEQ ID NO 676
<211> LENGTH: 12
<212> TYPE: PRT
<213> ORGANISM: Homo sapiens

<400> SEQUENCE: 676

Gln Thr Val Leu Tyr Ser Ser Asp Asn Lys Asn Tyr
1 5 10

<210> SEQ ID NO 677
<211> LENGTH: 7
<212> TYPE: PRT
<213> ORGANISM: Homo sapiens

<400> SEQUENCE: 677

Gln Ser Ile Ser Ser Ser Tyr
1 5

<210> SEQ ID NO 678
<211> LENGTH: 6
<212> TYPE: PRT
<213> ORGANISM: Homo sapiens

<400> SEQUENCE: 678

Gln Ser Ile Ser Ser Trp
1 5

<210> SEQ ID NO 679
<211> LENGTH: 6
<212> TYPE: PRT
<213> ORGANISM: Homo sapiens

<400> SEQUENCE: 679

Gln Gly Ile Ser Ser Tyr
1 5

<210> SEQ ID NO 680
<211> LENGTH: 6
<212> TYPE: PRT
<213> ORGANISM: Homo sapiens

<400> SEQUENCE: 680

Gln Gly Phe Ser Asn Tyr
1 5

<210> SEQ ID NO 681
<211> LENGTH: 11
<212> TYPE: PRT
<213> ORGANISM: Homo sapiens

<400> SEQUENCE: 681

Gln Ser Leu Leu His Ser Asn Gly Tyr Asn Tyr
1 5 10

<210> SEQ ID NO 682
<211> LENGTH: 11
<212> TYPE: PRT
<213> ORGANISM: Homo sapiens

<400> SEQUENCE: 682

Gln Ser Leu Leu His Ser Asn Gly Tyr Asn Tyr
1 5 10

<210> SEQ ID NO 683
<211> LENGTH: 11
<212> TYPE: PRT
<213> ORGANISM: Homo sapiens

<400> SEQUENCE: 683

Gln Ser Leu Leu His Ser Asn Gly Tyr Asn Tyr
1 5 10

<210> SEQ ID NO 684
<211> LENGTH: 12
<212> TYPE: PRT
<213> ORGANISM: Homo sapiens

<400> SEQUENCE: 684

Gln Ser Val Leu Tyr Ser Ser Asn Asn Lys Asn Tyr
1 5 10

<210> SEQ ID NO 685
<211> LENGTH: 6
<212> TYPE: PRT
<213> ORGANISM: Homo sapiens

<400> SEQUENCE: 685

Gln Asp Ile Ser Asn Tyr
1 5

<210> SEQ ID NO 686
<211> LENGTH: 11
<212> TYPE: PRT
<213> ORGANISM: Homo sapiens

<400> SEQUENCE: 686

Gln Ser Leu Leu His Ser Asn Gly Tyr Asn Tyr
1 5 10

<210> SEQ ID NO 687
<211> LENGTH: 11
<212> TYPE: PRT
<213> ORGANISM: Homo sapiens

<400> SEQUENCE: 687

Gln Ser Leu Leu His Ser Asn Gly Tyr Asn Tyr
1 5 10

<210> SEQ ID NO 688
<211> LENGTH: 12
<212> TYPE: PRT
<213> ORGANISM: Homo sapiens

<400> SEQUENCE: 688

Gln Ser Val Leu Tyr Ser Ser Asn Asn Lys Asn Tyr
1 5 10

<210> SEQ ID NO 689
<211> LENGTH: 11
<212> TYPE: PRT
<213> ORGANISM: Homo sapiens

<400> SEQUENCE: 689

Gln Ser Leu Leu His Ser Asn Gly Tyr Asn Tyr
1 5 10

<210> SEQ ID NO 690
<211> LENGTH: 12
<212> TYPE: PRT
<213> ORGANISM: Homo sapiens

<400> SEQUENCE: 690

Gln Ser Leu Leu Asp Ser Asp Asp Gly Asn Thr Tyr
1 5 10

<210> SEQ ID NO 691
<211> LENGTH: 12
<212> TYPE: PRT
<213> ORGANISM: Homo sapiens

<400> SEQUENCE: 691

Gln Ser Leu Leu Asp Ser Asp Asp Gly Asn Thr Tyr
1 5 10

<210> SEQ ID NO 692
<211> LENGTH: 12
<212> TYPE: PRT
<213> ORGANISM: Homo sapiens

<400> SEQUENCE: 692

Gln Ser Val Leu Tyr Ser Ser Asn Asn Lys Asn Tyr
1 5 10

<210> SEQ ID NO 693
<211> LENGTH: 6
<212> TYPE: PRT
<213> ORGANISM: Homo sapiens

<400> SEQUENCE: 693

Gln Gly Ile Ser Ser Trp
1 5

<210> SEQ ID NO 694
<211> LENGTH: 11
<212> TYPE: PRT
<213> ORGANISM: Homo sapiens

<400> SEQUENCE: 694

Gln Ser Leu Leu His Ser Asn Gly Tyr Asn Tyr
1 5 10

<210> SEQ ID NO 695
<211> LENGTH: 12
<212> TYPE: PRT
<213> ORGANISM: Homo sapiens

<400> SEQUENCE: 695

Gln Ser Leu Leu Asp Ser Asp Asp Gly Asn Thr Tyr
1 5 10

<210> SEQ ID NO 696
<211> LENGTH: 11
<212> TYPE: PRT
<213> ORGANISM: Homo sapiens

<400> SEQUENCE: 696

Gln Ser Leu Leu His Ser Asn Gly Tyr Asn Tyr
1 5 10

<210> SEQ ID NO 697
<211> LENGTH: 7
<212> TYPE: PRT
<213> ORGANISM: Homo sapiens

<400> SEQUENCE: 697

Gln Asn Val Ser Ser Thr Tyr
1 5

<210> SEQ ID NO 698
<211> LENGTH: 7
<212> TYPE: PRT
<213> ORGANISM: Homo sapiens

<400> SEQUENCE: 698

Gln Ser Val Ser Ser Ser Tyr
1 5

<210> SEQ ID NO 699
<211> LENGTH: 11
<212> TYPE: PRT
<213> ORGANISM: Homo sapiens

<400> SEQUENCE: 699

Gln Ser Leu Leu Tyr Ser Asn Gly Tyr Asn Tyr
1 5 10

<210> SEQ ID NO 700
<211> LENGTH: 8
<212> TYPE: PRT
<213> ORGANISM: Homo sapiens

<400> SEQUENCE: 700

Ser Ser Asn Ile Gly Ser Asn Thr
1 5

<210> SEQ ID NO 701
<211> LENGTH: 8
<212> TYPE: PRT
<213> ORGANISM: Homo sapiens

<400> SEQUENCE: 701

Ser Ser Asn Ile Gly Ser Asn Thr
1 5

<210> SEQ ID NO 702
<211> LENGTH: 8
<212> TYPE: PRT
<213> ORGANISM: Homo sapiens

<400> SEQUENCE: 702

Ser Ser Asn Ile Gly Ser Asn Thr
1 5

<210> SEQ ID NO 703
<211> LENGTH: 8
<212> TYPE: PRT
<213> ORGANISM: Homo sapiens

<400> SEQUENCE: 703

Ser Ser Asn Ile Gly Ser Asn Ser
1 5

-continued

<210> SEQ ID NO 704
<211> LENGTH: 8
<212> TYPE: PRT
<213> ORGANISM: Homo sapiens

<400> SEQUENCE: 704

Ser Ser Asn Ile Gly Ser Asn Thr
1 5

<210> SEQ ID NO 705
<211> LENGTH: 8
<212> TYPE: PRT
<213> ORGANISM: Homo sapiens

<400> SEQUENCE: 705

Ser Ser Asn Ile Gly Ser Asn Ala
1 5

<210> SEQ ID NO 706
<211> LENGTH: 8
<212> TYPE: PRT
<213> ORGANISM: Homo sapiens

<400> SEQUENCE: 706

Ser Ser Asn Ile Gly Ser Asn Thr
1 5

<210> SEQ ID NO 707
<211> LENGTH: 8
<212> TYPE: PRT
<213> ORGANISM: Homo sapiens

<400> SEQUENCE: 707

Ser Ser Asn Ile Gly Asn Asn Ala
1 5

<210> SEQ ID NO 708
<211> LENGTH: 8
<212> TYPE: PRT
<213> ORGANISM: Homo sapiens

<400> SEQUENCE: 708

Ser Ser Asn Ile Gly Ser Asn Thr
1 5

<210> SEQ ID NO 709
<211> LENGTH: 8
<212> TYPE: PRT
<213> ORGANISM: Homo sapiens

<400> SEQUENCE: 709

Ser Ser Asn Ile Gly Ser Asn Thr
1 5

<210> SEQ ID NO 710
<211> LENGTH: 8
<212> TYPE: PRT
<213> ORGANISM: Homo sapiens

<400> SEQUENCE: 710

Ser Ser Asn Ile Gly Ser Asn Thr
1 5

<210> SEQ ID NO 711
<211> LENGTH: 8

<212> TYPE: PRT
<213> ORGANISM: Homo sapiens

<400> SEQUENCE: 711

Ser Ser Asn Ile Gly Ser Asn Thr
1               5

<210> SEQ ID NO 712
<211> LENGTH: 8
<212> TYPE: PRT
<213> ORGANISM: Homo sapiens

<400> SEQUENCE: 712

Ser Ser Asn Ile Gly Ser Asn Thr
1               5

<210> SEQ ID NO 713
<211> LENGTH: 8
<212> TYPE: PRT
<213> ORGANISM: Homo sapiens

<400> SEQUENCE: 713

Ser Ser Asn Ile Gly Ser Asn Thr
1               5

<210> SEQ ID NO 714
<211> LENGTH: 8
<212> TYPE: PRT
<213> ORGANISM: Homo sapiens

<400> SEQUENCE: 714

Ser Ser Asn Ile Gly Ser Asn Thr
1               5

<210> SEQ ID NO 715
<211> LENGTH: 8
<212> TYPE: PRT
<213> ORGANISM: Homo sapiens

<400> SEQUENCE: 715

Ser Ser Asn Ile Gly Ser Asn Thr
1               5

<210> SEQ ID NO 716
<211> LENGTH: 9
<212> TYPE: PRT
<213> ORGANISM: Homo sapiens

<400> SEQUENCE: 716

Ser Ser Asp Val Gly Ser Tyr Asn Leu
1               5

<210> SEQ ID NO 717
<211> LENGTH: 8
<212> TYPE: PRT
<213> ORGANISM: Homo sapiens

<400> SEQUENCE: 717

Ser Ser Asn Ile Gly Ser Asn Thr
1               5

<210> SEQ ID NO 718
<211> LENGTH: 8
<212> TYPE: PRT
<213> ORGANISM: Homo sapiens

<400> SEQUENCE: 718

Ser Ser Asn Ile Gly Ser Asn Thr
1 5

<210> SEQ ID NO 719
<211> LENGTH: 8
<212> TYPE: PRT
<213> ORGANISM: Homo sapiens

<400> SEQUENCE: 719

Ser Ser Asn Ile Gly Ser Asn Thr
1 5

<210> SEQ ID NO 720
<211> LENGTH: 8
<212> TYPE: PRT
<213> ORGANISM: Homo sapiens

<400> SEQUENCE: 720

Ser Ser Asn Ile Gly Ser Asn Thr
1 5

<210> SEQ ID NO 721
<211> LENGTH: 9
<212> TYPE: PRT
<213> ORGANISM: Homo sapiens

<400> SEQUENCE: 721

Ser Ser Asp Val Gly Ser Tyr Asn Leu
1 5

<210> SEQ ID NO 722
<211> LENGTH: 8
<212> TYPE: PRT
<213> ORGANISM: Homo sapiens

<400> SEQUENCE: 722

Ser Ser Asn Ile Gly Ser Asn Ala
1 5

<210> SEQ ID NO 723
<211> LENGTH: 8
<212> TYPE: PRT
<213> ORGANISM: Homo sapiens

<400> SEQUENCE: 723

Ser Ser Asn Ile Gly Ser Asn Thr
1 5

<210> SEQ ID NO 724
<211> LENGTH: 8
<212> TYPE: PRT
<213> ORGANISM: Homo sapiens

<400> SEQUENCE: 724

Ser Ser Asn Ile Gly Ser Asn Thr
1 5

<210> SEQ ID NO 725
<211> LENGTH: 8
<212> TYPE: PRT
<213> ORGANISM: Homo sapiens

<400> SEQUENCE: 725

Ser Ser Asn Ile Gly Ser Asn Thr
1 5

<210> SEQ ID NO 726
<211> LENGTH: 8
<212> TYPE: PRT
<213> ORGANISM: Homo sapiens

<400> SEQUENCE: 726

Ser Ser Asn Ile Gly Ser Asn Thr
1 5

<210> SEQ ID NO 727
<211> LENGTH: 8
<212> TYPE: PRT
<213> ORGANISM: Homo sapiens

<400> SEQUENCE: 727

Ser Ser Asn Ile Gly Ser Asn Thr
1 5

<210> SEQ ID NO 728
<211> LENGTH: 8
<212> TYPE: PRT
<213> ORGANISM: Homo sapiens

<400> SEQUENCE: 728

Ser Ser Asn Ile Gly Ser Asn Thr
1 5

<210> SEQ ID NO 729
<211> LENGTH: 8
<212> TYPE: PRT
<213> ORGANISM: Homo sapiens

<400> SEQUENCE: 729

Ser Ser Asn Ile Gly Ser Asn Thr
1 5

<210> SEQ ID NO 730
<211> LENGTH: 8
<212> TYPE: PRT
<213> ORGANISM: Homo sapiens

<400> SEQUENCE: 730

Ser Ser Asn Ile Gly Ser Asn Thr
1 5

<210> SEQ ID NO 731
<211> LENGTH: 8
<212> TYPE: PRT
<213> ORGANISM: Homo sapiens

<400> SEQUENCE: 731

Ser Ser Asn Ile Gly Ser Asn Ser
1 5

<210> SEQ ID NO 732
<211> LENGTH: 8
<212> TYPE: PRT
<213> ORGANISM: Homo sapiens

<400> SEQUENCE: 732

Ser Ser Asn Ile Gly Ser Asn Thr 1 5

<210> SEQ ID NO 733
<211> LENGTH: 8
<212> TYPE: PRT
<213> ORGANISM: Homo sapiens

<400> SEQUENCE: 733

Ser Ser Asn Ile Gly Ser Asn Tyr
1 5

<210> SEQ ID NO 734
<211> LENGTH: 8
<212> TYPE: PRT
<213> ORGANISM: Homo sapiens

<400> SEQUENCE: 734

Ser Ser Asn Ile Gly Ser Asn Ala
1 5

<210> SEQ ID NO 735
<211> LENGTH: 8
<212> TYPE: PRT
<213> ORGANISM: Homo sapiens

<400> SEQUENCE: 735

Ser Ser Asn Ile Gly Ser Asn Thr
1 5

<210> SEQ ID NO 736
<211> LENGTH: 8
<212> TYPE: PRT
<213> ORGANISM: Homo sapiens

<400> SEQUENCE: 736

Ser Ser Asn Ile Gly Ser Asn Thr
1 5

<210> SEQ ID NO 737
<211> LENGTH: 8
<212> TYPE: PRT
<213> ORGANISM: Homo sapiens

<400> SEQUENCE: 737

Ser Ser Asn Ile Gly Ser Asn Tyr
1 5

<210> SEQ ID NO 738
<211> LENGTH: 8
<212> TYPE: PRT
<213> ORGANISM: Homo sapiens

<400> SEQUENCE: 738

Ser Ser Asn Ile Gly Ser Asn Thr
1 5

<210> SEQ ID NO 739
<211> LENGTH: 8
<212> TYPE: PRT
<213> ORGANISM: Homo sapiens

<400> SEQUENCE: 739

Ser Ser Asn Ile Gly Ser Asn Thr
1 5

<210> SEQ ID NO 740
<211> LENGTH: 8
<212> TYPE: PRT
<213> ORGANISM: Homo sapiens

<400> SEQUENCE: 740

Ser Ser Asn Ile Gly Ser Asn Thr
1 5

<210> SEQ ID NO 741
<211> LENGTH: 8
<212> TYPE: PRT
<213> ORGANISM: Homo sapiens

<400> SEQUENCE: 741

Ser Phe Asn Ile Gly Gly Asn Thr
1 5

<210> SEQ ID NO 742
<211> LENGTH: 8
<212> TYPE: PRT
<213> ORGANISM: Homo sapiens

<400> SEQUENCE: 742

Ser Ser Asn Ile Gly Ser Asn Thr
1 5

<210> SEQ ID NO 743
<211> LENGTH: 6
<212> TYPE: PRT
<213> ORGANISM: Homo sapiens

<400> SEQUENCE: 743

Ser Leu Arg Ser Tyr Tyr
1 5

<210> SEQ ID NO 744
<211> LENGTH: 8
<212> TYPE: PRT
<213> ORGANISM: Homo sapiens

<400> SEQUENCE: 744

Ser Ser Asn Ile Gly Ser Asn Thr
1 5

<210> SEQ ID NO 745
<211> LENGTH: 8
<212> TYPE: PRT
<213> ORGANISM: Homo sapiens

<400> SEQUENCE: 745

Asn Ser Asn Ile Gly Ser Asn Thr
1 5

<210> SEQ ID NO 746
<211> LENGTH: 8
<212> TYPE: PRT
<213> ORGANISM: Homo sapiens

<400> SEQUENCE: 746

Ser Ser Asn Ile Gly Ser Asn Thr
1 5

<210> SEQ ID NO 747

<211> LENGTH: 8
<212> TYPE: PRT
<213> ORGANISM: Homo sapiens

<400> SEQUENCE: 747

Ser Ser Asn Ile Gly Ser Asn Thr
1 5

<210> SEQ ID NO 748
<211> LENGTH: 8
<212> TYPE: PRT
<213> ORGANISM: Homo sapiens

<400> SEQUENCE: 748

Ser Ser Asn Ile Gly Ser Asn Tyr
1 5

<210> SEQ ID NO 749
<211> LENGTH: 8
<212> TYPE: PRT
<213> ORGANISM: Homo sapiens

<400> SEQUENCE: 749

Ser Ser Asn Ile Gly Ser Asn Thr
1 5

<210> SEQ ID NO 750
<211> LENGTH: 8
<212> TYPE: PRT
<213> ORGANISM: Homo sapiens

<400> SEQUENCE: 750

Ser Ser Asn Ile Gly Ser Asn Thr
1 5

<210> SEQ ID NO 751
<211> LENGTH: 8
<212> TYPE: PRT
<213> ORGANISM: Homo sapiens

<400> SEQUENCE: 751

Ser Ser Asn Ile Gly Ser Asn Thr
1 5

<210> SEQ ID NO 752
<211> LENGTH: 8
<212> TYPE: PRT
<213> ORGANISM: Homo sapiens

<400> SEQUENCE: 752

Ser Ser Asn Ile Gly Ser Asn Thr
1 5

<210> SEQ ID NO 753
<211> LENGTH: 6
<212> TYPE: PRT
<213> ORGANISM: Homo sapiens

<400> SEQUENCE: 753

Asn Ile Gly Ser Lys Ala
1 5

<210> SEQ ID NO 754
<211> LENGTH: 8
<212> TYPE: PRT

<213> ORGANISM: Homo sapiens

<400> SEQUENCE: 754

Ser Ser Asn Ile Gly Ser Asn Thr
1 5

<210> SEQ ID NO 755
<211> LENGTH: 8
<212> TYPE: PRT
<213> ORGANISM: Homo sapiens

<400> SEQUENCE: 755

Ser Ser Asn Ile Gly Ser Asn Thr
1 5

<210> SEQ ID NO 756
<211> LENGTH: 8
<212> TYPE: PRT
<213> ORGANISM: Homo sapiens

<400> SEQUENCE: 756

Ser Ser Asn Ile Gly Ser Asn Thr
1 5

<210> SEQ ID NO 757
<211> LENGTH: 8
<212> TYPE: PRT
<213> ORGANISM: Homo sapiens

<400> SEQUENCE: 757

Ser Ser Asn Ile Gly Ser Asn Thr
1 5

<210> SEQ ID NO 758
<211> LENGTH: 8
<212> TYPE: PRT
<213> ORGANISM: Homo sapiens

<400> SEQUENCE: 758

Ser Ser Asn Ile Gly Ser Asn Thr
1 5

<210> SEQ ID NO 759
<211> LENGTH: 8
<212> TYPE: PRT
<213> ORGANISM: Homo sapiens

<400> SEQUENCE: 759

Ser Ser Asn Ile Gly Ser Asn Thr
1 5

<210> SEQ ID NO 760
<211> LENGTH: 18
<212> TYPE: DNA
<213> ORGANISM: Homo sapiens

<400> SEQUENCE: 760
caggacatta gcgactat 18

<210> SEQ ID NO 761
<211> LENGTH: 36
<212> TYPE: DNA
<213> ORGANISM: Homo sapiens

<400> SEQUENCE: 761
cagagcctct tggatagtga tgatggaaac acctat 36

<210> SEQ ID NO 762
<211> LENGTH: 36
<212> TYPE: DNA
<213> ORGANISM: Homo sapiens

<400> SEQUENCE: 762
cagagtgttt tatacagttc caacaaaaag aactac 36

<210> SEQ ID NO 763
<211> LENGTH: 21
<212> TYPE: DNA
<213> ORGANISM: Homo sapiens

<400> SEQUENCE: 763
cagagtgtta gcagcagcta c 21

<210> SEQ ID NO 764
<211> LENGTH: 21
<212> TYPE: DNA
<213> ORGANISM: Homo sapiens

<400> SEQUENCE: 764
cagagtgtta gcagcagcta c 21

<210> SEQ ID NO 765
<211> LENGTH: 33
<212> TYPE: DNA
<213> ORGANISM: Homo sapiens

<400> SEQUENCE: 765
cagagcctcc tgcatagtaa tggatacaac tat 33

<210> SEQ ID NO 766
<211> LENGTH: 18
<212> TYPE: DNA
<213> ORGANISM: Homo sapiens

<400> SEQUENCE: 766
ccgggtatta gcagctgg 18

<210> SEQ ID NO 767
<211> LENGTH: 36
<212> TYPE: DNA
<213> ORGANISM: Homo sapiens

<400> SEQUENCE: 767
cagagtgttt tatacagctc caacaataag aactac 36

<210> SEQ ID NO 768
<211> LENGTH: 18
<212> TYPE: DNA
<213> ORGANISM: Homo sapiens

<400> SEQUENCE: 768
cagagtatta gtagctgg 18

<210> SEQ ID NO 769
<211> LENGTH: 18
<212> TYPE: DNA
<213> ORGANISM: Homo sapiens

<400> SEQUENCE: 769
caggacatta gcgactat 18

<210> SEQ ID NO 770
<211> LENGTH: 18
<212> TYPE: DNA
<213> ORGANISM: Homo sapiens

<400> SEQUENCE: 770
cagggtatta gcagttat 18

<210> SEQ ID NO 771
<211> LENGTH: 33
<212> TYPE: DNA
<213> ORGANISM: Homo sapiens

<400> SEQUENCE: 771
cagagcctcc tgtatagtaa tggatacaac tat 33

<210> SEQ ID NO 772
<211> LENGTH: 18
<212> TYPE: DNA
<213> ORGANISM: Homo sapiens

<400> SEQUENCE: 772
cagagtatta gtagctgg 18

<210> SEQ ID NO 773
<211> LENGTH: 18
<212> TYPE: DNA
<213> ORGANISM: Homo sapiens

<400> SEQUENCE: 773
cagagtatta gtagctgg 18

<210> SEQ ID NO 774
<211> LENGTH: 36
<212> TYPE: DNA
<213> ORGANISM: Homo sapiens

<400> SEQUENCE: 774
cagagcctct tggatagtga tgatggaaac acctat 36

<210> SEQ ID NO 775
<211> LENGTH: 18
<212> TYPE: DNA
<213> ORGANISM: Homo sapiens

<400> SEQUENCE: 775
cagagtatta gtgactgg 18

<210> SEQ ID NO 776
<211> LENGTH: 21
<212> TYPE: DNA
<213> ORGANISM: Homo sapiens

<400> SEQUENCE: 776
cagagtgtta gcagcaccta c 21

<210> SEQ ID NO 777
<211> LENGTH: 18
<212> TYPE: DNA
<213> ORGANISM: Homo sapiens

<400> SEQUENCE: 777
caggacatta gcaactat 18

<210> SEQ ID NO 778
<211> LENGTH: 21
<212> TYPE: DNA
<213> ORGANISM: Homo sapiens

<400> SEQUENCE: 778
cagagtgtta gcagcagcta c 21

<210> SEQ ID NO 779
<211> LENGTH: 36
<212> TYPE: DNA
<213> ORGANISM: Homo sapiens

<400> SEQUENCE: 779
cagagtgttt tatacagctc caacaataag aactac 36

<210> SEQ ID NO 780
<211> LENGTH: 21
<212> TYPE: DNA
<213> ORGANISM: Homo sapiens

<400> SEQUENCE: 780
cagagtgtta gcagcagcta c 21

<210> SEQ ID NO 781
<211> LENGTH: 36
<212> TYPE: DNA
<213> ORGANISM: Homo sapiens

<400> SEQUENCE: 781
cagagtgttt tatacagctc caacaataag aactac 36

<210> SEQ ID NO 782
<211> LENGTH: 21
<212> TYPE: DNA
<213> ORGANISM: Homo sapiens

<400> SEQUENCE: 782
cagagtgtta gcagcagcta c 21

<210> SEQ ID NO 783
<211> LENGTH: 36
<212> TYPE: DNA
<213> ORGANISM: Homo sapiens

<400> SEQUENCE: 783
cagagtgttt tatacagctc caacaataag aactac 36

<210> SEQ ID NO 784
<211> LENGTH: 36
<212> TYPE: DNA
<213> ORGANISM: Homo sapiens

<400> SEQUENCE: 784
cagactgttt tatacagctc cgacaataag aactac 36

<210> SEQ ID NO 785
<211> LENGTH: 21
<212> TYPE: DNA

<213> ORGANISM: Homo sapiens

<400> SEQUENCE: 785
cagagtatta gcagcagcta c 21

<210> SEQ ID NO 786
<211> LENGTH: 18
<212> TYPE: DNA
<213> ORGANISM: Homo sapiens

<400> SEQUENCE: 786
cagagtatta gtagctgg 18

<210> SEQ ID NO 787
<211> LENGTH: 18
<212> TYPE: DNA
<213> ORGANISM: Homo sapiens

<400> SEQUENCE: 787
cagggcatta gcagttat 18

<210> SEQ ID NO 788
<211> LENGTH: 18
<212> TYPE: DNA
<213> ORGANISM: Homo sapiens

<400> SEQUENCE: 788
cagggcttta gcaattat 18

<210> SEQ ID NO 789
<211> LENGTH: 33
<212> TYPE: DNA
<213> ORGANISM: Homo sapiens

<400> SEQUENCE: 789
cagagcctcc tgcatagtaa tggatacaac tat 33

<210> SEQ ID NO 790
<211> LENGTH: 33
<212> TYPE: DNA
<213> ORGANISM: Homo sapiens

<400> SEQUENCE: 790
cagagcctcc tgcatagtaa tggatacaac tat 33

<210> SEQ ID NO 791
<211> LENGTH: 33
<212> TYPE: DNA
<213> ORGANISM: Homo sapiens

<400> SEQUENCE: 791
cagagcctcc tgcatagtaa tggatacaac tat 33

<210> SEQ ID NO 792
<211> LENGTH: 36
<212> TYPE: DNA
<213> ORGANISM: Homo sapiens

<400> SEQUENCE: 792
cagagtgttt tatacagctc caacaataaa aactac 36

<210> SEQ ID NO 793
<211> LENGTH: 18

<212> TYPE: DNA
<213> ORGANISM: Homo sapiens

<400> SEQUENCE: 793
caggacatta gcaactat 18

<210> SEQ ID NO 794
<211> LENGTH: 33
<212> TYPE: DNA
<213> ORGANISM: Homo sapiens

<400> SEQUENCE: 794
cagagcctcc tgcatagtaa tggatacaac tat 33

<210> SEQ ID NO 795
<211> LENGTH: 33
<212> TYPE: DNA
<213> ORGANISM: Homo sapiens

<400> SEQUENCE: 795
cagagcctcc tgcatagtaa tggatacaac tat 33

<210> SEQ ID NO 796
<211> LENGTH: 36
<212> TYPE: DNA
<213> ORGANISM: Homo sapiens

<400> SEQUENCE: 796
cagagtgttt tatacagctc caacaataag aactac 36

<210> SEQ ID NO 797
<211> LENGTH: 33
<212> TYPE: DNA
<213> ORGANISM: Homo sapiens

<400> SEQUENCE: 797
cagagcctcc tgcatagtaa tggatacaac tat 33

<210> SEQ ID NO 798
<211> LENGTH: 36
<212> TYPE: DNA
<213> ORGANISM: Homo sapiens

<400> SEQUENCE: 798
cagagcctct tggatagtga tgatggaaac acctat 36

<210> SEQ ID NO 799
<211> LENGTH: 36
<212> TYPE: DNA
<213> ORGANISM: Homo sapiens

<400> SEQUENCE: 799
cagagcctct tggatagtga tgatggaaac acctat 36

<210> SEQ ID NO 800
<211> LENGTH: 36
<212> TYPE: DNA
<213> ORGANISM: Homo sapiens

<400> SEQUENCE: 800
cagagtgttt tatacagctc caacaataaa aactac 36

<210> SEQ ID NO 801

<211> LENGTH: 18
<212> TYPE: DNA
<213> ORGANISM: Homo sapiens

<400> SEQUENCE: 801
cagggtatta gcagctgg 18

<210> SEQ ID NO 802
<211> LENGTH: 33
<212> TYPE: DNA
<213> ORGANISM: Homo sapiens

<400> SEQUENCE: 802
cagagcctcc tccatagtaa tggatacaac tat 33

<210> SEQ ID NO 803
<211> LENGTH: 36
<212> TYPE: DNA
<213> ORGANISM: Homo sapiens

<400> SEQUENCE: 803
cagagcctct tggatagtga tgatggaaac acctat 36

<210> SEQ ID NO 804
<211> LENGTH: 33
<212> TYPE: DNA
<213> ORGANISM: Homo sapiens

<400> SEQUENCE: 804
cagagcctcc tgcatagtaa tggatacaac tat 33

<210> SEQ ID NO 805
<211> LENGTH: 21
<212> TYPE: DNA
<213> ORGANISM: Homo sapiens

<400> SEQUENCE: 805
cagaatgtta gcagcaccta c 21

<210> SEQ ID NO 806
<211> LENGTH: 21
<212> TYPE: DNA
<213> ORGANISM: Homo sapiens

<400> SEQUENCE: 806
cagagtgtta gcagcagcta c 21

<210> SEQ ID NO 807
<211> LENGTH: 33
<212> TYPE: DNA
<213> ORGANISM: Homo sapiens

<400> SEQUENCE: 807
cagagcctcc tctatagtaa tggatacaac tat 33

<210> SEQ ID NO 808
<211> LENGTH: 24
<212> TYPE: DNA
<213> ORGANISM: Homo sapiens

<400> SEQUENCE: 808
agctccaaca tcggaagtaa tact 24

<210> SEQ ID NO 809
<211> LENGTH: 24
<212> TYPE: DNA
<213> ORGANISM: Homo sapiens

<400> SEQUENCE: 809
agctccaaca tcggaagtaa tact 24

<210> SEQ ID NO 810
<211> LENGTH: 24
<212> TYPE: DNA
<213> ORGANISM: Homo sapiens

<400> SEQUENCE: 810
agctccaaca tcggaagtaa tact 24

<210> SEQ ID NO 811
<211> LENGTH: 24
<212> TYPE: DNA
<213> ORGANISM: Homo sapiens

<400> SEQUENCE: 811
agctccaaca tcggaagtaa ttct 24

<210> SEQ ID NO 812
<211> LENGTH: 24
<212> TYPE: DNA
<213> ORGANISM: Homo sapiens

<400> SEQUENCE: 812
agttccaaca tcggaagtaa tact 24

<210> SEQ ID NO 813
<211> LENGTH: 24
<212> TYPE: DNA
<213> ORGANISM: Homo sapiens

<400> SEQUENCE: 813
agctccaaca tcggaagtaa tgct 24

<210> SEQ ID NO 814
<211> LENGTH: 24
<212> TYPE: DNA
<213> ORGANISM: Homo sapiens

<400> SEQUENCE: 814
agctccaaca tcggaagtaa tact 24

<210> SEQ ID NO 815
<211> LENGTH: 24
<212> TYPE: DNA
<213> ORGANISM: Homo sapiens

<400> SEQUENCE: 815
agctccaaca tcggaaataa tgct 24

<210> SEQ ID NO 816
<211> LENGTH: 24
<212> TYPE: DNA
<213> ORGANISM: Homo sapiens

<400> SEQUENCE: 816
agctccaaca tcggaagtaa tact 24

<210> SEQ ID NO 817
<211> LENGTH: 24
<212> TYPE: DNA
<213> ORGANISM: Homo sapiens

<400> SEQUENCE: 817
agctccaaca tcggaagtaa tact 24

<210> SEQ ID NO 818
<211> LENGTH: 24
<212> TYPE: DNA
<213> ORGANISM: Homo sapiens

<400> SEQUENCE: 818
agctccaaca tcggaagtaa tact 24

<210> SEQ ID NO 819
<211> LENGTH: 24
<212> TYPE: DNA
<213> ORGANISM: Homo sapiens

<400> SEQUENCE: 819
agctccaaca tcggaagtaa tact 24

<210> SEQ ID NO 820
<211> LENGTH: 24
<212> TYPE: DNA
<213> ORGANISM: Homo sapiens

<400> SEQUENCE: 820
agctccaaca tcggaagtaa tact 24

<210> SEQ ID NO 821
<211> LENGTH: 24
<212> TYPE: DNA
<213> ORGANISM: Homo sapiens

<400> SEQUENCE: 821
agctccaata tcggaagtaa tact 24

<210> SEQ ID NO 822
<211> LENGTH: 24
<212> TYPE: DNA
<213> ORGANISM: Homo sapiens

<400> SEQUENCE: 822
agctccaaca tcggaagtaa tact 24

<210> SEQ ID NO 823
<211> LENGTH: 24
<212> TYPE: DNA
<213> ORGANISM: Homo sapiens

<400> SEQUENCE: 823
agctccaaca tcggaagtaa tact 24

<210> SEQ ID NO 824
<211> LENGTH: 27
<212> TYPE: DNA
<213> ORGANISM: Homo sapiens

<400> SEQUENCE: 824
agcagtgatg ttgggagtta taacctt 27

<210> SEQ ID NO 825
<211> LENGTH: 24
<212> TYPE: DNA
<213> ORGANISM: Homo sapiens

<400> SEQUENCE: 825
agctccaaca tcggaagtaa tact 24

<210> SEQ ID NO 826
<211> LENGTH: 24
<212> TYPE: DNA
<213> ORGANISM: Homo sapiens

<400> SEQUENCE: 826
agctccaaca tcggaagtaa tact 24

<210> SEQ ID NO 827
<211> LENGTH: 24
<212> TYPE: DNA
<213> ORGANISM: Homo sapiens

<400> SEQUENCE: 827
agctccaaca tcggaagtaa tact 24

<210> SEQ ID NO 828
<211> LENGTH: 24
<212> TYPE: DNA
<213> ORGANISM: Homo sapiens

<400> SEQUENCE: 828
agctccaaca tcggaagtaa tact 24

<210> SEQ ID NO 829
<211> LENGTH: 27
<212> TYPE: DNA
<213> ORGANISM: Homo sapiens

<400> SEQUENCE: 829
agcagtgatg ttgggagtta taacctt 27

<210> SEQ ID NO 830
<211> LENGTH: 24
<212> TYPE: DNA
<213> ORGANISM: Homo sapiens

<400> SEQUENCE: 830
agctccaaca tcggaagtaa tgct 24

<210> SEQ ID NO 831
<211> LENGTH: 24
<212> TYPE: DNA
<213> ORGANISM: Homo sapiens

<400> SEQUENCE: 831
agctccaaca tcggaagtaa tact 24

<210> SEQ ID NO 832
<211> LENGTH: 24
<212> TYPE: DNA
<213> ORGANISM: Homo sapiens

<400> SEQUENCE: 832
agctccaaca tcggaagtaa tact 24

<210> SEQ ID NO 833
<211> LENGTH: 24
<212> TYPE: DNA
<213> ORGANISM: Homo sapiens

<400> SEQUENCE: 833
agctccaaca tcggaagtaa tact 24

<210> SEQ ID NO 834
<211> LENGTH: 24
<212> TYPE: DNA
<213> ORGANISM: Homo sapiens

<400> SEQUENCE: 834
agctccaaca tcggaagtaa tact 24

<210> SEQ ID NO 835
<211> LENGTH: 24
<212> TYPE: DNA
<213> ORGANISM: Homo sapiens

<400> SEQUENCE: 835
agctccaaca tcggaagtaa tact 24

<210> SEQ ID NO 836
<211> LENGTH: 24
<212> TYPE: DNA
<213> ORGANISM: Homo sapiens

<400> SEQUENCE: 836
agctccaaca tcggaagtaa tact 24

<210> SEQ ID NO 837
<211> LENGTH: 24
<212> TYPE: DNA
<213> ORGANISM: Homo sapiens

<400> SEQUENCE: 837
agctccaaca tcggaagtaa tact 24

<210> SEQ ID NO 838
<211> LENGTH: 24
<212> TYPE: DNA
<213> ORGANISM: Homo sapiens

<400> SEQUENCE: 838
agctccaaca tcggaagtaa tact 24

<210> SEQ ID NO 839
<211> LENGTH: 24
<212> TYPE: DNA
<213> ORGANISM: Homo sapiens

<400> SEQUENCE: 839
agctccaaca tcggaagtaa ttct 24

<210> SEQ ID NO 840
<211> LENGTH: 24
<212> TYPE: DNA
<213> ORGANISM: Homo sapiens

<400> SEQUENCE: 840
agctccaaca tcggaagtaa tact 24

<210> SEQ ID NO 841
<211> LENGTH: 24
<212> TYPE: DNA
<213> ORGANISM: Homo sapiens

<400> SEQUENCE: 841
agctccaaca tcggaagtaa ttat 24

<210> SEQ ID NO 842
<211> LENGTH: 24
<212> TYPE: DNA
<213> ORGANISM: Homo sapiens

<400> SEQUENCE: 842
agctccaaca tcggaagtaa tgct 24

<210> SEQ ID NO 843
<211> LENGTH: 24
<212> TYPE: DNA
<213> ORGANISM: Homo sapiens

<400> SEQUENCE: 843
agctccaaca tcggaagtaa tact 24

<210> SEQ ID NO 844
<211> LENGTH: 24
<212> TYPE: DNA
<213> ORGANISM: Homo sapiens

<400> SEQUENCE: 844
agctccaaca tcggaagtaa tact 24

<210> SEQ ID NO 845
<211> LENGTH: 24
<212> TYPE: DNA
<213> ORGANISM: Homo sapiens

<400> SEQUENCE: 845
agctccaaca tcggaagtaa ttat 24

<210> SEQ ID NO 846
<211> LENGTH: 24
<212> TYPE: DNA
<213> ORGANISM: Homo sapiens

<400> SEQUENCE: 846
agctccaaca tcggaagtaa tact 24

<210> SEQ ID NO 847
<211> LENGTH: 24
<212> TYPE: DNA
<213> ORGANISM: Homo sapiens

<400> SEQUENCE: 847
agctccaaca tcggaagtaa tact 24

<210> SEQ ID NO 848
<211> LENGTH: 24
<212> TYPE: DNA
<213> ORGANISM: Homo sapiens

<400> SEQUENCE: 848
agctccaaca tcggaagtaa tact 24

<210> SEQ ID NO 849
<211> LENGTH: 24
<212> TYPE: DNA
<213> ORGANISM: Homo sapiens

<400> SEQUENCE: 849
agtttcaaca tcggaggtaa tact 24

<210> SEQ ID NO 850
<211> LENGTH: 24
<212> TYPE: DNA
<213> ORGANISM: Homo sapiens

<400> SEQUENCE: 850
agctccaaca tcggaagtaa tact 24

<210> SEQ ID NO 851
<211> LENGTH: 18
<212> TYPE: DNA
<213> ORGANISM: Homo sapiens

<400> SEQUENCE: 851
agcctcagaa gctattat 18

<210> SEQ ID NO 852
<211> LENGTH: 24
<212> TYPE: DNA
<213> ORGANISM: Homo sapiens

<400> SEQUENCE: 852
agctccaaca tcggaagtaa tact 24

<210> SEQ ID NO 853
<211> LENGTH: 24
<212> TYPE: DNA
<213> ORGANISM: Homo sapiens

<400> SEQUENCE: 853
aattccaaca tcggaagtaa tact 24

<210> SEQ ID NO 854
<211> LENGTH: 24
<212> TYPE: DNA
<213> ORGANISM: Homo sapiens

<400> SEQUENCE: 854
agctccaaca tcggaagtaa tact 24

<210> SEQ ID NO 855
<211> LENGTH: 24
<212> TYPE: DNA
<213> ORGANISM: Homo sapiens

<400> SEQUENCE: 855
agctccaaca tcggaagtaa tact 24

<210> SEQ ID NO 856
<211> LENGTH: 24
<212> TYPE: DNA
<213> ORGANISM: Homo sapiens

<400> SEQUENCE: 856
agctccaaca tcggaagtaa ttat 24

<210> SEQ ID NO 857
<211> LENGTH: 24
<212> TYPE: DNA
<213> ORGANISM: Homo sapiens

<400> SEQUENCE: 857
agctccaaca tcggaagtaa cact 24

<210> SEQ ID NO 858
<211> LENGTH: 24
<212> TYPE: DNA
<213> ORGANISM: Homo sapiens

<400> SEQUENCE: 858
agctccaaca tcggaagtaa tact 24

<210> SEQ ID NO 859
<211> LENGTH: 24
<212> TYPE: DNA
<213> ORGANISM: Homo sapiens

<400> SEQUENCE: 859
agctccaaca tcggaagtaa tact 24

<210> SEQ ID NO 860
<211> LENGTH: 24
<212> TYPE: DNA
<213> ORGANISM: Homo sapiens

<400> SEQUENCE: 860
agctccaaca tcggaagtaa tact 24

<210> SEQ ID NO 861
<211> LENGTH: 18
<212> TYPE: DNA
<213> ORGANISM: Homo sapiens

<400> SEQUENCE: 861
aacattggaa gtaaagct 18

<210> SEQ ID NO 862
<211> LENGTH: 24
<212> TYPE: DNA
<213> ORGANISM: Homo sapiens

<400> SEQUENCE: 862
agctccaaca tcggaagtaa tact 24

<210> SEQ ID NO 863
<211> LENGTH: 24
<212> TYPE: DNA
<213> ORGANISM: Homo sapiens

<400> SEQUENCE: 863
agctccaaca tcggaagtaa tact 24

<210> SEQ ID NO 864
<211> LENGTH: 24
<212> TYPE: DNA

<213> ORGANISM: Homo sapiens

<400> SEQUENCE: 864
agctccaaca tcggaagtaa tact 24

<210> SEQ ID NO 865
<211> LENGTH: 24
<212> TYPE: DNA
<213> ORGANISM: Homo sapiens

<400> SEQUENCE: 865
agctccaaca tcggaagtaa tact 24

<210> SEQ ID NO 866
<211> LENGTH: 24
<212> TYPE: DNA
<213> ORGANISM: Homo sapiens

<400> SEQUENCE: 866
agctccaaca tcggaagtaa tact 24

<210> SEQ ID NO 867
<211> LENGTH: 24
<212> TYPE: DNA
<213> ORGANISM: Homo sapiens

<400> SEQUENCE: 867
agctccaaca tcggaagtaa tact 24

<210> SEQ ID NO 868
<211> LENGTH: 10
<212> TYPE: PRT
<213> ORGANISM: Homo sapiens

<400> SEQUENCE: 868

Ile Lys Ser Lys Thr Asp Gly Gly Thr Thr
1 5 10

<210> SEQ ID NO 869
<211> LENGTH: 8
<212> TYPE: PRT
<213> ORGANISM: Homo sapiens

<400> SEQUENCE: 869

Ile Asn Pro Ile Ser Gly Gly Thr
1 5

<210> SEQ ID NO 870
<211> LENGTH: 10
<212> TYPE: PRT
<213> ORGANISM: Homo sapiens

<400> SEQUENCE: 870

Val Lys Ser Lys Thr Asp Gly Gly Thr Thr
1 5 10

<210> SEQ ID NO 871
<211> LENGTH: 7
<212> TYPE: PRT
<213> ORGANISM: Homo sapiens

<400> SEQUENCE: 871

Ile Phe Ser Ser Gly Ser Thr
1 5

<210> SEQ ID NO 872
<211> LENGTH: 7
<212> TYPE: PRT
<213> ORGANISM: Homo sapiens

<400> SEQUENCE: 872

Ile Tyr Thr Ser Gly Ser Thr
1               5

<210> SEQ ID NO 873
<211> LENGTH: 10
<212> TYPE: PRT
<213> ORGANISM: Homo sapiens

<400> SEQUENCE: 873

Ile Arg Ser Lys Ala Tyr Gly Gly Thr Thr
1               5                   10

<210> SEQ ID NO 874
<211> LENGTH: 8
<212> TYPE: PRT
<213> ORGANISM: Homo sapiens

<400> SEQUENCE: 874

Ile Asn Pro Asn Ser Gly Gly Thr
1               5

<210> SEQ ID NO 875
<211> LENGTH: 10
<212> TYPE: PRT
<213> ORGANISM: Homo sapiens

<400> SEQUENCE: 875

Ile Lys Ser Lys Thr Asp Gly Gly Thr Thr
1               5                   10

<210> SEQ ID NO 876
<211> LENGTH: 7
<212> TYPE: PRT
<213> ORGANISM: Homo sapiens

<400> SEQUENCE: 876

Ile His Tyr Ser Gly Ser Thr
1               5

<210> SEQ ID NO 877
<211> LENGTH: 8
<212> TYPE: PRT
<213> ORGANISM: Homo sapiens

<400> SEQUENCE: 877

Ile Ser Pro Ser Ser Ser Thr Ile
1               5

<210> SEQ ID NO 878
<211> LENGTH: 7
<212> TYPE: PRT
<213> ORGANISM: Homo sapiens

<400> SEQUENCE: 878

Ile Asp Trp Asp Asp Asp Lys
1               5

<210> SEQ ID NO 879
<211> LENGTH: 7
<212> TYPE: PRT
<213> ORGANISM: Homo sapiens

<400> SEQUENCE: 879

Ile Tyr Thr Ser Gly Thr Thr
1 5

<210> SEQ ID NO 880
<211> LENGTH: 7
<212> TYPE: PRT
<213> ORGANISM: Homo sapiens

<400> SEQUENCE: 880

Ile Tyr Thr Ser Gly Ser Thr
1 5

<210> SEQ ID NO 881
<211> LENGTH: 7
<212> TYPE: PRT
<213> ORGANISM: Homo sapiens

<400> SEQUENCE: 881

Val Ser Tyr Ser Gly Gly Thr
1 5

<210> SEQ ID NO 882
<211> LENGTH: 8
<212> TYPE: PRT
<213> ORGANISM: Homo sapiens

<400> SEQUENCE: 882

Ile Asn Pro Asn Arg Gly Asp Thr
1 5

<210> SEQ ID NO 883
<211> LENGTH: 7
<212> TYPE: PRT
<213> ORGANISM: Homo sapiens

<400> SEQUENCE: 883

Phe Ser Tyr Asn Gly Asn Thr
1 5

<210> SEQ ID NO 884
<211> LENGTH: 7
<212> TYPE: PRT
<213> ORGANISM: Homo sapiens

<400> SEQUENCE: 884

Ile Tyr Thr Ser Gly Ser Thr
1 5

<210> SEQ ID NO 885
<211> LENGTH: 7
<212> TYPE: PRT
<213> ORGANISM: Homo sapiens

<400> SEQUENCE: 885

Ile Gly Thr Ala Gly Asp Thr
1 5

<210> SEQ ID NO 886
<211> LENGTH: 7

<212> TYPE: PRT
<213> ORGANISM: Homo sapiens

<400> SEQUENCE: 886

Ile Asn His Ser Gly Ser Thr
1 5

<210> SEQ ID NO 887
<211> LENGTH: 10
<212> TYPE: PRT
<213> ORGANISM: Homo sapiens

<400> SEQUENCE: 887

Ile Lys Ser Lys Thr Asp Gly Gly Thr Thr
1 5 10

<210> SEQ ID NO 888
<211> LENGTH: 7
<212> TYPE: PRT
<213> ORGANISM: Homo sapiens

<400> SEQUENCE: 888

Ile Asn His Ser Gly Ser Thr
1 5

<210> SEQ ID NO 889
<211> LENGTH: 8
<212> TYPE: PRT
<213> ORGANISM: Homo sapiens

<400> SEQUENCE: 889

Ile Asn Ser Asp Gly Ser Ser Thr
1 5

<210> SEQ ID NO 890
<211> LENGTH: 8
<212> TYPE: PRT
<213> ORGANISM: Homo sapiens

<400> SEQUENCE: 890

Ile Ser Ser Ser Ser Ser Tyr Ile
1 5

<210> SEQ ID NO 891
<211> LENGTH: 7
<212> TYPE: PRT
<213> ORGANISM: Homo sapiens

<400> SEQUENCE: 891

Ile Tyr Trp Asn Asp Asp Lys
1 5

<210> SEQ ID NO 892
<211> LENGTH: 8
<212> TYPE: PRT
<213> ORGANISM: Homo sapiens

<400> SEQUENCE: 892

Ile Asn Pro Asn Ser Gly Gly Thr
1 5

<210> SEQ ID NO 893
<211> LENGTH: 7
<212> TYPE: PRT
<213> ORGANISM: Homo sapiens

<400> SEQUENCE: 893

Ile Tyr Tyr Ser Gly Ser Thr
1 5

<210> SEQ ID NO 894
<211> LENGTH: 7
<212> TYPE: PRT
<213> ORGANISM: Homo sapiens

<400> SEQUENCE: 894

Ile Ser Tyr Ser Gly Gly Thr
1 5

<210> SEQ ID NO 895
<211> LENGTH: 8
<212> TYPE: PRT
<213> ORGANISM: Homo sapiens

<400> SEQUENCE: 895

Ile Ser Ser Ser Ser Thr Tyr Ile
1 5

<210> SEQ ID NO 896
<211> LENGTH: 7
<212> TYPE: PRT
<213> ORGANISM: Homo sapiens

<400> SEQUENCE: 896

Ile Tyr Thr Ser Gly Ser Thr
1 5

<210> SEQ ID NO 897
<211> LENGTH: 8
<212> TYPE: PRT
<213> ORGANISM: Homo sapiens

<400> SEQUENCE: 897

Ile Ser Ser Ser Ser Ser Tyr Ile
1 5

<210> SEQ ID NO 898
<211> LENGTH: 10
<212> TYPE: PRT
<213> ORGANISM: Homo sapiens

<400> SEQUENCE: 898

Ile Arg Ser Lys Ala Tyr Gly Gly Thr Thr
1 5 10

<210> SEQ ID NO 899
<211> LENGTH: 10
<212> TYPE: PRT
<213> ORGANISM: Homo sapiens

<400> SEQUENCE: 899

Ile Asn Ser Lys Thr Asp Gly Gly Thr Thr
1 5 10

<210> SEQ ID NO 900
<211> LENGTH: 8
<212> TYPE: PRT
<213> ORGANISM: Homo sapiens

<400> SEQUENCE: 900

Ile Asn Pro Asn Ser Gly Gly Thr
1 5

<210> SEQ ID NO 901
<211> LENGTH: 8
<212> TYPE: PRT
<213> ORGANISM: Homo sapiens

<400> SEQUENCE: 901

Ile Ser Ser Ser Ser Ser Thr Ile
1 5

<210> SEQ ID NO 902
<211> LENGTH: 7
<212> TYPE: PRT
<213> ORGANISM: Homo sapiens

<400> SEQUENCE: 902

Ile Tyr Tyr Arg Gly Ser Thr
1 5

<210> SEQ ID NO 903
<211> LENGTH: 8
<212> TYPE: PRT
<213> ORGANISM: Homo sapiens

<400> SEQUENCE: 903

Ile Lys Gln Asp Gly Ser Glu Lys
1 5

<210> SEQ ID NO 904
<211> LENGTH: 10
<212> TYPE: PRT
<213> ORGANISM: Homo sapiens

<400> SEQUENCE: 904

Ile Lys Ser Lys Thr Asp Gly Gly Thr Thr
1 5 10

<210> SEQ ID NO 905
<211> LENGTH: 8
<212> TYPE: PRT
<213> ORGANISM: Homo sapiens

<400> SEQUENCE: 905

Ile Ser Ser Ser Ser Ser Tyr Ile
1 5

<210> SEQ ID NO 906
<211> LENGTH: 8
<212> TYPE: PRT
<213> ORGANISM: Homo sapiens

<400> SEQUENCE: 906

Ile Asn Pro Asn Ser Gly Gly Thr
1 5

<210> SEQ ID NO 907
<211> LENGTH: 8
<212> TYPE: PRT
<213> ORGANISM: Homo sapiens

<400> SEQUENCE: 907

Ile Asn Pro Asn Ser Gly Gly Thr 1 5

<210> SEQ ID NO 908
<211> LENGTH: 7
<212> TYPE: PRT
<213> ORGANISM: Homo sapiens

<400> SEQUENCE: 908

Ile Tyr Trp Asn Asp Asp Lys
1 5

<210> SEQ ID NO 909
<211> LENGTH: 8
<212> TYPE: PRT
<213> ORGANISM: Homo sapiens

<400> SEQUENCE: 909

Ile Trp Tyr Asp Gly Ser Ile Lys
1 5

<210> SEQ ID NO 910
<211> LENGTH: 8
<212> TYPE: PRT
<213> ORGANISM: Homo sapiens

<400> SEQUENCE: 910

Ile Lys Gln Asp Gly Ser Glu Lys
1 5

<210> SEQ ID NO 911
<211> LENGTH: 8
<212> TYPE: PRT
<213> ORGANISM: Homo sapiens

<400> SEQUENCE: 911

Ile Asn Pro Asn Ser Gly Gly Thr
1 5

<210> SEQ ID NO 912
<211> LENGTH: 8
<212> TYPE: PRT
<213> ORGANISM: Homo sapiens

<400> SEQUENCE: 912

Ile Ser Tyr Asp Gly Ser Asn Lys
1 5

<210> SEQ ID NO 913
<211> LENGTH: 7
<212> TYPE: PRT
<213> ORGANISM: Homo sapiens

<400> SEQUENCE: 913

Ile Phe Tyr Ser Gly Ser Ile
1 5

<210> SEQ ID NO 914
<211> LENGTH: 7
<212> TYPE: PRT
<213> ORGANISM: Homo sapiens

<400> SEQUENCE: 914

Ile Tyr Ser Ser Gly Ser Ile
1 5

<210> SEQ ID NO 915
<211> LENGTH: 8
<212> TYPE: PRT
<213> ORGANISM: Homo sapiens

<400> SEQUENCE: 915

Ile Trp Tyr Asp Gly Ser Asn Glu
1               5

<210> SEQ ID NO 916
<211> LENGTH: 7
<212> TYPE: PRT
<213> ORGANISM: Homo sapiens

<400> SEQUENCE: 916

Phe Tyr Tyr Ser Gly Ser Thr
1               5

<210> SEQ ID NO 917
<211> LENGTH: 7
<212> TYPE: PRT
<213> ORGANISM: Homo sapiens

<400> SEQUENCE: 917

Ile Tyr Tyr Ser Gly Ser Thr
1               5

<210> SEQ ID NO 918
<211> LENGTH: 7
<212> TYPE: PRT
<213> ORGANISM: Homo sapiens

<400> SEQUENCE: 918

Ile Tyr Thr Ser Gly Ser Thr
1               5

<210> SEQ ID NO 919
<211> LENGTH: 7
<212> TYPE: PRT
<213> ORGANISM: Homo sapiens

<400> SEQUENCE: 919

Ile Tyr Ile Ser Gly Ser Ile
1               5

<210> SEQ ID NO 920
<211> LENGTH: 7
<212> TYPE: PRT
<213> ORGANISM: Homo sapiens

<400> SEQUENCE: 920

Ile Tyr Tyr Ser Gly Ile Thr
1               5

<210> SEQ ID NO 921
<211> LENGTH: 7
<212> TYPE: PRT
<213> ORGANISM: Homo sapiens

<400> SEQUENCE: 921

Ile Tyr Thr Ser Gly Thr Thr
1               5

<210> SEQ ID NO 922

<211> LENGTH: 8
<212> TYPE: PRT
<213> ORGANISM: Homo sapiens

<400> SEQUENCE: 922

Ile Asn Pro Asn Ser Gly Gly Ala
1 5

<210> SEQ ID NO 923
<211> LENGTH: 7
<212> TYPE: PRT
<213> ORGANISM: Homo sapiens

<400> SEQUENCE: 923

Ile Phe Tyr Ser Gly Ser Thr
1 5

<210> SEQ ID NO 924
<211> LENGTH: 7
<212> TYPE: PRT
<213> ORGANISM: Homo sapiens

<400> SEQUENCE: 924

Ile Tyr Ile Ser Gly Thr Thr
1 5

<210> SEQ ID NO 925
<211> LENGTH: 7
<212> TYPE: PRT
<213> ORGANISM: Homo sapiens

<400> SEQUENCE: 925

Ile Tyr Thr Ser Gly Ser Thr
1 5

<210> SEQ ID NO 926
<211> LENGTH: 7
<212> TYPE: PRT
<213> ORGANISM: Homo sapiens

<400> SEQUENCE: 926

Ile Tyr Thr Ser Gly Ser Thr
1 5

<210> SEQ ID NO 927
<211> LENGTH: 8
<212> TYPE: PRT
<213> ORGANISM: Homo sapiens

<400> SEQUENCE: 927

Ile Ser Ser Ser Ser Ser Thr Ile
1 5

<210> SEQ ID NO 928
<211> LENGTH: 7
<212> TYPE: PRT
<213> ORGANISM: Homo sapiens

<400> SEQUENCE: 928

Ile Tyr Thr Ser Gly Ser Thr
1 5

<210> SEQ ID NO 929
<211> LENGTH: 7
<212> TYPE: PRT

<213> ORGANISM: Homo sapiens

<400> SEQUENCE: 929

Ile Tyr Ser Ser Gly Thr Thr
1               5

<210> SEQ ID NO 930
<211> LENGTH: 7
<212> TYPE: PRT
<213> ORGANISM: Homo sapiens

<400> SEQUENCE: 930

Ile Tyr Thr Ser Gly Ser Thr
1               5

<210> SEQ ID NO 931
<211> LENGTH: 7
<212> TYPE: PRT
<213> ORGANISM: Homo sapiens

<400> SEQUENCE: 931

Ile Tyr Thr Ser Gly Ser Thr
1               5

<210> SEQ ID NO 932
<211> LENGTH: 7
<212> TYPE: PRT
<213> ORGANISM: Homo sapiens

<400> SEQUENCE: 932

Ile Tyr Thr Ser Gly Asn Thr
1               5

<210> SEQ ID NO 933
<211> LENGTH: 7
<212> TYPE: PRT
<213> ORGANISM: Homo sapiens

<400> SEQUENCE: 933

Ile Tyr Thr Ser Gly Ser Thr
1               5

<210> SEQ ID NO 934
<211> LENGTH: 8
<212> TYPE: PRT
<213> ORGANISM: Homo sapiens

<400> SEQUENCE: 934

Ile Ser Ser Ser Ser Asn Tyr Ile
1               5

<210> SEQ ID NO 935
<211> LENGTH: 7
<212> TYPE: PRT
<213> ORGANISM: Homo sapiens

<400> SEQUENCE: 935

Phe Tyr Tyr Ser Gly Ser Thr
1               5

<210> SEQ ID NO 936
<211> LENGTH: 7
<212> TYPE: PRT
<213> ORGANISM: Homo sapiens

<400> SEQUENCE: 936

Ile Tyr Thr Ser Gly Ser Thr
1 5

<210> SEQ ID NO 937
<211> LENGTH: 7
<212> TYPE: PRT
<213> ORGANISM: Homo sapiens

<400> SEQUENCE: 937

Ile Tyr Thr Ser Gly Asn Thr
1 5

<210> SEQ ID NO 938
<211> LENGTH: 7
<212> TYPE: PRT
<213> ORGANISM: Homo sapiens

<400> SEQUENCE: 938

Ile Tyr Thr Ser Gly Ser Thr
1 5

<210> SEQ ID NO 939
<211> LENGTH: 8
<212> TYPE: PRT
<213> ORGANISM: Homo sapiens

<400> SEQUENCE: 939

Ile Asn Pro Asn Ser Gly Gly Thr
1 5

<210> SEQ ID NO 940
<211> LENGTH: 8
<212> TYPE: PRT
<213> ORGANISM: Homo sapiens

<400> SEQUENCE: 940

Ile Asn Pro Asn Ser Gly Gly Thr
1 5

<210> SEQ ID NO 941
<211> LENGTH: 7
<212> TYPE: PRT
<213> ORGANISM: Homo sapiens

<400> SEQUENCE: 941

Ile Tyr Thr Ser Gly Ser Thr
1 5

<210> SEQ ID NO 942
<211> LENGTH: 7
<212> TYPE: PRT
<213> ORGANISM: Homo sapiens

<400> SEQUENCE: 942

Leu Phe Thr Ser Gly Ser Thr
1 5

<210> SEQ ID NO 943
<211> LENGTH: 7
<212> TYPE: PRT
<213> ORGANISM: Homo sapiens

<400> SEQUENCE: 943

Ile Tyr Thr Ser Gly Ser Thr
1 5

<210> SEQ ID NO 944
<211> LENGTH: 7
<212> TYPE: PRT
<213> ORGANISM: Homo sapiens

<400> SEQUENCE: 944

Ile Tyr Thr Ser Gly Ser Thr
1 5

<210> SEQ ID NO 945
<211> LENGTH: 7
<212> TYPE: PRT
<213> ORGANISM: Homo sapiens

<400> SEQUENCE: 945

Ile Tyr Tyr Ser Gly Ser Thr
1 5

<210> SEQ ID NO 946
<211> LENGTH: 7
<212> TYPE: PRT
<213> ORGANISM: Homo sapiens

<400> SEQUENCE: 946

Ile Tyr Thr Ser Gly Tyr Thr
1 5

<210> SEQ ID NO 947
<211> LENGTH: 7
<212> TYPE: PRT
<213> ORGANISM: Homo sapiens

<400> SEQUENCE: 947

Ile Tyr Tyr Ser Gly Ser Thr
1 5

<210> SEQ ID NO 948
<211> LENGTH: 7
<212> TYPE: PRT
<213> ORGANISM: Homo sapiens

<400> SEQUENCE: 948

Ile Tyr Tyr Ser Gly Ser Thr
1 5

<210> SEQ ID NO 949
<211> LENGTH: 8
<212> TYPE: PRT
<213> ORGANISM: Homo sapiens

<400> SEQUENCE: 949

Ile Ser Ser Ser Ser Ala Ile Ile
1 5

<210> SEQ ID NO 950
<211> LENGTH: 8
<212> TYPE: PRT
<213> ORGANISM: Homo sapiens

<400> SEQUENCE: 950

Ile Lys Gln Asp Gly Ser Glu Lys
1 5

<210> SEQ ID NO 951
<211> LENGTH: 8
<212> TYPE: PRT
<213> ORGANISM: Homo sapiens

<400> SEQUENCE: 951

Ile Tyr Pro Gly Asp Ser Asp Thr
1               5

<210> SEQ ID NO 952
<211> LENGTH: 8
<212> TYPE: PRT
<213> ORGANISM: Homo sapiens

<400> SEQUENCE: 952

Ile Asn Pro Asn Ser Gly Gly Thr
1               5

<210> SEQ ID NO 953
<211> LENGTH: 7
<212> TYPE: PRT
<213> ORGANISM: Homo sapiens

<400> SEQUENCE: 953

Ile Tyr Tyr Thr Gly Ser Thr
1               5

<210> SEQ ID NO 954
<211> LENGTH: 7
<212> TYPE: PRT
<213> ORGANISM: Homo sapiens

<400> SEQUENCE: 954

Ile Tyr Ala Ser Gly Gly Thr
1               5

<210> SEQ ID NO 955
<211> LENGTH: 7
<212> TYPE: PRT
<213> ORGANISM: Homo sapiens

<400> SEQUENCE: 955

Ile Tyr Tyr Ser Gly Ser Thr
1               5

<210> SEQ ID NO 956
<211> LENGTH: 7
<212> TYPE: PRT
<213> ORGANISM: Homo sapiens

<400> SEQUENCE: 956

Ile Tyr Ala Ser Gly Ser Thr
1               5

<210> SEQ ID NO 957
<211> LENGTH: 8
<212> TYPE: PRT
<213> ORGANISM: Homo sapiens

<400> SEQUENCE: 957

Ile Ser Ser Ser Ser Ser Thr Ile
1               5

<210> SEQ ID NO 958
<211> LENGTH: 7
<212> TYPE: PRT
<213> ORGANISM: Homo sapiens

<400> SEQUENCE: 958

Ile Tyr Thr Ser Gly Ser Ile
1 5

<210> SEQ ID NO 959
<211> LENGTH: 7
<212> TYPE: PRT
<213> ORGANISM: Homo sapiens

<400> SEQUENCE: 959

Val Tyr Tyr Ser Gly Ser Thr
1 5

<210> SEQ ID NO 960
<211> LENGTH: 7
<212> TYPE: PRT
<213> ORGANISM: Homo sapiens

<400> SEQUENCE: 960

Ile Tyr Thr Ser Gly Ser Thr
1 5

<210> SEQ ID NO 961
<211> LENGTH: 7
<212> TYPE: PRT
<213> ORGANISM: Homo sapiens

<400> SEQUENCE: 961

Ile Tyr Thr Gly Gly Ser Thr
1 5

<210> SEQ ID NO 962
<211> LENGTH: 7
<212> TYPE: PRT
<213> ORGANISM: Homo sapiens

<400> SEQUENCE: 962

Ile Tyr Thr Ser Gly Ser Thr
1 5

<210> SEQ ID NO 963
<211> LENGTH: 7
<212> TYPE: PRT
<213> ORGANISM: Homo sapiens

<400> SEQUENCE: 963

Ile Tyr Thr Ser Gly Ser Thr
1 5

<210> SEQ ID NO 964
<211> LENGTH: 7
<212> TYPE: PRT
<213> ORGANISM: Homo sapiens

<400> SEQUENCE: 964

Ile Tyr Thr Ser Gly Ser Thr
1 5

<210> SEQ ID NO 965
<211> LENGTH: 8

<212> TYPE: PRT
<213> ORGANISM: Homo sapiens

<400> SEQUENCE: 965

Ile Ser Ser Ser Ser Ser Thr Ile
1               5

<210> SEQ ID NO 966
<211> LENGTH: 8
<212> TYPE: PRT
<213> ORGANISM: Homo sapiens

<400> SEQUENCE: 966

Ile Ser Asp Ser Ser Asp Tyr Ile
1               5

<210> SEQ ID NO 967
<211> LENGTH: 7
<212> TYPE: PRT
<213> ORGANISM: Homo sapiens

<400> SEQUENCE: 967

Ile Tyr Tyr Ser Gly Ser Thr
1               5

<210> SEQ ID NO 968
<211> LENGTH: 7
<212> TYPE: PRT
<213> ORGANISM: Homo sapiens

<400> SEQUENCE: 968

Ile Tyr Thr Ser Gly Asn Thr
1               5

<210> SEQ ID NO 969
<211> LENGTH: 7
<212> TYPE: PRT
<213> ORGANISM: Homo sapiens

<400> SEQUENCE: 969

Ile Tyr Tyr Ser Gly Thr Thr
1               5

<210> SEQ ID NO 970
<211> LENGTH: 7
<212> TYPE: PRT
<213> ORGANISM: Homo sapiens

<400> SEQUENCE: 970

Ile Tyr Thr Ser Gly Ser Thr
1               5

<210> SEQ ID NO 971
<211> LENGTH: 8
<212> TYPE: PRT
<213> ORGANISM: Homo sapiens

<400> SEQUENCE: 971

Ile Ser Ser Ser Ser Ser Tyr Ile
1               5

<210> SEQ ID NO 972
<211> LENGTH: 7
<212> TYPE: PRT
<213> ORGANISM: Homo sapiens

<400> SEQUENCE: 972

Ile Tyr Thr Ser Gly Ser Thr
1               5

<210> SEQ ID NO 973
<211> LENGTH: 7
<212> TYPE: PRT
<213> ORGANISM: Homo sapiens

<400> SEQUENCE: 973

Ile Tyr Thr Ser Gly Ser Thr
1               5

<210> SEQ ID NO 974
<211> LENGTH: 7
<212> TYPE: PRT
<213> ORGANISM: Homo sapiens

<400> SEQUENCE: 974

Phe Tyr Thr Ser Gly Ser Thr
1               5

<210> SEQ ID NO 975
<211> LENGTH: 7
<212> TYPE: PRT
<213> ORGANISM: Homo sapiens

<400> SEQUENCE: 975

Ile Tyr Tyr Ile Gly Ser Thr
1               5

<210> SEQ ID NO 976
<211> LENGTH: 30
<212> TYPE: DNA
<213> ORGANISM: Homo sapiens

<400> SEQUENCE: 976
attaaaagca aaactgatgg tgggacaaca 30

<210> SEQ ID NO 977
<211> LENGTH: 24
<212> TYPE: DNA
<213> ORGANISM: Homo sapiens

<400> SEQUENCE: 977
atcaacccta tcagtggtgg caca 24

<210> SEQ ID NO 978
<211> LENGTH: 30
<212> TYPE: DNA
<213> ORGANISM: Homo sapiens

<400> SEQUENCE: 978
gttaaaagca aaactgatgg tgggacaaca 30

<210> SEQ ID NO 979
<211> LENGTH: 21
<212> TYPE: DNA
<213> ORGANISM: Homo sapiens

<400> SEQUENCE: 979
atctttagca gtgggagcac c 21

<210> SEQ ID NO 980
<211> LENGTH: 21
<212> TYPE: DNA
<213> ORGANISM: Homo sapiens

<400> SEQUENCE: 980
atctatacca gtgggagcac c 21

<210> SEQ ID NO 981
<211> LENGTH: 30
<212> TYPE: DNA
<213> ORGANISM: Homo sapiens

<400> SEQUENCE: 981
attagaagca aagcttatgg tgggacaaca 30

<210> SEQ ID NO 982
<211> LENGTH: 24
<212> TYPE: DNA
<213> ORGANISM: Homo sapiens

<400> SEQUENCE: 982
atcaacccta acagtggtgg caca 24

<210> SEQ ID NO 983
<211> LENGTH: 30
<212> TYPE: DNA
<213> ORGANISM: Homo sapiens

<400> SEQUENCE: 983
attaaaagca aaactgatgg tgggacaaca 30

<210> SEQ ID NO 984
<211> LENGTH: 21
<212> TYPE: DNA
<213> ORGANISM: Homo sapiens

<400> SEQUENCE: 984
atccattaca gtgggagcac c 21

<210> SEQ ID NO 985
<211> LENGTH: 24
<212> TYPE: DNA
<213> ORGANISM: Homo sapiens

<400> SEQUENCE: 985
attagtccta gtagtagtac cata 24

<210> SEQ ID NO 986
<211> LENGTH: 21
<212> TYPE: DNA
<213> ORGANISM: Homo sapiens

<400> SEQUENCE: 986
attgattggg atgatgataa a 21

<210> SEQ ID NO 987
<211> LENGTH: 21
<212> TYPE: DNA
<213> ORGANISM: Homo sapiens

<400> SEQUENCE: 987
atctatacca gtgggaccac c 21

<210> SEQ ID NO 988
<211> LENGTH: 21
<212> TYPE: DNA
<213> ORGANISM: Homo sapiens

<400> SEQUENCE: 988
atctatacca gtgggagcac c 21

<210> SEQ ID NO 989
<211> LENGTH: 21
<212> TYPE: DNA
<213> ORGANISM: Homo sapiens

<400> SEQUENCE: 989
gtctcttaca gtgggggcac c 21

<210> SEQ ID NO 990
<211> LENGTH: 24
<212> TYPE: DNA
<213> ORGANISM: Homo sapiens

<400> SEQUENCE: 990
atcaacccta acagaggtga caca 24

<210> SEQ ID NO 991
<211> LENGTH: 21
<212> TYPE: DNA
<213> ORGANISM: Homo sapiens

<400> SEQUENCE: 991
ttctcttaca atgggaacac c 21

<210> SEQ ID NO 992
<211> LENGTH: 21
<212> TYPE: DNA
<213> ORGANISM: Homo sapiens

<400> SEQUENCE: 992
atctatacca gtgggagcac c 21

<210> SEQ ID NO 993
<211> LENGTH: 21
<212> TYPE: DNA
<213> ORGANISM: Homo sapiens

<400> SEQUENCE: 993
attggtactg ctggtgacac a 21

<210> SEQ ID NO 994
<211> LENGTH: 21
<212> TYPE: DNA
<213> ORGANISM: Homo sapiens

<400> SEQUENCE: 994
atcaatcata gtggaagcac c 21

<210> SEQ ID NO 995
<211> LENGTH: 30
<212> TYPE: DNA
<213> ORGANISM: Homo sapiens

<400> SEQUENCE: 995
attaaaagca aaactgatgg tgggacaaca 30

<210> SEQ ID NO 996
<211> LENGTH: 21
<212> TYPE: DNA
<213> ORGANISM: Homo sapiens

<400> SEQUENCE: 996
atcaatcata gtggaagcac c 21

<210> SEQ ID NO 997
<211> LENGTH: 24
<212> TYPE: DNA
<213> ORGANISM: Homo sapiens

<400> SEQUENCE: 997
attaatagtg atgggagtag caca 24

<210> SEQ ID NO 998
<211> LENGTH: 24
<212> TYPE: DNA
<213> ORGANISM: Homo sapiens

<400> SEQUENCE: 998
attagtagta gtagtagtta cata 24

<210> SEQ ID NO 999
<211> LENGTH: 21
<212> TYPE: DNA
<213> ORGANISM: Homo sapiens

<400> SEQUENCE: 999
atttattgga atgatgataa g 21

<210> SEQ ID NO 1000
<211> LENGTH: 24
<212> TYPE: DNA
<213> ORGANISM: Homo sapiens

<400> SEQUENCE: 1000
atcaacccta acagtggtgg caca 24

<210> SEQ ID NO 1001
<211> LENGTH: 21
<212> TYPE: DNA
<213> ORGANISM: Homo sapiens

<400> SEQUENCE: 1001
atctattaca gtgggagcac c 21

<210> SEQ ID NO 1002
<211> LENGTH: 21
<212> TYPE: DNA
<213> ORGANISM: Homo sapiens

<400> SEQUENCE: 1002
atctcttaca gtgggggcac c 21

<210> SEQ ID NO 1003
<211> LENGTH: 24
<212> TYPE: DNA
<213> ORGANISM: Homo sapiens

<400> SEQUENCE: 1003
attagtagta gtagtactta cata 24

<210> SEQ ID NO 1004
<211> LENGTH: 21
<212> TYPE: DNA
<213> ORGANISM: Homo sapiens

<400> SEQUENCE: 1004
atctatacca gtgggagcac c 21

<210> SEQ ID NO 1005
<211> LENGTH: 24
<212> TYPE: DNA
<213> ORGANISM: Homo sapiens

<400> SEQUENCE: 1005
attagtagta gtagtagtta cata 24

<210> SEQ ID NO 1006
<211> LENGTH: 30
<212> TYPE: DNA
<213> ORGANISM: Homo sapiens

<400> SEQUENCE: 1006
attagaagca aagcttatgg tgggacaaca 30

<210> SEQ ID NO 1007
<211> LENGTH: 30
<212> TYPE: DNA
<213> ORGANISM: Homo sapiens

<400> SEQUENCE: 1007
attaatagca aaactgatgg tgggacaaca 30

<210> SEQ ID NO 1008
<211> LENGTH: 24
<212> TYPE: DNA
<213> ORGANISM: Homo sapiens

<400> SEQUENCE: 1008
atcaacccta acagtggtgg caca 24

<210> SEQ ID NO 1009
<211> LENGTH: 24
<212> TYPE: DNA
<213> ORGANISM: Homo sapiens

<400> SEQUENCE: 1009
attagtagta gtagtagtac cata 24

<210> SEQ ID NO 1010
<211> LENGTH: 21
<212> TYPE: DNA
<213> ORGANISM: Homo sapiens

<400> SEQUENCE: 1010
atctattaca gggggagcac c 21

<210> SEQ ID NO 1011
<211> LENGTH: 24
<212> TYPE: DNA
<213> ORGANISM: Homo sapiens

<400> SEQUENCE: 1011
ataaagcaag atggaagtga gaaa 24

<210> SEQ ID NO 1012
<211> LENGTH: 30
<212> TYPE: DNA
<213> ORGANISM: Homo sapiens

<400> SEQUENCE: 1012
attaaaagca aaactgatgg tgggacaaca 30

<210> SEQ ID NO 1013
<211> LENGTH: 24
<212> TYPE: DNA
<213> ORGANISM: Homo sapiens

<400> SEQUENCE: 1013
attagtagta gtagtagtta cata 24

<210> SEQ ID NO 1014
<211> LENGTH: 24
<212> TYPE: DNA
<213> ORGANISM: Homo sapiens

<400> SEQUENCE: 1014
atcaacccta acagtggtgg caca 24

<210> SEQ ID NO 1015
<211> LENGTH: 24
<212> TYPE: DNA
<213> ORGANISM: Homo sapiens

<400> SEQUENCE: 1015
atcaacccta acagtggtgg caca 24

<210> SEQ ID NO 1016
<211> LENGTH: 21
<212> TYPE: DNA
<213> ORGANISM: Homo sapiens

<400> SEQUENCE: 1016
atttattgga atgatgataa g 21

<210> SEQ ID NO 1017
<211> LENGTH: 24
<212> TYPE: DNA
<213> ORGANISM: Homo sapiens

<400> SEQUENCE: 1017
atatggtatg atggaagtat taaa 24

<210> SEQ ID NO 1018
<211> LENGTH: 24
<212> TYPE: DNA
<213> ORGANISM: Homo sapiens

<400> SEQUENCE: 1018
ataaagcaag atggaagtga gaaa 24

<210> SEQ ID NO 1019
<211> LENGTH: 24
<212> TYPE: DNA
<213> ORGANISM: Homo sapiens

<400> SEQUENCE: 1019
atcaacccta acagtggtgg caca 24

<210> SEQ ID NO 1020
<211> LENGTH: 24
<212> TYPE: DNA
<213> ORGANISM: Homo sapiens

<400> SEQUENCE: 1020
atatcatatg atggaagtaa taaa 24

<210> SEQ ID NO 1021
<211> LENGTH: 21
<212> TYPE: DNA
<213> ORGANISM: Homo sapiens

<400> SEQUENCE: 1021
atcttttaca gtgggagcat c 21

<210> SEQ ID NO 1022
<211> LENGTH: 21
<212> TYPE: DNA
<213> ORGANISM: Homo sapiens

<400> SEQUENCE: 1022
atctatagca gtgggagcat t 21

<210> SEQ ID NO 1023
<211> LENGTH: 24
<212> TYPE: DNA
<213> ORGANISM: Homo sapiens

<400> SEQUENCE: 1023
atatggtatg atggaagtaa tgaa 24

<210> SEQ ID NO 1024
<211> LENGTH: 21
<212> TYPE: DNA
<213> ORGANISM: Homo sapiens

<400> SEQUENCE: 1024
ttctattaca gtgggagcac c 21

<210> SEQ ID NO 1025
<211> LENGTH: 21
<212> TYPE: DNA
<213> ORGANISM: Homo sapiens

<400> SEQUENCE: 1025
atctattaca gtgggagtac c 21

<210> SEQ ID NO 1026
<211> LENGTH: 21
<212> TYPE: DNA
<213> ORGANISM: Homo sapiens

<400> SEQUENCE: 1026
atctatacca gtgggagcac c 21

<210> SEQ ID NO 1027
<211> LENGTH: 21
<212> TYPE: DNA

<213> ORGANISM: Homo sapiens

<400> SEQUENCE: 1027
atttatatca gtgggagtat t 21

<210> SEQ ID NO 1028
<211> LENGTH: 21
<212> TYPE: DNA
<213> ORGANISM: Homo sapiens

<400> SEQUENCE: 1028
atctattaca gtgggatcac c 21

<210> SEQ ID NO 1029
<211> LENGTH: 21
<212> TYPE: DNA
<213> ORGANISM: Homo sapiens

<400> SEQUENCE: 1029
atctatacca gtgggaccac c 21

<210> SEQ ID NO 1030
<211> LENGTH: 24
<212> TYPE: DNA
<213> ORGANISM: Homo sapiens

<400> SEQUENCE: 1030
atcaacccta acagtggtgg cgca 24

<210> SEQ ID NO 1031
<211> LENGTH: 21
<212> TYPE: DNA
<213> ORGANISM: Homo sapiens

<400> SEQUENCE: 1031
atcttttaca gtgggagcac a 21

<210> SEQ ID NO 1032
<211> LENGTH: 21
<212> TYPE: DNA
<213> ORGANISM: Homo sapiens

<400> SEQUENCE: 1032
atctatatta gtgggaccac c 21

<210> SEQ ID NO 1033
<211> LENGTH: 21
<212> TYPE: DNA
<213> ORGANISM: Homo sapiens

<400> SEQUENCE: 1033
atctatacca gtgggagcac c 21

<210> SEQ ID NO 1034
<211> LENGTH: 21
<212> TYPE: DNA
<213> ORGANISM: Homo sapiens

<400> SEQUENCE: 1034
atctatacca gtgggagcac c 21

<210> SEQ ID NO 1035
<211> LENGTH: 24

<212> TYPE: DNA
<213> ORGANISM: Homo sapiens

<400> SEQUENCE: 1035
attagtagta gtagtagtac cata 24

<210> SEQ ID NO 1036
<211> LENGTH: 21
<212> TYPE: DNA
<213> ORGANISM: Homo sapiens

<400> SEQUENCE: 1036
atctatacca gtgggagcac c 21

<210> SEQ ID NO 1037
<211> LENGTH: 21
<212> TYPE: DNA
<213> ORGANISM: Homo sapiens

<400> SEQUENCE: 1037
atctatagca gtgggaccac c 21

<210> SEQ ID NO 1038
<211> LENGTH: 21
<212> TYPE: DNA
<213> ORGANISM: Homo sapiens

<400> SEQUENCE: 1038
atctatacca gtgggagcac c 21

<210> SEQ ID NO 1039
<211> LENGTH: 21
<212> TYPE: DNA
<213> ORGANISM: Homo sapiens

<400> SEQUENCE: 1039
atctatacca gtgggagcac c 21

<210> SEQ ID NO 1040
<211> LENGTH: 21
<212> TYPE: DNA
<213> ORGANISM: Homo sapiens

<400> SEQUENCE: 1040
atctatacca gtgggaacac c 21

<210> SEQ ID NO 1041
<211> LENGTH: 21
<212> TYPE: DNA
<213> ORGANISM: Homo sapiens

<400> SEQUENCE: 1041
atctatacca gtgggagcac c 21

<210> SEQ ID NO 1042
<211> LENGTH: 24
<212> TYPE: DNA
<213> ORGANISM: Homo sapiens

<400> SEQUENCE: 1042
attagtagta gtagtaatta cata 24

<210> SEQ ID NO 1043

<211> LENGTH: 21
<212> TYPE: DNA
<213> ORGANISM: Homo sapiens

<400> SEQUENCE: 1043
ttctattaca gtgggagtac c 21

<210> SEQ ID NO 1044
<211> LENGTH: 21
<212> TYPE: DNA
<213> ORGANISM: Homo sapiens

<400> SEQUENCE: 1044
atctatacca gtgggagcac c 21

<210> SEQ ID NO 1045
<211> LENGTH: 21
<212> TYPE: DNA
<213> ORGANISM: Homo sapiens

<400> SEQUENCE: 1045
atctatacca gtgggaacac c 21

<210> SEQ ID NO 1046
<211> LENGTH: 21
<212> TYPE: DNA
<213> ORGANISM: Homo sapiens

<400> SEQUENCE: 1046
atctatacca gtgggagcac c 21

<210> SEQ ID NO 1047
<211> LENGTH: 24
<212> TYPE: DNA
<213> ORGANISM: Homo sapiens

<400> SEQUENCE: 1047
atcaacccta acagtggtgg caca 24

<210> SEQ ID NO 1048
<211> LENGTH: 24
<212> TYPE: DNA
<213> ORGANISM: Homo sapiens

<400> SEQUENCE: 1048
atcaacccta acagtggtgg caca 24

<210> SEQ ID NO 1049
<211> LENGTH: 21
<212> TYPE: DNA
<213> ORGANISM: Homo sapiens

<400> SEQUENCE: 1049
atctatacca gtgggagcac c 21

<210> SEQ ID NO 1050
<211> LENGTH: 21
<212> TYPE: DNA
<213> ORGANISM: Homo sapiens

<400> SEQUENCE: 1050
ctctttacca gtgggagcac c 21

<210> SEQ ID NO 1051
<211> LENGTH: 21
<212> TYPE: DNA
<213> ORGANISM: Homo sapiens

<400> SEQUENCE: 1051
atctatacca gtgggagcac c 21

<210> SEQ ID NO 1052
<211> LENGTH: 21
<212> TYPE: DNA
<213> ORGANISM: Homo sapiens

<400> SEQUENCE: 1052
atctatacca gtgggagcac c 21

<210> SEQ ID NO 1053
<211> LENGTH: 21
<212> TYPE: DNA
<213> ORGANISM: Homo sapiens

<400> SEQUENCE: 1053
atctattaca gtgggagcac c 21

<210> SEQ ID NO 1054
<211> LENGTH: 21
<212> TYPE: DNA
<213> ORGANISM: Homo sapiens

<400> SEQUENCE: 1054
atctatacca gtgggtacac c 21

<210> SEQ ID NO 1055
<211> LENGTH: 21
<212> TYPE: DNA
<213> ORGANISM: Homo sapiens

<400> SEQUENCE: 1055
atctattaca gtgggagcac c 21

<210> SEQ ID NO 1056
<211> LENGTH: 21
<212> TYPE: DNA
<213> ORGANISM: Homo sapiens

<400> SEQUENCE: 1056
atctattaca gtgggagcac c 21

<210> SEQ ID NO 1057
<211> LENGTH: 24
<212> TYPE: DNA
<213> ORGANISM: Homo sapiens

<400> SEQUENCE: 1057
attagtagta gtagtgctat cata 24

<210> SEQ ID NO 1058
<211> LENGTH: 24
<212> TYPE: DNA
<213> ORGANISM: Homo sapiens

<400> SEQUENCE: 1058
ataaagcaag atggaagtga gaaa 24

<210> SEQ ID NO 1059
<211> LENGTH: 24
<212> TYPE: DNA
<213> ORGANISM: Homo sapiens

<400> SEQUENCE: 1059
atctatcctg gtgactctga tacc 24

<210> SEQ ID NO 1060
<211> LENGTH: 24
<212> TYPE: DNA
<213> ORGANISM: Homo sapiens

<400> SEQUENCE: 1060
atcaacccta acagtggtgg caca 24

<210> SEQ ID NO 1061
<211> LENGTH: 21
<212> TYPE: DNA
<213> ORGANISM: Homo sapiens

<400> SEQUENCE: 1061
atctattaca ctgggagtac c 21

<210> SEQ ID NO 1062
<211> LENGTH: 21
<212> TYPE: DNA
<213> ORGANISM: Homo sapiens

<400> SEQUENCE: 1062
atctatgcca gtgggggcac c 21

<210> SEQ ID NO 1063
<211> LENGTH: 21
<212> TYPE: DNA
<213> ORGANISM: Homo sapiens

<400> SEQUENCE: 1063
atctattata gtgggagcac c 21

<210> SEQ ID NO 1064
<211> LENGTH: 21
<212> TYPE: DNA
<213> ORGANISM: Homo sapiens

<400> SEQUENCE: 1064
atctatgcca gtgggagcac c 21

<210> SEQ ID NO 1065
<211> LENGTH: 24
<212> TYPE: DNA
<213> ORGANISM: Homo sapiens

<400> SEQUENCE: 1065
attagtagta gtagtagtac cata 24

<210> SEQ ID NO 1066
<211> LENGTH: 21
<212> TYPE: DNA
<213> ORGANISM: Homo sapiens

<400> SEQUENCE: 1066
atctatacca gtgggagtat c 21

<210> SEQ ID NO 1067
<211> LENGTH: 21
<212> TYPE: DNA
<213> ORGANISM: Homo sapiens

<400> SEQUENCE: 1067
gtctattaca gtgggagcac c 21

<210> SEQ ID NO 1068
<211> LENGTH: 21
<212> TYPE: DNA
<213> ORGANISM: Homo sapiens

<400> SEQUENCE: 1068
atctatacca gtgggagcac c 21

<210> SEQ ID NO 1069
<211> LENGTH: 21
<212> TYPE: DNA
<213> ORGANISM: Homo sapiens

<400> SEQUENCE: 1069
atctataccg gtgggagcac c 21

<210> SEQ ID NO 1070
<211> LENGTH: 21
<212> TYPE: DNA
<213> ORGANISM: Homo sapiens

<400> SEQUENCE: 1070
atctatacca gtgggagcac c 21

<210> SEQ ID NO 1071
<211> LENGTH: 21
<212> TYPE: DNA
<213> ORGANISM: Homo sapiens

<400> SEQUENCE: 1071
atctatacca gtgggagcac c 21

<210> SEQ ID NO 1072
<211> LENGTH: 21
<212> TYPE: DNA
<213> ORGANISM: Homo sapiens

<400> SEQUENCE: 1072
atctatacca gtgggagcac c 21

<210> SEQ ID NO 1073
<211> LENGTH: 24
<212> TYPE: DNA
<213> ORGANISM: Homo sapiens

<400> SEQUENCE: 1073
attagtagta gtagtagtac cata 24

<210> SEQ ID NO 1074
<211> LENGTH: 24
<212> TYPE: DNA
<213> ORGANISM: Homo sapiens

<400> SEQUENCE: 1074
attagtgata gtagtgatta cata 24

<210> SEQ ID NO 1075
<211> LENGTH: 21
<212> TYPE: DNA
<213> ORGANISM: Homo sapiens

<400> SEQUENCE: 1075
atctattata gtgggagcac c 21

<210> SEQ ID NO 1076
<211> LENGTH: 21
<212> TYPE: DNA
<213> ORGANISM: Homo sapiens

<400> SEQUENCE: 1076
atctatacca gtgggaacac c 21

<210> SEQ ID NO 1077
<211> LENGTH: 21
<212> TYPE: DNA
<213> ORGANISM: Homo sapiens

<400> SEQUENCE: 1077
atctattaca gtgggaccac c 21

<210> SEQ ID NO 1078
<211> LENGTH: 21
<212> TYPE: DNA
<213> ORGANISM: Homo sapiens

<400> SEQUENCE: 1078
atctatacca gtgggagcac c 21

<210> SEQ ID NO 1079
<211> LENGTH: 24
<212> TYPE: DNA
<213> ORGANISM: Homo sapiens

<400> SEQUENCE: 1079
attagtagta gtagtagtta cata 24

<210> SEQ ID NO 1080
<211> LENGTH: 21
<212> TYPE: DNA
<213> ORGANISM: Homo sapiens

<400> SEQUENCE: 1080
atctatacca gtgggagcac c 21

<210> SEQ ID NO 1081
<211> LENGTH: 21
<212> TYPE: DNA
<213> ORGANISM: Homo sapiens

<400> SEQUENCE: 1081
atctatacca gtgggagcac c 21

<210> SEQ ID NO 1082
<211> LENGTH: 21
<212> TYPE: DNA
<213> ORGANISM: Homo sapiens

<400> SEQUENCE: 1082
ttctatacca gtgggagcac c 21

<210> SEQ ID NO 1083
<211> LENGTH: 21
<212> TYPE: DNA
<213> ORGANISM: Homo sapiens

<400> SEQUENCE: 1083
atctattaca ttgggagcac c 21

<210> SEQ ID NO 1084
<211> LENGTH: 3
<212> TYPE: PRT
<213> ORGANISM: Homo sapiens

<400> SEQUENCE: 1084

Asp Glu Ser
1

<210> SEQ ID NO 1085
<211> LENGTH: 3
<212> TYPE: PRT
<213> ORGANISM: Homo sapiens

<400> SEQUENCE: 1085

Thr Leu Ser
1

<210> SEQ ID NO 1086
<211> LENGTH: 3
<212> TYPE: PRT
<213> ORGANISM: Homo sapiens

<400> SEQUENCE: 1086

Trp Ala Ser
1

<210> SEQ ID NO 1087
<211> LENGTH: 3
<212> TYPE: PRT
<213> ORGANISM: Homo sapiens

<400> SEQUENCE: 1087

Gly Ala Ser
1

<210> SEQ ID NO 1088
<211> LENGTH: 3
<212> TYPE: PRT
<213> ORGANISM: Homo sapiens

<400> SEQUENCE: 1088

Gly Ala Ser
1

<210> SEQ ID NO 1089
<211> LENGTH: 3
<212> TYPE: PRT
<213> ORGANISM: Homo sapiens

<400> SEQUENCE: 1089

Leu Gly Ser
1

<210> SEQ ID NO 1090
<211> LENGTH: 3
<212> TYPE: PRT
<213> ORGANISM: Homo sapiens

<400> SEQUENCE: 1090

Ala Ala Ser
1

<210> SEQ ID NO 1091
<211> LENGTH: 3
<212> TYPE: PRT
<213> ORGANISM: Homo sapiens

<400> SEQUENCE: 1091

Trp Ala Ser
1

<210> SEQ ID NO 1092
<211> LENGTH: 3
<212> TYPE: PRT
<213> ORGANISM: Homo sapiens

<400> SEQUENCE: 1092

Met Ala Ser
1

<210> SEQ ID NO 1093
<211> LENGTH: 3
<212> TYPE: PRT
<213> ORGANISM: Homo sapiens

<400> SEQUENCE: 1093

Asp Ala Ser
1

<210> SEQ ID NO 1094
<211> LENGTH: 3
<212> TYPE: PRT
<213> ORGANISM: Homo sapiens

<400> SEQUENCE: 1094

Ala Ala Ser
1

<210> SEQ ID NO 1095
<211> LENGTH: 3
<212> TYPE: PRT
<213> ORGANISM: Homo sapiens

<400> SEQUENCE: 1095

Leu Gly Ser
1

<210> SEQ ID NO 1096
<211> LENGTH: 3
<212> TYPE: PRT
<213> ORGANISM: Homo sapiens

<400> SEQUENCE: 1096

Lys Ala Ser
1

<210> SEQ ID NO 1097

<211> LENGTH: 3
<212> TYPE: PRT
<213> ORGANISM: Homo sapiens

<400> SEQUENCE: 1097

Lys Ala Ser
1

<210> SEQ ID NO 1098
<211> LENGTH: 3
<212> TYPE: PRT
<213> ORGANISM: Homo sapiens

<400> SEQUENCE: 1098

Thr Leu Ser
1

<210> SEQ ID NO 1099
<211> LENGTH: 3
<212> TYPE: PRT
<213> ORGANISM: Homo sapiens

<400> SEQUENCE: 1099

Lys Ala Ser
1

<210> SEQ ID NO 1100
<211> LENGTH: 3
<212> TYPE: PRT
<213> ORGANISM: Homo sapiens

<400> SEQUENCE: 1100

Gly Ala Ser
1

<210> SEQ ID NO 1101
<211> LENGTH: 3
<212> TYPE: PRT
<213> ORGANISM: Homo sapiens

<400> SEQUENCE: 1101

Asp Ala Ser
1

<210> SEQ ID NO 1102
<211> LENGTH: 3
<212> TYPE: PRT
<213> ORGANISM: Homo sapiens

<400> SEQUENCE: 1102

Gly Ala Ser
1

<210> SEQ ID NO 1103
<211> LENGTH: 3
<212> TYPE: PRT
<213> ORGANISM: Homo sapiens

<400> SEQUENCE: 1103

Trp Ala Ser
1

<210> SEQ ID NO 1104
<211> LENGTH: 3
<212> TYPE: PRT

<213> ORGANISM: Homo sapiens

<400> SEQUENCE: 1104

Gly Ala Ser
1

<210> SEQ ID NO 1105
<211> LENGTH: 3
<212> TYPE: PRT
<213> ORGANISM: Homo sapiens

<400> SEQUENCE: 1105

Trp Ala Ser
1

<210> SEQ ID NO 1106
<211> LENGTH: 3
<212> TYPE: PRT
<213> ORGANISM: Homo sapiens

<400> SEQUENCE: 1106

Gly Ala Ser
1

<210> SEQ ID NO 1107
<211> LENGTH: 3
<212> TYPE: PRT
<213> ORGANISM: Homo sapiens

<400> SEQUENCE: 1107

Trp Ala Ser
1

<210> SEQ ID NO 1108
<211> LENGTH: 3
<212> TYPE: PRT
<213> ORGANISM: Homo sapiens

<400> SEQUENCE: 1108

Trp Ala Ser
1

<210> SEQ ID NO 1109
<211> LENGTH: 3
<212> TYPE: PRT
<213> ORGANISM: Homo sapiens

<400> SEQUENCE: 1109

Gly Ala Ser
1

<210> SEQ ID NO 1110
<211> LENGTH: 3
<212> TYPE: PRT
<213> ORGANISM: Homo sapiens

<400> SEQUENCE: 1110

Lys Ala Ser
1

<210> SEQ ID NO 1111
<211> LENGTH: 3
<212> TYPE: PRT
<213> ORGANISM: Homo sapiens

<400> SEQUENCE: 1111

Ala Ala Ser
1

<210> SEQ ID NO 1112
<211> LENGTH: 3
<212> TYPE: PRT
<213> ORGANISM: Homo sapiens

<400> SEQUENCE: 1112

Ala Ala Ser
1

<210> SEQ ID NO 1113
<211> LENGTH: 3
<212> TYPE: PRT
<213> ORGANISM: Homo sapiens

<400> SEQUENCE: 1113

Leu Asp Ser
1

<210> SEQ ID NO 1114
<211> LENGTH: 3
<212> TYPE: PRT
<213> ORGANISM: Homo sapiens

<400> SEQUENCE: 1114

Leu Gly Ser
1

<210> SEQ ID NO 1115
<211> LENGTH: 3
<212> TYPE: PRT
<213> ORGANISM: Homo sapiens

<400> SEQUENCE: 1115

Leu Gly Ser
1

<210> SEQ ID NO 1116
<211> LENGTH: 3
<212> TYPE: PRT
<213> ORGANISM: Homo sapiens

<400> SEQUENCE: 1116

Trp Ala Ser
1

<210> SEQ ID NO 1117
<211> LENGTH: 3
<212> TYPE: PRT
<213> ORGANISM: Homo sapiens

<400> SEQUENCE: 1117

Asp Ala Ser
1

<210> SEQ ID NO 1118
<211> LENGTH: 3
<212> TYPE: PRT
<213> ORGANISM: Homo sapiens

<400> SEQUENCE: 1118

Leu Gly Ser
1

<210> SEQ ID NO 1119
<211> LENGTH: 3
<212> TYPE: PRT
<213> ORGANISM: Homo sapiens

<400> SEQUENCE: 1119

Leu Gly Ser
1

<210> SEQ ID NO 1120
<211> LENGTH: 3
<212> TYPE: PRT
<213> ORGANISM: Homo sapiens

<400> SEQUENCE: 1120

Trp Ala Ser
1

<210> SEQ ID NO 1121
<211> LENGTH: 3
<212> TYPE: PRT
<213> ORGANISM: Homo sapiens

<400> SEQUENCE: 1121

Leu Gly Ser
1

<210> SEQ ID NO 1122
<211> LENGTH: 3
<212> TYPE: PRT
<213> ORGANISM: Homo sapiens

<400> SEQUENCE: 1122

Thr Leu Ser
1

<210> SEQ ID NO 1123
<211> LENGTH: 3
<212> TYPE: PRT
<213> ORGANISM: Homo sapiens

<400> SEQUENCE: 1123

Thr Leu Ser
1

<210> SEQ ID NO 1124
<211> LENGTH: 3
<212> TYPE: PRT
<213> ORGANISM: Homo sapiens

<400> SEQUENCE: 1124

Trp Ala Ser
1

<210> SEQ ID NO 1125
<211> LENGTH: 3
<212> TYPE: PRT
<213> ORGANISM: Homo sapiens

<400> SEQUENCE: 1125

Ala Ala Ser
1

<210> SEQ ID NO 1126
<211> LENGTH: 3
<212> TYPE: PRT
<213> ORGANISM: Homo sapiens

<400> SEQUENCE: 1126

Leu Gly Ser
1

<210> SEQ ID NO 1127
<211> LENGTH: 3
<212> TYPE: PRT
<213> ORGANISM: Homo sapiens

<400> SEQUENCE: 1127

Thr Leu Ser
1

<210> SEQ ID NO 1128
<211> LENGTH: 3
<212> TYPE: PRT
<213> ORGANISM: Homo sapiens

<400> SEQUENCE: 1128

Leu Ala Ser
1

<210> SEQ ID NO 1129
<211> LENGTH: 3
<212> TYPE: PRT
<213> ORGANISM: Homo sapiens

<400> SEQUENCE: 1129

Gly Ala Ser
1

<210> SEQ ID NO 1130
<211> LENGTH: 3
<212> TYPE: PRT
<213> ORGANISM: Homo sapiens

<400> SEQUENCE: 1130

Gly Ala Ser
1

<210> SEQ ID NO 1131
<211> LENGTH: 3
<212> TYPE: PRT
<213> ORGANISM: Homo sapiens

<400> SEQUENCE: 1131

Leu Gly Ser
1

<210> SEQ ID NO 1132
<211> LENGTH: 3
<212> TYPE: PRT
<213> ORGANISM: Homo sapiens

<400> SEQUENCE: 1132

Ser Asn Asn
1

<210> SEQ ID NO 1133
<211> LENGTH: 3
<212> TYPE: PRT
<213> ORGANISM: Homo sapiens

<400> SEQUENCE: 1133

Ser Asn Asn
1

<210> SEQ ID NO 1134
<211> LENGTH: 3
<212> TYPE: PRT
<213> ORGANISM: Homo sapiens

<400> SEQUENCE: 1134

Ser Asn Asn
1

<210> SEQ ID NO 1135
<211> LENGTH: 3
<212> TYPE: PRT
<213> ORGANISM: Homo sapiens

<400> SEQUENCE: 1135

Ser Asn Asn
1

<210> SEQ ID NO 1136
<211> LENGTH: 3
<212> TYPE: PRT
<213> ORGANISM: Homo sapiens

<400> SEQUENCE: 1136

Ser Asn Asn
1

<210> SEQ ID NO 1137
<211> LENGTH: 3
<212> TYPE: PRT
<213> ORGANISM: Homo sapiens

<400> SEQUENCE: 1137

Ser Asn Asn
1

<210> SEQ ID NO 1138
<211> LENGTH: 3
<212> TYPE: PRT
<213> ORGANISM: Homo sapiens

<400> SEQUENCE: 1138

Ser Asn Asn
1

<210> SEQ ID NO 1139
<211> LENGTH: 3
<212> TYPE: PRT
<213> ORGANISM: Homo sapiens

<400> SEQUENCE: 1139

Ser Asn Asn
1

<210> SEQ ID NO 1140
<211> LENGTH: 3

<212> TYPE: PRT
<213> ORGANISM: Homo sapiens

<400> SEQUENCE: 1140

Ser Asn Asn
1

<210> SEQ ID NO 1141
<211> LENGTH: 3
<212> TYPE: PRT
<213> ORGANISM: Homo sapiens

<400> SEQUENCE: 1141

Ser Asn Asn
1

<210> SEQ ID NO 1142
<211> LENGTH: 3
<212> TYPE: PRT
<213> ORGANISM: Homo sapiens

<400> SEQUENCE: 1142

Ser Asn Asn
1

<210> SEQ ID NO 1143
<211> LENGTH: 3
<212> TYPE: PRT
<213> ORGANISM: Homo sapiens

<400> SEQUENCE: 1143

Ser Asn Asn
1

<210> SEQ ID NO 1144
<211> LENGTH: 3
<212> TYPE: PRT
<213> ORGANISM: Homo sapiens

<400> SEQUENCE: 1144

Ser Asn Asn
1

<210> SEQ ID NO 1145
<211> LENGTH: 3
<212> TYPE: PRT
<213> ORGANISM: Homo sapiens

<400> SEQUENCE: 1145

Ser Asn Asn
1

<210> SEQ ID NO 1146
<211> LENGTH: 3
<212> TYPE: PRT
<213> ORGANISM: Homo sapiens

<400> SEQUENCE: 1146

Ser Asn Asn
1

<210> SEQ ID NO 1147
<211> LENGTH: 3
<212> TYPE: PRT
<213> ORGANISM: Homo sapiens

<400> SEQUENCE: 1147

Ser Asn Asn
1

<210> SEQ ID NO 1148
<211> LENGTH: 3
<212> TYPE: PRT
<213> ORGANISM: Homo sapiens

<400> SEQUENCE: 1148

Glu Gly Ser
1

<210> SEQ ID NO 1149
<211> LENGTH: 3
<212> TYPE: PRT
<213> ORGANISM: Homo sapiens

<400> SEQUENCE: 1149

Ser Asn Asn
1

<210> SEQ ID NO 1150
<211> LENGTH: 3
<212> TYPE: PRT
<213> ORGANISM: Homo sapiens

<400> SEQUENCE: 1150

Ser Asn Asn
1

<210> SEQ ID NO 1151
<211> LENGTH: 3
<212> TYPE: PRT
<213> ORGANISM: Homo sapiens

<400> SEQUENCE: 1151

Ser Asn Asn
1

<210> SEQ ID NO 1152
<211> LENGTH: 3
<212> TYPE: PRT
<213> ORGANISM: Homo sapiens

<400> SEQUENCE: 1152

Ser Asn Asn
1

<210> SEQ ID NO 1153
<211> LENGTH: 3
<212> TYPE: PRT
<213> ORGANISM: Homo sapiens

<400> SEQUENCE: 1153

Glu Gly Ser
1

<210> SEQ ID NO 1154
<211> LENGTH: 3
<212> TYPE: PRT
<213> ORGANISM: Homo sapiens

<400> SEQUENCE: 1154

Ser Asn Asn
1

<210> SEQ ID NO 1155
<211> LENGTH: 3
<212> TYPE: PRT
<213> ORGANISM: Homo sapiens

<400> SEQUENCE: 1155

Ser Asn Asn
1

<210> SEQ ID NO 1156
<211> LENGTH: 3
<212> TYPE: PRT
<213> ORGANISM: Homo sapiens

<400> SEQUENCE: 1156

Ser Asn Asn
1

<210> SEQ ID NO 1157
<211> LENGTH: 3
<212> TYPE: PRT
<213> ORGANISM: Homo sapiens

<400> SEQUENCE: 1157

Ser Asn Asn
1

<210> SEQ ID NO 1158
<211> LENGTH: 3
<212> TYPE: PRT
<213> ORGANISM: Homo sapiens

<400> SEQUENCE: 1158

Ser Asn Asn
1

<210> SEQ ID NO 1159
<211> LENGTH: 3
<212> TYPE: PRT
<213> ORGANISM: Homo sapiens

<400> SEQUENCE: 1159

Ser Asn Asn
1

<210> SEQ ID NO 1160
<211> LENGTH: 3
<212> TYPE: PRT
<213> ORGANISM: Homo sapiens

<400> SEQUENCE: 1160

Ser Asn Asn
1

<210> SEQ ID NO 1161
<211> LENGTH: 3
<212> TYPE: PRT
<213> ORGANISM: Homo sapiens

<400> SEQUENCE: 1161

Ser Asn Asn

1

<210> SEQ ID NO 1162
<211> LENGTH: 3
<212> TYPE: PRT
<213> ORGANISM: Homo sapiens

<400> SEQUENCE: 1162

Ser Asn Asn
1

<210> SEQ ID NO 1163
<211> LENGTH: 3
<212> TYPE: PRT
<213> ORGANISM: Homo sapiens

<400> SEQUENCE: 1163

Ser Asn Asn
1

<210> SEQ ID NO 1164
<211> LENGTH: 3
<212> TYPE: PRT
<213> ORGANISM: Homo sapiens

<400> SEQUENCE: 1164

Ser Asn Asn
1

<210> SEQ ID NO 1165
<211> LENGTH: 3
<212> TYPE: PRT
<213> ORGANISM: Homo sapiens

<400> SEQUENCE: 1165

Ser Asn Asn
1

<210> SEQ ID NO 1166
<211> LENGTH: 3
<212> TYPE: PRT
<213> ORGANISM: Homo sapiens

<400> SEQUENCE: 1166

Ser Asn Asn
1

<210> SEQ ID NO 1167
<211> LENGTH: 3
<212> TYPE: PRT
<213> ORGANISM: Homo sapiens

<400> SEQUENCE: 1167

Ser Asn Asn
1

<210> SEQ ID NO 1168
<211> LENGTH: 3
<212> TYPE: PRT
<213> ORGANISM: Homo sapiens

<400> SEQUENCE: 1168

Ser Asn Asn
1

<210> SEQ ID NO 1169
<211> LENGTH: 3
<212> TYPE: PRT
<213> ORGANISM: Homo sapiens

<400> SEQUENCE: 1169

Ser Asn Asn
1

<210> SEQ ID NO 1170
<211> LENGTH: 3
<212> TYPE: PRT
<213> ORGANISM: Homo sapiens

<400> SEQUENCE: 1170

Ser Asn Asn
1

<210> SEQ ID NO 1171
<211> LENGTH: 3
<212> TYPE: PRT
<213> ORGANISM: Homo sapiens

<400> SEQUENCE: 1171

Ser Asn Asn
1

<210> SEQ ID NO 1172
<211> LENGTH: 3
<212> TYPE: PRT
<213> ORGANISM: Homo sapiens

<400> SEQUENCE: 1172

Ser Asn Asn
1

<210> SEQ ID NO 1173
<211> LENGTH: 3
<212> TYPE: PRT
<213> ORGANISM: Homo sapiens

<400> SEQUENCE: 1173

Ser Asn Asn
1

<210> SEQ ID NO 1174
<211> LENGTH: 3
<212> TYPE: PRT
<213> ORGANISM: Homo sapiens

<400> SEQUENCE: 1174

Ser Asn Asn
1

<210> SEQ ID NO 1175
<211> LENGTH: 3
<212> TYPE: PRT
<213> ORGANISM: Homo sapiens

<400> SEQUENCE: 1175

Gly Lys Asn
1

<210> SEQ ID NO 1176

<211> LENGTH: 3
<212> TYPE: PRT
<213> ORGANISM: Homo sapiens

<400> SEQUENCE: 1176

Ser Asn Asn
1

<210> SEQ ID NO 1177
<211> LENGTH: 3
<212> TYPE: PRT
<213> ORGANISM: Homo sapiens

<400> SEQUENCE: 1177

Ser Asn Asn
1

<210> SEQ ID NO 1178
<211> LENGTH: 3
<212> TYPE: PRT
<213> ORGANISM: Homo sapiens

<400> SEQUENCE: 1178

Ser Asn Asn
1

<210> SEQ ID NO 1179
<211> LENGTH: 3
<212> TYPE: PRT
<213> ORGANISM: Homo sapiens

<400> SEQUENCE: 1179

Ser Asn Asn
1

<210> SEQ ID NO 1180
<211> LENGTH: 3
<212> TYPE: PRT
<213> ORGANISM: Homo sapiens

<400> SEQUENCE: 1180

Ser Asn Asn
1

<210> SEQ ID NO 1181
<211> LENGTH: 3
<212> TYPE: PRT
<213> ORGANISM: Homo sapiens

<400> SEQUENCE: 1181

Ser Asn Asn
1

<210> SEQ ID NO 1182
<211> LENGTH: 3
<212> TYPE: PRT
<213> ORGANISM: Homo sapiens

<400> SEQUENCE: 1182

Ser Asn Asn
1

<210> SEQ ID NO 1183
<211> LENGTH: 3
<212> TYPE: PRT

<213> ORGANISM: Homo sapiens

<400> SEQUENCE: 1183

Ser Asn Asn
1

<210> SEQ ID NO 1184
<211> LENGTH: 3
<212> TYPE: PRT
<213> ORGANISM: Homo sapiens

<400> SEQUENCE: 1184

Ser Asn Asn
1

<210> SEQ ID NO 1185
<211> LENGTH: 3
<212> TYPE: PRT
<213> ORGANISM: Homo sapiens

<400> SEQUENCE: 1185

Ser Asp Ser
1

<210> SEQ ID NO 1186
<211> LENGTH: 3
<212> TYPE: PRT
<213> ORGANISM: Homo sapiens

<400> SEQUENCE: 1186

Ser Asn Asn
1

<210> SEQ ID NO 1187
<211> LENGTH: 3
<212> TYPE: PRT
<213> ORGANISM: Homo sapiens

<400> SEQUENCE: 1187

Ser Asn Asn
1

<210> SEQ ID NO 1188
<211> LENGTH: 3
<212> TYPE: PRT
<213> ORGANISM: Homo sapiens

<400> SEQUENCE: 1188

Ser Asn Asn
1

<210> SEQ ID NO 1189
<211> LENGTH: 3
<212> TYPE: PRT
<213> ORGANISM: Homo sapiens

<400> SEQUENCE: 1189

Ser Asn Asn
1

<210> SEQ ID NO 1190
<211> LENGTH: 3
<212> TYPE: PRT
<213> ORGANISM: Homo sapiens

<400> SEQUENCE: 1190

Ser Asn Asn
1

<210> SEQ ID NO 1191
<211> LENGTH: 3
<212> TYPE: PRT
<213> ORGANISM: Homo sapiens

<400> SEQUENCE: 1191

Ser Asn Asp
1

<210> SEQ ID NO 1192
<211> LENGTH: 9
<212> TYPE: DNA
<213> ORGANISM: Homo sapiens

<400> SEQUENCE: 1192 gatgaatcc 9

<210> SEQ ID NO 1193
<211> LENGTH: 9
<212> TYPE: DNA
<213> ORGANISM: Homo sapiens

<400> SEQUENCE: 1193 acgctttcc 9

<210> SEQ ID NO 1194
<211> LENGTH: 9
<212> TYPE: DNA
<213> ORGANISM: Homo sapiens

<400> SEQUENCE: 1194 tgggcatct 9

<210> SEQ ID NO 1195
<211> LENGTH: 9
<212> TYPE: DNA
<213> ORGANISM: Homo sapiens

<400> SEQUENCE: 1195 ggtgcatcc 9

<210> SEQ ID NO 1196
<211> LENGTH: 9
<212> TYPE: DNA
<213> ORGANISM: Homo sapiens

<400> SEQUENCE: 1196 ggtgcatcc 9

<210> SEQ ID NO 1197
<211> LENGTH: 9
<212> TYPE: DNA
<213> ORGANISM: Homo sapiens

<400> SEQUENCE: 1197 ttgggttct 9

<210> SEQ ID NO 1198
<211> LENGTH: 9

<212> TYPE: DNA
<213> ORGANISM: Homo sapiens

<400> SEQUENCE: 1198 gctgcatcc 9

<210> SEQ ID NO 1199
<211> LENGTH: 9
<212> TYPE: DNA
<213> ORGANISM: Homo sapiens

<400> SEQUENCE: 1199 tgggcatct 9

<210> SEQ ID NO 1200
<211> LENGTH: 9
<212> TYPE: DNA
<213> ORGANISM: Homo sapiens

<400> SEQUENCE: 1200 atggcgtct 9

<210> SEQ ID NO 1201
<211> LENGTH: 9
<212> TYPE: DNA
<213> ORGANISM: Homo sapiens

<400> SEQUENCE: 1201 gatgcatcc 9

<210> SEQ ID NO 1202
<211> LENGTH: 9
<212> TYPE: DNA
<213> ORGANISM: Homo sapiens

<400> SEQUENCE: 1202 gctgcatcc 9

<210> SEQ ID NO 1203
<211> LENGTH: 9
<212> TYPE: DNA
<213> ORGANISM: Homo sapiens

<400> SEQUENCE: 1203 ttgggttct 9

<210> SEQ ID NO 1204
<211> LENGTH: 9
<212> TYPE: DNA
<213> ORGANISM: Homo sapiens

<400> SEQUENCE: 1204 aaggcgtct 9

<210> SEQ ID NO 1205
<211> LENGTH: 9
<212> TYPE: DNA
<213> ORGANISM: Homo sapiens

<400> SEQUENCE: 1205 aaggcgtct 9

<210> SEQ ID NO 1206

<211> LENGTH: 9
<212> TYPE: DNA
<213> ORGANISM: Homo sapiens

<400> SEQUENCE: 1206 acgctttcc 9

<210> SEQ ID NO 1207
<211> LENGTH: 9
<212> TYPE: DNA
<213> ORGANISM: Homo sapiens

<400> SEQUENCE: 1207 aaggcgtct 9

<210> SEQ ID NO 1208
<211> LENGTH: 9
<212> TYPE: DNA
<213> ORGANISM: Homo sapiens

<400> SEQUENCE: 1208 ggtgcatcc 9

<210> SEQ ID NO 1209
<211> LENGTH: 9
<212> TYPE: DNA
<213> ORGANISM: Homo sapiens

<400> SEQUENCE: 1209 gatgcatcc 9

<210> SEQ ID NO 1210
<211> LENGTH: 9
<212> TYPE: DNA
<213> ORGANISM: Homo sapiens

<400> SEQUENCE: 1210 ggtgcatcc 9

<210> SEQ ID NO 1211
<211> LENGTH: 9
<212> TYPE: DNA
<213> ORGANISM: Homo sapiens

<400> SEQUENCE: 1211 tgggcatct 9

<210> SEQ ID NO 1212
<211> LENGTH: 9
<212> TYPE: DNA
<213> ORGANISM: Homo sapiens

<400> SEQUENCE: 1212 ggtgcatcc 9

<210> SEQ ID NO 1213
<211> LENGTH: 9
<212> TYPE: DNA
<213> ORGANISM: Homo sapiens

<400> SEQUENCE: 1213 tgggcatct 9

<210> SEQ ID NO 1214
<211> LENGTH: 9
<212> TYPE: DNA
<213> ORGANISM: Homo sapiens

<400> SEQUENCE: 1214 ggtgcatcc 9

<210> SEQ ID NO 1215
<211> LENGTH: 9
<212> TYPE: DNA
<213> ORGANISM: Homo sapiens

<400> SEQUENCE: 1215 tgggcatct 9

<210> SEQ ID NO 1216
<211> LENGTH: 9
<212> TYPE: DNA
<213> ORGANISM: Homo sapiens

<400> SEQUENCE: 1216 tgggcatct 9

<210> SEQ ID NO 1217
<211> LENGTH: 9
<212> TYPE: DNA
<213> ORGANISM: Homo sapiens

<400> SEQUENCE: 1217 ggtgcatcc 9

<210> SEQ ID NO 1218
<211> LENGTH: 9
<212> TYPE: DNA
<213> ORGANISM: Homo sapiens

<400> SEQUENCE: 1218 aaggcgtct 9

<210> SEQ ID NO 1219
<211> LENGTH: 9
<212> TYPE: DNA
<213> ORGANISM: Homo sapiens

<400> SEQUENCE: 1219 gctgcatcc 9

<210> SEQ ID NO 1220
<211> LENGTH: 9
<212> TYPE: DNA
<213> ORGANISM: Homo sapiens

<400> SEQUENCE: 1220 gctgcatcc 9

<210> SEQ ID NO 1221
<211> LENGTH: 9
<212> TYPE: DNA
<213> ORGANISM: Homo sapiens

<400> SEQUENCE: 1221 ttggattct 9

<210> SEQ ID NO 1222
<211> LENGTH: 9
<212> TYPE: DNA
<213> ORGANISM: Homo sapiens

<400> SEQUENCE: 1222 ttgggttct 9

<210> SEQ ID NO 1223
<211> LENGTH: 9
<212> TYPE: DNA
<213> ORGANISM: Homo sapiens

<400> SEQUENCE: 1223 ttgggttct 9

<210> SEQ ID NO 1224
<211> LENGTH: 9
<212> TYPE: DNA
<213> ORGANISM: Homo sapiens

<400> SEQUENCE: 1224 tgggcatct 9

<210> SEQ ID NO 1225
<211> LENGTH: 9
<212> TYPE: DNA
<213> ORGANISM: Homo sapiens

<400> SEQUENCE: 1225 gatgcatcc 9

<210> SEQ ID NO 1226
<211> LENGTH: 9
<212> TYPE: DNA
<213> ORGANISM: Homo sapiens

<400> SEQUENCE: 1226 ttgggttct 9

<210> SEQ ID NO 1227
<211> LENGTH: 9
<212> TYPE: DNA
<213> ORGANISM: Homo sapiens

<400> SEQUENCE: 1227 ttgggttct 9

<210> SEQ ID NO 1228
<211> LENGTH: 9
<212> TYPE: DNA
<213> ORGANISM: Homo sapiens

<400> SEQUENCE: 1228 tgggcatct 9

<210> SEQ ID NO 1229
<211> LENGTH: 9
<212> TYPE: DNA
<213> ORGANISM: Homo sapiens

<400> SEQUENCE: 1229 ttgggttct 9

<210> SEQ ID NO 1230
<211> LENGTH: 9
<212> TYPE: DNA
<213> ORGANISM: Homo sapiens

<400> SEQUENCE: 1230 acgctttcc 9

<210> SEQ ID NO 1231
<211> LENGTH: 9
<212> TYPE: DNA
<213> ORGANISM: Homo sapiens

<400> SEQUENCE: 1231 acgctttcc 9

<210> SEQ ID NO 1232
<211> LENGTH: 9
<212> TYPE: DNA
<213> ORGANISM: Homo sapiens

<400> SEQUENCE: 1232 tgggcatct 9

<210> SEQ ID NO 1233
<211> LENGTH: 9
<212> TYPE: DNA
<213> ORGANISM: Homo sapiens

<400> SEQUENCE: 1233 gctgcatcc 9

<210> SEQ ID NO 1234
<211> LENGTH: 9
<212> TYPE: DNA
<213> ORGANISM: Homo sapiens

<400> SEQUENCE: 1234 ttgggttct 9

<210> SEQ ID NO 1235
<211> LENGTH: 9
<212> TYPE: DNA
<213> ORGANISM: Homo sapiens

<400> SEQUENCE: 1235 acgctttcc 9

<210> SEQ ID NO 1236
<211> LENGTH: 9
<212> TYPE: DNA
<213> ORGANISM: Homo sapiens

<400> SEQUENCE: 1236 ttggcttct 9

<210> SEQ ID NO 1237
<211> LENGTH: 9
<212> TYPE: DNA
<213> ORGANISM: Homo sapiens

<400> SEQUENCE: 1237 ggtgcatcc 9

<210> SEQ ID NO 1238
<211> LENGTH: 9
<212> TYPE: DNA
<213> ORGANISM: Homo sapiens

<400> SEQUENCE: 1238 ggtgcatcc 9

<210> SEQ ID NO 1239
<211> LENGTH: 9
<212> TYPE: DNA
<213> ORGANISM: Homo sapiens

<400> SEQUENCE: 1239 ttgggttct 9

<210> SEQ ID NO 1240
<211> LENGTH: 9
<212> TYPE: DNA
<213> ORGANISM: Homo sapiens

<400> SEQUENCE: 1240 agtaataat 9

<210> SEQ ID NO 1241
<211> LENGTH: 9
<212> TYPE: DNA
<213> ORGANISM: Homo sapiens

<400> SEQUENCE: 1241 agtaataat 9

<210> SEQ ID NO 1242
<211> LENGTH: 9
<212> TYPE: DNA
<213> ORGANISM: Homo sapiens

<400> SEQUENCE: 1242 agtaataat 9

<210> SEQ ID NO 1243
<211> LENGTH: 9
<212> TYPE: DNA
<213> ORGANISM: Homo sapiens

<400> SEQUENCE: 1243 agtaataat 9

<210> SEQ ID NO 1244
<211> LENGTH: 9
<212> TYPE: DNA
<213> ORGANISM: Homo sapiens

<400> SEQUENCE: 1244 agtaataat 9

<210> SEQ ID NO 1245
<211> LENGTH: 9
<212> TYPE: DNA
<213> ORGANISM: Homo sapiens

<400> SEQUENCE: 1245 agtaataat 9

<210> SEQ ID NO 1246
<211> LENGTH: 9
<212> TYPE: DNA
<213> ORGANISM: Homo sapiens

<400> SEQUENCE: 1246 agtaataat 9

<210> SEQ ID NO 1247
<211> LENGTH: 9
<212> TYPE: DNA
<213> ORGANISM: Homo sapiens

<400> SEQUENCE: 1247 agtaataat 9

<210> SEQ ID NO 1248
<211> LENGTH: 9
<212> TYPE: DNA
<213> ORGANISM: Homo sapiens

<400> SEQUENCE: 1248 agtaataat 9

<210> SEQ ID NO 1249
<211> LENGTH: 9
<212> TYPE: DNA
<213> ORGANISM: Homo sapiens

<400> SEQUENCE: 1249 agtaataat 9

<210> SEQ ID NO 1250
<211> LENGTH: 9
<212> TYPE: DNA
<213> ORGANISM: Homo sapiens

<400> SEQUENCE: 1250 agtaataat 9

<210> SEQ ID NO 1251
<211> LENGTH: 9
<212> TYPE: DNA
<213> ORGANISM: Homo sapiens

<400> SEQUENCE: 1251 agtaataat 9

<210> SEQ ID NO 1252
<211> LENGTH: 9
<212> TYPE: DNA
<213> ORGANISM: Homo sapiens

<400> SEQUENCE: 1252 agtaataat 9

<210> SEQ ID NO 1253
<211> LENGTH: 9
<212> TYPE: DNA
<213> ORGANISM: Homo sapiens

<400> SEQUENCE: 1253 agtaataat 9

<210> SEQ ID NO 1254
<211> LENGTH: 9
<212> TYPE: DNA
<213> ORGANISM: Homo sapiens

<400> SEQUENCE: 1254 agtaataat 9

<210> SEQ ID NO 1255
<211> LENGTH: 9
<212> TYPE: DNA
<213> ORGANISM: Homo sapiens

<400> SEQUENCE: 1255 agtaataat 9

<210> SEQ ID NO 1256
<211> LENGTH: 9
<212> TYPE: DNA
<213> ORGANISM: Homo sapiens

<400> SEQUENCE: 1256 gagggcagt 9

<210> SEQ ID NO 1257
<211> LENGTH: 9
<212> TYPE: DNA
<213> ORGANISM: Homo sapiens

<400> SEQUENCE: 1257 agtaataat 9

<210> SEQ ID NO 1258
<211> LENGTH: 9
<212> TYPE: DNA
<213> ORGANISM: Homo sapiens

<400> SEQUENCE: 1258 agtaataat 9

<210> SEQ ID NO 1259
<211> LENGTH: 9
<212> TYPE: DNA
<213> ORGANISM: Homo sapiens

<400> SEQUENCE: 1259 agtaataat 9

<210> SEQ ID NO 1260
<211> LENGTH: 9
<212> TYPE: DNA
<213> ORGANISM: Homo sapiens

<400> SEQUENCE: 1260 agtaataat 9

<210> SEQ ID NO 1261
<211> LENGTH: 9
<212> TYPE: DNA
<213> ORGANISM: Homo sapiens

<400> SEQUENCE: 1261 gagggcagt 9

<210> SEQ ID NO 1262
<211> LENGTH: 9
<212> TYPE: DNA
<213> ORGANISM: Homo sapiens

<400> SEQUENCE: 1262 agtaataat 9

<210> SEQ ID NO 1263
<211> LENGTH: 9
<212> TYPE: DNA
<213> ORGANISM: Homo sapiens

<400> SEQUENCE: 1263 agtaataat 9

<210> SEQ ID NO 1264
<211> LENGTH: 9
<212> TYPE: DNA
<213> ORGANISM: Homo sapiens

<400> SEQUENCE: 1264 agtaataat 9

<210> SEQ ID NO 1265
<211> LENGTH: 9
<212> TYPE: DNA
<213> ORGANISM: Homo sapiens

<400> SEQUENCE: 1265 agtaataat 9

<210> SEQ ID NO 1266
<211> LENGTH: 9
<212> TYPE: DNA
<213> ORGANISM: Homo sapiens

<400> SEQUENCE: 1266 agtaataat 9

<210> SEQ ID NO 1267
<211> LENGTH: 9
<212> TYPE: DNA
<213> ORGANISM: Homo sapiens

<400> SEQUENCE: 1267 agtaataat 9

<210> SEQ ID NO 1268
<211> LENGTH: 9
<212> TYPE: DNA
<213> ORGANISM: Homo sapiens

<400> SEQUENCE: 1268 agtaataat 9

<210> SEQ ID NO 1269
<211> LENGTH: 9
<212> TYPE: DNA

<213> ORGANISM: Homo sapiens

<400> SEQUENCE: 1269 agtaataat 9

<210> SEQ ID NO 1270
<211> LENGTH: 9
<212> TYPE: DNA
<213> ORGANISM: Homo sapiens

<400> SEQUENCE: 1270 agtaataat 9

<210> SEQ ID NO 1271
<211> LENGTH: 9
<212> TYPE: DNA
<213> ORGANISM: Homo sapiens

<400> SEQUENCE: 1271 agtaataat 9

<210> SEQ ID NO 1272
<211> LENGTH: 9
<212> TYPE: DNA
<213> ORGANISM: Homo sapiens

<400> SEQUENCE: 1272 agtaataat 9

<210> SEQ ID NO 1273
<211> LENGTH: 9
<212> TYPE: DNA
<213> ORGANISM: Homo sapiens

<400> SEQUENCE: 1273 agtaataat 9

<210> SEQ ID NO 1274
<211> LENGTH: 9
<212> TYPE: DNA
<213> ORGANISM: Homo sapiens

<400> SEQUENCE: 1274 agtaataat 9

<210> SEQ ID NO 1275
<211> LENGTH: 9
<212> TYPE: DNA
<213> ORGANISM: Homo sapiens

<400> SEQUENCE: 1275 agtaataat 9

<210> SEQ ID NO 1276
<211> LENGTH: 9
<212> TYPE: DNA
<213> ORGANISM: Homo sapiens

<400> SEQUENCE: 1276 agtaataat 9

<210> SEQ ID NO 1277
<211> LENGTH: 9

<212> TYPE: DNA
<213> ORGANISM: Homo sapiens

<400> SEQUENCE: 1277 agtaataat 9

<210> SEQ ID NO 1278
<211> LENGTH: 9
<212> TYPE: DNA
<213> ORGANISM: Homo sapiens

<400> SEQUENCE: 1278 agtaataat 9

<210> SEQ ID NO 1279
<211> LENGTH: 9
<212> TYPE: DNA
<213> ORGANISM: Homo sapiens

<400> SEQUENCE: 1279 agtaataat 9

<210> SEQ ID NO 1280
<211> LENGTH: 9
<212> TYPE: DNA
<213> ORGANISM: Homo sapiens

<400> SEQUENCE: 1280 agtaataat 9

<210> SEQ ID NO 1281
<211> LENGTH: 9
<212> TYPE: DNA
<213> ORGANISM: Homo sapiens

<400> SEQUENCE: 1281 agtaataat 9

<210> SEQ ID NO 1282
<211> LENGTH: 9
<212> TYPE: DNA
<213> ORGANISM: Homo sapiens

<400> SEQUENCE: 1282 agtaataat 9

<210> SEQ ID NO 1283
<211> LENGTH: 9
<212> TYPE: DNA
<213> ORGANISM: Homo sapiens

<400> SEQUENCE: 1283 ggtaaaaac 9

<210> SEQ ID NO 1284
<211> LENGTH: 9
<212> TYPE: DNA
<213> ORGANISM: Homo sapiens

<400> SEQUENCE: 1284 agtaataat 9

<210> SEQ ID NO 1285

<211> LENGTH: 9
<212> TYPE: DNA
<213> ORGANISM: Homo sapiens

<400> SEQUENCE: 1285 agtaataat 9

<210> SEQ ID NO 1286
<211> LENGTH: 9
<212> TYPE: DNA
<213> ORGANISM: Homo sapiens

<400> SEQUENCE: 1286 agtaataat 9

<210> SEQ ID NO 1287
<211> LENGTH: 9
<212> TYPE: DNA
<213> ORGANISM: Homo sapiens

<400> SEQUENCE: 1287 agtaataat 9

<210> SEQ ID NO 1288
<211> LENGTH: 9
<212> TYPE: DNA
<213> ORGANISM: Homo sapiens

<400> SEQUENCE: 1288 agtaataat 9

<210> SEQ ID NO 1289
<211> LENGTH: 9
<212> TYPE: DNA
<213> ORGANISM: Homo sapiens

<400> SEQUENCE: 1289 agtaataat 9

<210> SEQ ID NO 1290
<211> LENGTH: 9
<212> TYPE: DNA
<213> ORGANISM: Homo sapiens

<400> SEQUENCE: 1290 agtaataat 9

<210> SEQ ID NO 1291
<211> LENGTH: 9
<212> TYPE: DNA
<213> ORGANISM: Homo sapiens

<400> SEQUENCE: 1291 agtaataat 9

<210> SEQ ID NO 1292
<211> LENGTH: 9
<212> TYPE: DNA
<213> ORGANISM: Homo sapiens

<400> SEQUENCE: 1292 agtaataat 9

<210> SEQ ID NO 1293
<211> LENGTH: 9
<212> TYPE: DNA
<213> ORGANISM: Homo sapiens

<400> SEQUENCE: 1293 agcgatagc 9

<210> SEQ ID NO 1294
<211> LENGTH: 9
<212> TYPE: DNA
<213> ORGANISM: Homo sapiens

<400> SEQUENCE: 1294 agtaataat 9

<210> SEQ ID NO 1295
<211> LENGTH: 9
<212> TYPE: DNA
<213> ORGANISM: Homo sapiens

<400> SEQUENCE: 1295 agtaataat 9

<210> SEQ ID NO 1296
<211> LENGTH: 9
<212> TYPE: DNA
<213> ORGANISM: Homo sapiens

<400> SEQUENCE: 1296 agtaataat 9

<210> SEQ ID NO 1297
<211> LENGTH: 9
<212> TYPE: DNA
<213> ORGANISM: Homo sapiens

<400> SEQUENCE: 1297 agtaataat 9

<210> SEQ ID NO 1298
<211> LENGTH: 9
<212> TYPE: DNA
<213> ORGANISM: Homo sapiens

<400> SEQUENCE: 1298 agtaataat 9

<210> SEQ ID NO 1299
<211> LENGTH: 9
<212> TYPE: DNA
<213> ORGANISM: Homo sapiens

<400> SEQUENCE: 1299 agtaatgat 9

<210> SEQ ID NO 1300
<211> LENGTH: 13
<212> TYPE: PRT
<213> ORGANISM: Homo sapiens

<400> SEQUENCE: 1300

Thr Thr Asn Asp Tyr Gly Asp Tyr Glu Ala Phe Asp Ile
1 5 10

<210> SEQ ID NO 1301
<211> LENGTH: 11
<212> TYPE: PRT
<213> ORGANISM: Homo sapiens

<400> SEQUENCE: 1301

Ala Arg Gln Asp Asn Trp Asn Tyr Phe Asp Tyr
1 5 10

<210> SEQ ID NO 1302
<211> LENGTH: 14
<212> TYPE: PRT
<213> ORGANISM: Homo sapiens

<400> SEQUENCE: 1302

Thr Thr Asn Asp Tyr Gly Gly Pro Val Asp Ala Phe Asp Ile
1 5 10

<210> SEQ ID NO 1303
<211> LENGTH: 10
<212> TYPE: PRT
<213> ORGANISM: Homo sapiens

<400> SEQUENCE: 1303

Ala Arg Gly Gly Val Thr Trp Phe Asp Pro
1 5 10

<210> SEQ ID NO 1304
<211> LENGTH: 10
<212> TYPE: PRT
<213> ORGANISM: Homo sapiens

<400> SEQUENCE: 1304

Ala Arg Gly Gly Ile Thr Trp Phe Asp Pro
1 5 10

<210> SEQ ID NO 1305
<211> LENGTH: 11
<212> TYPE: PRT
<213> ORGANISM: Homo sapiens

<400> SEQUENCE: 1305

Thr Arg Glu Gly Ser Phe Gly Ala Leu Asp Ile
1 5 10

<210> SEQ ID NO 1306
<211> LENGTH: 12
<212> TYPE: PRT
<213> ORGANISM: Homo sapiens

<400> SEQUENCE: 1306

Ala Arg Gly Gly Tyr Ser Gly Pro Tyr Phe Asp Tyr
1 5 10

<210> SEQ ID NO 1307
<211> LENGTH: 13
<212> TYPE: PRT
<213> ORGANISM: Homo sapiens

<400> SEQUENCE: 1307

Thr Thr Gly Asp Tyr Ser Tyr Thr Asp Ala Phe Asp Ile
1 5 10

<210> SEQ ID NO 1308
<211> LENGTH: 6
<212> TYPE: PRT
<213> ORGANISM: Homo sapiens

<400> SEQUENCE: 1308

Ala Arg Gly Phe Asp Tyr
1               5

<210> SEQ ID NO 1309
<211> LENGTH: 17
<212> TYPE: PRT
<213> ORGANISM: Homo sapiens

<400> SEQUENCE: 1309

Ala Arg Asp Phe Pro His Asp Tyr Gly Tyr Tyr Pro His Tyr Phe Asp
1               5                   10                  15

Tyr

<210> SEQ ID NO 1310
<211> LENGTH: 10
<212> TYPE: PRT
<213> ORGANISM: Homo sapiens

<400> SEQUENCE: 1310

Ala Arg Thr Gln Leu Gly Ile Ala Asp Tyr
1               5                   10

<210> SEQ ID NO 1311
<211> LENGTH: 14
<212> TYPE: PRT
<213> ORGANISM: Homo sapiens

<400> SEQUENCE: 1311

Ala Thr Leu Ser Gly Thr Asn Trp Gly Ser Pro Phe Asp Tyr
1               5                   10

<210> SEQ ID NO 1312
<211> LENGTH: 19
<212> TYPE: PRT
<213> ORGANISM: Homo sapiens

<400> SEQUENCE: 1312

Ala Arg Glu Ile Leu Val Val Val Ala Ala Thr Arg Thr Gly Gly Val
1               5                   10                  15

Phe Asp Ile

<210> SEQ ID NO 1313
<211> LENGTH: 6
<212> TYPE: PRT
<213> ORGANISM: Homo sapiens

<400> SEQUENCE: 1313

Ala Arg Gly Phe Asp Tyr
1               5

<210> SEQ ID NO 1314
<211> LENGTH: 12
<212> TYPE: PRT
<213> ORGANISM: Homo sapiens

<400> SEQUENCE: 1314

Ala Arg Asp Leu Glu Gly Gly Gly Pro Phe Asp Tyr
1               5                   10

<210> SEQ ID NO 1315
<211> LENGTH: 6
<212> TYPE: PRT
<213> ORGANISM: Homo sapiens

<400> SEQUENCE: 1315

Thr Arg Gly Met Asp Val
1 5

<210> SEQ ID NO 1316
<211> LENGTH: 11
<212> TYPE: PRT
<213> ORGANISM: Homo sapiens

<400> SEQUENCE: 1316

Ala Arg Asp Arg Thr Phe Tyr Ala Phe Asp Met
1 5 10

<210> SEQ ID NO 1317
<211> LENGTH: 13
<212> TYPE: PRT
<213> ORGANISM: Homo sapiens

<400> SEQUENCE: 1317

Ala Arg Gly His Ile Val Val Val Thr Ala Met Asp Tyr
1 5 10

<210> SEQ ID NO 1318
<211> LENGTH: 9
<212> TYPE: PRT
<213> ORGANISM: Homo sapiens

<400> SEQUENCE: 1318

Ala Arg Glu Ala Asp Ala Phe Asp Ile
1 5

<210> SEQ ID NO 1319
<211> LENGTH: 13
<212> TYPE: PRT
<213> ORGANISM: Homo sapiens

<400> SEQUENCE: 1319

Thr Thr Ser Asp Tyr Gly Asp Phe Asp Ala Phe Asp Ile
1 5 10

<210> SEQ ID NO 1320
<211> LENGTH: 9
<212> TYPE: PRT
<213> ORGANISM: Homo sapiens

<400> SEQUENCE: 1320

Ala Arg Glu Ala Asp Ala Phe Asp Ile
1 5

<210> SEQ ID NO 1321
<211> LENGTH: 12
<212> TYPE: PRT
<213> ORGANISM: Homo sapiens

<400> SEQUENCE: 1321

Ala Arg Asp Gly Gly Thr Thr Gly Ala Phe Asp Ile
1 5 10

<210> SEQ ID NO 1322
<211> LENGTH: 15
<212> TYPE: PRT
<213> ORGANISM: Homo sapiens

<400> SEQUENCE: 1322

Ala Arg Ala Gly Ala Val Ala Ala Leu Tyr Asn Trp Phe Asp Pro
1 5 10 15

<210> SEQ ID NO 1323
<211> LENGTH: 12
<212> TYPE: PRT
<213> ORGANISM: Homo sapiens

<400> SEQUENCE: 1323

Ala His Ser Pro Arg Tyr Ser Gly Tyr Phe Asp Tyr
1 5 10

<210> SEQ ID NO 1324
<211> LENGTH: 11
<212> TYPE: PRT
<213> ORGANISM: Homo sapiens

<400> SEQUENCE: 1324

Ala Arg Glu Ser Pro Tyr Trp Tyr Phe Asp Leu
1 5 10

<210> SEQ ID NO 1325
<211> LENGTH: 11
<212> TYPE: PRT
<213> ORGANISM: Homo sapiens

<400> SEQUENCE: 1325

Ala Arg Trp Arg Thr Phe Tyr Gly Met Asp Val
1 5 10

<210> SEQ ID NO 1326
<211> LENGTH: 7
<212> TYPE: PRT
<213> ORGANISM: Homo sapiens

<400> SEQUENCE: 1326

Ala Arg Glu Leu Gly Asn Tyr
1 5

<210> SEQ ID NO 1327
<211> LENGTH: 16
<212> TYPE: PRT
<213> ORGANISM: Homo sapiens

<400> SEQUENCE: 1327

Ala Arg Asp Ser Gly Thr Tyr Pro Tyr Tyr Tyr Phe Gly Met Asp Val
1 5 10 15

<210> SEQ ID NO 1328
<211> LENGTH: 11
<212> TYPE: PRT
<213> ORGANISM: Homo sapiens

<400> SEQUENCE: 1328

Ala Arg Asp Arg Ser Phe Tyr Gly Met Asp Val
1 5 10

<210> SEQ ID NO 1329
<211> LENGTH: 13

<212> TYPE: PRT
<213> ORGANISM: Homo sapiens

<400> SEQUENCE: 1329

Ala Arg Gly Gly Ser Phe Pro Tyr Asn Trp Phe Asp Pro
1               5                   10

<210> SEQ ID NO 1330
<211> LENGTH: 11
<212> TYPE: PRT
<213> ORGANISM: Homo sapiens

<400> SEQUENCE: 1330

Thr Arg Glu Gly Ser Phe Gly Ala Leu Asp Ile
1               5                   10

<210> SEQ ID NO 1331
<211> LENGTH: 12
<212> TYPE: PRT
<213> ORGANISM: Homo sapiens

<400> SEQUENCE: 1331

Thr Thr Asp Gly Val Tyr Pro Asp Val Phe Asp Ile
1               5                   10

<210> SEQ ID NO 1332
<211> LENGTH: 11
<212> TYPE: PRT
<213> ORGANISM: Homo sapiens

<400> SEQUENCE: 1332

Ala Arg Leu Ser Pro Tyr Trp Tyr Phe Asp Leu
1               5                   10

<210> SEQ ID NO 1333
<211> LENGTH: 19
<212> TYPE: PRT
<213> ORGANISM: Homo sapiens

<400> SEQUENCE: 1333

Ala Arg Glu Gly Glu Arg Phe Cys Gly Ala Asp Cys Tyr Pro His Trp
1               5                   10                  15

Phe Asp Pro

<210> SEQ ID NO 1334
<211> LENGTH: 20
<212> TYPE: PRT
<213> ORGANISM: Homo sapiens

<400> SEQUENCE: 1334

Ala Arg Asp Asn Trp Asn Tyr Gly Gly Pro Thr Tyr Tyr Tyr Tyr Tyr
1               5                   10                  15

Gly Met Asp Val
            20

<210> SEQ ID NO 1335
<211> LENGTH: 9
<212> TYPE: PRT
<213> ORGANISM: Homo sapiens

<400> SEQUENCE: 1335

Ala Ser Gly Tyr His Leu Phe Asp Tyr
1               5

<210> SEQ ID NO 1336
<211> LENGTH: 13
<212> TYPE: PRT
<213> ORGANISM: Homo sapiens

<400> SEQUENCE: 1336

Thr Ser Thr Asp Tyr Gly Asp Tyr Asp Ala Phe Asp Ile
1 5 10

<210> SEQ ID NO 1337
<211> LENGTH: 13
<212> TYPE: PRT
<213> ORGANISM: Homo sapiens

<400> SEQUENCE: 1337

Ala Arg Gly Gly Ser Tyr Pro Tyr Asn Trp Phe Asp Pro
1 5 10

<210> SEQ ID NO 1338
<211> LENGTH: 11
<212> TYPE: PRT
<213> ORGANISM: Homo sapiens

<400> SEQUENCE: 1338

Ala Arg Asp Asn His Asp Gly Ala Phe Asp Ile
1 5 10

<210> SEQ ID NO 1339
<211> LENGTH: 12
<212> TYPE: PRT
<213> ORGANISM: Homo sapiens

<400> SEQUENCE: 1339

Ala Arg Asp Glu Asp Ser Gly Ser Tyr Phe Asp Tyr
1 5 10

<210> SEQ ID NO 1340
<211> LENGTH: 13
<212> TYPE: PRT
<213> ORGANISM: Homo sapiens

<400> SEQUENCE: 1340

Ala His Gln Glu Arg Arg Ser Gly Trp Ser Phe Asp Tyr
1 5 10

<210> SEQ ID NO 1341
<211> LENGTH: 19
<212> TYPE: PRT
<213> ORGANISM: Homo sapiens

<400> SEQUENCE: 1341

Ala Arg Ala Thr Tyr Tyr Tyr Asp Ser Ser Gly Tyr Tyr Ser Asn Trp
1 5 10 15

Phe Asp Pro

<210> SEQ ID NO 1342
<211> LENGTH: 9
<212> TYPE: PRT
<213> ORGANISM: Homo sapiens

<400> SEQUENCE: 1342

Ala Ser Gly Tyr His Leu Phe Asp Tyr
1 5

<210> SEQ ID NO 1343
<211> LENGTH: 11
<212> TYPE: PRT
<213> ORGANISM: Homo sapiens

<400> SEQUENCE: 1343

Ala Arg Lys Asn Pro Trp Gly His Phe Asp Tyr
1 5 10

<210> SEQ ID NO 1344
<211> LENGTH: 11
<212> TYPE: PRT
<213> ORGANISM: Homo sapiens

<400> SEQUENCE: 1344

Ala Arg Asp Gly Thr Gly Asp Ala Leu Asp Ile
1 5 10

<210> SEQ ID NO 1345
<211> LENGTH: 11
<212> TYPE: PRT
<213> ORGANISM: Homo sapiens

<400> SEQUENCE: 1345

Ala Arg Asp Arg Thr Phe Tyr Gly Met Asp Val
1 5 10

<210> SEQ ID NO 1346
<211> LENGTH: 11
<212> TYPE: PRT
<213> ORGANISM: Homo sapiens

<400> SEQUENCE: 1346

Ala Arg Asp Arg Ala Phe Tyr Gly Met Asp Val
1 5 10

<210> SEQ ID NO 1347
<211> LENGTH: 10
<212> TYPE: PRT
<213> ORGANISM: Homo sapiens

<400> SEQUENCE: 1347

Ala Arg Asp Arg Ala Trp Gly Ser Gly Asp
1 5 10

<210> SEQ ID NO 1348
<211> LENGTH: 11
<212> TYPE: PRT
<213> ORGANISM: Homo sapiens

<400> SEQUENCE: 1348

Ala Arg Ser Arg Leu Gly Ser Ile Phe Asp Tyr
1 5 10

<210> SEQ ID NO 1349
<211> LENGTH: 11
<212> TYPE: PRT
<213> ORGANISM: Homo sapiens

<400> SEQUENCE: 1349

Ala Arg Gly Arg Leu Asn Gly Ala Phe Asp Tyr
1 5 10

<210> SEQ ID NO 1350

<211> LENGTH: 11
<212> TYPE: PRT
<213> ORGANISM: Homo sapiens

<400> SEQUENCE: 1350

Ala Arg Glu Arg Leu Thr Gly Phe Phe Asp Tyr
1 5 10

<210> SEQ ID NO 1351
<211> LENGTH: 11
<212> TYPE: PRT
<213> ORGANISM: Homo sapiens

<400> SEQUENCE: 1351

Ala Arg Asp Arg Val Gly Met Thr Phe Asp Ile
1 5 10

<210> SEQ ID NO 1352
<211> LENGTH: 11
<212> TYPE: PRT
<213> ORGANISM: Homo sapiens

<400> SEQUENCE: 1352

Ala Arg Gly Arg Ile Ile Gly Ala Phe Asp Ile
1 5 10

<210> SEQ ID NO 1353
<211> LENGTH: 10
<212> TYPE: PRT
<213> ORGANISM: Homo sapiens

<400> SEQUENCE: 1353

Ala Arg Glu Arg Val Ile Trp Phe Asp Pro
1 5 10

<210> SEQ ID NO 1354
<211> LENGTH: 10
<212> TYPE: PRT
<213> ORGANISM: Homo sapiens

<400> SEQUENCE: 1354

Ala Arg Gly Arg Leu Thr Phe Phe Asp Tyr
1 5 10

<210> SEQ ID NO 1355
<211> LENGTH: 11
<212> TYPE: PRT
<213> ORGANISM: Homo sapiens

<400> SEQUENCE: 1355

Ala Arg Gly Arg Leu Gly Asn Tyr Phe Asp Tyr
1 5 10

<210> SEQ ID NO 1356
<211> LENGTH: 11
<212> TYPE: PRT
<213> ORGANISM: Homo sapiens

<400> SEQUENCE: 1356

Ala Arg Glu Arg Leu Val Arg Ala Phe Asp Ile
1 5 10

<210> SEQ ID NO 1357
<211> LENGTH: 11
<212> TYPE: PRT

<213> ORGANISM: Homo sapiens

<400> SEQUENCE: 1357

Ala Arg Glu Gly Val Thr Gly Gly Phe Asp Pro
1 5 10

<210> SEQ ID NO 1358
<211> LENGTH: 11
<212> TYPE: PRT
<213> ORGANISM: Homo sapiens

<400> SEQUENCE: 1358

Ala Arg Leu Thr Val Val Gly Ala Leu Asp Tyr
1 5 10

<210> SEQ ID NO 1359
<211> LENGTH: 11
<212> TYPE: PRT
<213> ORGANISM: Homo sapiens

<400> SEQUENCE: 1359

Ala Arg Asp Arg Leu Gly Ile Pro Phe Asp Tyr
1 5 10

<210> SEQ ID NO 1360
<211> LENGTH: 10
<212> TYPE: PRT
<213> ORGANISM: Homo sapiens

<400> SEQUENCE: 1360

Ala Arg Glu Arg Ile Asn Trp Phe Asp Pro
1 5 10

<210> SEQ ID NO 1361
<211> LENGTH: 11
<212> TYPE: PRT
<213> ORGANISM: Homo sapiens

<400> SEQUENCE: 1361

Ala Arg Glu Arg Ile Thr Gly His Phe Asp Tyr
1 5 10

<210> SEQ ID NO 1362
<211> LENGTH: 11
<212> TYPE: PRT
<213> ORGANISM: Homo sapiens

<400> SEQUENCE: 1362

Ala Arg Glu Val Leu Gly Tyr Tyr Phe Asp Tyr
1 5 10

<210> SEQ ID NO 1363
<211> LENGTH: 10
<212> TYPE: PRT
<213> ORGANISM: Homo sapiens

<400> SEQUENCE: 1363

Ala Arg Glu Arg Leu Tyr Gly Met Asp Val
1 5 10

<210> SEQ ID NO 1364
<211> LENGTH: 13
<212> TYPE: PRT
<213> ORGANISM: Homo sapiens

<400> SEQUENCE: 1364

Ala Arg Val Gly Ala Ile Gly Val Asp Ala Phe Asp Ile
1 5 10

<210> SEQ ID NO 1365
<211> LENGTH: 10
<212> TYPE: PRT
<213> ORGANISM: Homo sapiens

<400> SEQUENCE: 1365

Ala Arg Glu Arg Ile Ile Trp Phe Asp Pro
1 5 10

<210> SEQ ID NO 1366
<211> LENGTH: 11
<212> TYPE: PRT
<213> ORGANISM: Homo sapiens

<400> SEQUENCE: 1366

Ala Arg Asp Arg Leu Gly Ile Pro Phe Asp Tyr
1 5 10

<210> SEQ ID NO 1367
<211> LENGTH: 11
<212> TYPE: PRT
<213> ORGANISM: Homo sapiens

<400> SEQUENCE: 1367

Ala Arg Gly Lys Val Gly Val Pro Phe Asp Tyr
1 5 10

<210> SEQ ID NO 1368
<211> LENGTH: 11
<212> TYPE: PRT
<213> ORGANISM: Homo sapiens

<400> SEQUENCE: 1368

Ala Arg Glu Gly Val Thr Gly Gly Phe Asp Pro
1 5 10

<210> SEQ ID NO 1369
<211> LENGTH: 13
<212> TYPE: PRT
<213> ORGANISM: Homo sapiens

<400> SEQUENCE: 1369

Ala Arg Val Gly Ala Ile Gly Val Asp Ala Phe Asp Ile
1 5 10

<210> SEQ ID NO 1370
<211> LENGTH: 11
<212> TYPE: PRT
<213> ORGANISM: Homo sapiens

<400> SEQUENCE: 1370

Ala Arg Glu Arg Leu Thr Gly Ala Phe Asp Ile
1 5 10

<210> SEQ ID NO 1371
<211> LENGTH: 10
<212> TYPE: PRT
<213> ORGANISM: Homo sapiens

<400> SEQUENCE: 1371

Ala Arg Gly Arg Leu Thr Phe Phe Asp Tyr
1 5 10

<210> SEQ ID NO 1372
<211> LENGTH: 10
<212> TYPE: PRT
<213> ORGANISM: Homo sapiens

<400> SEQUENCE: 1372

Ala Arg Gly Arg Leu Thr Phe Phe Asp Tyr
1 5 10

<210> SEQ ID NO 1373
<211> LENGTH: 11
<212> TYPE: PRT
<213> ORGANISM: Homo sapiens

<400> SEQUENCE: 1373

Ala Arg Glu Arg Ile Thr Ser Phe Phe Asp Pro
1 5 10

<210> SEQ ID NO 1374
<211> LENGTH: 11
<212> TYPE: PRT
<213> ORGANISM: Homo sapiens

<400> SEQUENCE: 1374

Ala Arg Glu Arg Leu Thr Gly Tyr Phe Asp Tyr
1 5 10

<210> SEQ ID NO 1375
<211> LENGTH: 11
<212> TYPE: PRT
<213> ORGANISM: Homo sapiens

<400> SEQUENCE: 1375

Ala Arg Glu Arg Leu Val Ile Ala Phe Asp Ile
1 5 10

<210> SEQ ID NO 1376
<211> LENGTH: 11
<212> TYPE: PRT
<213> ORGANISM: Homo sapiens

<400> SEQUENCE: 1376

Ala Arg Asp Arg Leu Gly Arg Ala Phe Asp Ile
1 5 10

<210> SEQ ID NO 1377
<211> LENGTH: 11
<212> TYPE: PRT
<213> ORGANISM: Homo sapiens

<400> SEQUENCE: 1377

Ala Arg Gly Arg Leu Thr Gly His Phe Asp Tyr
1 5 10

<210> SEQ ID NO 1378
<211> LENGTH: 11
<212> TYPE: PRT
<213> ORGANISM: Homo sapiens

<400> SEQUENCE: 1378

Ala Arg Glu Arg Leu Gly Ala Phe Phe Asp Tyr
1 5 10

<210> SEQ ID NO 1379
<211> LENGTH: 11
<212> TYPE: PRT
<213> ORGANISM: Homo sapiens

<400> SEQUENCE: 1379

Ala Arg Ile Thr Val Thr Ser Ala Phe Asp Ile
1 5 10

<210> SEQ ID NO 1380
<211> LENGTH: 11
<212> TYPE: PRT
<213> ORGANISM: Homo sapiens

<400> SEQUENCE: 1380

Ala Arg Ser Thr Val Val Asn Ala Phe Asp Ile
1 5 10

<210> SEQ ID NO 1381
<211> LENGTH: 19
<212> TYPE: PRT
<213> ORGANISM: Homo sapiens

<400> SEQUENCE: 1381

Ala Arg Asp Leu Pro Ile Thr Met Ile Val Val Val Met Pro Asp Ala
1 5 10 15

Phe Asp Ile

<210> SEQ ID NO 1382
<211> LENGTH: 10
<212> TYPE: PRT
<213> ORGANISM: Homo sapiens

<400> SEQUENCE: 1382

Ala Arg Asp Arg Leu Gly Ile Phe Asp Tyr
1 5 10

<210> SEQ ID NO 1383
<211> LENGTH: 10
<212> TYPE: PRT
<213> ORGANISM: Homo sapiens

<400> SEQUENCE: 1383

Ala Arg His Arg Leu Gly Phe Phe Asp Tyr
1 5 10

<210> SEQ ID NO 1384
<211> LENGTH: 11
<212> TYPE: PRT
<213> ORGANISM: Homo sapiens

<400> SEQUENCE: 1384

Ala Arg Leu Tyr Tyr Tyr Tyr Asn Met Asp Val
1 5 10

<210> SEQ ID NO 1385
<211> LENGTH: 12
<212> TYPE: PRT
<213> ORGANISM: Homo sapiens

<400> SEQUENCE: 1385

Ala Arg Gly Trp Trp Glu Leu Thr Phe Phe Asp Tyr
1 5 10

<210> SEQ ID NO 1386
<211> LENGTH: 10
<212> TYPE: PRT
<213> ORGANISM: Homo sapiens

<400> SEQUENCE: 1386

Ala Arg Asn Arg Leu Gly Ile Tyr Asp Tyr
1 5 10

<210> SEQ ID NO 1387
<211> LENGTH: 11
<212> TYPE: PRT
<213> ORGANISM: Homo sapiens

<400> SEQUENCE: 1387

Ala Arg Ala Leu Leu Thr Gly Gly Phe Ala Tyr
1 5 10

<210> SEQ ID NO 1388
<211> LENGTH: 11
<212> TYPE: PRT
<213> ORGANISM: Homo sapiens

<400> SEQUENCE: 1388

Ala Arg Glu Arg Val Gly Ile Tyr Phe Asp Tyr
1 5 10

<210> SEQ ID NO 1389
<211> LENGTH: 18
<212> TYPE: PRT
<213> ORGANISM: Homo sapiens

<400> SEQUENCE: 1389

Ala Arg Asp Ser Thr Met Ile Val Val Val Lys Val Pro Asp Ala Phe
1 5 10 15

Asp Ile

<210> SEQ ID NO 1390
<211> LENGTH: 11
<212> TYPE: PRT
<213> ORGANISM: Homo sapiens

<400> SEQUENCE: 1390

Ala Arg Glu Gly Ile Leu Gly Tyr Phe Asp Tyr
1 5 10

<210> SEQ ID NO 1391
<211> LENGTH: 11
<212> TYPE: PRT
<213> ORGANISM: Homo sapiens

<400> SEQUENCE: 1391

Ala Arg Asp Arg Leu Gly Ile Ala Phe Asp Ile
1 5 10

<210> SEQ ID NO 1392
<211> LENGTH: 12
<212> TYPE: PRT
<213> ORGANISM: Homo sapiens

<400> SEQUENCE: 1392

Ala Arg Glu Arg Thr Val Val Thr Tyr Phe Asp Tyr
1 5 10

<210> SEQ ID NO 1393
<211> LENGTH: 11
<212> TYPE: PRT
<213> ORGANISM: Homo sapiens

<400> SEQUENCE: 1393

Ala Arg Glu Arg Leu Thr Gly Tyr Phe Asp Tyr
1 5 10

<210> SEQ ID NO 1394
<211> LENGTH: 10
<212> TYPE: PRT
<213> ORGANISM: Homo sapiens

<400> SEQUENCE: 1394

Ala Arg Ser Arg Leu Gly Ile Phe Asp Tyr
1 5 10

<210> SEQ ID NO 1395
<211> LENGTH: 11
<212> TYPE: PRT
<213> ORGANISM: Homo sapiens

<400> SEQUENCE: 1395

Ala Arg Glu Arg Met Ala Thr Ile Phe Asp Tyr
1 5 10

<210> SEQ ID NO 1396
<211> LENGTH: 10
<212> TYPE: PRT
<213> ORGANISM: Homo sapiens

<400> SEQUENCE: 1396

Ala Arg Glu Gly Leu Arg Gly Phe Asp Pro
1 5 10

<210> SEQ ID NO 1397
<211> LENGTH: 18
<212> TYPE: PRT
<213> ORGANISM: Homo sapiens

<400> SEQUENCE: 1397

Ala Arg Asp Tyr Tyr Gly Ser Ser Gly Tyr Tyr Tyr Pro His Ala Phe
1 5 10 15

Asp Ile

<210> SEQ ID NO 1398
<211> LENGTH: 9
<212> TYPE: PRT
<213> ORGANISM: Homo sapiens

<400> SEQUENCE: 1398

Ala Arg Gly Gly Leu Arg Phe Asp Tyr
1 5

<210> SEQ ID NO 1399
<211> LENGTH: 11
<212> TYPE: PRT
<213> ORGANISM: Homo sapiens

<400> SEQUENCE: 1399

Ala Arg Ala Leu Leu Thr Gly Gly Phe Ala Tyr
1 5 10

<210> SEQ ID NO 1400
<211> LENGTH: 11
<212> TYPE: PRT
<213> ORGANISM: Homo sapiens

<400> SEQUENCE: 1400

Ala Arg Glu Arg Leu Thr Gly Tyr Phe Asp Tyr
1               5                   10

<210> SEQ ID NO 1401
<211> LENGTH: 11
<212> TYPE: PRT
<213> ORGANISM: Homo sapiens

<400> SEQUENCE: 1401

Ala Arg Ala Leu Ile Val Gly Ala Phe Ala Tyr
1               5                   10

<210> SEQ ID NO 1402
<211> LENGTH: 11
<212> TYPE: PRT
<213> ORGANISM: Homo sapiens

<400> SEQUENCE: 1402

Ala Arg Glu Gly Ile Val Gly Ala Phe His Tyr
1               5                   10

<210> SEQ ID NO 1403
<211> LENGTH: 11
<212> TYPE: PRT
<213> ORGANISM: Homo sapiens

<400> SEQUENCE: 1403

Ala Arg Glu Arg Leu Gly Arg Ala Phe Asp Ile
1               5                   10

<210> SEQ ID NO 1404
<211> LENGTH: 11
<212> TYPE: PRT
<213> ORGANISM: Homo sapiens

<400> SEQUENCE: 1404

Ala Arg Glu Arg Leu Gly Met Phe Phe Asp Tyr
1               5                   10

<210> SEQ ID NO 1405
<211> LENGTH: 11
<212> TYPE: PRT
<213> ORGANISM: Homo sapiens

<400> SEQUENCE: 1405

Ala Arg Glu Arg Leu Gly Met Phe Phe Asp Tyr
1               5                   10

<210> SEQ ID NO 1406
<211> LENGTH: 11
<212> TYPE: PRT
<213> ORGANISM: Homo sapiens

<400> SEQUENCE: 1406

Ala Arg Glu Gly Ile Leu Gly Tyr Phe Asp Tyr
1               5                   10

<210> SEQ ID NO 1407
<211> LENGTH: 11
<212> TYPE: PRT
<213> ORGANISM: Homo sapiens

<400> SEQUENCE: 1407

Ala Arg Gly Arg Leu Thr Tyr Ala Phe Asp Ile
1               5                   10

<210> SEQ ID NO 1408
<211> LENGTH: 39
<212> TYPE: DNA
<213> ORGANISM: Homo sapiens

<400> SEQUENCE: 1408
accaccaatg actacggtga ctacgaggct tttgatatc 39

<210> SEQ ID NO 1409
<211> LENGTH: 33
<212> TYPE: DNA
<213> ORGANISM: Homo sapiens

<400> SEQUENCE: 1409
gcgagacagg ataactggaa ctactttgac tac 33

<210> SEQ ID NO 1410
<211> LENGTH: 42
<212> TYPE: DNA
<213> ORGANISM: Homo sapiens

<400> SEQUENCE: 1410
accactaatg actacggtgg tcccgttgat gcttttgata tc 42

<210> SEQ ID NO 1411
<211> LENGTH: 30
<212> TYPE: DNA
<213> ORGANISM: Homo sapiens

<400> SEQUENCE: 1411
gcgagggggg gggtcacttg gttcgacccc 30

<210> SEQ ID NO 1412
<211> LENGTH: 30
<212> TYPE: DNA
<213> ORGANISM: Homo sapiens

<400> SEQUENCE: 1412
gcgagggggg ggattacttg gttcgacccc 30

<210> SEQ ID NO 1413
<211> LENGTH: 33
<212> TYPE: DNA
<213> ORGANISM: Homo sapiens

<400> SEQUENCE: 1413
actagagagg gtagttttgg tgctcttgat atc 33

<210> SEQ ID NO 1414
<211> LENGTH: 36
<212> TYPE: DNA
<213> ORGANISM: Homo sapiens

<400> SEQUENCE: 1414
gcgagagggg ggtatagtgg gccctacttt gactac 36

<210> SEQ ID NO 1415
<211> LENGTH: 39
<212> TYPE: DNA
<213> ORGANISM: Homo sapiens

<400> SEQUENCE: 1415
accacagggg actacagtta cactgatgct tttgatatc 39

<210> SEQ ID NO 1416
<211> LENGTH: 18
<212> TYPE: DNA
<213> ORGANISM: Homo sapiens

<400> SEQUENCE: 1416
gcgaggggat ttgactac 18

<210> SEQ ID NO 1417
<211> LENGTH: 51
<212> TYPE: DNA
<213> ORGANISM: Homo sapiens

<400> SEQUENCE: 1417
gcgagagatt ttccccatga ctacggttac taccctcact actttgacta c 51

<210> SEQ ID NO 1418
<211> LENGTH: 30
<212> TYPE: DNA
<213> ORGANISM: Homo sapiens

<400> SEQUENCE: 1418
gcacggaccc aactggggat cgcggactac 30

<210> SEQ ID NO 1419
<211> LENGTH: 42
<212> TYPE: DNA
<213> ORGANISM: Homo sapiens

<400> SEQUENCE: 1419
gcgacattgt ctggtacgaa ctggggaagt ccctttgact ac 42

<210> SEQ ID NO 1420
<211> LENGTH: 57
<212> TYPE: DNA
<213> ORGANISM: Homo sapiens

<400> SEQUENCE: 1420
gcgagagaga ttttagtggt ggtagctgct actcgaactg gggggtttt tgatatc 57

<210> SEQ ID NO 1421
<211> LENGTH: 18
<212> TYPE: DNA
<213> ORGANISM: Homo sapiens

<400> SEQUENCE: 1421
gcgaggggat ttgactac 18

<210> SEQ ID NO 1422
<211> LENGTH: 36
<212> TYPE: DNA
<213> ORGANISM: Homo sapiens

<400> SEQUENCE: 1422
gcgagagatc tcgaaggggg ggggcctttt gactac 36

<210> SEQ ID NO 1423
<211> LENGTH: 18
<212> TYPE: DNA
<213> ORGANISM: Homo sapiens

<400> SEQUENCE: 1423
acgaggggta tggacgtc 18

<210> SEQ ID NO 1424
<211> LENGTH: 33
<212> TYPE: DNA
<213> ORGANISM: Homo sapiens

<400> SEQUENCE: 1424
gcgagagatc gaacttttta tgcttttgat atg 33

<210> SEQ ID NO 1425
<211> LENGTH: 39
<212> TYPE: DNA
<213> ORGANISM: Homo sapiens

<400> SEQUENCE: 1425
gcaagaggtc atattgtggt ggtgactgct atggactac 39

<210> SEQ ID NO 1426
<211> LENGTH: 27
<212> TYPE: DNA
<213> ORGANISM: Homo sapiens

<400> SEQUENCE: 1426
gcgagagagg ctgatgcttt tgatatc 27

<210> SEQ ID NO 1427
<211> LENGTH: 39
<212> TYPE: DNA
<213> ORGANISM: Homo sapiens

<400> SEQUENCE: 1427
accacctctg actacggtga ctttgatgct tttgatatc 39

<210> SEQ ID NO 1428
<211> LENGTH: 27
<212> TYPE: DNA
<213> ORGANISM: Homo sapiens

<400> SEQUENCE: 1428
gcgagagagg ctgatgcttt tgatatc 27

<210> SEQ ID NO 1429
<211> LENGTH: 36
<212> TYPE: DNA
<213> ORGANISM: Homo sapiens

<400> SEQUENCE: 1429
gcaagagatg gaggaactac tggtgctttt gatatc 36

<210> SEQ ID NO 1430
<211> LENGTH: 45
<212> TYPE: DNA
<213> ORGANISM: Homo sapiens

<400> SEQUENCE: 1430
gcgagagctg gagcagtggc tgccctgtac aactggttcg acccc 45

<210> SEQ ID NO 1431
<211> LENGTH: 36
<212> TYPE: DNA
<213> ORGANISM: Homo sapiens

<400> SEQUENCE: 1431
gcacacagcc cccgatatag tggctacttt gactac 36

<210> SEQ ID NO 1432
<211> LENGTH: 33
<212> TYPE: DNA
<213> ORGANISM: Homo sapiens

<400> SEQUENCE: 1432
gcgagagaat ctccttactg gtacttcgat ctc 33

<210> SEQ ID NO 1433
<211> LENGTH: 33
<212> TYPE: DNA
<213> ORGANISM: Homo sapiens

<400> SEQUENCE: 1433
gcgagatgga gaacctttta cggtatggac gtc 33

<210> SEQ ID NO 1434
<211> LENGTH: 21
<212> TYPE: DNA
<213> ORGANISM: Homo sapiens

<400> SEQUENCE: 1434
gcgagagaac tggggaacta c 21

<210> SEQ ID NO 1435
<211> LENGTH: 48
<212> TYPE: DNA
<213> ORGANISM: Homo sapiens

<400> SEQUENCE: 1435
gcgagagata gtgggaccta cccctactac tacttcggta tggacgtc 48

<210> SEQ ID NO 1436
<211> LENGTH: 33
<212> TYPE: DNA
<213> ORGANISM: Homo sapiens

<400> SEQUENCE: 1436
gcgagagata ggagttttta cggtatggac gtc 33

<210> SEQ ID NO 1437
<211> LENGTH: 39
<212> TYPE: DNA
<213> ORGANISM: Homo sapiens

<400> SEQUENCE: 1437
gcgagaggtg ggagcttccc ttataactgg ttcgacccc 39

<210> SEQ ID NO 1438
<211> LENGTH: 33
<212> TYPE: DNA
<213> ORGANISM: Homo sapiens

<400> SEQUENCE: 1438
actagagagg gtagttttgg tgctcttgat atc 33

<210> SEQ ID NO 1439
<211> LENGTH: 36
<212> TYPE: DNA
<213> ORGANISM: Homo sapiens

<400> SEQUENCE: 1439
accacagatg gggtataccc cgatgttttt gatatc 36

<210> SEQ ID NO 1440
<211> LENGTH: 33
<212> TYPE: DNA
<213> ORGANISM: Homo sapiens

<400> SEQUENCE: 1440
gcgagattat ccccttactg gtacttcgat ctc 33

<210> SEQ ID NO 1441
<211> LENGTH: 57
<212> TYPE: DNA
<213> ORGANISM: Homo sapiens

<400> SEQUENCE: 1441
gcgagagaag gggagagatt ttgtggtgct gactgctatc cccactggtt cgacccc 57

<210> SEQ ID NO 1442
<211> LENGTH: 60
<212> TYPE: DNA
<213> ORGANISM: Homo sapiens

<400> SEQUENCE: 1442
gcgagagata actggaacta cggagggccc acttactact actactacgg tatggacgtc 60

<210> SEQ ID NO 1443
<211> LENGTH: 27
<212> TYPE: DNA
<213> ORGANISM: Homo sapiens

<400> SEQUENCE: 1443
gcgagcggat accatttatt tgactac 27

<210> SEQ ID NO 1444
<211> LENGTH: 39
<212> TYPE: DNA
<213> ORGANISM: Homo sapiens

<400> SEQUENCE: 1444
acctcaacgg actacggtga ctacgatgct tttgatatc 39

<210> SEQ ID NO 1445
<211> LENGTH: 39
<212> TYPE: DNA
<213> ORGANISM: Homo sapiens

<400> SEQUENCE: 1445
gcgagaggtg ggagctaccc ttataactgg ttcgacccc 39

<210> SEQ ID NO 1446
<211> LENGTH: 33
<212> TYPE: DNA
<213> ORGANISM: Homo sapiens

<400> SEQUENCE: 1446
gcgagagata accacgacgg tgcttttgat atc 33

<210> SEQ ID NO 1447
<211> LENGTH: 36
<212> TYPE: DNA
<213> ORGANISM: Homo sapiens

<400> SEQUENCE: 1447
gcgagagatg aggatagtgg gagctacttt gactac 36

<210> SEQ ID NO 1448
<211> LENGTH: 39
<212> TYPE: DNA
<213> ORGANISM: Homo sapiens

<400> SEQUENCE: 1448
gcacatcaag agaggcgcag tggctggtcc tttgactac 39

<210> SEQ ID NO 1449
<211> LENGTH: 57
<212> TYPE: DNA
<213> ORGANISM: Homo sapiens

<400> SEQUENCE: 1449
gcgagagcta cgtattacta tgatagtagt ggttattact ctaactggtt cgacccc 57

<210> SEQ ID NO 1450
<211> LENGTH: 27
<212> TYPE: DNA
<213> ORGANISM: Homo sapiens

<400> SEQUENCE: 1450
gcgagcggat accatttatt tgactac 27

<210> SEQ ID NO 1451
<211> LENGTH: 33
<212> TYPE: DNA
<213> ORGANISM: Homo sapiens

<400> SEQUENCE: 1451
gcgagaaaga atccctgggg tcactttgac tac 33

<210> SEQ ID NO 1452
<211> LENGTH: 33
<212> TYPE: DNA
<213> ORGANISM: Homo sapiens

<400> SEQUENCE: 1452
gcgagagatg ggactgggga tgctttggat atc 33

<210> SEQ ID NO 1453
<211> LENGTH: 33
<212> TYPE: DNA
<213> ORGANISM: Homo sapiens

<400> SEQUENCE: 1453
gcgagagatc ggacctttta cggtatggac gtc 33

<210> SEQ ID NO 1454
<211> LENGTH: 33
<212> TYPE: DNA

<213> ORGANISM: Homo sapiens

<400> SEQUENCE: 1454
gcgagagatc gggcttttta cggtatggac gtc 33

<210> SEQ ID NO 1455
<211> LENGTH: 30
<212> TYPE: DNA
<213> ORGANISM: Homo sapiens

<400> SEQUENCE: 1455
gcgagagatc gagcctgggg atcaggagac 30

<210> SEQ ID NO 1456
<211> LENGTH: 33
<212> TYPE: DNA
<213> ORGANISM: Homo sapiens

<400> SEQUENCE: 1456
gcgaggagcc ggttggggag catatttgac tac 33

<210> SEQ ID NO 1457
<211> LENGTH: 33
<212> TYPE: DNA
<213> ORGANISM: Homo sapiens

<400> SEQUENCE: 1457
gcgagaggac gtctaaatgg ggcctttgac tac 33

<210> SEQ ID NO 1458
<211> LENGTH: 33
<212> TYPE: DNA
<213> ORGANISM: Homo sapiens

<400> SEQUENCE: 1458
gcgagagaaa ggctaactgg gttctttgac tac 33

<210> SEQ ID NO 1459
<211> LENGTH: 33
<212> TYPE: DNA
<213> ORGANISM: Homo sapiens

<400> SEQUENCE: 1459
gcgagagatc gggtggggat gacttttgat atc 33

<210> SEQ ID NO 1460
<211> LENGTH: 33
<212> TYPE: DNA
<213> ORGANISM: Homo sapiens

<400> SEQUENCE: 1460
gcgagagggc gtattattgg agcttttgat atc 33

<210> SEQ ID NO 1461
<211> LENGTH: 30
<212> TYPE: DNA
<213> ORGANISM: Homo sapiens

<400> SEQUENCE: 1461
gcgagagaaa gggtaatttg gttcgacccc 30

<210> SEQ ID NO 1462
<211> LENGTH: 30

<212> TYPE: DNA
<213> ORGANISM: Homo sapiens

<400> SEQUENCE: 1462
gcgagaggaa ggctaacttt ctttgactac 30

<210> SEQ ID NO 1463
<211> LENGTH: 33
<212> TYPE: DNA
<213> ORGANISM: Homo sapiens

<400> SEQUENCE: 1463
gcgagaggga gactggggaa ctactttgac tac 33

<210> SEQ ID NO 1464
<211> LENGTH: 33
<212> TYPE: DNA
<213> ORGANISM: Homo sapiens

<400> SEQUENCE: 1464
gcgagagaaa ggctggtgag ggcttttgat atc 33

<210> SEQ ID NO 1465
<211> LENGTH: 33
<212> TYPE: DNA
<213> ORGANISM: Homo sapiens

<400> SEQUENCE: 1465
gcgagagagg gagtaacggg tgggttcgac ccc 33

<210> SEQ ID NO 1466
<211> LENGTH: 33
<212> TYPE: DNA
<213> ORGANISM: Homo sapiens

<400> SEQUENCE: 1466
gcgagattga ccgtagtggg agctcttgac tac 33

<210> SEQ ID NO 1467
<211> LENGTH: 33
<212> TYPE: DNA
<213> ORGANISM: Homo sapiens

<400> SEQUENCE: 1467
gcgagagata ggctggggat accctttgac tac 33

<210> SEQ ID NO 1468
<211> LENGTH: 30
<212> TYPE: DNA
<213> ORGANISM: Homo sapiens

<400> SEQUENCE: 1468
gcgagagaaa ggatcaactg gttcgacccc 30

<210> SEQ ID NO 1469
<211> LENGTH: 33
<212> TYPE: DNA
<213> ORGANISM: Homo sapiens

<400> SEQUENCE: 1469
gcgagagaga ggataactgg gcactttgac tac 33

<210> SEQ ID NO 1470

<211> LENGTH: 33
<212> TYPE: DNA
<213> ORGANISM: Homo sapiens

<400> SEQUENCE: 1470
gcgagagagg tactggggta ctactttgac tac 33

<210> SEQ ID NO 1471
<211> LENGTH: 30
<212> TYPE: DNA
<213> ORGANISM: Homo sapiens

<400> SEQUENCE: 1471
gcgagagaaa gactctacgg tatggacgtc 30

<210> SEQ ID NO 1472
<211> LENGTH: 39
<212> TYPE: DNA
<213> ORGANISM: Homo sapiens

<400> SEQUENCE: 1472
gcgagagtgg gagctatcgg ggttgatgct tttgatatc 39

<210> SEQ ID NO 1473
<211> LENGTH: 30
<212> TYPE: DNA
<213> ORGANISM: Homo sapiens

<400> SEQUENCE: 1473
gcgagagaaa ggataatttg gttcgacccc 30

<210> SEQ ID NO 1474
<211> LENGTH: 33
<212> TYPE: DNA
<213> ORGANISM: Homo sapiens

<400> SEQUENCE: 1474
gcgagagatc gattggggat cccctttgac tac 33

<210> SEQ ID NO 1475
<211> LENGTH: 33
<212> TYPE: DNA
<213> ORGANISM: Homo sapiens

<400> SEQUENCE: 1475
gcgagaggga aggtcggggt cccttttgac tac 33

<210> SEQ ID NO 1476
<211> LENGTH: 33
<212> TYPE: DNA
<213> ORGANISM: Homo sapiens

<400> SEQUENCE: 1476
gcgagagagg gagtaacggg tgggttcgac ccc 33

<210> SEQ ID NO 1477
<211> LENGTH: 39
<212> TYPE: DNA
<213> ORGANISM: Homo sapiens

<400> SEQUENCE: 1477
gcgagagtgg gagctatcgg ggttgatgct tttgatatc 39

<210> SEQ ID NO 1478
<211> LENGTH: 33
<212> TYPE: DNA
<213> ORGANISM: Homo sapiens

<400> SEQUENCE: 1478
gcgagagaga ggttaactgg cgcttttgat atc 33

<210> SEQ ID NO 1479
<211> LENGTH: 30
<212> TYPE: DNA
<213> ORGANISM: Homo sapiens

<400> SEQUENCE: 1479
gcgagaggaa ggctaacttt ctttgactac 30

<210> SEQ ID NO 1480
<211> LENGTH: 30
<212> TYPE: DNA
<213> ORGANISM: Homo sapiens

<400> SEQUENCE: 1480
gcgagaggaa ggctaacttt ctttgactac 30

<210> SEQ ID NO 1481
<211> LENGTH: 33
<212> TYPE: DNA
<213> ORGANISM: Homo sapiens

<400> SEQUENCE: 1481
gcgagagaaa ggattacttc gtttttcgac ccc 33

<210> SEQ ID NO 1482
<211> LENGTH: 33
<212> TYPE: DNA
<213> ORGANISM: Homo sapiens

<400> SEQUENCE: 1482
gcgagagaga gactaactgg gtactttgac tac 33

<210> SEQ ID NO 1483
<211> LENGTH: 33
<212> TYPE: DNA
<213> ORGANISM: Homo sapiens

<400> SEQUENCE: 1483
gcgagagaac gactggtgat agcttttgat atc 33

<210> SEQ ID NO 1484
<211> LENGTH: 33
<212> TYPE: DNA
<213> ORGANISM: Homo sapiens

<400> SEQUENCE: 1484
gcgagagaca gactggggag ggcttttgat atc 33

<210> SEQ ID NO 1485
<211> LENGTH: 33
<212> TYPE: DNA
<213> ORGANISM: Homo sapiens

<400> SEQUENCE: 1485
gcgagagggc ggctaactgg tcactttgac tac 33

<210> SEQ ID NO 1486
<211> LENGTH: 33
<212> TYPE: DNA
<213> ORGANISM: Homo sapiens

<400> SEQUENCE: 1486
gcgagagaga ggttgggagc tttctttgac tac 33

<210> SEQ ID NO 1487
<211> LENGTH: 33
<212> TYPE: DNA
<213> ORGANISM: Homo sapiens

<400> SEQUENCE: 1487
gcgagaatta cggtgacttc tgcttttgat atc 33

<210> SEQ ID NO 1488
<211> LENGTH: 33
<212> TYPE: DNA
<213> ORGANISM: Homo sapiens

<400> SEQUENCE: 1488
gcgagaagta cggtggtaaa tgcttttgat atc 33

<210> SEQ ID NO 1489
<211> LENGTH: 57
<212> TYPE: DNA
<213> ORGANISM: Homo sapiens

<400> SEQUENCE: 1489
gcgagagatc tccccattac tatgatagta gtggttatgc ctgatgcttt tgatatc 57

<210> SEQ ID NO 1490
<211> LENGTH: 30
<212> TYPE: DNA
<213> ORGANISM: Homo sapiens

<400> SEQUENCE: 1490
gcgagagata gactggggat atttgactac 30

<210> SEQ ID NO 1491
<211> LENGTH: 30
<212> TYPE: DNA
<213> ORGANISM: Homo sapiens

<400> SEQUENCE: 1491
gcgagacatc gactggggtt ctttgactac 30

<210> SEQ ID NO 1492
<211> LENGTH: 33
<212> TYPE: DNA
<213> ORGANISM: Homo sapiens

<400> SEQUENCE: 1492
gcgaggcttt actactacta caatatggac gtc 33

<210> SEQ ID NO 1493
<211> LENGTH: 36
<212> TYPE: DNA
<213> ORGANISM: Homo sapiens

<400> SEQUENCE: 1493
gcgagagggt ggtgggagct aactttcttt gactac 36

<210> SEQ ID NO 1494
<211> LENGTH: 30
<212> TYPE: DNA
<213> ORGANISM: Homo sapiens

<400> SEQUENCE: 1494
gcgagaaatc ggctggggat ctatgactac 30

<210> SEQ ID NO 1495
<211> LENGTH: 33
<212> TYPE: DNA
<213> ORGANISM: Homo sapiens

<400> SEQUENCE: 1495
gcgagagccc tccttacggg agggtttgcc tat 33

<210> SEQ ID NO 1496
<211> LENGTH: 33
<212> TYPE: DNA
<213> ORGANISM: Homo sapiens

<400> SEQUENCE: 1496
gcgagagaga gggtgggaat ctactttgac tac 33

<210> SEQ ID NO 1497
<211> LENGTH: 54
<212> TYPE: DNA
<213> ORGANISM: Homo sapiens

<400> SEQUENCE: 1497
gcgagagata gtactatgat agtagtggtt aaggttcctg atgcttttga tatc 54

<210> SEQ ID NO 1498
<211> LENGTH: 33
<212> TYPE: DNA
<213> ORGANISM: Homo sapiens

<400> SEQUENCE: 1498
gcgagagagg ggatactggg gtactttgac tac 33

<210> SEQ ID NO 1499
<211> LENGTH: 33
<212> TYPE: DNA
<213> ORGANISM: Homo sapiens

<400> SEQUENCE: 1499
gcgagagata gactgggaat agcttttgat atc 33

<210> SEQ ID NO 1500
<211> LENGTH: 36
<212> TYPE: DNA
<213> ORGANISM: Homo sapiens

<400> SEQUENCE: 1500
gcgagagaga ggacggtggt aacctacttt gactac 36

<210> SEQ ID NO 1501
<211> LENGTH: 33
<212> TYPE: DNA
<213> ORGANISM: Homo sapiens

<400> SEQUENCE: 1501
gcgagagagc ggctaactgg gtactttgac tac 33

<210> SEQ ID NO 1502
<211> LENGTH: 30
<212> TYPE: DNA
<213> ORGANISM: Homo sapiens

<400> SEQUENCE: 1502
gcgagatccc gtctggggat ctttgactac 30

<210> SEQ ID NO 1503
<211> LENGTH: 33
<212> TYPE: DNA
<213> ORGANISM: Homo sapiens

<400> SEQUENCE: 1503
gcgagagaac ggatggctac aatctttgac tac 33

<210> SEQ ID NO 1504
<211> LENGTH: 30
<212> TYPE: DNA
<213> ORGANISM: Homo sapiens

<400> SEQUENCE: 1504
gcgagagagg gacttcgggg attcgacccc 30

<210> SEQ ID NO 1505
<211> LENGTH: 54
<212> TYPE: DNA
<213> ORGANISM: Homo sapiens

<400> SEQUENCE: 1505
gcgagagatt actatggtag tagtggttat tactaccctc atgcttttga tatc 54

<210> SEQ ID NO 1506
<211> LENGTH: 27
<212> TYPE: DNA
<213> ORGANISM: Homo sapiens

<400> SEQUENCE: 1506
gcgagaggcg gactacggtt tgactac 27

<210> SEQ ID NO 1507
<211> LENGTH: 33
<212> TYPE: DNA
<213> ORGANISM: Homo sapiens

<400> SEQUENCE: 1507
gcgagagccc tccttacggg agggtttgcc tat 33

<210> SEQ ID NO 1508
<211> LENGTH: 33
<212> TYPE: DNA
<213> ORGANISM: Homo sapiens

<400> SEQUENCE: 1508
gcgagagaac ggctaactgg gtactttgac tac 33

<210> SEQ ID NO 1509
<211> LENGTH: 33
<212> TYPE: DNA
<213> ORGANISM: Homo sapiens

<400> SEQUENCE: 1509
gcgagagccc ttatagtggg agcttttgcc tac 33

<210> SEQ ID NO 1510
<211> LENGTH: 33
<212> TYPE: DNA
<213> ORGANISM: Homo sapiens

<400> SEQUENCE: 1510
gcgagagagg gtatagtggg agctttccac tat 33

<210> SEQ ID NO 1511
<211> LENGTH: 33
<212> TYPE: DNA
<213> ORGANISM: Homo sapiens

<400> SEQUENCE: 1511
gcgagagaga ggctggggag ggcttttgat atc 33

<210> SEQ ID NO 1512
<211> LENGTH: 33
<212> TYPE: DNA
<213> ORGANISM: Homo sapiens

<400> SEQUENCE: 1512
gcgagagaga ggctggggat gttctttgac tac 33

<210> SEQ ID NO 1513
<211> LENGTH: 33
<212> TYPE: DNA
<213> ORGANISM: Homo sapiens

<400> SEQUENCE: 1513
gcgagagaga ggctggggat gttctttgac tac 33

<210> SEQ ID NO 1514
<211> LENGTH: 33
<212> TYPE: DNA
<213> ORGANISM: Homo sapiens

<400> SEQUENCE: 1514
gcgagagagg ggatactggg gtattttgac tat 33

<210> SEQ ID NO 1515
<211> LENGTH: 33
<212> TYPE: DNA
<213> ORGANISM: Homo sapiens

<400> SEQUENCE: 1515
gcgcgaggaa ggctaactta tgcttttgat atc 33

<210> SEQ ID NO 1516
<211> LENGTH: 8
<212> TYPE: PRT
<213> ORGANISM: Homo sapiens

<400> SEQUENCE: 1516

Gln Gln Tyr Asp Asn Leu Leu Thr
1 5

<210> SEQ ID NO 1517
<211> LENGTH: 9
<212> TYPE: PRT
<213> ORGANISM: Homo sapiens

<400> SEQUENCE: 1517

Met Gln Arg Ile Glu Phe Pro Phe Thr
1               5

<210> SEQ ID NO 1518
<211> LENGTH: 9
<212> TYPE: PRT
<213> ORGANISM: Homo sapiens

<400> SEQUENCE: 1518

Gln Gln Tyr Tyr Ser Thr Pro Phe Thr
1               5

<210> SEQ ID NO 1519
<211> LENGTH: 8
<212> TYPE: PRT
<213> ORGANISM: Homo sapiens

<400> SEQUENCE: 1519

Gln Gln Tyr Gly Ser Ser Leu Thr
1               5

<210> SEQ ID NO 1520
<211> LENGTH: 8
<212> TYPE: PRT
<213> ORGANISM: Homo sapiens

<400> SEQUENCE: 1520

Gln Gln Tyr Gly Ser Ser Leu Thr
1               5

<210> SEQ ID NO 1521
<211> LENGTH: 9
<212> TYPE: PRT
<213> ORGANISM: Homo sapiens

<400> SEQUENCE: 1521

Met Gln Ala Leu Gln Thr Pro Leu Thr
1               5

<210> SEQ ID NO 1522
<211> LENGTH: 9
<212> TYPE: PRT
<213> ORGANISM: Homo sapiens

<400> SEQUENCE: 1522

Gln Gln Ala Tyr Ser Phe Pro Tyr Thr
1               5

<210> SEQ ID NO 1523
<211> LENGTH: 9
<212> TYPE: PRT
<213> ORGANISM: Homo sapiens

<400> SEQUENCE: 1523

Gln Gln Tyr Tyr Ser Thr Pro Leu Thr
1               5

<210> SEQ ID NO 1524
<211> LENGTH: 8
<212> TYPE: PRT
<213> ORGANISM: Homo sapiens

<400> SEQUENCE: 1524

Gln Gln Tyr Asn Ser Tyr Trp Thr
1 5

<210> SEQ ID NO 1525
<211> LENGTH: 9
<212> TYPE: PRT
<213> ORGANISM: Homo sapiens

<400> SEQUENCE: 1525

Gln Gln Tyr Asp Asn Leu Pro Pro Thr
1 5

<210> SEQ ID NO 1526
<211> LENGTH: 9
<212> TYPE: PRT
<213> ORGANISM: Homo sapiens

<400> SEQUENCE: 1526

Gln Gln Tyr Tyr Ser Tyr Pro Phe Thr
1 5

<210> SEQ ID NO 1527
<211> LENGTH: 9
<212> TYPE: PRT
<213> ORGANISM: Homo sapiens

<400> SEQUENCE: 1527

Met Gln Ala Leu Gln Thr Pro Leu Thr
1 5

<210> SEQ ID NO 1528
<211> LENGTH: 8
<212> TYPE: PRT
<213> ORGANISM: Homo sapiens

<400> SEQUENCE: 1528

Gln Gln Phe Asn Ser Tyr Trp Thr
1 5

<210> SEQ ID NO 1529
<211> LENGTH: 8
<212> TYPE: PRT
<213> ORGANISM: Homo sapiens

<400> SEQUENCE: 1529

Gln Gln Tyr Asn Ser Tyr Trp Thr
1 5

<210> SEQ ID NO 1530
<211> LENGTH: 9
<212> TYPE: PRT
<213> ORGANISM: Homo sapiens

<400> SEQUENCE: 1530

Met Gln Arg Ile Glu Phe Pro Ser Thr
1 5

<210> SEQ ID NO 1531
<211> LENGTH: 8
<212> TYPE: PRT
<213> ORGANISM: Homo sapiens

<400> SEQUENCE: 1531

Gln Gln Tyr Asn Ser His Trp Thr 1 5

<210> SEQ ID NO 1532
<211> LENGTH: 9
<212> TYPE: PRT
<213> ORGANISM: Homo sapiens

<400> SEQUENCE: 1532

Gln Gln Tyr Gly Ser Ser Pro Tyr Thr
1 5

<210> SEQ ID NO 1533
<211> LENGTH: 9
<212> TYPE: PRT
<213> ORGANISM: Homo sapiens

<400> SEQUENCE: 1533

Gln Gln Tyr Asp Asn Leu Pro Leu Thr
1 5

<210> SEQ ID NO 1534
<211> LENGTH: 9
<212> TYPE: PRT
<213> ORGANISM: Homo sapiens

<400> SEQUENCE: 1534

Gln Gln Tyr Gly Ser Ser Pro Tyr Thr
1 5

<210> SEQ ID NO 1535
<211> LENGTH: 9
<212> TYPE: PRT
<213> ORGANISM: Homo sapiens

<400> SEQUENCE: 1535

Gln Gln Tyr Tyr Tyr Thr Pro Tyr Thr
1 5

<210> SEQ ID NO 1536
<211> LENGTH: 9
<212> TYPE: PRT
<213> ORGANISM: Homo sapiens

<400> SEQUENCE: 1536

Gln Gln Tyr Gly Ser Ser Pro Tyr Thr
1 5

<210> SEQ ID NO 1537
<211> LENGTH: 9
<212> TYPE: PRT
<213> ORGANISM: Homo sapiens

<400> SEQUENCE: 1537

Gln Gln Tyr Tyr Ser Thr Pro Leu Thr
1 5

<210> SEQ ID NO 1538
<211> LENGTH: 9
<212> TYPE: PRT
<213> ORGANISM: Homo sapiens

<400> SEQUENCE: 1538

Gln Gln Tyr Gly Ser Ser Leu Phe Thr
1 5

<210> SEQ ID NO 1539
<211> LENGTH: 9
<212> TYPE: PRT
<213> ORGANISM: Homo sapiens

<400> SEQUENCE: 1539

Gln Gln Tyr Tyr Ser Thr Pro Tyr Thr
1 5

<210> SEQ ID NO 1540
<211> LENGTH: 9
<212> TYPE: PRT
<213> ORGANISM: Homo sapiens

<400> SEQUENCE: 1540

Gln Gln Tyr Tyr Ser Thr Pro Arg Thr
1 5

<210> SEQ ID NO 1541
<211> LENGTH: 9
<212> TYPE: PRT
<213> ORGANISM: Homo sapiens

<400> SEQUENCE: 1541

Gln Gln Tyr Gly Ser Ser Pro Tyr Thr
1 5

<210> SEQ ID NO 1542
<211> LENGTH: 8
<212> TYPE: PRT
<213> ORGANISM: Homo sapiens

<400> SEQUENCE: 1542

Gln Gln Tyr Asn Ser Tyr Trp Thr
1 5

<210> SEQ ID NO 1543
<211> LENGTH: 9
<212> TYPE: PRT
<213> ORGANISM: Homo sapiens

<400> SEQUENCE: 1543

Gln Gln Leu Asn Thr Tyr Pro Arg Thr
1 5

<210> SEQ ID NO 1544
<211> LENGTH: 9
<212> TYPE: PRT
<213> ORGANISM: Homo sapiens

<400> SEQUENCE: 1544

Gln Lys Tyr Asn Ser Ala Pro Leu Thr
1 5

<210> SEQ ID NO 1545
<211> LENGTH: 9
<212> TYPE: PRT
<213> ORGANISM: Homo sapiens

<400> SEQUENCE: 1545

Met Gln Thr Leu Gln Thr Pro Tyr Thr
1 5

<210> SEQ ID NO 1546

<211> LENGTH: 9
<212> TYPE: PRT
<213> ORGANISM: Homo sapiens

<400> SEQUENCE: 1546

Met Gln Ala Leu Gln Thr Pro Leu Thr
1 5

<210> SEQ ID NO 1547
<211> LENGTH: 9
<212> TYPE: PRT
<213> ORGANISM: Homo sapiens

<400> SEQUENCE: 1547

Met Gln Ala Leu Gln Thr Pro Leu Thr
1 5

<210> SEQ ID NO 1548
<211> LENGTH: 9
<212> TYPE: PRT
<213> ORGANISM: Homo sapiens

<400> SEQUENCE: 1548

Gln Gln Tyr Tyr Ser Thr Pro Pro Thr
1 5

<210> SEQ ID NO 1549
<211> LENGTH: 9
<212> TYPE: PRT
<213> ORGANISM: Homo sapiens

<400> SEQUENCE: 1549

Gln Gln Tyr Asp Asn Leu Pro Ile Thr
1 5

<210> SEQ ID NO 1550
<211> LENGTH: 10
<212> TYPE: PRT
<213> ORGANISM: Homo sapiens

<400> SEQUENCE: 1550

Met Gln Ala Leu Gln Thr Pro Pro Tyr Thr
1 5 10

<210> SEQ ID NO 1551
<211> LENGTH: 9
<212> TYPE: PRT
<213> ORGANISM: Homo sapiens

<400> SEQUENCE: 1551

Met Gln Ala Leu Gln Thr Pro Leu Thr
1 5

<210> SEQ ID NO 1552
<211> LENGTH: 9
<212> TYPE: PRT
<213> ORGANISM: Homo sapiens

<400> SEQUENCE: 1552

Gln Gln Tyr Tyr Arg Thr Met Tyr Thr
1 5

<210> SEQ ID NO 1553
<211> LENGTH: 9
<212> TYPE: PRT

<213> ORGANISM: Homo sapiens

<400> SEQUENCE: 1553

Met Gln Thr Leu Gln Ile Pro Tyr Thr
1               5

<210> SEQ ID NO 1554
<211> LENGTH: 9
<212> TYPE: PRT
<213> ORGANISM: Homo sapiens

<400> SEQUENCE: 1554

Met Gln Arg Ile Glu Phe Pro Leu Thr
1               5

<210> SEQ ID NO 1555
<211> LENGTH: 9
<212> TYPE: PRT
<213> ORGANISM: Homo sapiens

<400> SEQUENCE: 1555

Met Gln Arg Ile Glu Phe Pro Ile Thr
1               5

<210> SEQ ID NO 1556
<211> LENGTH: 9
<212> TYPE: PRT
<213> ORGANISM: Homo sapiens

<400> SEQUENCE: 1556

Gln Gln Tyr Tyr Ser Ser Pro Trp Thr
1               5

<210> SEQ ID NO 1557
<211> LENGTH: 9
<212> TYPE: PRT
<213> ORGANISM: Homo sapiens

<400> SEQUENCE: 1557

Gln Gln Ala Asn Thr Phe Pro Phe Thr
1               5

<210> SEQ ID NO 1558
<211> LENGTH: 9
<212> TYPE: PRT
<213> ORGANISM: Homo sapiens

<400> SEQUENCE: 1558

Leu Gln Ala Leu Gln Thr Pro Leu Thr
1               5

<210> SEQ ID NO 1559
<211> LENGTH: 9
<212> TYPE: PRT
<213> ORGANISM: Homo sapiens

<400> SEQUENCE: 1559

Met Gln Arg Ile Glu Phe Pro Tyr Thr
1               5

<210> SEQ ID NO 1560
<211> LENGTH: 9
<212> TYPE: PRT
<213> ORGANISM: Homo sapiens

<400> SEQUENCE: 1560

Met Gln Ala Leu Gln Thr Pro Leu Ile
1               5

<210> SEQ ID NO 1561
<211> LENGTH: 9
<212> TYPE: PRT
<213> ORGANISM: Homo sapiens

<400> SEQUENCE: 1561

Gln Gln Tyr Gly Ser Ser Pro Arg Thr
1               5

<210> SEQ ID NO 1562
<211> LENGTH: 9
<212> TYPE: PRT
<213> ORGANISM: Homo sapiens

<400> SEQUENCE: 1562

Gln Gln Tyr Gly Asn Ser Pro Leu Thr
1               5

<210> SEQ ID NO 1563
<211> LENGTH: 9
<212> TYPE: PRT
<213> ORGANISM: Homo sapiens

<400> SEQUENCE: 1563

Met Gln Ala Leu Gln Thr Pro Trp Thr
1               5

<210> SEQ ID NO 1564
<211> LENGTH: 11
<212> TYPE: PRT
<213> ORGANISM: Homo sapiens

<400> SEQUENCE: 1564

Ala Ala Trp Asp Asp Ser Leu Asn Gly Pro Val
1               5                   10

<210> SEQ ID NO 1565
<211> LENGTH: 11
<212> TYPE: PRT
<213> ORGANISM: Homo sapiens

<400> SEQUENCE: 1565

Ala Ala Trp Asp Asp Ser Leu Asn Gly Pro Val
1               5                   10

<210> SEQ ID NO 1566
<211> LENGTH: 11
<212> TYPE: PRT
<213> ORGANISM: Homo sapiens

<400> SEQUENCE: 1566

Ala Ala Trp Asp Asp Ser Leu Asn Gly Pro Val
1               5                   10

<210> SEQ ID NO 1567
<211> LENGTH: 11
<212> TYPE: PRT
<213> ORGANISM: Homo sapiens

<400> SEQUENCE: 1567

Ala Ala Trp Asp Asp Ser Leu Asn Gly Pro Val
1 5 10

<210> SEQ ID NO 1568
<211> LENGTH: 11
<212> TYPE: PRT
<213> ORGANISM: Homo sapiens

<400> SEQUENCE: 1568

Ala Ala Trp Asp Asp Ser Leu Asn Gly Pro Val
1 5 10

<210> SEQ ID NO 1569
<211> LENGTH: 11
<212> TYPE: PRT
<213> ORGANISM: Homo sapiens

<400> SEQUENCE: 1569

Ala Ala Trp Asp Asp Ser Leu Asn Gly Pro Val
1 5 10

<210> SEQ ID NO 1570
<211> LENGTH: 11
<212> TYPE: PRT
<213> ORGANISM: Homo sapiens

<400> SEQUENCE: 1570

Ala Ala Trp Asp Asp Ser Leu Asn Gly Val Val
1 5 10

<210> SEQ ID NO 1571
<211> LENGTH: 11
<212> TYPE: PRT
<213> ORGANISM: Homo sapiens

<400> SEQUENCE: 1571

Ala Ala Trp Asp Asp Ser Leu Asn Gly Pro Val
1 5 10

<210> SEQ ID NO 1572
<211> LENGTH: 11
<212> TYPE: PRT
<213> ORGANISM: Homo sapiens

<400> SEQUENCE: 1572

Ala Ala Trp Asp Asp Ser Leu Asn Gly Val Val
1 5 10

<210> SEQ ID NO 1573
<211> LENGTH: 11
<212> TYPE: PRT
<213> ORGANISM: Homo sapiens

<400> SEQUENCE: 1573

Ala Ala Trp Asp Asp Ser Leu Asn Gly Pro Val
1 5 10

<210> SEQ ID NO 1574
<211> LENGTH: 11
<212> TYPE: PRT
<213> ORGANISM: Homo sapiens

<400> SEQUENCE: 1574

Ala Ala Trp Asp Asp Ser Leu Asn Gly Pro Val
1 5 10

<210> SEQ ID NO 1575
<211> LENGTH: 11
<212> TYPE: PRT
<213> ORGANISM: Homo sapiens

<400> SEQUENCE: 1575

Ala Ala Trp Asp Asp Ser Leu Asn Gly Tyr Val
1 5 10

<210> SEQ ID NO 1576
<211> LENGTH: 11
<212> TYPE: PRT
<213> ORGANISM: Homo sapiens

<400> SEQUENCE: 1576

Ala Ala Trp His Asp Ser Leu Asn Gly Val Val
1 5 10

<210> SEQ ID NO 1577
<211> LENGTH: 10
<212> TYPE: PRT
<213> ORGANISM: Homo sapiens

<400> SEQUENCE: 1577

Ala Ala Trp Asp Asp Ser Leu Asn Gly Val
1 5 10

<210> SEQ ID NO 1578
<211> LENGTH: 11
<212> TYPE: PRT
<213> ORGANISM: Homo sapiens

<400> SEQUENCE: 1578

Ala Ala Trp Asp Asp Ser Leu Asn Gly Val Val
1 5 10

<210> SEQ ID NO 1579
<211> LENGTH: 11
<212> TYPE: PRT
<213> ORGANISM: Homo sapiens

<400> SEQUENCE: 1579

Ala Ala Trp Asp Asp Ser Leu Asn Gly Val Val
1 5 10

<210> SEQ ID NO 1580
<211> LENGTH: 11
<212> TYPE: PRT
<213> ORGANISM: Homo sapiens

<400> SEQUENCE: 1580

Cys Ser Tyr Ala Gly Ser Ser Thr Phe Val Val
1 5 10

<210> SEQ ID NO 1581
<211> LENGTH: 11
<212> TYPE: PRT
<213> ORGANISM: Homo sapiens

<400> SEQUENCE: 1581

Ala Ala Trp Asp Asp Ser Leu Asn Gly Pro Val
1 5 10

<210> SEQ ID NO 1582
<211> LENGTH: 11
<212> TYPE: PRT
<213> ORGANISM: Homo sapiens

<400> SEQUENCE: 1582

Ala Ala Trp Asp Asp Ser Leu Asn Gly Tyr Val
1 5 10

<210> SEQ ID NO 1583
<211> LENGTH: 11
<212> TYPE: PRT
<213> ORGANISM: Homo sapiens

<400> SEQUENCE: 1583

Ala Ala Trp Asp Asp Ser Leu Asn Gly Pro Val
1 5 10

<210> SEQ ID NO 1584
<211> LENGTH: 11
<212> TYPE: PRT
<213> ORGANISM: Homo sapiens

<400> SEQUENCE: 1584

Ala Ala Trp Asp Asp Ser Leu Asn Gly Pro Val
1 5 10

<210> SEQ ID NO 1585
<211> LENGTH: 11
<212> TYPE: PRT
<213> ORGANISM: Homo sapiens

<400> SEQUENCE: 1585

Cys Ser Tyr Ala Gly Ser Ser Thr Phe Val Val
1 5 10

<210> SEQ ID NO 1586
<211> LENGTH: 11
<212> TYPE: PRT
<213> ORGANISM: Homo sapiens

<400> SEQUENCE: 1586

Ala Ala Trp Asp Asp Ser Leu Asn Gly Pro Val
1 5 10

<210> SEQ ID NO 1587
<211> LENGTH: 11
<212> TYPE: PRT
<213> ORGANISM: Homo sapiens

<400> SEQUENCE: 1587

Ala Ala Trp Asp Asp Ser Leu Asn Gly Val Val
1 5 10

<210> SEQ ID NO 1588
<211> LENGTH: 11
<212> TYPE: PRT
<213> ORGANISM: Homo sapiens

<400> SEQUENCE: 1588

Ala Ala Trp Asp Asp Ser Leu Asn Gly Val Val
1 5 10

<210> SEQ ID NO 1589
<211> LENGTH: 11

<212> TYPE: PRT
<213> ORGANISM: Homo sapiens

<400> SEQUENCE: 1589

Ala Ala Trp Asp Asp Ser Leu Asn Gly Pro Val
1 5 10

<210> SEQ ID NO 1590
<211> LENGTH: 11
<212> TYPE: PRT
<213> ORGANISM: Homo sapiens

<400> SEQUENCE: 1590

Ala Ala Trp Asp Asp Ser Leu Asn Gly Pro Val
1 5 10

<210> SEQ ID NO 1591
<211> LENGTH: 11
<212> TYPE: PRT
<213> ORGANISM: Homo sapiens

<400> SEQUENCE: 1591

Ala Ala Trp Asp Asp Ser Leu Asn Gly Pro Val
1 5 10

<210> SEQ ID NO 1592
<211> LENGTH: 11
<212> TYPE: PRT
<213> ORGANISM: Homo sapiens

<400> SEQUENCE: 1592

Ala Ala Trp His Asp Ser Leu Asn Gly Arg Val
1 5 10

<210> SEQ ID NO 1593
<211> LENGTH: 11
<212> TYPE: PRT
<213> ORGANISM: Homo sapiens

<400> SEQUENCE: 1593

Ala Ala Trp Asp Asp Ser Leu Asn Gly Pro Val
1 5 10

<210> SEQ ID NO 1594
<211> LENGTH: 11
<212> TYPE: PRT
<213> ORGANISM: Homo sapiens

<400> SEQUENCE: 1594

Ala Ala Trp Asp Asp Ser Leu Asn Gly Pro Val
1 5 10

<210> SEQ ID NO 1595
<211> LENGTH: 11
<212> TYPE: PRT
<213> ORGANISM: Homo sapiens

<400> SEQUENCE: 1595

Ala Ala Trp Asp Asp Ser Leu Asn Gly Pro Val
1 5 10

<210> SEQ ID NO 1596
<211> LENGTH: 11
<212> TYPE: PRT
<213> ORGANISM: Homo sapiens

<400> SEQUENCE: 1596

Ala Ala Trp Asp Asp Ser Leu Asn Gly Pro Val
1 5 10

<210> SEQ ID NO 1597
<211> LENGTH: 11
<212> TYPE: PRT
<213> ORGANISM: Homo sapiens

<400> SEQUENCE: 1597

Ala Ala Trp Asp Asp Ser Leu Ser Gly Leu Val
1 5 10

<210> SEQ ID NO 1598
<211> LENGTH: 11
<212> TYPE: PRT
<213> ORGANISM: Homo sapiens

<400> SEQUENCE: 1598

Ala Ala Trp Asp Asp Ser Leu Ser Gly Val Val
1 5 10

<210> SEQ ID NO 1599
<211> LENGTH: 11
<212> TYPE: PRT
<213> ORGANISM: Homo sapiens

<400> SEQUENCE: 1599

Ala Ala Trp Asp Asp Ser Leu Asn Gly Pro Val
1 5 10

<210> SEQ ID NO 1600
<211> LENGTH: 11
<212> TYPE: PRT
<213> ORGANISM: Homo sapiens

<400> SEQUENCE: 1600

Ala Ala Trp Asp Asp Ser Leu Asn Gly Pro Val
1 5 10

<210> SEQ ID NO 1601
<211> LENGTH: 11
<212> TYPE: PRT
<213> ORGANISM: Homo sapiens

<400> SEQUENCE: 1601

Ala Ala Trp Asp Asp Ser Leu Ser Gly Val Val
1 5 10

<210> SEQ ID NO 1602
<211> LENGTH: 11
<212> TYPE: PRT
<213> ORGANISM: Homo sapiens

<400> SEQUENCE: 1602

Ala Ala Trp Asp Asp Arg Leu Asn Gly Pro Val
1 5 10

<210> SEQ ID NO 1603
<211> LENGTH: 11
<212> TYPE: PRT
<213> ORGANISM: Homo sapiens

<400> SEQUENCE: 1603

Ala Ala Trp Asp Asp Ser Leu Asn Gly Pro Val
1 5 10

<210> SEQ ID NO 1604
<211> LENGTH: 11
<212> TYPE: PRT
<213> ORGANISM: Homo sapiens

<400> SEQUENCE: 1604

Ala Ala Trp Asp Asp Ser Leu Asn Gly Pro Val
1 5 10

<210> SEQ ID NO 1605
<211> LENGTH: 11
<212> TYPE: PRT
<213> ORGANISM: Homo sapiens

<400> SEQUENCE: 1605

Ala Ala Trp Asp Asp Ser Leu Asn Gly Pro Val
1 5 10

<210> SEQ ID NO 1606
<211> LENGTH: 11
<212> TYPE: PRT
<213> ORGANISM: Homo sapiens

<400> SEQUENCE: 1606

Ala Ala Trp Asp Asp Ser Leu Ser Gly Pro Val
1 5 10

<210> SEQ ID NO 1607
<211> LENGTH: 12
<212> TYPE: PRT
<213> ORGANISM: Homo sapiens

<400> SEQUENCE: 1607

Asn Ser Gln Asp Asn Ser Gly Asn His Leu Val Val
1 5 10

<210> SEQ ID NO 1608
<211> LENGTH: 11
<212> TYPE: PRT
<213> ORGANISM: Homo sapiens

<400> SEQUENCE: 1608

Ala Ala Trp Asp Asp Ser Leu Asn Gly Pro Val
1 5 10

<210> SEQ ID NO 1609
<211> LENGTH: 11
<212> TYPE: PRT
<213> ORGANISM: Homo sapiens

<400> SEQUENCE: 1609

Ala Ala Trp Tyr Asp Ser Leu Asn Gly Pro Val
1 5 10

<210> SEQ ID NO 1610
<211> LENGTH: 11
<212> TYPE: PRT
<213> ORGANISM: Homo sapiens

<400> SEQUENCE: 1610

Ala Ala Trp Asp Asp Ser Leu Asn Gly Pro Val 1 5 10

<210> SEQ ID NO 1611
<211> LENGTH: 11
<212> TYPE: PRT
<213> ORGANISM: Homo sapiens

<400> SEQUENCE: 1611

Ala Ala Trp Asp Asp Ser Leu Asn Gly Val Val
1 5 10

<210> SEQ ID NO 1612
<211> LENGTH: 11
<212> TYPE: PRT
<213> ORGANISM: Homo sapiens

<400> SEQUENCE: 1612

Ala Ala Trp Asp Asp Ser Leu Ser Gly Val Val
1 5 10

<210> SEQ ID NO 1613
<211> LENGTH: 11
<212> TYPE: PRT
<213> ORGANISM: Homo sapiens

<400> SEQUENCE: 1613

Ala Ala Trp Asp Asp Ser Leu Asn Gly Pro Val
1 5 10

<210> SEQ ID NO 1614
<211> LENGTH: 11
<212> TYPE: PRT
<213> ORGANISM: Homo sapiens

<400> SEQUENCE: 1614

Ala Ala Trp Asp Asp Ser Leu Asn Gly Trp Val
1 5 10

<210> SEQ ID NO 1615
<211> LENGTH: 11
<212> TYPE: PRT
<213> ORGANISM: Homo sapiens

<400> SEQUENCE: 1615

Ala Ala Trp Asp Asp Ser Leu Asn Gly Pro Val
1 5 10

<210> SEQ ID NO 1616
<211> LENGTH: 11
<212> TYPE: PRT
<213> ORGANISM: Homo sapiens

<400> SEQUENCE: 1616

Ala Ala Trp Asp Asp Ser Leu Asn Gly Pro Val
1 5 10

<210> SEQ ID NO 1617
<211> LENGTH: 11
<212> TYPE: PRT
<213> ORGANISM: Homo sapiens

<400> SEQUENCE: 1617

Gln Val Trp Asp Ser Ser Ser Asp His Arg Val
1 5 10

<210> SEQ ID NO 1618
<211> LENGTH: 11
<212> TYPE: PRT
<213> ORGANISM: Homo sapiens

<400> SEQUENCE: 1618

Ala Pro Trp Asp Asp Ser Leu Asn Gly Val Val
1 5 10

<210> SEQ ID NO 1619
<211> LENGTH: 11
<212> TYPE: PRT
<213> ORGANISM: Homo sapiens

<400> SEQUENCE: 1619

Ala Ala Trp Asp Asp Ser Leu Asn Ser Trp Val
1 5 10

<210> SEQ ID NO 1620
<211> LENGTH: 11
<212> TYPE: PRT
<213> ORGANISM: Homo sapiens

<400> SEQUENCE: 1620

Ala Ala Arg Asp Asp Ser Leu Asn Gly Val Val
1 5 10

<210> SEQ ID NO 1621
<211> LENGTH: 11
<212> TYPE: PRT
<213> ORGANISM: Homo sapiens

<400> SEQUENCE: 1621

Ala Ala Arg Asp Asp Ser Leu Asn Gly Val Val
1 5 10

<210> SEQ ID NO 1622
<211> LENGTH: 11
<212> TYPE: PRT
<213> ORGANISM: Homo sapiens

<400> SEQUENCE: 1622

Ala Ala Trp Asp Asp Ser Leu Asn Gly Pro Val
1 5 10

<210> SEQ ID NO 1623
<211> LENGTH: 11
<212> TYPE: PRT
<213> ORGANISM: Homo sapiens

<400> SEQUENCE: 1623

Ala Ala Trp Asp Asp Ser Leu Asn Gly Val Val
1 5 10

<210> SEQ ID NO 1624
<211> LENGTH: 24
<212> TYPE: DNA
<213> ORGANISM: Homo sapiens

<400> SEQUENCE: 1624
caacagtatg ataatcttct cact 24

<210> SEQ ID NO 1625
<211> LENGTH: 27

<212> TYPE: DNA
<213> ORGANISM: Homo sapiens

<400> SEQUENCE: 1625
atgcaacgta tagagtttcc gttcact 27

<210> SEQ ID NO 1626
<211> LENGTH: 27
<212> TYPE: DNA
<213> ORGANISM: Homo sapiens

<400> SEQUENCE: 1626
cagcaatatt atagtactcc gttcact 27

<210> SEQ ID NO 1627
<211> LENGTH: 24
<212> TYPE: DNA
<213> ORGANISM: Homo sapiens

<400> SEQUENCE: 1627
cagcagtatg gtagctcgct cact 24

<210> SEQ ID NO 1628
<211> LENGTH: 24
<212> TYPE: DNA
<213> ORGANISM: Homo sapiens

<400> SEQUENCE: 1628
cagcagtatg gtagctcgct cact 24

<210> SEQ ID NO 1629
<211> LENGTH: 27
<212> TYPE: DNA
<213> ORGANISM: Homo sapiens

<400> SEQUENCE: 1629
atgcaagctc tacaaactcc gctcact 27

<210> SEQ ID NO 1630
<211> LENGTH: 27
<212> TYPE: DNA
<213> ORGANISM: Homo sapiens

<400> SEQUENCE: 1630
caacaggctt acagtttccc gtacact 27

<210> SEQ ID NO 1631
<211> LENGTH: 27
<212> TYPE: DNA
<213> ORGANISM: Homo sapiens

<400> SEQUENCE: 1631
cagcaatatt atagtactcc gctcact 27

<210> SEQ ID NO 1632
<211> LENGTH: 24
<212> TYPE: DNA
<213> ORGANISM: Homo sapiens

<400> SEQUENCE: 1632
caacagtata atagttattg gacg 24

<210> SEQ ID NO 1633

<211> LENGTH: 27
<212> TYPE: DNA
<213> ORGANISM: Homo sapiens

<400> SEQUENCE: 1633
caacagtatg ataatctccc tcccact 27

<210> SEQ ID NO 1634
<211> LENGTH: 27
<212> TYPE: DNA
<213> ORGANISM: Homo sapiens

<400> SEQUENCE: 1634
caacagtatt atagttaccc attcact 27

<210> SEQ ID NO 1635
<211> LENGTH: 27
<212> TYPE: DNA
<213> ORGANISM: Homo sapiens

<400> SEQUENCE: 1635
atgcaagctc tacaaactcc gctcact 27

<210> SEQ ID NO 1636
<211> LENGTH: 24
<212> TYPE: DNA
<213> ORGANISM: Homo sapiens

<400> SEQUENCE: 1636
caacagttta atagttattg gacg 24

<210> SEQ ID NO 1637
<211> LENGTH: 24
<212> TYPE: DNA
<213> ORGANISM: Homo sapiens

<400> SEQUENCE: 1637
caacagtata atagttattg gacg 24

<210> SEQ ID NO 1638
<211> LENGTH: 27
<212> TYPE: DNA
<213> ORGANISM: Homo sapiens

<400> SEQUENCE: 1638
atgcaacgta tagagtttcc ttcgacc 27

<210> SEQ ID NO 1639
<211> LENGTH: 24
<212> TYPE: DNA
<213> ORGANISM: Homo sapiens

<400> SEQUENCE: 1639
caacagtata atagtcattg gacg 24

<210> SEQ ID NO 1640
<211> LENGTH: 27
<212> TYPE: DNA
<213> ORGANISM: Homo sapiens

<400> SEQUENCE: 1640
cagcagtatg gtagctcacc gtacact 27

<210> SEQ ID NO 1641
<211> LENGTH: 27
<212> TYPE: DNA
<213> ORGANISM: Homo sapiens

<400> SEQUENCE: 1641
caacagtatg ataatctccc tctcact 27

<210> SEQ ID NO 1642
<211> LENGTH: 27
<212> TYPE: DNA
<213> ORGANISM: Homo sapiens

<400> SEQUENCE: 1642
cagcagtatg gtagctcacc gtacact 27

<210> SEQ ID NO 1643
<211> LENGTH: 27
<212> TYPE: DNA
<213> ORGANISM: Homo sapiens

<400> SEQUENCE: 1643
cagcaatatt attatactcc gtacact 27

<210> SEQ ID NO 1644
<211> LENGTH: 27
<212> TYPE: DNA
<213> ORGANISM: Homo sapiens

<400> SEQUENCE: 1644
cagcagtatg gtagctcacc gtacact 27

<210> SEQ ID NO 1645
<211> LENGTH: 27
<212> TYPE: DNA
<213> ORGANISM: Homo sapiens

<400> SEQUENCE: 1645
cagcaatatt atagtactcc gctcact 27

<210> SEQ ID NO 1646
<211> LENGTH: 27
<212> TYPE: DNA
<213> ORGANISM: Homo sapiens

<400> SEQUENCE: 1646
cagcagtatg gtagctcact attcact 27

<210> SEQ ID NO 1647
<211> LENGTH: 27
<212> TYPE: DNA
<213> ORGANISM: Homo sapiens

<400> SEQUENCE: 1647
cagcaatatt atagtactcc gtacact 27

<210> SEQ ID NO 1648
<211> LENGTH: 27
<212> TYPE: DNA
<213> ORGANISM: Homo sapiens

<400> SEQUENCE: 1648
cagcaatatt atagtactcc tcggacg 27

<210> SEQ ID NO 1649
<211> LENGTH: 27
<212> TYPE: DNA
<213> ORGANISM: Homo sapiens

<400> SEQUENCE: 1649
cagcagtatg gtagctcacc gtacact 27

<210> SEQ ID NO 1650
<211> LENGTH: 24
<212> TYPE: DNA
<213> ORGANISM: Homo sapiens

<400> SEQUENCE: 1650
caacagtata atagttattg gacg 24

<210> SEQ ID NO 1651
<211> LENGTH: 27
<212> TYPE: DNA
<213> ORGANISM: Homo sapiens

<400> SEQUENCE: 1651
caacagctta atacttaccc tcggacg 27

<210> SEQ ID NO 1652
<211> LENGTH: 27
<212> TYPE: DNA
<213> ORGANISM: Homo sapiens

<400> SEQUENCE: 1652
caaaagtata acagtgcccc gctcact 27

<210> SEQ ID NO 1653
<211> LENGTH: 27
<212> TYPE: DNA
<213> ORGANISM: Homo sapiens

<400> SEQUENCE: 1653
atgcaaactc tacaaactcc gtacact 27

<210> SEQ ID NO 1654
<211> LENGTH: 27
<212> TYPE: DNA
<213> ORGANISM: Homo sapiens

<400> SEQUENCE: 1654
atgcaagctc tacaaactcc gctcact 27

<210> SEQ ID NO 1655
<211> LENGTH: 27
<212> TYPE: DNA
<213> ORGANISM: Homo sapiens

<400> SEQUENCE: 1655
atgcaagctc tacaaactcc gctcact 27

<210> SEQ ID NO 1656
<211> LENGTH: 27
<212> TYPE: DNA
<213> ORGANISM: Homo sapiens

<400> SEQUENCE: 1656
cagcaatatt atagtactcc tccgacg 27

<210> SEQ ID NO 1657
<211> LENGTH: 27
<212> TYPE: DNA
<213> ORGANISM: Homo sapiens

<400> SEQUENCE: 1657
caacagtatg ataatctccc catcacc 27

<210> SEQ ID NO 1658
<211> LENGTH: 30
<212> TYPE: DNA
<213> ORGANISM: Homo sapiens

<400> SEQUENCE: 1658
atgcaagctc tacaaactcc tccgtacact 30

<210> SEQ ID NO 1659
<211> LENGTH: 27
<212> TYPE: DNA
<213> ORGANISM: Homo sapiens

<400> SEQUENCE: 1659
atgcaagctc tacaaactcc actcact 27

<210> SEQ ID NO 1660
<211> LENGTH: 27
<212> TYPE: DNA
<213> ORGANISM: Homo sapiens

<400> SEQUENCE: 1660
cagcaatatt atcgtactat gtacact 27

<210> SEQ ID NO 1661
<211> LENGTH: 27
<212> TYPE: DNA
<213> ORGANISM: Homo sapiens

<400> SEQUENCE: 1661
atgcaaactc tacaaattcc gtatact 27

<210> SEQ ID NO 1662
<211> LENGTH: 27
<212> TYPE: DNA
<213> ORGANISM: Homo sapiens

<400> SEQUENCE: 1662
atgcaacgta tagagtttcc tctcact 27

<210> SEQ ID NO 1663
<211> LENGTH: 27
<212> TYPE: DNA
<213> ORGANISM: Homo sapiens

<400> SEQUENCE: 1663
atgcaacgta tagagtttcc gatcacc 27

<210> SEQ ID NO 1664
<211> LENGTH: 27
<212> TYPE: DNA
<213> ORGANISM: Homo sapiens

<400> SEQUENCE: 1664
cagcaatatt atagttctcc gtggacg 27

<210> SEQ ID NO 1665
<211> LENGTH: 27
<212> TYPE: DNA
<213> ORGANISM: Homo sapiens

<400> SEQUENCE: 1665
caacaggcta acactttccc cttcact 27

<210> SEQ ID NO 1666
<211> LENGTH: 27
<212> TYPE: DNA
<213> ORGANISM: Homo sapiens

<400> SEQUENCE: 1666
ttgcaagctc tacaaactcc gctcact 27

<210> SEQ ID NO 1667
<211> LENGTH: 27
<212> TYPE: DNA
<213> ORGANISM: Homo sapiens

<400> SEQUENCE: 1667
atgcaacgta tagagtttcc ttacact 27

<210> SEQ ID NO 1668
<211> LENGTH: 27
<212> TYPE: DNA
<213> ORGANISM: Homo sapiens

<400> SEQUENCE: 1668
atgcaagctc tacaaactcc gctcatt 27

<210> SEQ ID NO 1669
<211> LENGTH: 27
<212> TYPE: DNA
<213> ORGANISM: Homo sapiens

<400> SEQUENCE: 1669
cagcagtatg gtagctcccc tcggacg 27

<210> SEQ ID NO 1670
<211> LENGTH: 27
<212> TYPE: DNA
<213> ORGANISM: Homo sapiens

<400> SEQUENCE: 1670
cagcagtatg gtaactcacc gctcact 27

<210> SEQ ID NO 1671
<211> LENGTH: 27
<212> TYPE: DNA
<213> ORGANISM: Homo sapiens

<400> SEQUENCE: 1671
atgcaagctc tacaaacccc gtggacg 27

<210> SEQ ID NO 1672
<211> LENGTH: 33
<212> TYPE: DNA
<213> ORGANISM: Homo sapiens

<400> SEQUENCE: 1672
gcagcatggg atgacagcct gaatggtccg gtg 33

<210> SEQ ID NO 1673
<211> LENGTH: 33
<212> TYPE: DNA
<213> ORGANISM: Homo sapiens

<400> SEQUENCE: 1673
gcagcatggg atgacagtct gaatggtccg gtg 33

<210> SEQ ID NO 1674
<211> LENGTH: 33
<212> TYPE: DNA
<213> ORGANISM: Homo sapiens

<400> SEQUENCE: 1674
gcagcatggg atgacagcct gaatggtccg gta 33

<210> SEQ ID NO 1675
<211> LENGTH: 33
<212> TYPE: DNA
<213> ORGANISM: Homo sapiens

<400> SEQUENCE: 1675
gcagcatggg atgacagcct gaatggtccg gta 33

<210> SEQ ID NO 1676
<211> LENGTH: 33
<212> TYPE: DNA
<213> ORGANISM: Homo sapiens

<400> SEQUENCE: 1676
gcagcatggg atgacagcct gaatggtccg gta 33

<210> SEQ ID NO 1677
<211> LENGTH: 33
<212> TYPE: DNA
<213> ORGANISM: Homo sapiens

<400> SEQUENCE: 1677
gcagcatggg atgacagcct gaatggtccg gta 33

<210> SEQ ID NO 1678
<211> LENGTH: 33
<212> TYPE: DNA
<213> ORGANISM: Homo sapiens

<400> SEQUENCE: 1678
gcagcatggg atgacagcct gaatggtgtg gta 33

<210> SEQ ID NO 1679
<211> LENGTH: 33
<212> TYPE: DNA
<213> ORGANISM: Homo sapiens

<400> SEQUENCE: 1679
gcagcatggg atgacagcct gaatggtccg gtt 33

<210> SEQ ID NO 1680
<211> LENGTH: 33
<212> TYPE: DNA
<213> ORGANISM: Homo sapiens

<400> SEQUENCE: 1680
gcagcatggg atgacagcct gaatggtgtg gta 33

<210> SEQ ID NO 1681
<211> LENGTH: 33
<212> TYPE: DNA
<213> ORGANISM: Homo sapiens

<400> SEQUENCE: 1681
gcagcatggg atgacagcct gaatggtccg gta 33

<210> SEQ ID NO 1682
<211> LENGTH: 33
<212> TYPE: DNA
<213> ORGANISM: Homo sapiens

<400> SEQUENCE: 1682
gcagcatggg atgacagcct gaatggtccg gta 33

<210> SEQ ID NO 1683
<211> LENGTH: 33
<212> TYPE: DNA
<213> ORGANISM: Homo sapiens

<400> SEQUENCE: 1683
gcagcatggg atgacagcct gaatggttat gtc 33

<210> SEQ ID NO 1684
<211> LENGTH: 33
<212> TYPE: DNA
<213> ORGANISM: Homo sapiens

<400> SEQUENCE: 1684
gcagcatggc atgacagcct gaatggtgtg gtt 33

<210> SEQ ID NO 1685
<211> LENGTH: 30
<212> TYPE: DNA
<213> ORGANISM: Homo sapiens

<400> SEQUENCE: 1685
gcggcatggg atgacagtct gaatggtgtg 30

<210> SEQ ID NO 1686
<211> LENGTH: 33
<212> TYPE: DNA
<213> ORGANISM: Homo sapiens

<400> SEQUENCE: 1686
gcagcatggg atgacagcct gaatggtgtg gta 33

<210> SEQ ID NO 1687
<211> LENGTH: 33
<212> TYPE: DNA
<213> ORGANISM: Homo sapiens

<400> SEQUENCE: 1687
gcagcatggg atgacagcct gaatggtgtg gta 33

<210> SEQ ID NO 1688
<211> LENGTH: 33
<212> TYPE: DNA
<213> ORGANISM: Homo sapiens

<400> SEQUENCE: 1688
tgctcatatg caggtagtag cactttcgtg gta 33

<210> SEQ ID NO 1689
<211> LENGTH: 33
<212> TYPE: DNA
<213> ORGANISM: Homo sapiens

<400> SEQUENCE: 1689
gcagcatggg atgacagcct gaatggtccg gta 33

<210> SEQ ID NO 1690
<211> LENGTH: 33
<212> TYPE: DNA
<213> ORGANISM: Homo sapiens

<400> SEQUENCE: 1690
gcagcatggg atgacagcct gaatggttat gtc 33

<210> SEQ ID NO 1691
<211> LENGTH: 33
<212> TYPE: DNA
<213> ORGANISM: Homo sapiens

<400> SEQUENCE: 1691
gcagcatggg atgacagcct gaatggtccg gtg 33

<210> SEQ ID NO 1692
<211> LENGTH: 33
<212> TYPE: DNA
<213> ORGANISM: Homo sapiens

<400> SEQUENCE: 1692
gcagcatggg atgacagcct gaatggtccg gta 33

<210> SEQ ID NO 1693
<211> LENGTH: 33
<212> TYPE: DNA
<213> ORGANISM: Homo sapiens

<400> SEQUENCE: 1693
tgctcatatg caggtagtag cactttcgtg gta 33

<210> SEQ ID NO 1694
<211> LENGTH: 33
<212> TYPE: DNA
<213> ORGANISM: Homo sapiens

<400> SEQUENCE: 1694
gcagcatggg atgacagcct gaatggtccg gtg 33

<210> SEQ ID NO 1695
<211> LENGTH: 33
<212> TYPE: DNA
<213> ORGANISM: Homo sapiens

<400> SEQUENCE: 1695
gcagcatggg atgacagcct gaatggtgtg gta 33

<210> SEQ ID NO 1696
<211> LENGTH: 33
<212> TYPE: DNA

<213> ORGANISM: Homo sapiens

<400> SEQUENCE: 1696
gcagcatggg atgacagcct gaatggtgtg gta 33

<210> SEQ ID NO 1697
<211> LENGTH: 33
<212> TYPE: DNA
<213> ORGANISM: Homo sapiens

<400> SEQUENCE: 1697
gcagcatggg atgacagcct gaatggtccg gta 33

<210> SEQ ID NO 1698
<211> LENGTH: 33
<212> TYPE: DNA
<213> ORGANISM: Homo sapiens

<400> SEQUENCE: 1698
gcagcatggg atgacagcct gaatggtccg gtg 33

<210> SEQ ID NO 1699
<211> LENGTH: 33
<212> TYPE: DNA
<213> ORGANISM: Homo sapiens

<400> SEQUENCE: 1699
gcagcatggg atgacagcct gaatggtccg gta 33

<210> SEQ ID NO 1700
<211> LENGTH: 33
<212> TYPE: DNA
<213> ORGANISM: Homo sapiens

<400> SEQUENCE: 1700
gcagcatggc atgacagcct gaatggtcgg gtg 33

<210> SEQ ID NO 1701
<211> LENGTH: 33
<212> TYPE: DNA
<213> ORGANISM: Homo sapiens

<400> SEQUENCE: 1701
gcagcatggg atgacagcct gaatggtccg gta 33

<210> SEQ ID NO 1702
<211> LENGTH: 33
<212> TYPE: DNA
<213> ORGANISM: Homo sapiens

<400> SEQUENCE: 1702
gcagcatggg atgacagcct gaatggtccg gta 33

<210> SEQ ID NO 1703
<211> LENGTH: 33
<212> TYPE: DNA
<213> ORGANISM: Homo sapiens

<400> SEQUENCE: 1703
gcagcatggg atgacagcct gaatggtccg gtg 33

<210> SEQ ID NO 1704
<211> LENGTH: 33

<212> TYPE: DNA
<213> ORGANISM: Homo sapiens

<400> SEQUENCE: 1704
gcagcatggg atgacagcct gaatggtccg gta 33

<210> SEQ ID NO 1705
<211> LENGTH: 33
<212> TYPE: DNA
<213> ORGANISM: Homo sapiens

<400> SEQUENCE: 1705
gcagcatggg atgacagcct gagtggtctg gta 33

<210> SEQ ID NO 1706
<211> LENGTH: 33
<212> TYPE: DNA
<213> ORGANISM: Homo sapiens

<400> SEQUENCE: 1706
gcagcatggg atgacagcct gagtggtgtg gta 33

<210> SEQ ID NO 1707
<211> LENGTH: 33
<212> TYPE: DNA
<213> ORGANISM: Homo sapiens

<400> SEQUENCE: 1707
gcagcatggg atgacagcct gaatggtccg gta 33

<210> SEQ ID NO 1708
<211> LENGTH: 33
<212> TYPE: DNA
<213> ORGANISM: Homo sapiens

<400> SEQUENCE: 1708
gcagcatggg atgacagcct gaatggtccg gta 33

<210> SEQ ID NO 1709
<211> LENGTH: 33
<212> TYPE: DNA
<213> ORGANISM: Homo sapiens

<400> SEQUENCE: 1709
gcagcatggg atgacagcct gagtggtgtg gta 33

<210> SEQ ID NO 1710
<211> LENGTH: 33
<212> TYPE: DNA
<213> ORGANISM: Homo sapiens

<400> SEQUENCE: 1710
gcagcatggg atgacagact gaatggtccg gtg 33

<210> SEQ ID NO 1711
<211> LENGTH: 33
<212> TYPE: DNA
<213> ORGANISM: Homo sapiens

<400> SEQUENCE: 1711
gcagcatggg atgacagcct gaatggtccg gtg 33

<210> SEQ ID NO 1712

<211> LENGTH: 33
<212> TYPE: DNA
<213> ORGANISM: Homo sapiens

<400> SEQUENCE: 1712
gcagcatggg atgacagcct gaatggtccg gtg 33

<210> SEQ ID NO 1713
<211> LENGTH: 33
<212> TYPE: DNA
<213> ORGANISM: Homo sapiens

<400> SEQUENCE: 1713
gcagcatggg atgacagcct gaatggtccg gtg 33

<210> SEQ ID NO 1714
<211> LENGTH: 33
<212> TYPE: DNA
<213> ORGANISM: Homo sapiens

<400> SEQUENCE: 1714
gcagcatggg atgacagcct gagtggtccg gta 33

<210> SEQ ID NO 1715
<211> LENGTH: 36
<212> TYPE: DNA
<213> ORGANISM: Homo sapiens

<400> SEQUENCE: 1715
aactcccagg acaacagtgg taaccatcta gtggta 36

<210> SEQ ID NO 1716
<211> LENGTH: 33
<212> TYPE: DNA
<213> ORGANISM: Homo sapiens

<400> SEQUENCE: 1716
gcagcatggg atgacagcct gaatggtccg gta 33

<210> SEQ ID NO 1717
<211> LENGTH: 33
<212> TYPE: DNA
<213> ORGANISM: Homo sapiens

<400> SEQUENCE: 1717
gcagcatggt atgacagcct gaatggtccg gtg 33

<210> SEQ ID NO 1718
<211> LENGTH: 33
<212> TYPE: DNA
<213> ORGANISM: Homo sapiens

<400> SEQUENCE: 1718
gcagcatggg atgacagcct gaatggtccg gtg 33

<210> SEQ ID NO 1719
<211> LENGTH: 33
<212> TYPE: DNA
<213> ORGANISM: Homo sapiens

<400> SEQUENCE: 1719
gcagcatggg atgacagcct gaatggtgtg gta 33

<210> SEQ ID NO 1720
<211> LENGTH: 33
<212> TYPE: DNA
<213> ORGANISM: Homo sapiens

<400> SEQUENCE: 1720
gcagcatggg atgacagcct gagtggtgtg gta 33

<210> SEQ ID NO 1721
<211> LENGTH: 33
<212> TYPE: DNA
<213> ORGANISM: Homo sapiens

<400> SEQUENCE: 1721
gcagcatggg atgacagcct gaatggtccg gta 33

<210> SEQ ID NO 1722
<211> LENGTH: 33
<212> TYPE: DNA
<213> ORGANISM: Homo sapiens

<400> SEQUENCE: 1722
gcagcatggg atgacagcct gaatggttgg gtg 33

<210> SEQ ID NO 1723
<211> LENGTH: 33
<212> TYPE: DNA
<213> ORGANISM: Homo sapiens

<400> SEQUENCE: 1723
gcagcatggg atgacagcct gaatggtccg gtg 33

<210> SEQ ID NO 1724
<211> LENGTH: 33
<212> TYPE: DNA
<213> ORGANISM: Homo sapiens

<400> SEQUENCE: 1724
gcagcatggg atgacagcct gaatggtccg gta 33

<210> SEQ ID NO 1725
<211> LENGTH: 33
<212> TYPE: DNA
<213> ORGANISM: Homo sapiens

<400> SEQUENCE: 1725
caggtgtggg acagtagtag tgatcatcgg gtg 33

<210> SEQ ID NO 1726
<211> LENGTH: 33
<212> TYPE: DNA
<213> ORGANISM: Homo sapiens

<400> SEQUENCE: 1726
gcaccatggg atgacagcct gaatggtgtg gta 33

<210> SEQ ID NO 1727
<211> LENGTH: 33
<212> TYPE: DNA
<213> ORGANISM: Homo sapiens

<400> SEQUENCE: 1727
gcagcatggg atgacagcct gaatagttgg gtg 33

-continued

```
<210> SEQ ID NO 1728
<211> LENGTH: 33
<212> TYPE: DNA
<213> ORGANISM: Homo sapiens

<400> SEQUENCE: 1728

gcagcacggg atgacagcct gaatggtgtg gta                              33


<210> SEQ ID NO 1729
<211> LENGTH: 33
<212> TYPE: DNA
<213> ORGANISM: Homo sapiens

<400> SEQUENCE: 1729

gcagcacggg atgacagcct gaatggtgtg gta                              33


<210> SEQ ID NO 1730
<211> LENGTH: 33
<212> TYPE: DNA
<213> ORGANISM: Homo sapiens

<400> SEQUENCE: 1730

gcagcatggg atgacagcct gaatggtccg gta                              33


<210> SEQ ID NO 1731
<211> LENGTH: 33
<212> TYPE: DNA
<213> ORGANISM: Homo sapiens

<400> SEQUENCE: 1731

gcagcatggg atgacagcct gaatggtgtg gta                              33
```